United States Patent
Benarous et al.

(10) Patent No.: US 9,475,802 B2
(45) Date of Patent: Oct. 25, 2016

(54) INHIBITORS OF VIRAL REPLICATION, THEIR PROCESS OF PREPARATION AND THEIR THERAPEUTICAL USES

(71) Applicant: LABORATOIRE BIODIM, Paris (FR)

(72) Inventors: Richard Benarous, Paris (FR); Francis Chevreuil, Chantilly (FR); Benoit Ledoussal, Pommerit Jaudy (FR); Sophie Chasset, Nandy (FR); Frédéric Le Strat, Combs-la-Ville (FR)

(73) Assignee: LABORATOIRE BIODIM, Paris (FR)

( * ) Notice: Subject to any disclaimer, the term of this patent is extended or adjusted under 35 U.S.C. 154(b) by 0 days.

(21) Appl. No.: 14/434,190

(22) PCT Filed: Oct. 11, 2013

(86) PCT No.: PCT/EP2013/071321
§ 371 (c)(1),
(2) Date: Apr. 8, 2015

(87) PCT Pub. No.: WO2014/057103
PCT Pub. Date: Apr. 17, 2014

(65) Prior Publication Data
US 2015/0274718 A1    Oct. 1, 2015

Related U.S. Application Data

(60) Provisional application No. 61/712,674, filed on Oct. 11, 2012.

(30) Foreign Application Priority Data

Oct. 11, 2012   (EP) ..................... 12306244

(51) Int. Cl.

| | | |
|---|---|---|
| C07D 471/04 | (2006.01) |
| C07D 417/04 | (2006.01) |
| A61K 31/352 | (2006.01) |
| A61K 31/381 | (2006.01) |
| A61K 31/415 | (2006.01) |
| A61K 31/4155 | (2006.01) |
| A61K 31/4418 | (2006.01) |
| A61K 31/4433 | (2006.01) |
| A61K 31/506 | (2006.01) |
| C07D 311/04 | (2006.01) |
| C07D 231/12 | (2006.01) |
| C07D 405/10 | (2006.01) |
| C07D 409/10 | (2006.01) |
| C07D 213/55 | (2006.01) |
| C07D 233/60 | (2006.01) |
| C07D 417/10 | (2006.01) |
| A61K 45/06 | (2006.01) |
| A61K 31/341 | (2006.01) |
| A61K 31/47 | (2006.01) |
| A61K 31/4709 | (2006.01) |
| A61K 31/4741 | (2006.01) |
| A61K 31/497 | (2006.01) |
| A61K 31/50 | (2006.01) |
| A61K 31/501 | (2006.01) |
| A61K 31/505 | (2006.01) |

(Continued)

(52) U.S. Cl.
CPC .......... *C07D 417/04* (2013.01); *A61K 31/341* (2013.01); *A61K 31/352* (2013.01); *A61K 31/381* (2013.01); *A61K 31/415* (2013.01); *A61K 31/4155* (2013.01); *A61K 31/437* (2013.01); *A61K 31/4409* (2013.01); *A61K 31/4418* (2013.01); *A61K 31/4433* (2013.01); *A61K 31/47* (2013.01); *A61K 31/4709* (2013.01); *A61K 31/4741* (2013.01); *A61K 31/497* (2013.01); *A61K 31/50* (2013.01); *A61K 31/501* (2013.01); *A61K 31/505* (2013.01); *A61K 31/506* (2013.01); *A61K 45/06* (2013.01); *C07D 213/55* (2013.01); *C07D 231/12* (2013.01); *C07D 233/60* (2013.01); *C07D 237/08* (2013.01); *C07D 239/26* (2013.01); *C07D 311/04* (2013.01); *C07D 311/74* (2013.01); *C07D 405/10* (2013.01); *C07D 409/10* (2013.01); *C07D 417/10* (2013.01)

(58) Field of Classification Search
None
See application file for complete search history.

(56) References Cited

U.S. PATENT DOCUMENTS

2008/0221159 A1   9/2008  Tsantrizos et al.
2010/0292227 A1   11/2010 Yoakim et al.

(Continued)

OTHER PUBLICATIONS

International Search Report for PCT/EP2013/071321 dated Nov. 12, 2013.

(Continued)

*Primary Examiner* — Karl J Puttlitz
(74) *Attorney, Agent, or Firm* — B. Aaron Schulman, Esq.; Stites & Harbison, PLLC

(57) ABSTRACT

Inhibitors of viral replication of formula (I), their process of preparation and their therapeutical uses. The present invention relates to compounds, their use in the treatment or the prevention of viral disorders, including HIV.

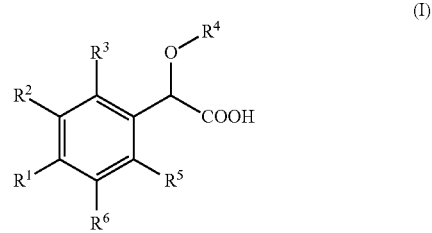

17 Claims, No Drawings

(51) Int. Cl.
  *A61K 31/437*  (2006.01)
  *A61K 31/4409* (2006.01)
  *C07D 237/08*  (2006.01)
  *C07D 239/26*  (2006.01)
  *C07D 311/74*  (2006.01)

(56) References Cited

U.S. PATENT DOCUMENTS

| | | |
|---|---|---|
| 2010/0305115 A1 | 12/2010 | Carson et al. |
| 2010/0311735 A1 | 12/2010 | Tsantrizos et al. |
| 2011/0028464 A1 | 2/2011 | Tsantrizos et al. |
| 2011/0118249 A1 | 5/2011 | Tsantrizos et al. |
| 2012/0059028 A1 | 3/2012 | Bardiot et al. |
| 2012/0129840 A1 | 5/2012 | Chaltin et al. |
| 2012/0225888 A1 | 9/2012 | Pendri et al. |
| 2012/0316161 A1 | 12/2012 | Carlens et al. |
| 2013/0190491 A1 | 7/2013 | Tsantrizos et al. |
| 2013/0197231 A1 | 8/2013 | Tsantrizos et al. |
| 2013/0203727 A1 | 8/2013 | Babaoglu et al. |
| 2013/0203747 A1 | 8/2013 | Yoakim et al. |
| 2013/0210801 A1 | 8/2013 | Babaoglu et al. |
| 2013/0289027 A1 | 10/2013 | De La Rosa et al. |
| 2014/0296272 A1 | 10/2014 | Bardiot et al. |

OTHER PUBLICATIONS

Cervia et al: "Enfuvirtide (T-20): A Novel Human Immunodeficiency Virus Type 1 Fusion Inhibitor", Clinical Infectious Diseases (Oct. 15, 2003), vol. 37, No. 8, pp. 1102-1106.

Christ et al: "Rational design of small-molecule inhibitors of the LEDGF/p75-integrase interaction and HIV replication"; Nature Chemical Biology, (May 16, 2010), pp. 1-7.

Hughes et al: "New Treatment Options for HIV Salvage Patients: An Overview of Second Generation PIs, NNRTIs, Integrase Inhibitors and CCR5 Antagonists", Journal of Infection, The British Infection Society, 2008, vol. 57, pp. 1-10.

Gregg S. Jones et al: "Preclinical Evaluation of GS-9160, a Novel Inhibitor of Human Immunodificiency Virus Type 1 Integrase" Antimicrobial Agents and Chemotherapy, (Mar. 2009), vol. 53, No. 3, pp. 1194-1203.

Adachi et al: "Production of acquired immunodeficiency syndrome-associated retrovirus in human and nonhuman cells transfected with an infectious molecular clone", Journal of Virology, American Society for Microbiology, (Aug. 1986), vol. 59, No. 2, pp. 284-291.

Lopez-Verges et al: "Tail-interacting protein TIP47 is a connector between Gag and Env and is required for Env incorporation into HIV-1 virions", PNAS, U S A., (Oct. 3, 2006), vol. 103, No. 40, pp. 14947-14952.

INHIBITORS OF VIRAL REPLICATION, THEIR PROCESS OF PREPARATION AND THEIR THERAPEUTICAL USES

The present invention relates to compounds, their use in the treatment or the prevention of viral disorders, including HIV. The present invention also relates to methods for the preparation of such compounds. The present invention also relates to pharmaceutical compositions comprising such compounds. The present invention also relates to the treatment of viral infections by the administration of a therapeutically efficient amount of such compounds.

The Acquired Immuno Deficiency Syndrome (AIDS) is a disease due to infection by the Human Immunodeficiency Virus (HIV). HIV is a retrovirus, belonging to the subclass of primate lentiviruses. Two types of HIV have been identified, HIV-1 and HIV-2. HIV-1 is responsible for the larger part of the AIDS global epidemic in the world, with virtually every country reporting cases.

Currently HIV infected patients are treated with Highly Active Anti Retroviral Therapies (HAART) that rely on a combination of several drugs belonging to different classes. Up to 2003, all approved anti-HIV drugs were inhibitors of the catalytic activity of two viral enzymes, Reverse Transcriptase (RT) inhibitors and Protease (PR) inhibitors. Reverse Transcriptase inhibitors include two different classes, Nucleoside/Nucleotide RT Inhibitors (NRTI) and Non Nucleoside RT Inhibitors (NNRTI). In 2003 a new class of Anti-retroviral drug (ARV), Fusion inhibitor (Enfuvirtide) was introduced (Cervia et al, Clin Infect Dis., 2003, 37(8): 1102-6). And lately, in 2007, two other classes of ARV were approved, Entry inhibitors (Maraviroc (Pfizer)) targeting the CCR5 co-receptor, and Integrase inhibitors (Raltegravir (Merck)) (Hughes et al, J Infect., 2008, 57(1):1-10). Although these three novel drugs were very useful to treat patients in therapeutic failure due to multiresistance to RT and PR inhibitors, resistance mutations against these drugs have already been reported.

Although the development of these potent anti-HIV drugs, has allowed HIV-infected people to live longer and to benefit of a higher quality of life, it is clear that these drugs do not cure the HIV infection. Moreover, their prolonged use often results in significant toxicity and in the emergence of drug-resistant viruses. Importantly, the ability of HIV to establish latent reservoirs early in the course of infection ensures the persistence of the virus even in the face of intensive drug therapy and vigorous antiviral immune response.

Thus, there is a continuous need for the development of novel anti-HIV therapies or a 2008, 13(3):393-416).

Document of Christ et al (Christ et al, Nat. Chem. Biol., 2010, 6: 442) and documents WO 2007131350, WO 2009062285, WO 2009062288, WO 2009062289, WO 2009062308, WO 2010130034, WO 2010130842, WO 2011015641, WO2011076765, WO 2012003498, WO 20120033735, WO 2012102985 describe partially or totally unsaturated heterocyclic derivatives as anti-HIV agents.

Document WO 2012003497 describes naphtyl derivatives as anti-HIV agents.

However, these compounds are different from the compounds according to the invention.

Surprisingly, the inventors have identified and prepared compounds having an improved antiviral activity, especially against HIV in comparison with prior art compounds.

SUMMARY OF THE INVENTION

The present invention relates to compounds that are able to totally or partially solve the above-mentioned problems and drawbacks.

The present invention provides antiviral agents, especially anti-retroviral agents, and more particularly anti-HIV compounds.

The compounds according the invention are inhibitors of HIV replication as assessed by HIV-1 replication assay as herein-detailed. These compounds are thus useful agents for treating or preventing virus, such as HIV, or other viral pathogenic diseases or disorders, by inhibiting replication of the virus into the host infected cells.

Therefore, the compounds according to the invention constitute a useful class of new potent antiviral compounds that can be used in the treatment and/or prevention of viral infections in animals, mammals and humans, more specifically for the treatment and/or prevention of HIV in humans.

The present invention further relates to such compounds for their use as a medicament (medicine), to the use of such compounds as medicaments (medicines), more specifically as antiviral agents, and to their use for the manufacture of medicaments for treating and/or preventing viral infections, in particular retroviral infections such as, but not limited to, HIV in humans.

The invention also relates to pharmaceutical composition comprising such compound as an active ingredient and at least a pharmaceutically acceptable carrier. This pharmaceutical composition further comprises at least a further antiviral agent.

The invention also relates to pharmaceutical compositions comprising such compounds in an antiviral effective amount, optionally in combination with at least one further antiviral agent.

The present invention further relates to such pharmaceutical composition for use for the prevention and/or the treatment of viral infection, preferably for the prevention and/or the treatment of retroviral infection, more preferably for the prevention and/or the treatment of an HIV infection.

The present invention further relates to such pharmaceutical composition for its use for the treatment of an HIV infection in a mammal being infected or having a risk to be infected by the HIV.

The present invention also relates to a method of treatment or prevention of viral infections, in particular retroviral infections such as, but not limited to HIV in humans by the administration of one or more such compounds, optionally in combination with one or more other antiviral agents, to a patient in need thereof.

The present invention also relates to a method of inhibiting the replication of HIV comprising exposing the virus to an effective amount of one or more such compounds under conditions where replication of HIV is inhibited.

The invention provides compounds comprising a 6-membered carbocycle, said compounds having a structure according to formula (I):

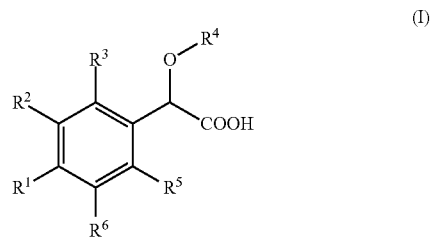

wherein:
- $R^1$ and $R^6$, identical or different, independently represent a hydrogen atom; —CN; —OH; —CF$_3$; a halogen atom; a linear or branched $C_1$-$C_3$ alkyl a linear or branched $C_1$-$C_3$ heteroalkyl;
- $R^2$, non-substituted or substituted by at least one $T^1$, represents a partially or totally unsaturated or aromatic 5-, 6- or 7-membered carbocycle; a partially or totally unsaturated or aromatic 5-, 6- or 7-membered heterocycle; a partially or totally unsaturated or aromatic 5-, 6- or 7-membered carbocycle fused with a saturated, partially or totally unsaturated or aromatic 5-, 6- or 7-membered carbocycle; a partially or totally unsaturated or aromatic 5-, 6- or 7-membered carbocycle fused with a saturated, partially or totally unsaturated or aromatic 5-, 6- or 7-membered heterocycle; a partially or totally unsaturated or aromatic 5-, 6- or 7-membered heterocycle fused with a saturated, partially or totally unsaturated or aromatic 5-, 6- or 7-membered carbocycle; a partially or totally unsaturated or aromatic 5-, 6- or 7-membered heterocycle fused with a saturated, partially or totally unsaturated or aromatic 5-, 6- or 7-membered heterocycle;
- $R^3$, non-substituted or substituted by at least one $T^2$, represents an aryl; an aryl fused with a saturated, partially or totally unsaturated or aromatic 5-, 6- or 7-membered carbocycle; an aryl fused with a saturated, partially or totally unsaturated or aromatic 5-, 6- or 7-membered heterocycle; an aryl fused with a saturated, partially or totally unsaturated or aromatic 4-, 5-, 6- or 7-membered heterocycle and further fused with a saturated, partially or totally unsaturated or aromatic 4-, 5-, 6- or 7-membered heterocycle; a heteroaryl; a heteroaryl fused with a saturated, partially or totally unsaturated or aromatic 5-, 6- or 7-membered carbocycle; a heteroaryl fused with a saturated, partially or totally unsaturated or aromatic 5-, 6- or 7-membered heterocycle; a $C_5$-$C_7$ cycloalkenyl; a $C_5$-$C_7$ cycloalkenyl fused with a saturated, partially or totally unsaturated or aromatic 4-, 5-, 6- or 7-membered heterocycle; or a saturated, partially or totally unsaturated or aromatic 5-, 6- or 7-membered heterocycle;
- $R^4$ represents a linear or branched $C_1$-$C_6$-alkyl; a linear or branched $C_1$-$C_6$ fluoroalkyl or a $C_3$-$C_6$ cycloalkyl;
- $R^5$ represents a halogen atom; —CF$_3$; a linear or branched $C_1$-$C_6$ alkyl; a linear or branched $C_2$-$C_6$ alkenyl; a linear or branched $C_2$-$C_6$ alkynyl; a linear or branched fluoroalkyl; a $C_3$-$C_6$ cycloalkyl; CH$_2$OH; or —CH$_2$—O—CH$_3$;
- $T^1$ independently represents a hydrogen atom; a halogen atom; an alkyl; —(X)$_x$—C$_1$-C$_6$ alkyl; a linear or branched fluoroalkyl; a linear or branched —O—C$_1$-C$_3$ fluoroalkyl; —(X)$_x$—C$_3$-C$_6$ cycloalkyl; —(X)$_x$—(CT$^5$T$^6$)$_y$-C$_3$-C$_6$ cycloalkyl; —(X)$_x$—(CT$^5$T$^6$)$_y$-aryl; —(X)$_x$—(CT$^5$T$^6$)$_y$CN; —(X)$_x$—(CT$^5$T$^6$)$_y$OT$^3$; —(X)$_x$—(CT$^5$T$^6$)$_y$ST$^3$; —(X)$_x$—(CT$^5$T$^6$)$_y$S(O)T$^3$; —(X)$_x$—(CT$^5$T$^6$)$_y$S(O)$_2$T$^3$; —(X)$_x$—(CT$^5$T$^6$)$_y$NT$^3$T$^4$; —(X)$_x$—(CT$^5$T$^6$)$_y$C(O)T$^3$; —(X)$_x$—(CT$^5$T$^6$)$_y$C(O)OT$^3$; —(X)$_x$—(CT$^5$T$^6$)$_y$C(O)NT$^3$T$^4$; —(X)$_x$—(CT$^5$T$^6$)$_y$NT$^3$C(O)NT$^3$T$^4$; —(X)$_x$—(CT$^5$T$^6$)$_y$NT$^3$C(O)T$^4$; —(X)$_x$—(CT$^5$T$^6$)$_y$NT$^3$C(O)OT$^4$; —(X)$_x$—(CT$^5$T$^6$)$_y$OC(O)NT$^3$T$^4$; —(X)$_x$—(CT$^5$T$^6$)$_y$S(O)$_2$NT$^3$T$^4$ or —(X)$_x$—(CT$^5$T$^6$)$_y$NT$^3$S(O)$_2$T$^4$;
- $T^2$ independently represents a hydrogen atom; a halogen atom; a linear or branched —O—C$_1$-C$_3$ alkyl; a linear or branched C$_1$-C$_3$ fluoroalkyl; a linear or branched —O—C$_1$-C$_3$ fluoroalkyl; a linear or branched C$_1$-C$_3$ alkyl; or —CN; optionally two geminal $T^2$ form with the carbon atom to which they are bonded, a $C_3$-$C_7$ cycloalkyl;
- X independently represents an oxygen atom; a sulphur atom; NT$^3$; S═O or S(O)$_2$;
- $T^3$ and $T^4$, identical or different, independently represent a hydrogen atom; a branched or linear $C_1$-$C_6$ alkyl or a $C_3$-$C_6$ cycloalkyl; optionally $T^3$, $T^4$ and the nitrogen atom to which they are bonded form a $C_4$-$C_6$ heterocycloalkyl;
- $T^5$ and $T^6$, identical or different, independently represent a hydrogen atom; a fluorine atom or a linear or branched $C_1$-$C_3$ alkyl or a $C_3$-$C_6$ cycloalkyl; optionally $T^5$, $T^6$ and the carbon atom to which they are bonded form a cyclopropyl;
- x independently represents 0 or 1;
- y independently represents 0, 1, 2 or 3; or
- $R^5$ and $R^6$ form, with the carbon atoms to which they are bonded, a heteroaryl comprising at least one nitrogen atom;

and a racemate, enantiomer, atropisomer, diastereoisomer or a pharmaceutically acceptable salt thereof.

The invention also provides compounds of formula (I) wherein;
- $R^1$ and $R^6$ represent a hydrogen atom;
- $R^2$, non-substituted or substituted by at least one $T^1$, represents a partially or totally unsaturated or aromatic 5-, 6- or 7-membered carbocycle; a partially or totally unsaturated or aromatic 5-, 6- or 7-membered heterocycle; a partially or totally unsaturated or aromatic 5-, 6- or 7-membered carbocycle fused with a saturated, partially or totally unsaturated or aromatic 5-, 6- or 7-membered carbocycle; a partially or totally unsaturated or aromatic 5-, 6- or 7-membered carbocycle fused with a saturated, partially or totally unsaturated or aromatic 5-, 6- or 7-membered heterocycle; a partially or totally unsaturated or aromatic 5-, 6- or 7-membered heterocycle fused with a saturated, partially or totally unsaturated or aromatic 5-, 6- or 7-membered carbocycle; a partially or totally unsaturated or aromatic 5-, 6- or 7-membered heterocycle fused with a saturated, partially or totally unsaturated or aromatic 5-, 6- or 7-membered heterocycle;
- $R^3$, non-substituted or substituted by at least one $T^2$, represents an aryl; an aryl fused with a saturated, partially or totally unsaturated or aromatic 5-, 6- or 7-membered carbocycle; an aryl fused with a saturated, partially or totally unsaturated or aromatic 5-, 6- or 7-membered heterocycle; an aryl fused with a saturated, partially or totally unsaturated or aromatic 4-, 5-, 6- or 7-membered heterocycle and further fused with a saturated, partially or totally unsaturated or aromatic 4-, 5-, 6- or 7-membered heterocycle; a heteroaryl; a heteroaryl fused with a saturated, partially or totally unsaturated or aromatic 5-, 6- or 7-membered carbocycle; a heteroaryl fused with a saturated, partially or totally unsaturated or aromatic 5-, 6- or 7-membered heterocycle; a $C_5$-$C_7$ cycloalkenyl; a $C_5$-$C_7$ cycloalkenyl fused with a saturated, partially or totally unsaturated or aromatic 4-, 5-, 6- or 7-membered heterocycle; or a saturated, partially or totally unsaturated or aromatic 5-, 6- or 7-membered heterocycle;
- $R^4$ represents a linear or branched $C_1$-$C_6$-alkyl; a linear or branched $C_1$-$C_6$ fluoroalkyl or a $C_3$-$C_6$ cycloalkyl;
- $R^5$ represents a halogen atom; a linear or branched $C_1$-$C_6$ alkyl; a linear or branched fluoroalkyl; a $C_3$-$C_6$ cycloalkyl or —CH$_2$OH;

$T^1$ independently represents a hydrogen atom; a halogen atom; an alkyl; —$(X)_x$—$C_1$-$C_6$ alkyl; a linear or branched fluoroalkyl; a linear or branched —O—$C_1$-$C_3$ fluoroalkyl; —$(X)_x$—$C_3$-$C_6$ cycloalkyl; —$(X)_x$—$(CT^5T^6)_y$-$C_3$-$C_6$ cycloalkyl; —$(X)_x$—$(CT^5T^6)_y$-aryl; —$(X)_x$—$(CT^5T^6)_y$CN; —$(X)_x$—$(CT^5T^6)_y$OT$^3$; —$(X)_x$—$(CT^5T^6)_y$ST$^3$; —$(X)_x$—$(CT^5T^6)_y$S(O)T$^3$; —$(X)_x$—$(CT^5T^6)_y$S(O)$_2$T$^3$; —$(X)_x$—$(CT^5T^6)_y$NT$^3$T$^4$; —$(X)_x$—$(CT^5T^6)_y$C(O)T$^3$; —$(X)_x$—$(CT^5T^6)_y$C(O)OT$^3$; —$(X)_x$—$(CT^5T^6)_y$C(O)NT$^3$T$^4$; —$(X)_x$—$(CT^5T^6)_y$NT$^3$C(O)NT$^3$T$^4$; —$(X)_x$—$(CT^5T^6)_y$NT$^3$C(O)T$^4$; —$(X)_x$—$(CT^5T^6)_y$NT$^3$C(O)OT$^4$; —$(X)_x$—$(CT^5T^6)_y$OC(O)NT$^3$T$^4$; —$(X)_x$—$(CT^5T^6)_y$ S(O)$_2$NT$^3$T$^4$ or —$(X)_x$—$(CT^5T^6)_y$NT$^3$S(O)$_2$T$^4$;

$T^2$ independently represents a hydrogen atom; a halogen atom; a linear or branched —O—$C_1$-$C_3$ alkyl; a linear or branched $C_1$-$C_3$ fluoroalkyl; a linear or branched —O—$C_1$-$C_3$ fluoroalkyl; a linear or branched $C_1$-$C_3$ alkyl; or —CN; optionally two geminal $T^2$ form with the carbon atom to which they are bonded, a $C_3$-$C_7$ cycloalkyl;

X independently represents an oxygen atom; a sulphur atom; NT$^3$; S═O or S(O)$_2$;

$T^3$ and $T^4$, identical or different, independently represent a hydrogen atom; a branched or linear $C_1$-$C_6$ alkyl or a $C_3$-$C_6$ cycloalkyl; optionally $T^3$, $T^4$ and the nitrogen atom to which they are bonded form a $C_4$-$C_6$ heterocycloalkyl;

$T^5$ and $T^6$, identical or different, independently represent a hydrogen atom; a fluorine atom or a linear or branched $C_1$-$C_3$ alkyl or a $C_3$-$C_6$ cycloalkyl; optionally $T^5$, $T^6$ and the carbon atom to which they are bonded form a cyclopropyl;

x independently represents 0 or 1;

y independently represents 0, 1, 2 or 3.

The invention also provides compounds of formula (I) wherein;

$R^1$ and $R^6$, identical or different, independently represent a hydrogen atom; —CN; —OH; —CF$_3$; a halogen atom; a linear or branched $C_1$-$C_3$ alkyl a linear or branched $C_1$-$C_3$ heteroalkyl;

$R^2$, non-substituted or substituted by at least one $T^1$, represents a partially or totally unsaturated or aromatic 5-, 6- or 7-membered carbocycle; a partially or totally unsaturated or aromatic 5-, 6- or 7-membered heterocycle; a partially or totally unsaturated or aromatic 5-, 6- or 7-membered carbocycle fused with a saturated, partially or totally unsaturated 5-, 6- or 7-membered carbocycle; a partially or totally unsaturated or aromatic 5-, 6- or 7-membered carbocycle fused with a saturated, partially or totally unsaturated 5-, 6- or 7-membered heterocycle; a partially or totally unsaturated or aromatic 5-, 6- or 7-membered heterocycle fused with a saturated, partially or totally unsaturated 5-, 6- or 7-membered carbocycle; a partially or totally unsaturated or aromatic 5-, 6- or 7-membered heterocycle fused with a saturated, partially or totally unsaturated 5-, 6- or 7-membered heterocycle;

$R^3$, non-substituted or substituted by at least one $T^2$, represents an aryl; an aryl fused with a saturated, partially or totally unsaturated or aromatic 5-, 6- or 7-membered carbocycle; an aryl fused with a saturated, partially or totally unsaturated or aromatic 5-, 6- or 7-membered heterocycle; a heteroaryl; a heteroaryl fused with a saturated, partially or totally unsaturated or aromatic 5-, 6- or 7-membered carbocycle; a heteroaryl fused with a saturated, partially or totally unsaturated or aromatic 5-, 6- or 7-membered heterocycle or a $C_3$-$C_7$ cycloalkenyl;

$R^4$ represents a linear or branched $C_1$-$C_6$-alkyl; a linear or branched $C_1$-$C_6$ fluoroalkyl or a $C_3$-$C_6$ cycloalkyl;

$R^5$ represents a halogen atom; a linear or branched $C_1$-$C_6$ alkyl; a linear or branched fluoroalkyl; a $C_3$-$C_6$ cycloalkyl or —CH$_2$OH;

$R^5$ and $R^6$ form, with the carbon atoms to which they are bonded, a heteroaryl comprising at least one nitrogen atom;

$T^1$ represents a hydrogen atom; a halogen atom; an alkyl; —$(X)_x$—$C_1$-$C_6$ alkyl; a linear or branched fluoroalkyl; a linear or branched —O—$C_1$-$C_3$ fluoroalkyl; —$(X)_x$—$C_3$-$C_6$ cycloalkyl; —$(X)_x$—$(CT^5T^6)_y$-aryl; —$(X)_x$—$(CT^5T^6)_y$CN; —$(X)_x$—$(CT^5T^6)_y$OT$^3$; —$(X)_x$—$(CT^5T^6)_y$ST$^3$; —$(X)_x$—$(CT^5T^6)_y$S(O)T$^3$; —$(X)_x$—$(CT^5T^6)_y$S(O)$_2$T$^3$; —$(X)_x$—$(CT^5T^6)_y$NT$^3$T$^4$; —$(X)_x$—$(CT^5T^6)_y$C(O)T$^3$; —$(X)_x$—$(CT^5T^6)_y$C(O)OT$^3$; —$(X)_x$—$(CT^5T^6)_y$C(O)NT$^3$T$^4$; —$(X)_x$—$(CT^5T^6)_y$NT$^3$C(O)NT$^3$T$^4$; —$(X)_x$—$(CT^5T^6)_y$NT$^3$C(O)T$^4$; —$(X)_x$—$(CT^5T^6)_y$NT$^3$C(O)OT$^4$; —$(X)_x$—$(CT^5T^6)_y$OC(O)NT$^3$T$^4$; —$(X)_x$—$(CT^5T^6)_y$ S(O)$_2$NT$^3$T$^4$ or —$(X)_x$—$(CT^5T^6)_y$NT$^3$S(O)$_2$T$^4$;

$T^2$ represents a hydrogen atom; a halogen atom; a linear or branched —O—$C_1$-$C_3$ alkyl; a linear or branched $C_1$-$C_3$ fluoroalkyl; a linear or branched —O—$C_1$-$C_3$ fluoroalkyl; a linear or branched $C_1$-$C_3$ alkyl; cyclopropyl or —CN;

X represents an oxygen atom; a sulphur atom; NT$^3$; S═O or S(O)$_2$;

$T^3$ and $T^4$, identical or different, independently represent a hydrogen atom; a branched or linear $C_1$-$C_6$ alkyl or a $C_3$-$C_6$ cycloalkyl;

$T^3$, $T^4$ and the nitrogen atom to which they are bonded form a $C_4$-$C_6$ heterocycloalkyl;

$T^5$ and $T^6$, identical or different, independently represent a hydrogen atom; a fluorine atom or a linear or branched $C_1$-$C_3$ alkyl or a $C_3$-$C_6$ cycloalkyl;

$T^5$, $T^6$ and the carbon atom to which they are bonded form a cyclopropyl;

x represents 0 or 1;

y represents 0, 1, 2 or 3;

and a racemate, enantiomer, isomer, atropisomer or diastereoisomer or a pharmaceutically acceptable salt thereof.

DETAILED DESCRIPTION OF THE INVENTION

Even if described in particular or preferred embodiments, the present invention is not to be understood as being limited to such particular or preferred embodiments.

The term "alkyl" as used herein, either alone or in combination with another radical, refers to acyclic, linear or branched chain alkyl radicals.

The term "heteroalkyl" as used herein, alone or in combination with another radical, refers to an acyclic alkyl wherein one or more carbon atoms are replaced by an oxygen, nitrogen or sulphur atom.

The term "cycloalkyl", as used herein, either alone or in combination with another radical, refers to a monocyclic or polycyclic saturated hydrocarbon radical.

The term "aryl", as used herein, either alone or in combination with another radical, refers to a carbocyclic aromatic monocyclic group containing 6 carbon atoms which can be fused with at least another saturated, unsaturated or aromatic carbocycle.

The term "carbocycle", as used herein and unless specified otherwise, either alone or in combination with another radical, refers to a 3- to 8-membered saturated, unsaturated or aromatic cyclic radical in which all of the ring members are carbon atoms and which can be fused with at least another carbocycle.

The term "heterocycle" as used herein means a saturated, unsaturated or aromatic ring system of 3 to 18 atoms including at least one N, O or S and which can be fused with at least another carbocycle or heterocycle.

The expression "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the present invention can be synthesized from the parent compound which contains a basic or acidic moiety by conventional chemical methods.

The term "enantiomer" is employed herein to refer to one of the two specific stereoisomers which is a non-superimposable mirror image with one other but is related to one other by reflection.

The term "diastereoisomer" is employed herein to refer to one of the stereoisomers which is a non-superimposable mirror image with one other but is not related to one other by reflection.

The term "racemate" is employed herein to refer to an equal amount of two specific enantiomers.

The term "atropisomer" is employed herein to refer to stereoisomer obtained by a sterically hindered single bond whereby the free rotation of functional groups on either side of this bond is not allowed.

The term "tautomer" is employed herein to refer to constitutional isomer obtained by a formal migration of a hydrogen atom or a proton accompanied by a switch of a single bond and adjacent double bond.

The term "treatment" as used herein is intended to mean the administration of a compound or composition according to the present invention to alleviate or eliminate symptoms of HIV infection and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectable levels in the blood, and the administration of a compound or composition according to the present invention to prevent perinatal transmission of HIV from mother to baby, by administration to the mother before giving birth and to the child within the first days of life.

The expression "therapeutically effective amount" refers to an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient Such a therapeutically effective amount can be determined routinely by one of ordinary skill in the art having regard to their own knowledge, the state of the art, and this disclosure.

The term "mammal" as used herein is intended to encompass humans, as well as non-human mammals which are susceptible to infection by HIV or non human equivalents of HIV. Non-human mammals include but are not limited to domestic animals, such as cows, pigs, dogs, cats, rabbits, rats and mice, and non domestic animals.

The compounds according to the invention are compounds of formula (I) as defined and including the embodiments described in the summary of the invention.

In particular, according to feature (a), the compounds according to the invention are compounds of formula (I) wherein $R^4$ represents tBu.

Particularly, according to feature (b), the compounds according to the invention are compounds of formula (I) wherein $R^2$, non-substituted or substituted by at least one $T^1$, represents a partially or totally unsaturated or aromatic 5-, 6- or 7-membered carbocycle; a partially or totally unsaturated or aromatic 5-, 6- or 7-membered heterocycle or a partially or totally unsaturated or aromatic 5-, 6- or 7-membered heterocycle fused with a saturated, partially or totally unsaturated 5-, 6- or 7-membered heterocycle;

$T^1$ represents a hydrogen atom; a halogen atom; —$CH_3$; —$CH_2F$; —$CHF_2$; —$CF_3$; —OMe; —$OCH_2F$; —$OCHF_2$; —$OCF_3$; —$(X)_x$—$C_3$-$C_6$ cycloalkyl; —$(X)_x$—$(CT^5T^6)_y$-aryl; —$(X)_x$—$(CT^5T^6)_y$CN; —$(X)_x$—$(CT^5T^6)_y$OT$^3$; —$(X)_x$—$(CT^5T^6)_y$ST$^3$; —$(X)_x$—$(CT^5T^6)_y$S(O)T$^3$; —$(X)_x$—$(CT^5T^6)_y$S(O)$_2$T$^3$; —$(X)_x$—$(CT^5T^6)_y$NT$^3$T$^4$; —$(X)_x$—$(CT^5T^6)_y$C(O)T$^3$; —$(X)_x$—$(CT^5T^6)_y$C(O)OT$^3$; —$(X)_x$—$(CT^5T^6)_y$C(O)NT$^3$T$^4$; —$(X)_x$—$(CT^5T^6)_y$NT$^3$C(O)NT$^3$T$^4$; —$(X)_x$—$(CT^5T^6)_y$NT$^3$C(O)T$^4$; —$(X)_x$—$(CT^5T^6)_y$NT$^3$C(O)OT$^4$; —$(X)_x$—$(CT^5T^6)_y$OC(O)NT$^3$T$^4$; —$(X)_x$—$(CT^5T^6)_y$ S(O)$_2$NT$^3$T$^4$ or —$(X)_x$—$(CT^5T^6)_y$NT$^3$S(O)$_2$T$^4$;

X independently represents an oxygen atom; a sulphur atom; NT$^3$; S=O or S(O)$_2$;

T$^3$ and T$^4$, identical or different, independently represent a hydrogen atom; a branched or linear $C_1$-$C_6$ alkyl or a $C_3$-$C_6$ cycloalkyl;

T$^3$, T$^4$ and the nitrogen atom to which they are bonded form a $C_4$-$C_6$ heterocycloalkyl;

T$^5$ and T$^6$, identical or different, independently represent a hydrogen atom; a fluorine atom or methyl;

x independently represents 0 or 1;

y independently represents 0, 1, 2 or 3.

Particularly, according to feature (c), the compounds according to the invention are compounds of formula (I) wherein $R^2$ represents a partially or totally unsaturated or aromatic 5-, 6- or 7-membered carbocycle; a partially or totally unsaturated or aromatic 5-, 6- or 7-membered heterocycle; a partially or totally unsaturated or aromatic 5-, 6- or 7-membered heterocycle fused with a saturated, partially or totally unsaturated or aromatic 5-, 6- or 7-membered heterocycle; or a partially or totally unsaturated or aromatic 5-, 6- or 7-membered heterocycle fused with a saturated, partially or totally unsaturated or aromatic 5-, 6- or 7-membered carbocycle;

$T^1$ independently represents a hydrogen atom; a halogen atom; —$CH_3$; —$CH_2CH_3$; —$(CH_2)_2CH_3$; —$CH(CH_3)_2$; —$CH_2CF_3$; —$OCH_3$; —$NH_2$; —$N(CH_3)_2$; —$CH_2F$; —$CHF_2$; —$CF_3$; —$OCH_2F$; —$OCHF_2$; —$OCF_3$; —$(X)_x$—$C_3$-$C_6$ cycloalkyl; —$(X)_x$—$(CT^5T^6)_y$-$C_3$-$C_6$ cycloalkyl; —$(X)_x$—$(CT^5T^6)_y$-aryl; —$(X)_x$—$(CT^5T^6)_y$CN; —$(X)_x$—$(CT^5T^6)_y$OT$^3$; —$(X)_x$—$(CT^5T^6)_y$ST$^3$; —$(X)_x$—$(CT^5T^6)_y$S(O)T$^3$; —$(X)_x$—$(CT^5T^6)_y$S(O)$_2$T$^3$; —$(X)_x$—$(CT^5T^6)_y$NT$^3$T$^4$; —$(X)_x$—$(CT^5T^6)_y$C(O)T$^3$; —$(X)_x$—$(CT^5T^6)_y$C(O)OT$^3$; —$(X)_x$—$(CT^5T^6)_y$C(O)NT$^3$T$^4$; —$(X)_x$—$(CT^5T^6)_y$NT$^3$C(O)NT$^3$T$^4$; —$(X)_x$—$(CT^5T^6)_y$NT$^3$C(O)T$^4$; —$(X)_x$—$(CT^5T^6)_y$NT$^3$C(O)OT$^4$; —$(X)_x$—$(CT^5T^6)_y$OC(O)NT$^3$T$^4$; —$(X)_x$—$(CT^5T^6)_y$S(O)$_2$NT$^3$T$^4$ or —$(X)_x$—$(CT^5T^6)_y$NT$^3$S(O)$_2$T$^4$;

X independently represents an oxygen atom; a sulphur atom; NT$^3$; S=O or S(O)$_2$;

$T^3$ and $T^4$, identical or different, independently represent a hydrogen atom; a branched or linear $C_1$-$C_6$ alkyl or a $C_3$-$C_6$ cycloalkyl;

$T^5$ and $T^6$, identical or different, independently represent a hydrogen atom; a fluorine atom or methyl;

x independently represents 0 or 1;

y independently represents 0, 1, 2 or 3.

Preferably, according to feature (d), the invention provides compounds of formula (I), wherein $R^3$, non-substituted or substituted by at least one $T^2$, represents an aryl fused with a saturated, partially or totally unsaturated or aromatic 5-, 6- or 7-membered heterocycle; or a $C_5$-$C_7$ cycloalkenyl.

More preferably, according to feature (e), the invention provides compounds of formula (I), wherein $R^3$, non-substituted or substituted by at least one $T^2$, represents a cyclohexenyl or a dihydrobenzopyranyl.

Preferably, according to feature (f), the invention provides compounds of formula (I), wherein $R^2$, non-substituted or substituted by at least one $T^1$, represents a partially or totally unsaturated or aromatic 5-, 6- or 7-membered heterocycle; a partially or totally unsaturated or aromatic 5-, 6- or 7-membered heterocycle fused with a saturated, partially or totally unsaturated or aromatic 5-, 6- or 7-membered heterocycle; or a partially or totally unsaturated or aromatic 5-, 6- or 7-membered heterocycle fused with a saturated, partially or totally unsaturated or aromatic 5-, 6- or 7-membered carbocycle.

More preferably, according to feature (g), the invention provides compounds of formula (I), wherein $R^2$, non-substituted or substituted by at least one $T^1$, represents a phenyl, a cyclohexenyl, a cyclopentenyl, a thiophenyl, a pyrazolyl, an isothiazolyl, a benzothiazolyl, a pyridinyl, a thiazolyl, an imidazolyl, a pyridinopyrazolyl, a pyrimidinyl, a pyranyl, a pyridinonyl, or a pyridazinyl.

More preferably, according to feature (h), the invention provides compounds of formula (I), wherein $R^2$, non-substituted or substituted by at least one $T^1$, represents a thiophenyl, a pyrazolyl, an isothiazolyl, a benzothiazolyl, a pyridinyl, a thiazolyl, an imidazolyl, a pyridinopyrazolyl, a pyrimidinyl, a pyranyl, a pyridinonyl, or a pyridazinyl.

Preferably, according to feature (i), the invention provides compounds of formula (I), wherein:
$T^1$ independently represents a hydrogen atom; a halogen atom; an alkyl; —$(X)_x$—$C_1$-$C_6$ alkyl; a linear or branched fluoroalkyl; —$(X)_x$—$C_3$-$C_6$ cycloalkyl; —$(X)_x$—$(CT^5T^6)_y$-$C_3$-$C_6$ cycloalkyl; —$(X)_x$—$(CT^5T^6)_y$OT$^3$; —$(X)_x$—$(CT^5T^6)_y$-aryl; —$(X)_x$—$(CT^5T^6)_y$NT$^3$T$^4$; —$(X)_x$—$(CT^5T^6)_y$C(O)OT$^3$; —$(X)_x$—$(CT^5T^6)_y$C(O)NT$^3$T$^4$; or —$(X)_x$—$(CT^5T^6)_y$NT$^3$C(O)T$^4$;

$T^2$ independently represents a hydrogen atom; a halogen atom; a linear or branched $C_1$-$C_3$ fluoroalkyl; or a linear or branched $C_1$-$C_3$ alkyl;

X represents an oxygen atom;

$T^3$ and $T^4$, identical or different, independently represent a hydrogen atom; or a branched or linear $C_1$-$C_6$ alkyl;

x independently represents 0 or 1;

y independently represents 0, 1, 2 or 3.

More preferably, according to feature (j), the invention provides compounds of formula (I), wherein:
$T^1$ independently represents a hydrogen atom; a fluorine atom; a bromine atom; a chlorine atom; —$CH_3$; —$CH_2CH_3$; —$(CH_2)_2CH_3$; —$CH_2CH(CH_3)_2$; —$CF_3$; —$CH_2CF_3$; —$OCH_3$; —$NH_2$; —$N(CH_3)_2$; a cyclopropyl; a phenyl; a benzyloxy; a benzyl; a methylcyclopropane; an ethylcyclopropane; a methylcyclobutane; —$C(O)OH$; —$C(O)NH_2$; —$C(O)NH(CH_3)$; or —$NHC(O)CH_3$;

$T^2$ represents a hydrogen atom.

Preferably, according to feature (k), the invention compounds of formula (I), wherein $R^5$ represents:
a linear or branched $C_1$-$C_3$ alkyl;
a linear or branched fluoroalkyl;
a halogen atom;
a $C_3$-$C_6$ cycloalkyl;
—$CH_2OH$.

Preferably, according to feature (l), the invention provides compounds of formula (I) wherein $R^5$ represents:
a linear or branched $C_1$-$C_3$ alkyl;
a linear or branched $C_1$-$C_3$ fluoroalkyl;
a halogen atom;
a $C_3$-$C_6$ cycloalkyl; or
—$CH_2OH$.

Advantageously, according to feature (m), the invention provides compounds of formula (I) wherein $R^5$ represent methyl; ethyl; —$CH_2F$; —$CHF_2$; —$CF_3$; —$CH_2CH_2F$; —$CH_2CHF_2$; —$CH_2CF_3$; —$CH_2OH$.

Advantageously, according to feature (n), the invention provides compounds of formula (I) wherein $R^5$ represents methyl or —$CF_3$.

Preferably, the invention provides compounds of formula (I) comprising the two features: (a) and (b); (a) and (c); (a) and (d); (a) and (e); (a) and (f); (a) and (g); (a) and (h); (a) and (i); (a) and (j); (a) and (k); (a) and (l); (a) and (m); (a) and (n); (b) and (d); (b) and (e); (b) and (k); (b) and (l); (b) and (m); (b) and (n); (c) and (d); (c) and (e); (c) and (k); (c) and (l); (c) and (m); (c) and (n); (d) and (f); (d) and (g); (d) and (h); (d) and (i); (d) and (j); (d) and (k); (d) and (l); (d) and (m); (d) and (n); (e) and (h); (e) and (f); (e) and (g); (e) and (h); (e) and (i); (e) and (j); (e) and (k); (e) and (l); (e) and (m); (e) and (n); (f) and (i); (f) and (j); (f) and (k); (f) and (l); (f) and (m); (f) and (n); (g) and (i); (g) and (j); (g) and (k); (g) and (l); (g) and (m); (g) and (n); (h) and (i); (h) and (j); (h) and (k); (h) and (l); (h) and (m); or (h) and (n).

Preferably, the invention provides compounds of formula (I) comprising the three features: (a), (b) and (d); (a), (b) and (e); (a), (b) and (k); (a), (b) and (l); (a), (b) and (m); (a), (b)

and (n); (a), (c) and (d); (a), (c) and (e); (a), (c) and (k); (a), (c) and (l); (a), (c) and (m); (a), (c) and (n); (a), (d) and (f); (a), (d) and (h); (a), (d) and (i); (a), (d) and (j); (a), (d) and (k); (a), (d) and (l); (a), (d) and (m); (a), (d) and (n); (a), (e) and (f); (a), (e) and (g); (a), (e) and (i); (a), (e) and (j); (a), (e) and (k); (a), (e) and (l); (a), (e) and (m); (a), (e) and (n); (a), (f) and (i); (a), (f) and (j); (a), (f) and (k); (a), (f) and (l); (a), (f) and (m); (a), (f) and (n). (a), (g) and (i); (a), (g) and (j); (a), (g) and (k); (a), (g) and (l); (a), (g) and (m); (a), (g) and (n); (a), (h) and (i); (a), (h) and (j); (a), (h) and (k); (a), (h) and (l); (a), (h) and (m); or (a), (h) and (n).

Preferably, the invention provides compounds of formula (I) comprising the four features: (a), (d), (f) and (i); (a), (d), (f) and (j); (a), (d), (f) and (k); (a), (d), (f) and (l); (a), (d), (f) and (m); (a), (d), (f) and (n); (a), (d), (g) and (i); (a), (d), (g) and (j); (a), (d), (g) and (k); (a), (d), (g) and (l); (a), (d), (g) and (m); (a), (d), (g) and (n); (a), (d), (h) and (i); (a), (d), (h) and (j); (a), (d), (h) and (k); (a), (d), (h) and (l); (a), (d), (h) and (m); (a), (d), (h) and (n); (a), (e), (f) and (i); (a), (e), (f) and (j); (a), (e), (f) and (k); (a), (e), (f) and (l); (a), (e), (f) and (m); (a), (e), (f) and (n); (a), (e), (g) and (i); (a), (e), (g) and (j); (a), (e), (g) and (k); (a), (e), (g) and (l); (a), (e), (g) and (m); (a), (e), (g) and (n); (a), (e), (h) and (i); (a), (e), (h) and (j); (a), (e), (h) and (k); (a), (e), (h) and (l); (a), (e), (h) and (m); or (a), (e), (h) and (n).

Preferably, the invention provides compounds of formula (I) comprising the five features: (a), (d), (f), (i) and (k); (a), (d), (f), (i) and (l); (a), (d), (f), (i) and (m); (a), (d), (f), (i) and (n); (a), (e), (f), (i) and (k); (a), (e), (f), (i) and (l); (a), (e), (f), (i) and (m); (a), (e), (f), (i) and (n); (a), (d), (g), (i) and (k); (a), (d), (g), (i) and (l); (a), (d), (g), (i) and (m); (a), (d), (g), (i) and (n); (a), (e), (g), (i) and (k); (a), (e), (g), (i) and (l); (a), (e), (g), (i) and (m); (a), (e), (g), (i) and (n); (a), (d), (f), (j) and (k); (a), (d), (f), (j) and (l); (a), (d), (f), (j) and (m); (a), (d), (f), (j) and (n); (a), (e), (f), (j) and (k); (a), (e), (f), (j) and (l); (a), (e), (f), (j) and (m); (a), (e), (f), (j) and (n); (a), (d), (g), (j) and (k); (a), (d), (g), (j) and (l); (a), (d), (g), (j) and (m); (a), (d), (g), (j) and (n); (a), (e), (g), (j) and (k); (a), (e), (g), (j) and (l); (a), (e), (g), (j) and (m); or (a), (e), (g), (j) and (n).

Advantageously, the invention provides compounds of formula (A), (B), (C), (D), (E) or (F)

wherein
a, b, c, d, e, f, g, h, i, j, k, l, m, n, o and p independently represent 0 or 1;
V represents a substituted or non-substituted partially or totally unsaturated carbocycle or a partially or totally unsaturated or aromatic heterocycle;
W represents a substituted or non-substituted partially unsaturated carbo- or heterocycle;
$Q^1$ represents $CR^7$ or N;
$Q^2$ represents $CR^8$ or N;
$Q^3$ represents $CR^9$ or N;
$Q^4$ represents $CR^{10}$ or N;
$Q^5$ represents $CR^{11}$ or N;
$Q^6$ represents $CR^{12}$ or N;
$Q^7$ represents $CR^{13}$, C=O, $NR^{13}$, N, S, O, S=O or $S(O)_2$;
$Q^8$ represents $CR^{14}$, C=O, $NR^{14}$, N, S, O, S=O or $S(O)_2$;

Q⁹ represents CR¹⁵, C=O, NR¹⁵, N, S, O, S=O or S(O)₂;

Q¹⁰ represents CR¹⁶, NR¹⁶, N, S, O, S=O or S(O)₂;

Q¹¹ represents C, CR¹⁷, N;

Q¹² represents C, CR¹⁸, C=O, N, NR¹⁸; O, S, S=O or S(O)₂;

Q¹³ represents C, CR¹⁹, C=O, N, NR¹⁹; O, S, S=O or S(O)₂;

Q¹⁴ represents C, CR²⁰, C=O, N, NR²⁰; O, S, S=O or S(O)₂;

Q¹⁵ represents C, CR²¹, C=O, N, NR²¹; O, S, S=O or S(O)₂;

Q¹⁶ represents C, CR²², C=O, N, NR²²; O, S, S=O or S(O)₂;

R⁷, R⁸, R⁹, R¹⁰, R¹¹, R¹², R¹³, R¹⁴, R¹⁵, R¹⁶, R¹⁷, R¹⁸, R¹⁹, R²⁰, R²¹ and R²², identical or different, independently represent a hydrogen atom; a halogen atom; —CH₃; —CH₂CH₃; —(CH₂)₂CH₃; —CH(CH₃)₂; —CH₂CF₃; —OCH₃; —NH₂; —N(CH₃)₂; —CH₂F; —CHF₂; —CF₃; —OCH₂F; —OCHF₂; —OCF₃; —(X)ₓ—C₃-C₆ cycloalkyl; —(X)ₓ—(CT⁵T⁶)ᵧ-C₃-C₆ cycloalkyl; —(X)ₓ—(CT⁵T⁶)ᵧ-aryl; —(X)ₓ—(CT⁵T⁶)ᵧCN; —(X)ₓ—(CT⁵T⁶)ᵧOT³; —(X)ₓ—(CT⁵T⁶)ᵧST³; —(X)ₓ—(CT⁵T⁶)ᵧS(O)T³; —(X)ₓ—(CT⁵T⁶)ᵧS(O)₂T³; —(X)ₓ—(CT⁵T⁶)ᵧNT³T⁴; —(X)ₓ—(CT⁵T⁶)ᵧC(O)T³; —(X)ₓ—(CT⁵T⁶)ᵧC(O)OT³; —(X)ₓ—(CT⁵T⁶)ᵧC(O)NT³T⁴; —(X)ₓ—(CT⁵T⁶)ᵧNT³C(O)NT³T⁴; —(X)ₓ—(CT⁵T⁶)ᵧNT³C(O)T⁴; —(X)ₓ—(CT⁵T⁶)ᵧNT³C(O)OT⁴; —(X)ₓ—(CT⁵T⁶)ᵧOC(O)NT³T⁴; —(X)ₓ—(CT⁵T⁶)ᵧS(O)₂NT³T⁴ or —(X)ₓ—(CT⁵T⁶)ᵧNT³S(O)₂T⁴;

T² independently represents a hydrogen atom; a halogen atom; a linear or branched C₁-C₃ alkyl; —CH₂F; —CHF₂; —CF₃; —OMe; —OCH₂F; —OCHF₂; —OCF₃; or —CN; optionally two geminal T² form with the carbon atom to which they are bonded, a C₃-C₇ cycloalkyl;

R¹, R³, R⁵, R⁶, X, x, y and T³ to T⁶ are independently defined as for the compounds of formula (I).

The invention provides compounds of formula (A), (B), (C), (D), (E) or (F), wherein:

R⁷, Q¹, Q² and R⁸ form a saturated, partially or totally unsaturated or aromatic 6-membered carbo- or heterocycle;

R⁸, Q², Q³ and R⁹ form a saturated, partially or totally unsaturated or aromatic 6-membered carbo- or heterocycle;

R⁹, Q³, Q⁴ and R¹⁰ form a saturated, partially or totally unsaturated or aromatic 6-membered carbo- or heterocycle;

R¹⁰, Q⁴, Q⁵ and R¹¹ form a saturated, partially or totally unsaturated or aromatic 6-membered carbo- or heterocycle;

R¹³, Q⁷, Q⁸ and R¹⁴ form a saturated, partially or totally unsaturated or aromatic 6-membered carbo- or heterocycle;

R¹⁴, Q⁸, Q⁹ and R¹⁵ form a saturated, partially or totally unsaturated or aromatic 6-membered carbo- or heterocycle;

R¹⁵, Q⁹, Q¹⁰ and R¹⁶ form a saturated, partially or totally unsaturated or aromatic 6-membered carbo- or heterocycle;

R¹⁸, Q¹², Q¹³ and R¹⁹ form a saturated, partially or totally unsaturated or aromatic 6-membered carbo- or heterocycle;

R¹⁹, Q¹³, Q¹⁴ and R²⁰ form a saturated, partially or totally unsaturated or aromatic 6-membered carbo- or heterocycle;

R²⁰, Q¹⁴, Q¹⁵ and R²¹ form a saturated, partially or totally unsaturated or aromatic 6-membered carbo- or heterocycle; or R²¹, Q¹⁵, Q¹⁶ and R²² form a saturated, partially or totally unsaturated or aromatic 6-membered carbo- or heterocycle.

More advantageously, the invention provides compounds of formula (A), (B), (C), (D), (E) or (F), wherein R⁷, R⁸, R⁹, R¹⁰, R¹¹, R¹², R¹³, R¹⁴, R¹⁵, R¹⁶, R¹⁷, R¹⁸, R¹⁹, R²⁰, R²¹ and R²², identical or different, independently represent a hydrogen atom; a halogen atom; a linear or branched C₁-C₆ alkyl; a linear or branched —O—C₁-C₆ alkyl; —(X)ₓ—(CT⁵T⁶)ᵧ-aryl; —C(O)NH₂.

More advantageously, the invention provides compounds of formula (A), (B), (C), (D), (E) or (F), wherein R⁷, R⁸, R⁹, R¹⁰, R¹¹, R¹², R¹³, R¹⁴, R¹⁵, R¹⁶, R¹⁷, R¹⁸, R¹⁹, R²⁰, R²¹ and R²², identical or different, independently represent a hydrogen atom; a halogen atom; a linear or branched C₁-C₆ alkyl; a linear or branched —O—C₁-C₆ alkyl; —(X)ₓ—C₃-C₆ cycloalkyl; —(X)ₓ—(CT⁵T⁶)ᵧ-C₃-C₆ cycloalkyl; —(X)ₓ—(CT⁵T⁶)ᵧ-aryl; —C(O)OH; —C(O)NH₂; —C(O)NH(CH₃); or —NHC(O)CH₃.

Preferably, the invention provides compounds of formulae (A1) to (A10), (B1) to (B15), (C1) to (C9), (D1) to (D10), (E1) to (E7) or (F1) to (F8)

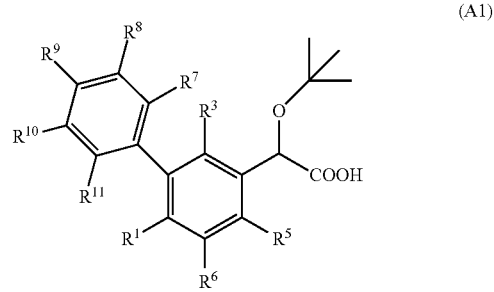

(A1)

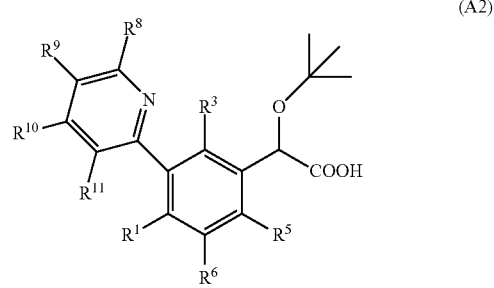

(A2)

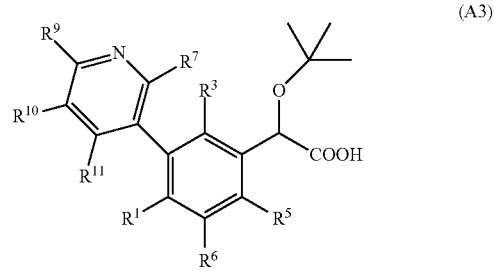

(A3)

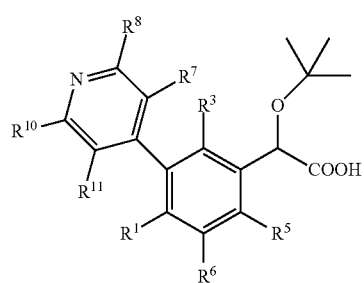 (A4)
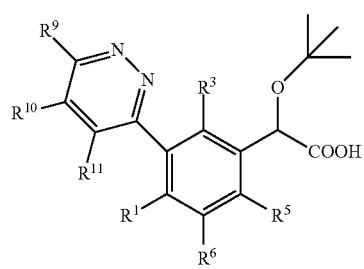 (A5)
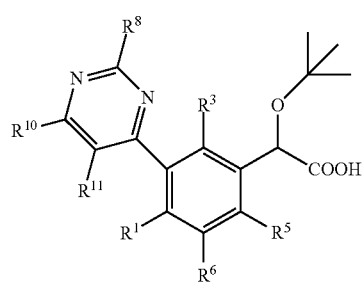 (A6)
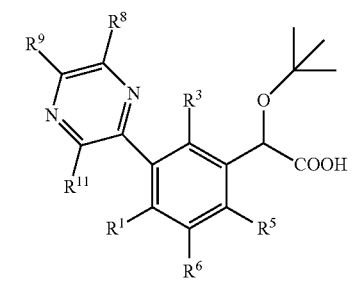 (A7)
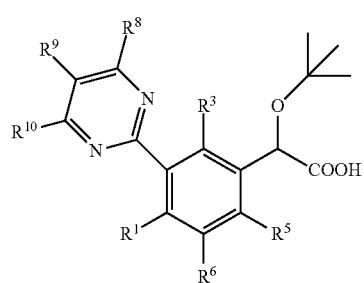 (A8)
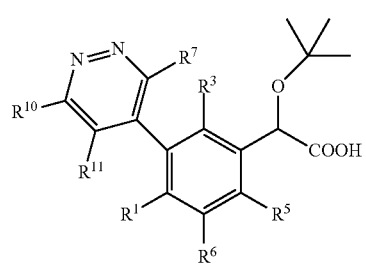 (A9)
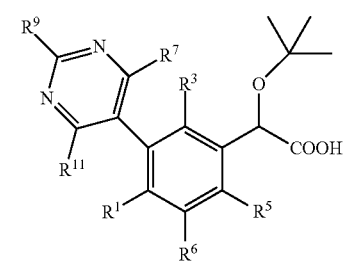 (A10)
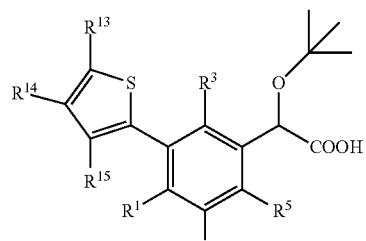 (B1)
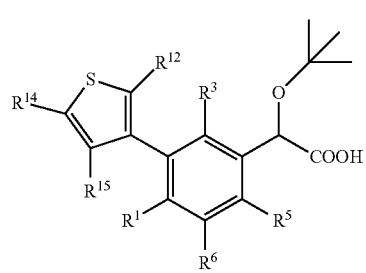 (B2)
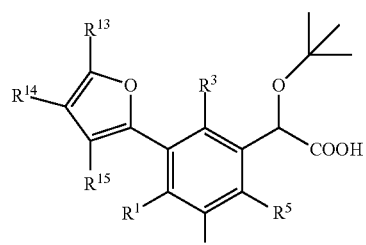 (B3)
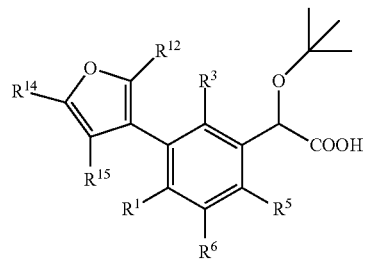 (B4)

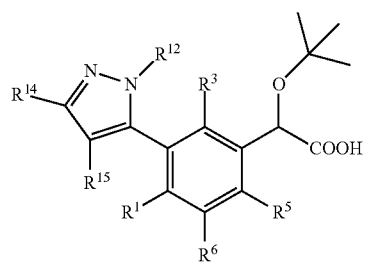
(B5)
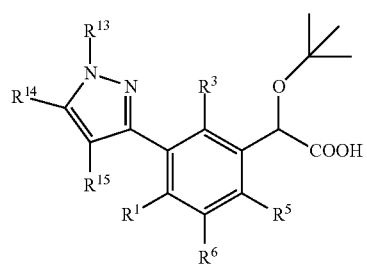
(B6)
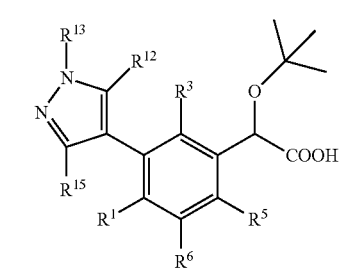
(B7)
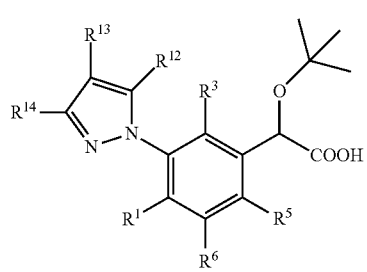
(B8)
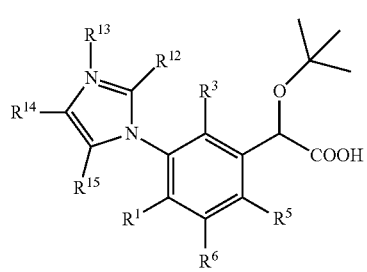
(B9)
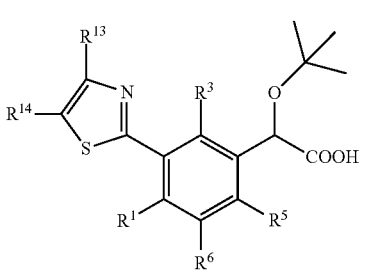
(B10)
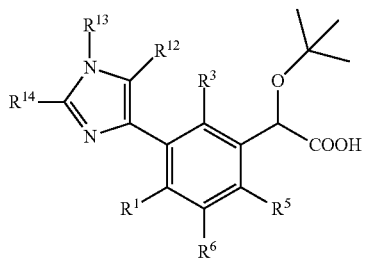
(B11)
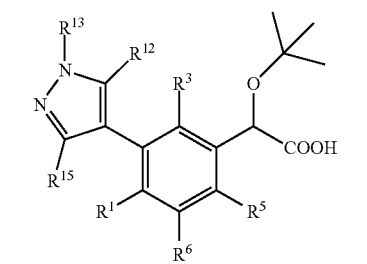
(B12)
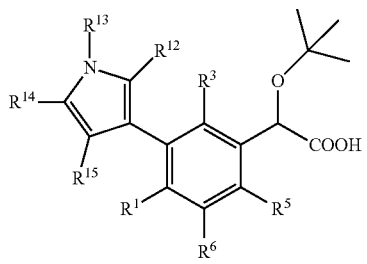
(B13)
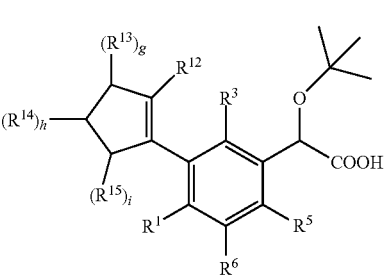
(B14)
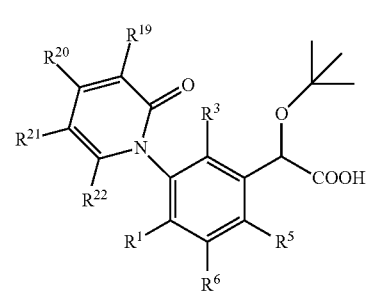
(B15)
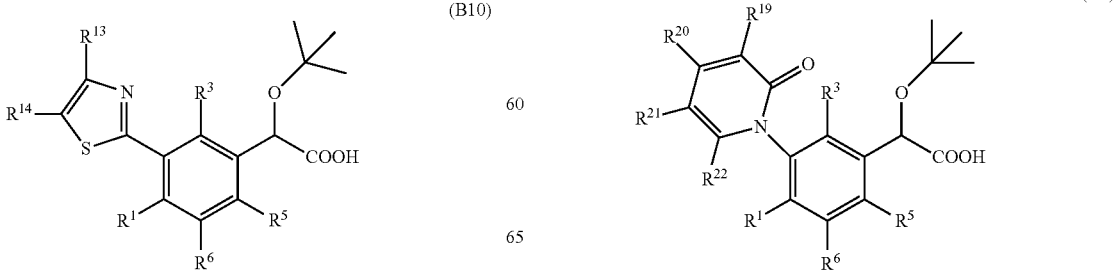
(C1)

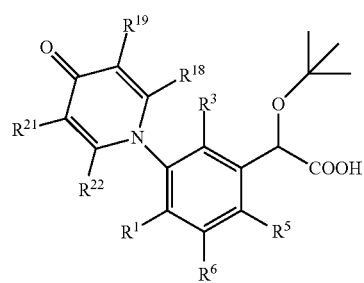
(C2)
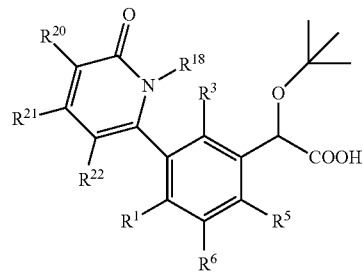
(C3)
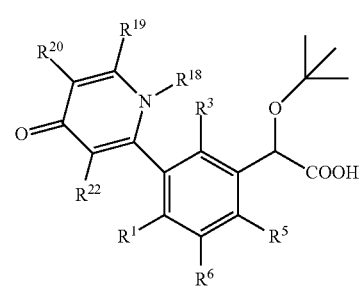
(C4)
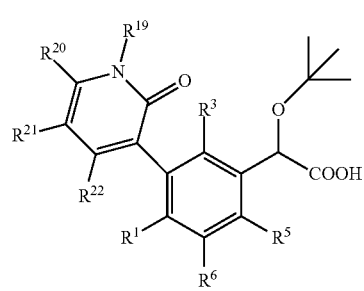
(C5)
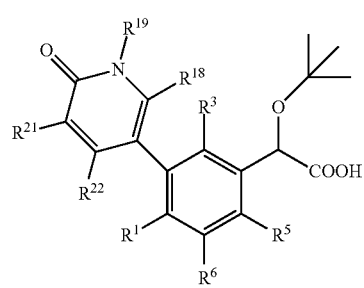
(C6)
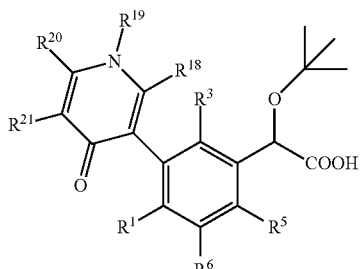
(C7)
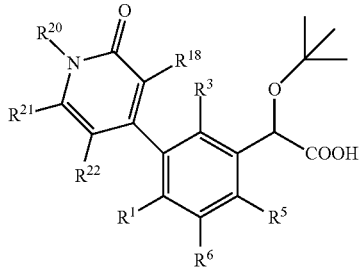
(C8)
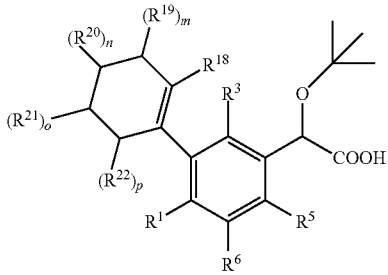
(C9)
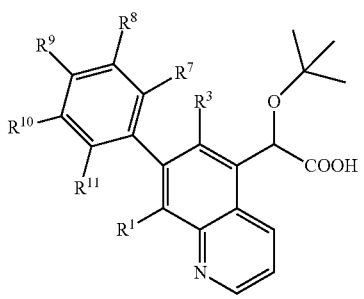
(D1)
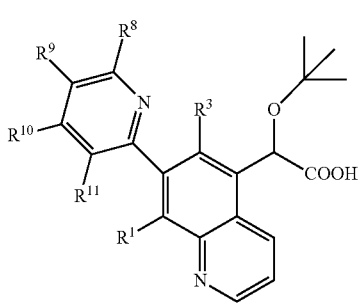
(D2)

-continued
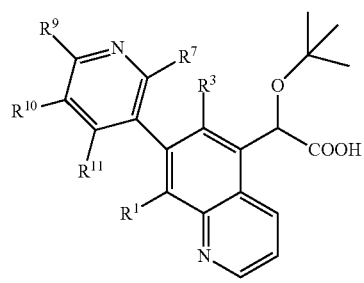 (D3)
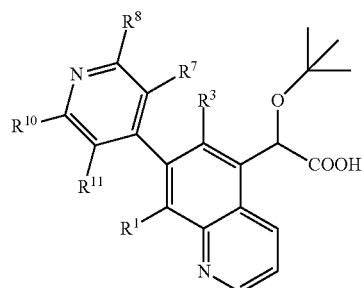 (D4)
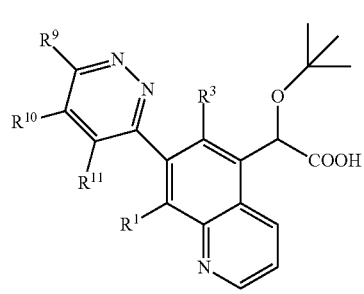 (D5)
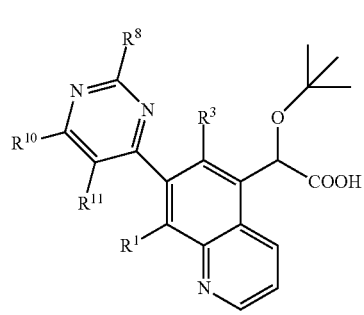 (D6)
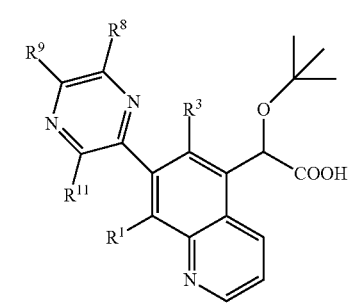 (D7)
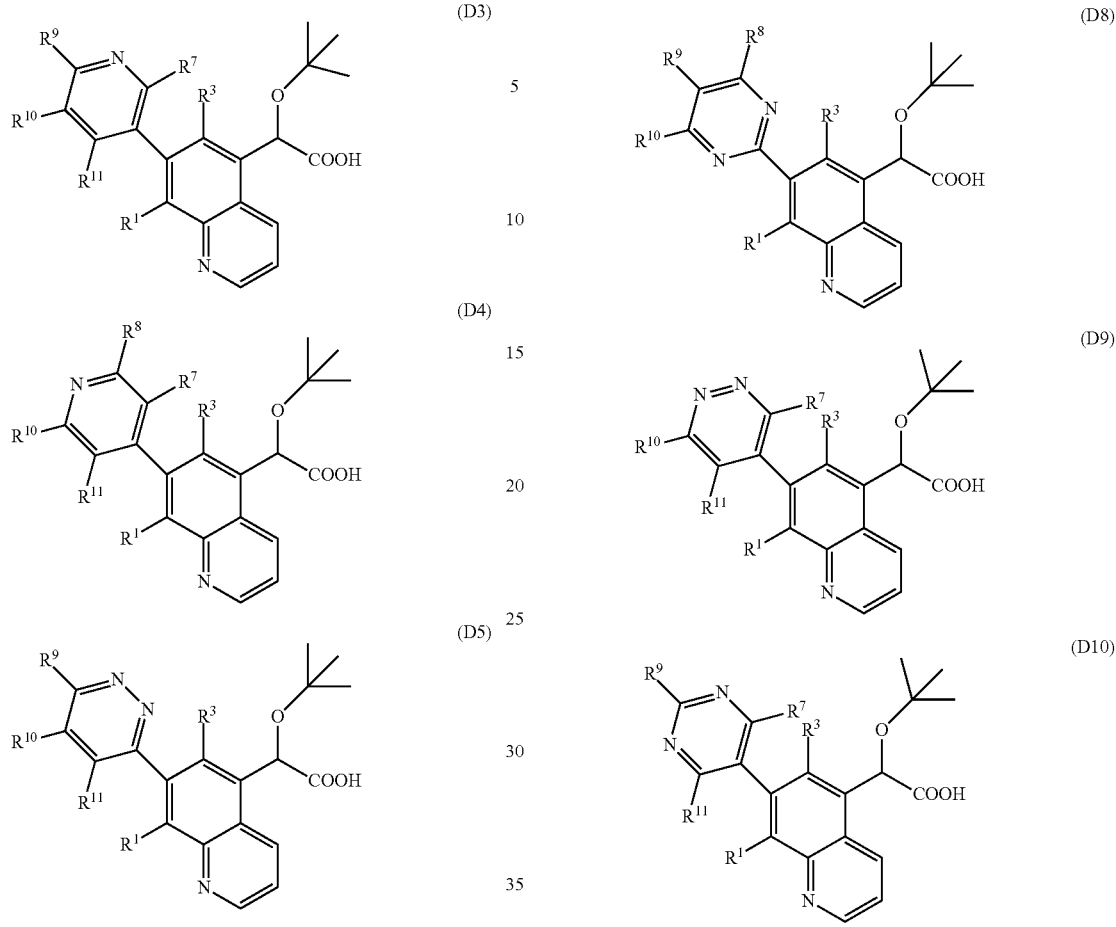 (D8) (D9) (D10)
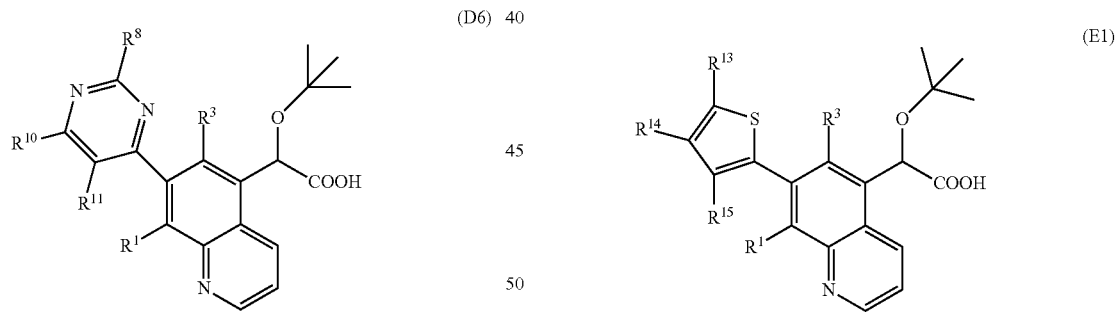 (E1)
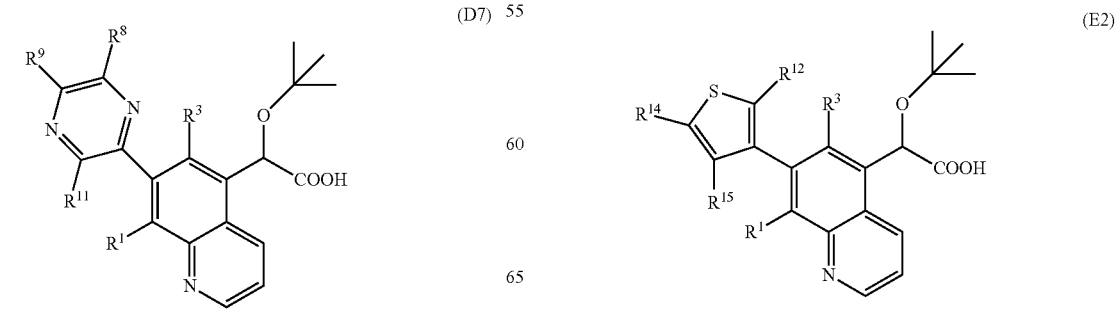 (E2)

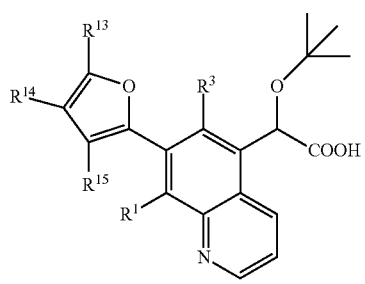
(E3)
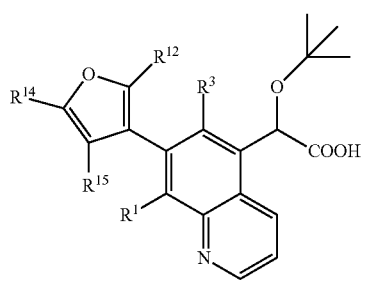
(E4)
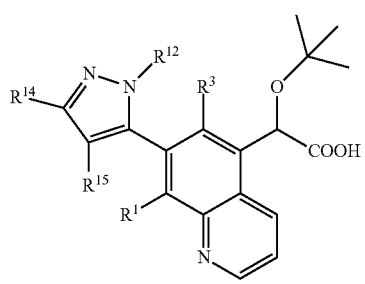
(E5)
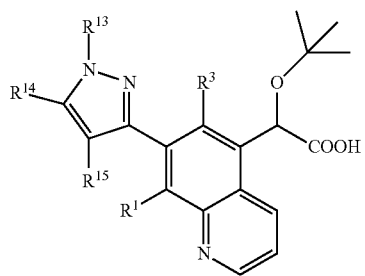
(E6)
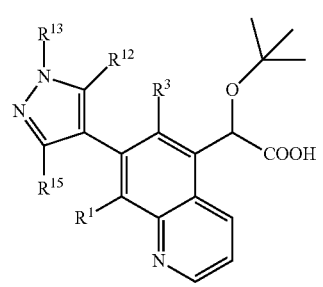
(E7)
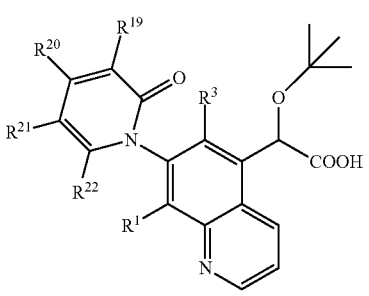
(F1)
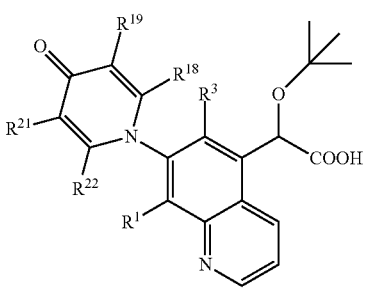
(F2)
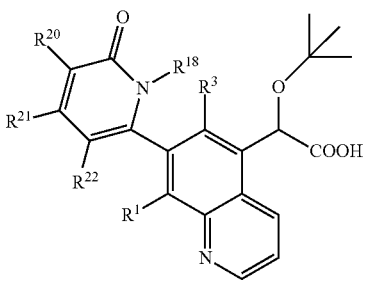
(F3)
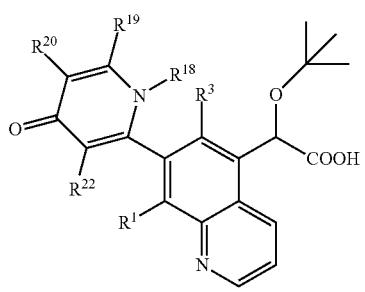
(F4)
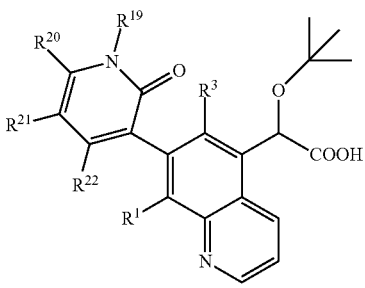
(F5)

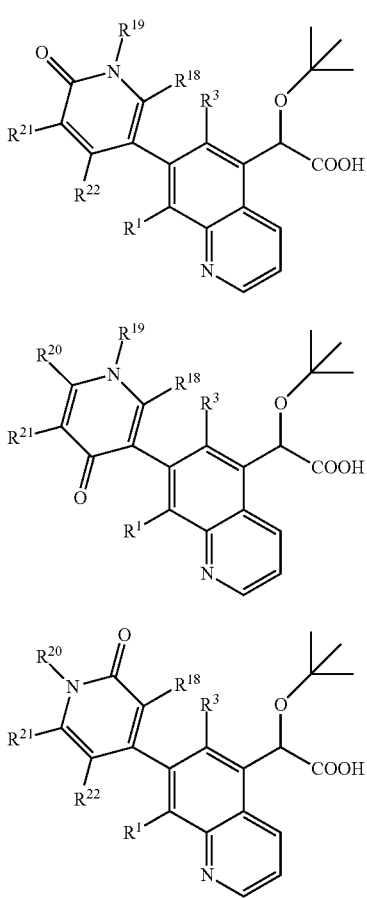

(F6)

(F7)

(F8)

wherein
R[7], R[8], R[9], R[10], R[11], R[12], R[13], R[14], R[15], R[16], R[17], R[18], R[19], R[20], R[21] and R[22], identical or different, independently represent a hydrogen atom; a halogen atom; —CH$_3$; —CH$_2$CH$_3$; —(CH$_2$)$_2$CH$_3$; —CH(CH$_3$)$_2$; —CH$_2$CF$_3$; —OCH$_3$; —NH$_2$; —N(CH$_3$)$_2$; —CH$_2$F; —CHF$_2$; —CF$_3$; —OCH$_2$F; —OCHF$_2$; —OCF$_3$; —(X)$_x$—C$_3$-C$_6$ cycloalkyl; —(X)$_x$—(CT$^5$T$^6$)$_y$-C$_3$-C$_6$ cycloalkyl; —(X)$_x$—(CT$^5$T$^6$)$_y$-aryl; —(X)$_x$—(CT$^5$T$^6$)$_y$ CN; —(X)$_x$—(CT$^5$T$^6$)$_y$OT$^3$; —(X)$_x$—(CT$^5$T$^6$)$_y$ST$^3$; —(X)$_x$—(CT$^5$T$^6$)$_y$S(O)T$^3$; —(X)$_x$—(CT$^5$T$^6$)$_y$S(O)$_2$T$^3$; —(X)$_x$—(CT$^5$T$^6$)$_y$NT$^3$T$^4$; —(X)$_x$—(CT$^5$T$^6$)$_y$C(O)T$^3$; —(X)$_x$—(CT$^5$T$^6$)$_y$C(O)OT$^3$; —(X)$_x$—(CT$^5$T$^6$)$_y$C(O)NT$^3$T$^4$; —(X)$_x$—(CT$^5$T$^6$)$_y$NT$^3$C(O)NT$^3$T$^4$; —(X)$_x$—(CT$^5$T$^6$)$_y$NT$^3$C(O)T$^4$; —(X)$_x$—(CT$^5$T$^6$)$_y$NT$^3$C(O)OT$^4$; —(X)$_x$—(CT$^5$T$^6$)$_y$OC(O)NT$^3$T$^4$; —(X)$_x$—(CT$^5$T$^6$)$_y$S(O)$_2$NT$^3$T$^4$ or —(X)$_x$—(CT$^5$T$^6$)$_y$NT$^3$S(O)$_2$T$^4$;

T$^2$ represents a hydrogen atom; a halogen atom; —CH$_2$F; —CHF$_2$; —CF$_3$; —OMe; —OCH$_2$F; —OCHF$_2$; —OCF$_3$; an alkyl; a linear or branched alkyl; a cycloalkyl; an alkoxy; a halogenoalkoxy or —CN;

R$^1$, R$^5$, R$^6$, T$^3$, T$^4$, T$^5$, T$^6$, X, x, y, g, h, i, l, m, n, o, p are as defined for compounds of formula (I), (A), (B), (C), (D), (E) or (F).

The invention also provides compounds of formulae (A1) to (A10), (B1) to (B15), (C1) to (C9), (D1) to (D10), (E1) to (E7) or (F1) to (F8) wherein:
R$^7$, R$^8$ and the carbon atoms to which they are bonded form a saturated, partially or totally unsaturated 6-membered carbo- or heterocycle;

R$^8$, R$^9$ and the carbon atoms to which they are bonded form a saturated, partially or totally unsaturated 6-membered carbo- or heterocycle R$^9$, R$^{10}$ and the carbon atoms to which they are bonded form a saturated, partially or totally unsaturated 6-membered carbo- or heterocycle;

R$^{10}$, R$^{11}$ and the carbon atoms to which they are bonded form a saturated, partially or totally unsaturated 6-membered carbo- or heterocycle; or R$^{12}$, R$^{13}$ and the carbon and nitrogen atoms to which they are bonded form a saturated, partially or totally unsaturated 6-membered carbo- or heterocycle.

More preferably, the invention provides compounds of formulae (A1) to (A10), (B1) to (B15), (C1) to (C9), (D1) to (D10), (E1) to (E7) or (F1) to (F8) wherein R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$ and R$^{22}$, identical or different, independently represent a hydrogen atom; a halogen atom; a linear or branched C$_1$-C$_6$ alkyl; a linear or branched —O—C$_1$-C$_6$ alkyl; a linear or branched —O—C$_1$-C$_{10}$ alkylaryl; —(X)$_x$—C$_3$-C$_6$ cycloalkyl; —(X)$_x$—(CT$^5$T$^6$)$_y$-C$_3$-C$_6$ cycloalkyl; —(X)$_x$—(CT$^5$T$^6$)$_y$-aryl; —C(O)OH; —C(O)NH$_2$; —C(O)NH(CH$_3$); or —NHC(O)CH$_3$.

Advantageously, the invention provides compounds of formulae (A1a) to (A10a), (A1b) to (A10b), (A1c) to (A10c), (A1d) to (A10d), (B1a) to (B15a), (B1b) to (B15b), (B1c) to (B15c), (B1d) to (B15d), (C1a) to (C9a), (C1b) to (C9b), (C1c) to (C9c), (C1d) to (C9d), (D1a) to (D10a), (D1b) to (D10b), (D1c) to (D10c), (D1d) to (D10d), (E1a) to (E7a), (E1b) to (E7b), (E1c) to (E7c), (E1d) to (E7d), (F1a) to (F8a), (F1b) to (F8b), (F1c) to (F8c) or (F1d) to (F8d):

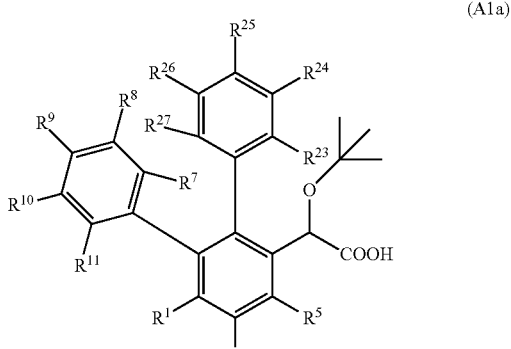

(A1a)

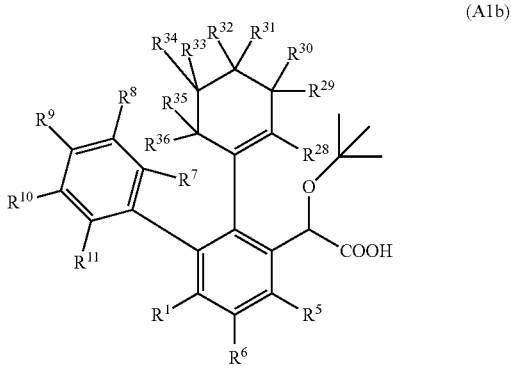

(A1b)

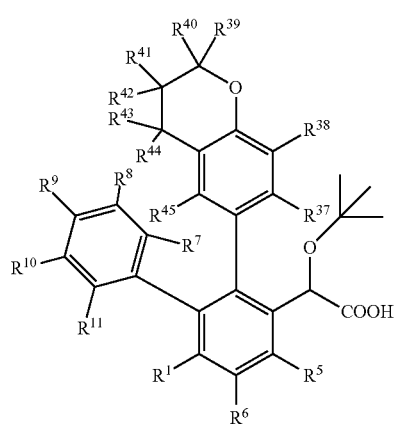
(A1c)
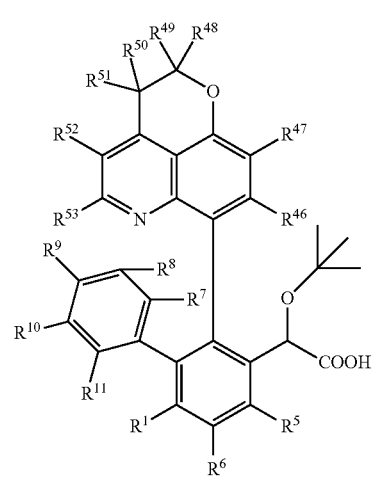
(A1d)
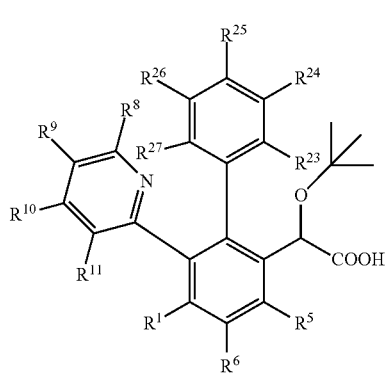
(A2a)
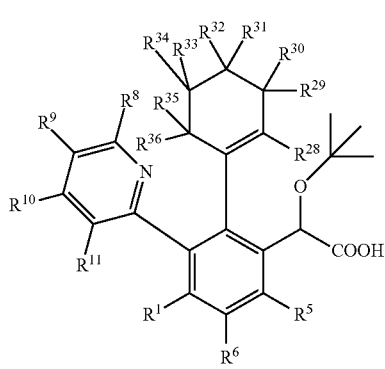
(A2b)
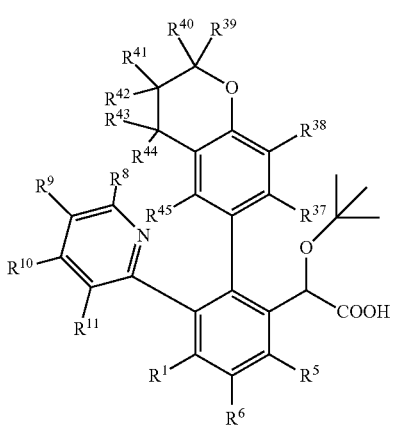
(A2c)
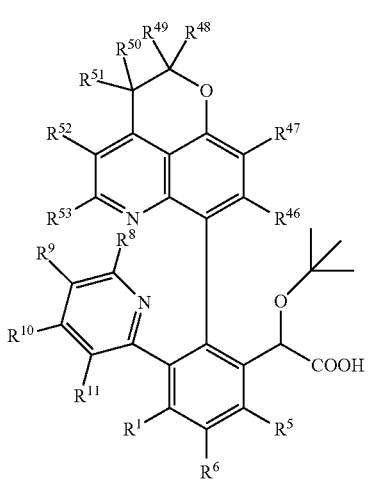
(A2d)
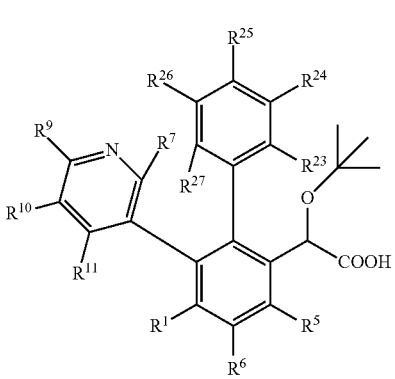
(A3a)
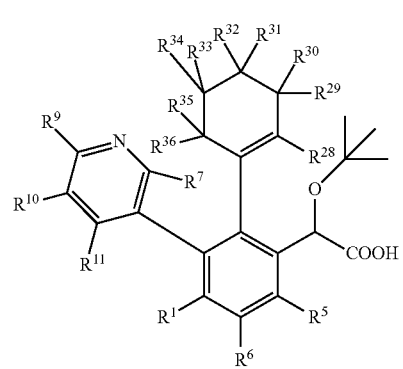
(A3b)

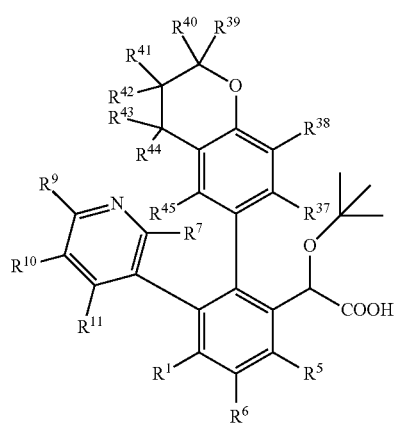
(A3c)
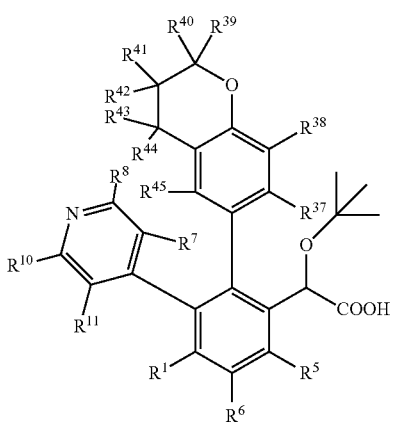
(A4c)
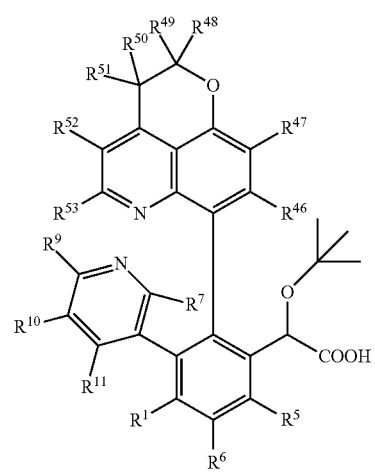
(A3d)
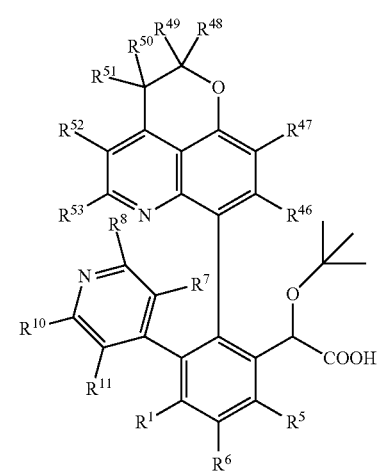
(A4d)
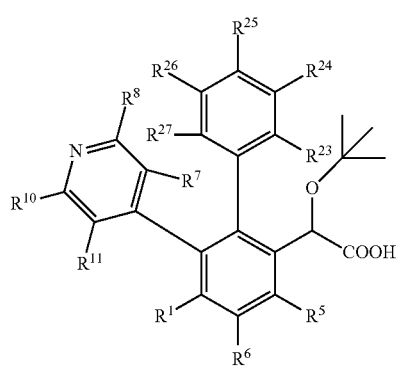
(A4a)
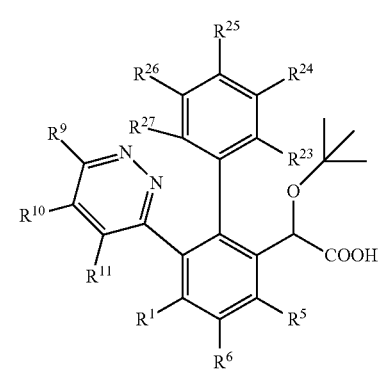
(A5a)
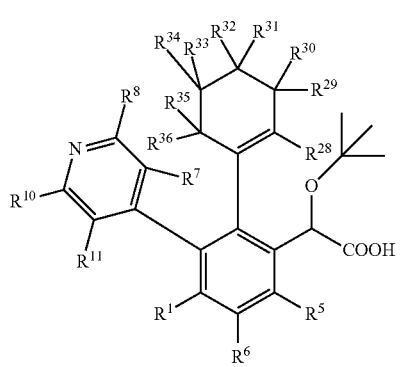
(A4b)
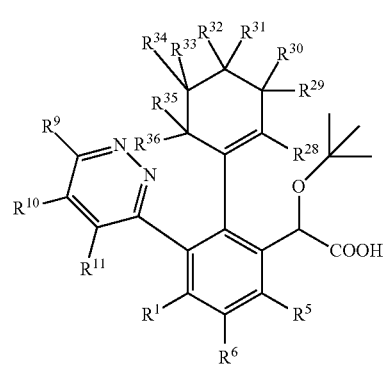
(A5b)

(A5c)
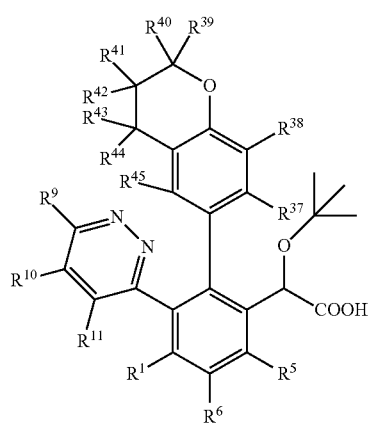
(A5d)
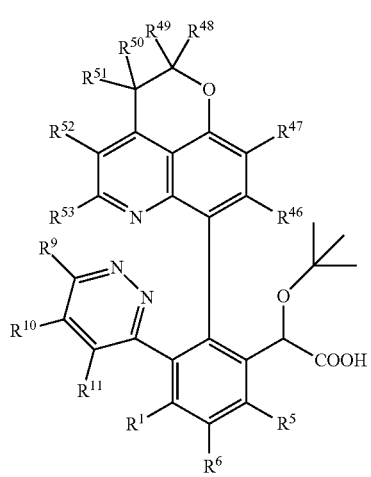
(A6a)
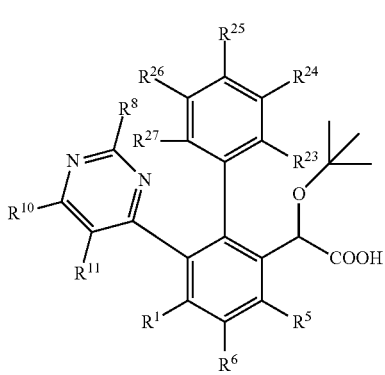
(A6b)
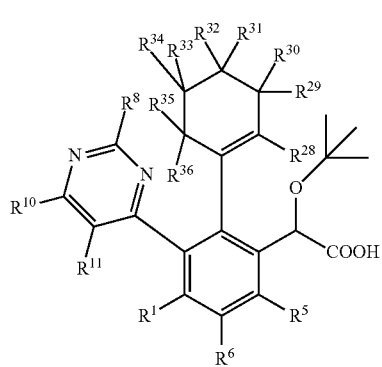
(A6c)
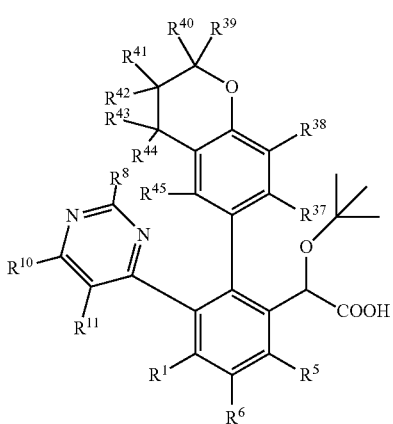
(A6d)
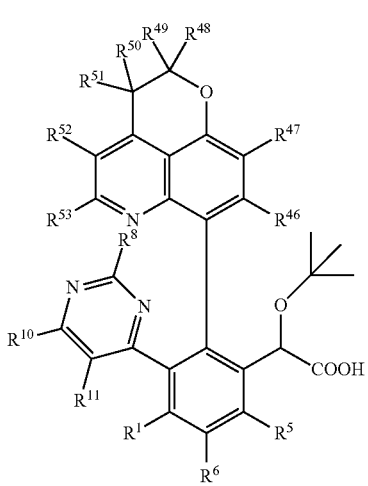
(A7a)
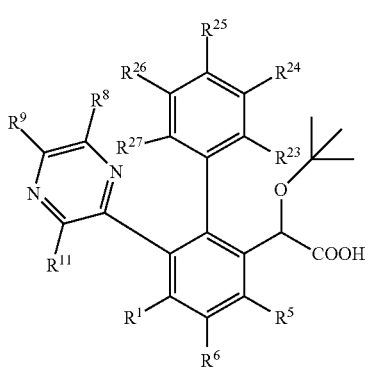
(A7b)
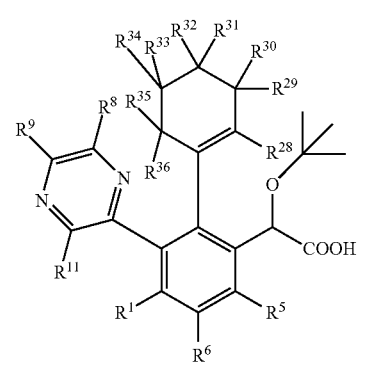

(A7c)
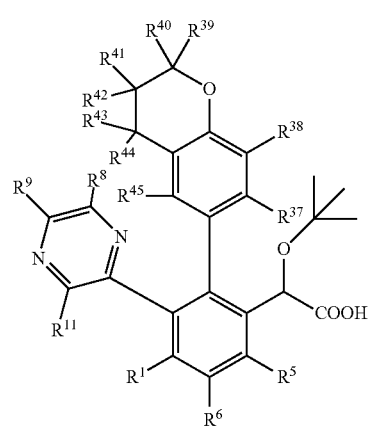
(A7d)
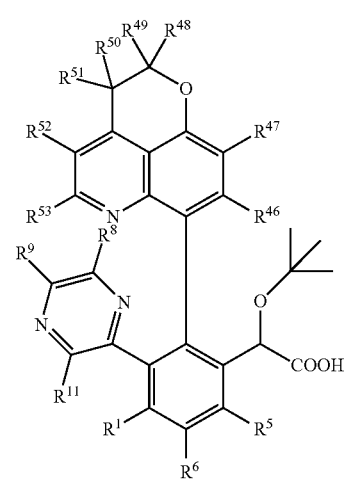
(A8a)
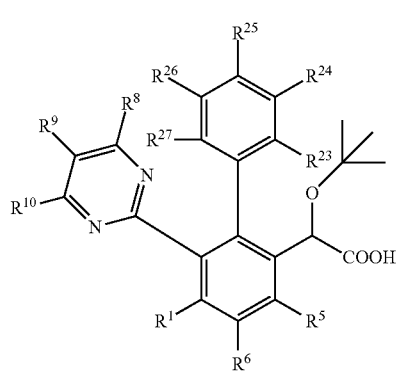
(A8b)
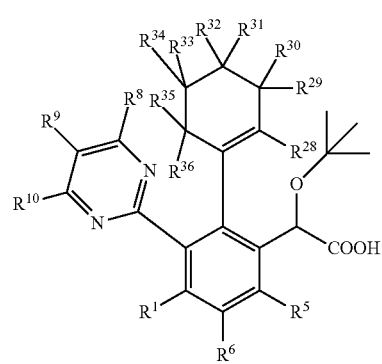
(A8c)
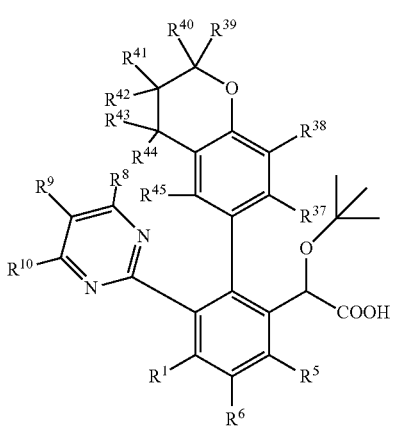
(A8d)
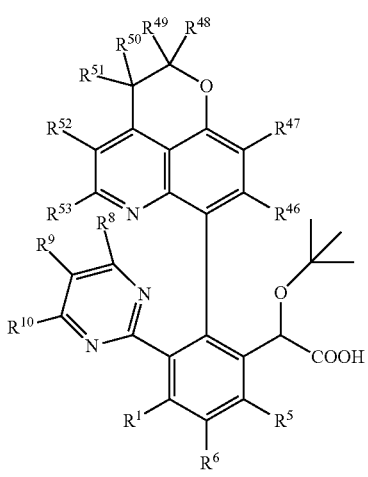
(A9a)
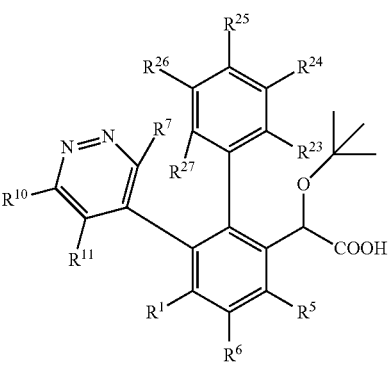
(A9b)
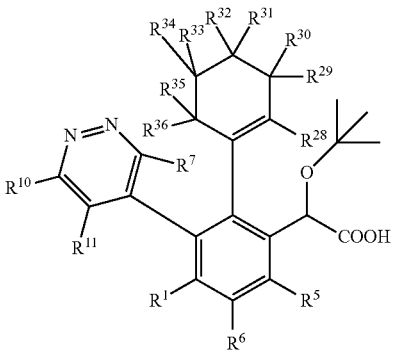

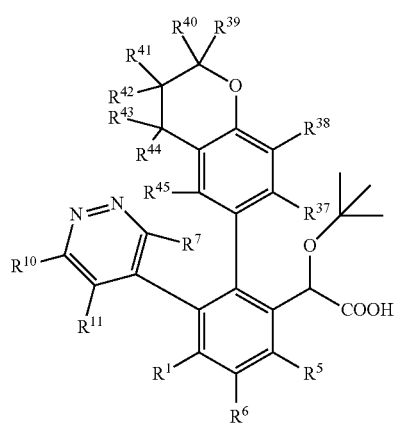
(A9c)
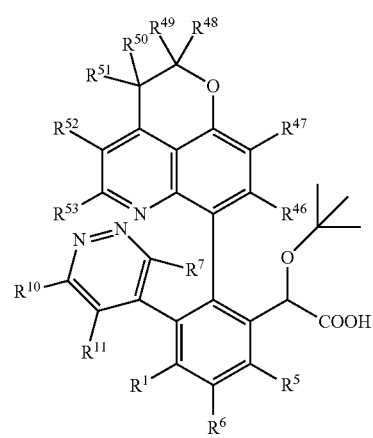
(A9d)
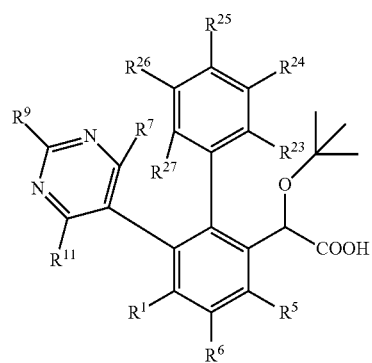
(A10a)
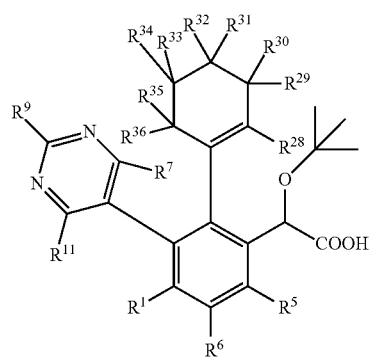
(A10b)
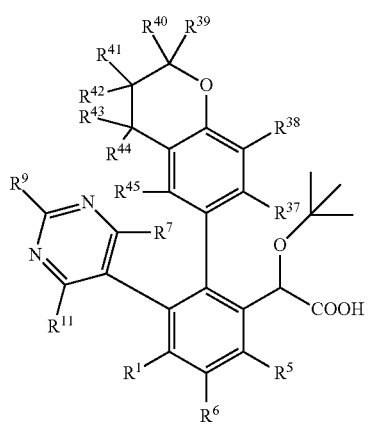
(A10c)
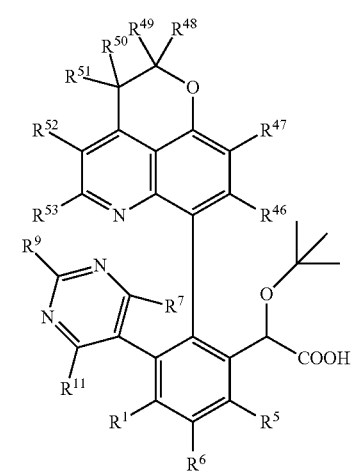
(A10d)
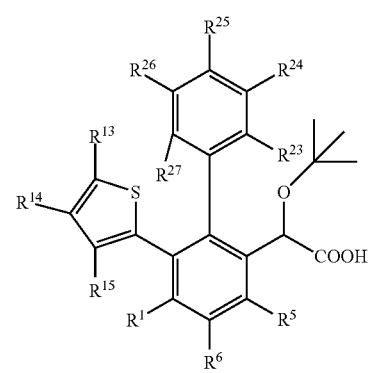
(B1a)
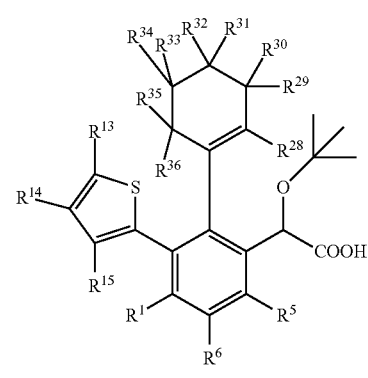
(B1b)

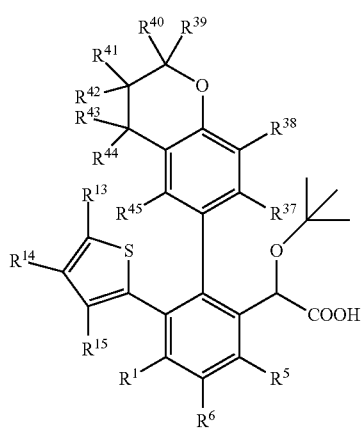 (B1c)
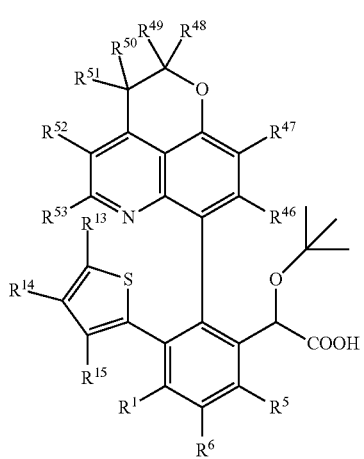 (B1d)
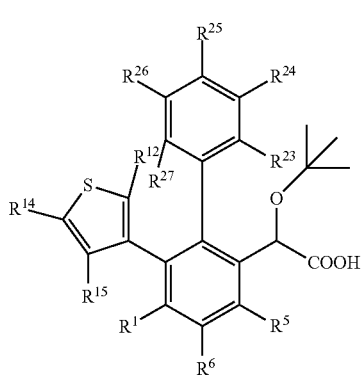 (B2a)
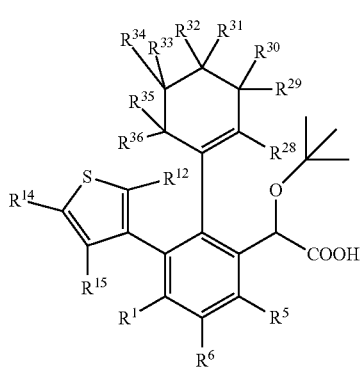 (B2b)
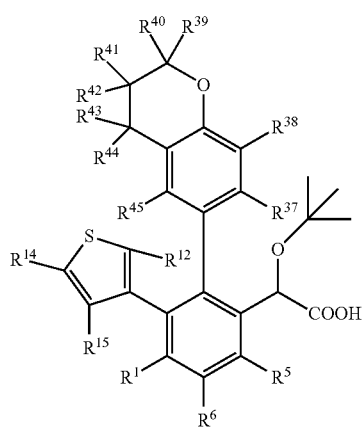 (B2c)
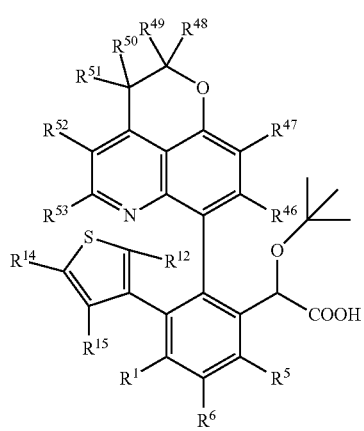 (B2d)
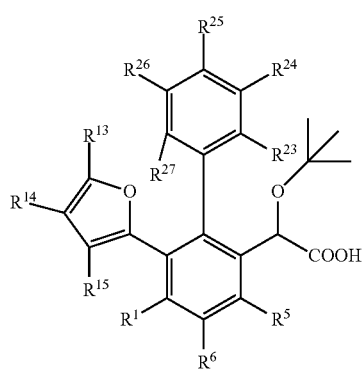 (B3a)
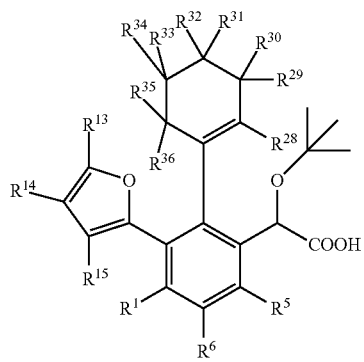 (B3b)

-continued
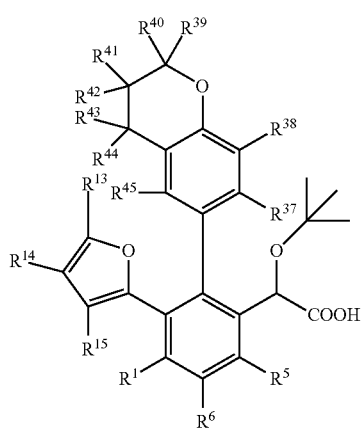
(B3c)
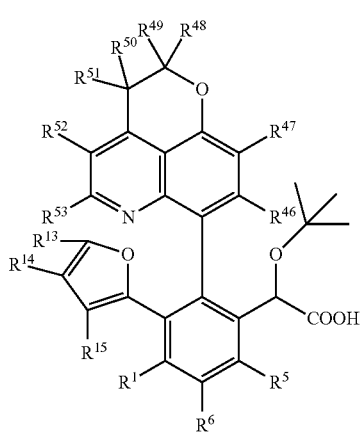
(B3d)
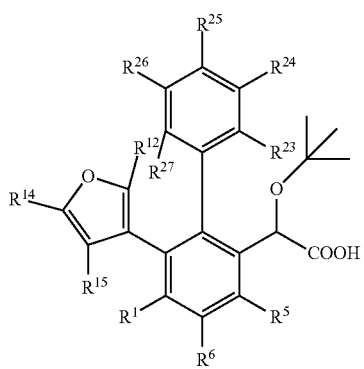
(B4a)
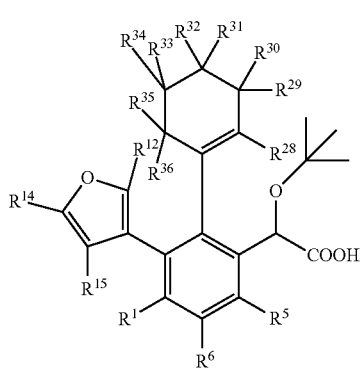
(B4b)
-continued
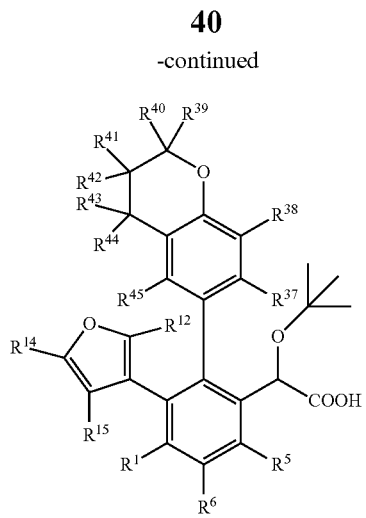
(B4c)
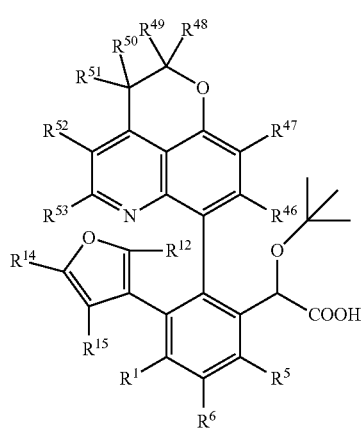
(B4d)
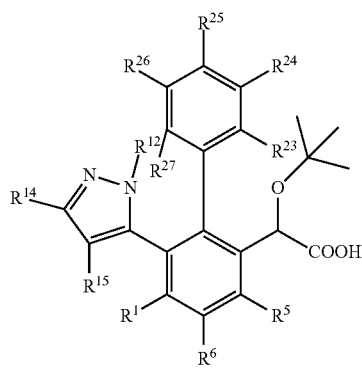
(B5a)
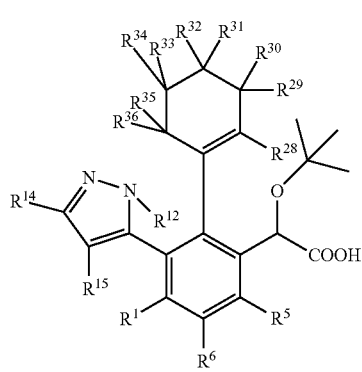
(B5b)

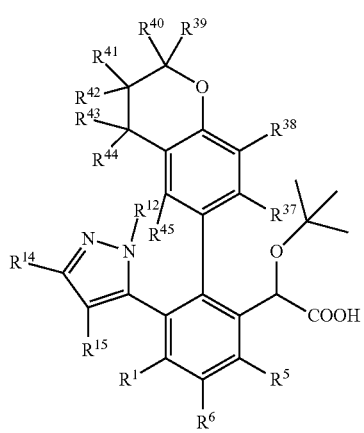
(B5c)
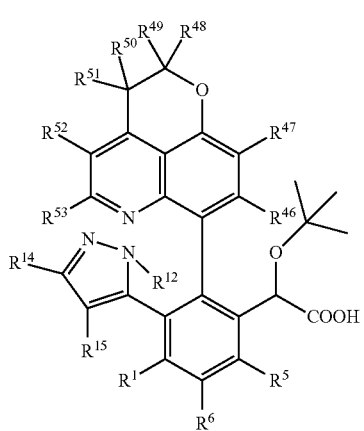
(B5d)
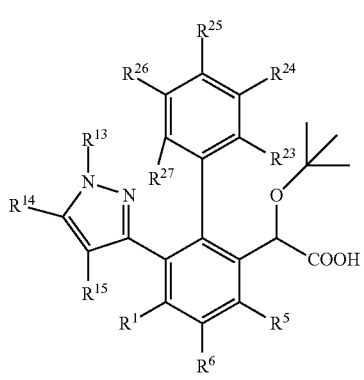
(B6a)
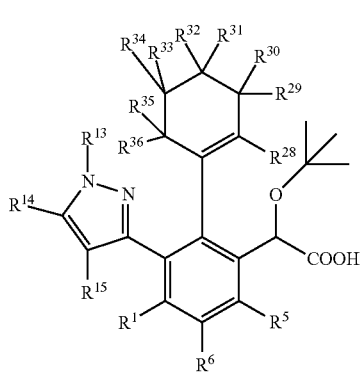
(B6b)
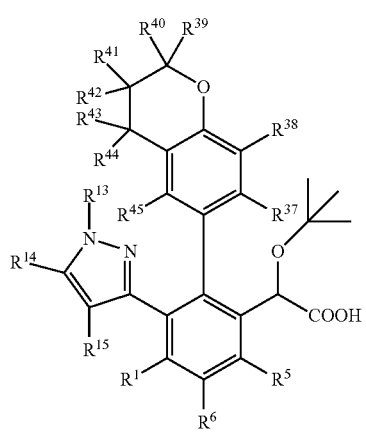
(B6c)
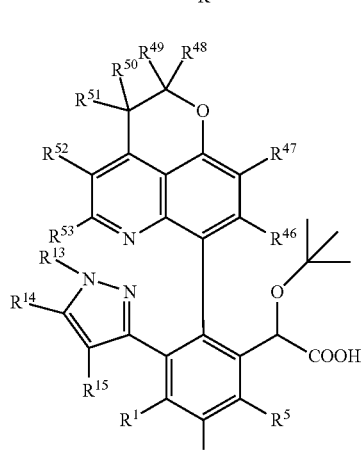
(B6d)
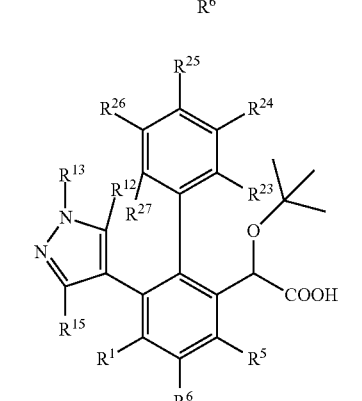
(B7a)
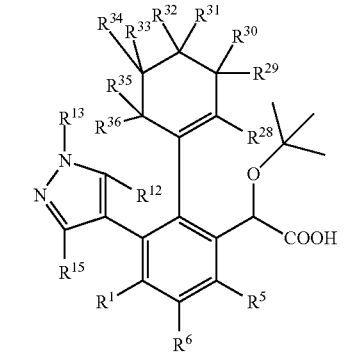
(B7b)

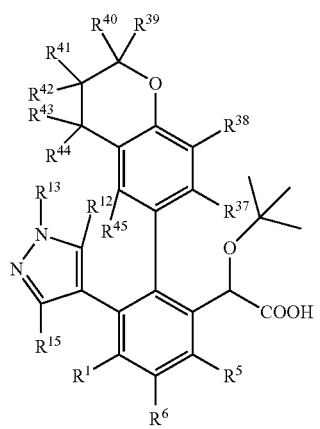
(B7c)
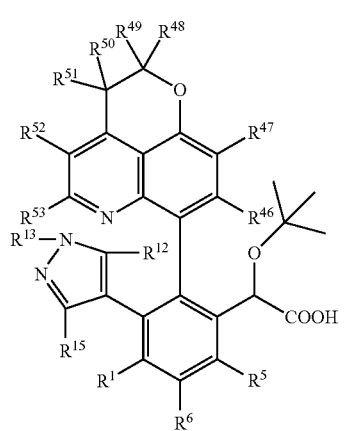
(B7d)
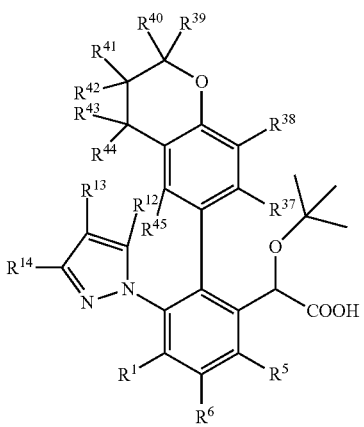
(B8c)
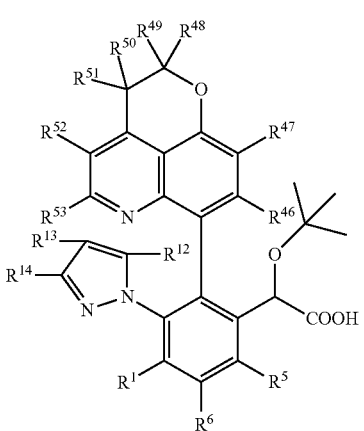
(B8d)
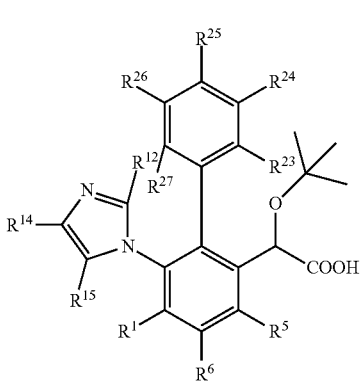
(B8a)
(B8b)
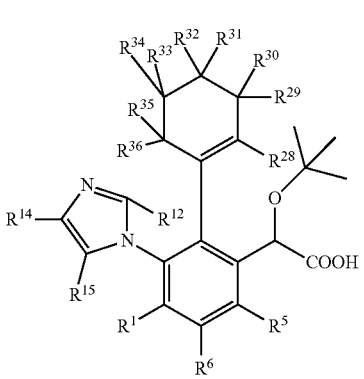
(B9a)
(B9b)

-continued
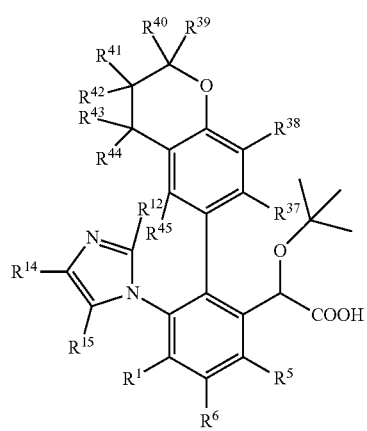
(B9c)
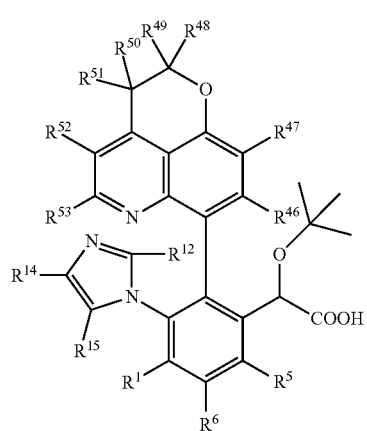
(B9d)
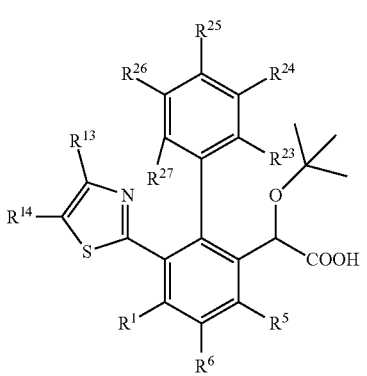
(B10a)
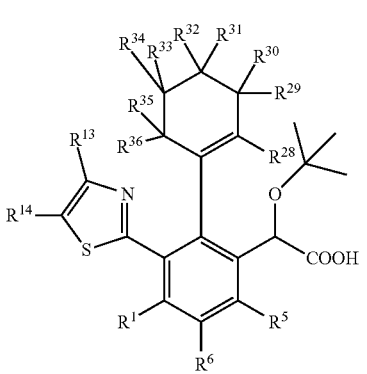
(B10b)
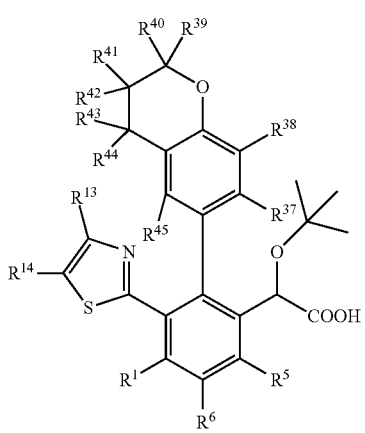
(B10c)
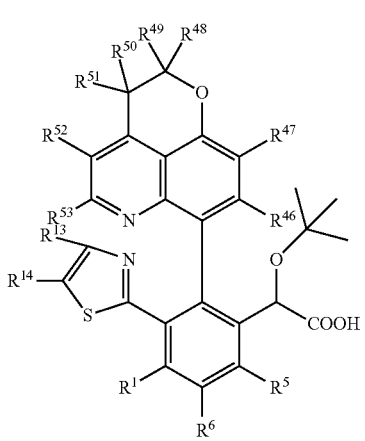
(B10d)
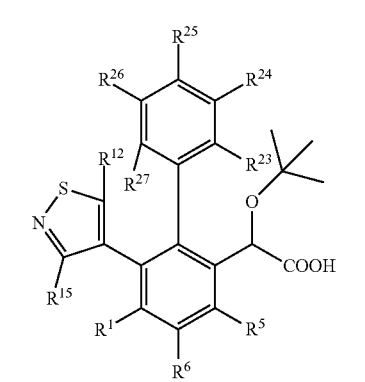
(B11a)
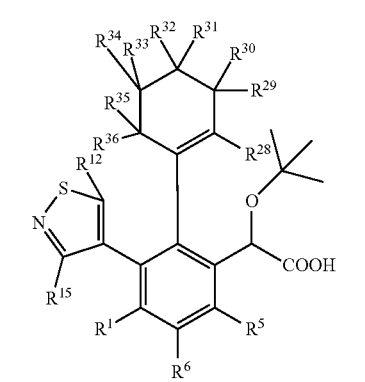
(B11b)

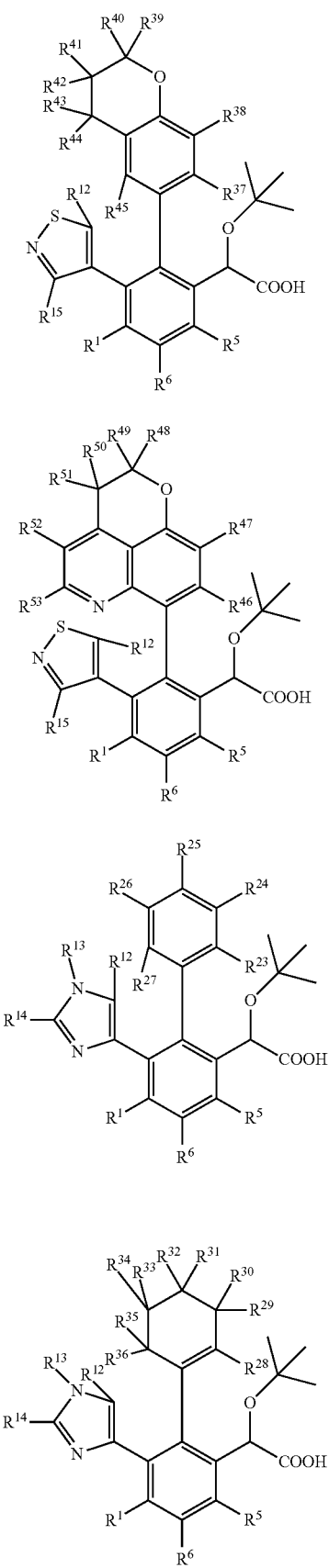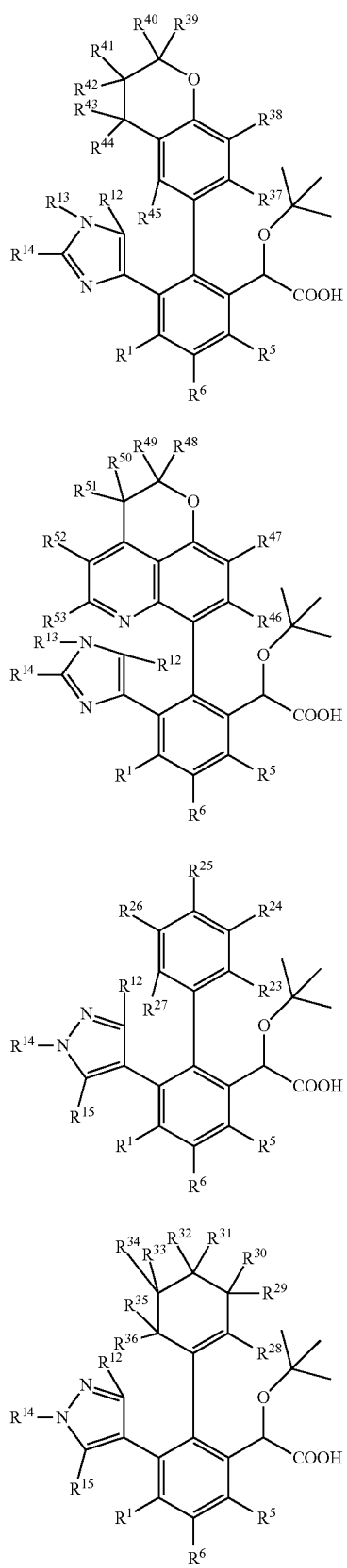

(B13c) 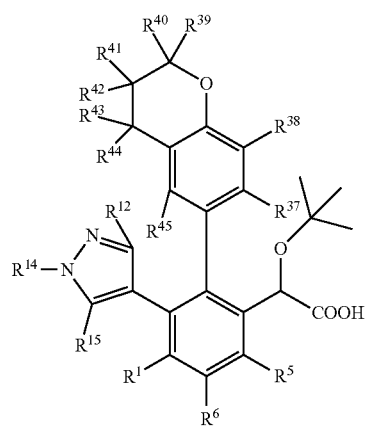
(B13d) 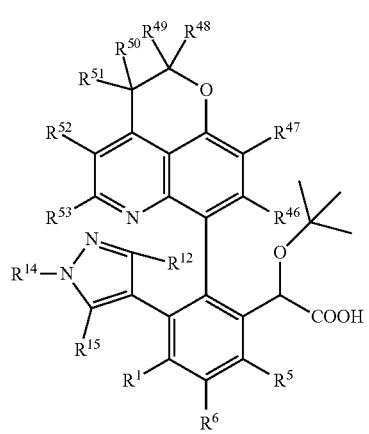
(B14a) 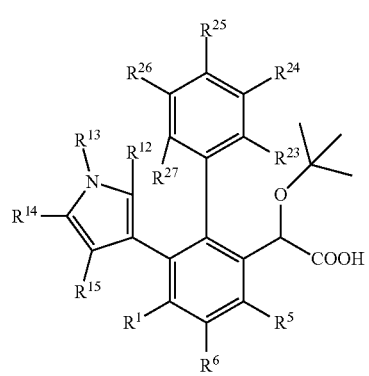
(B14b) 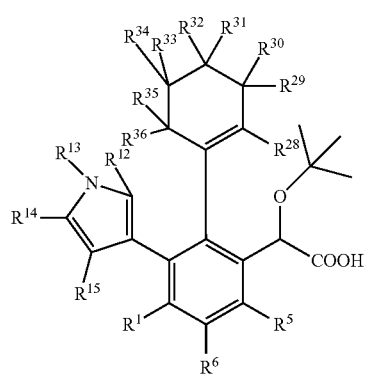
(B14c) 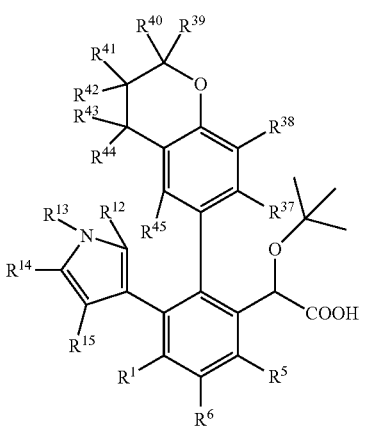
(B14d) 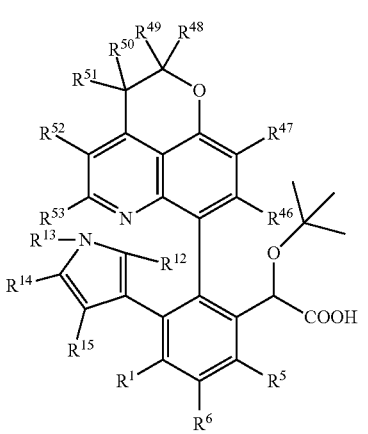
(B15a) 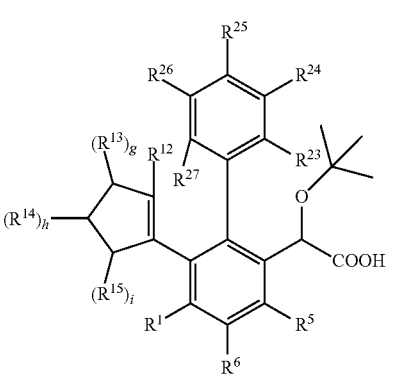
(B15b) 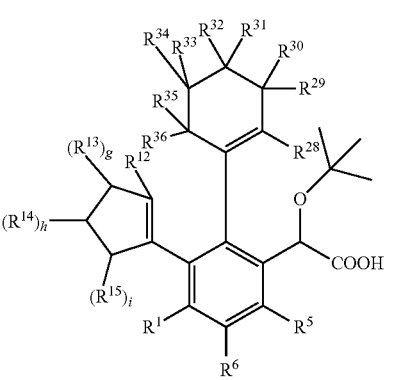

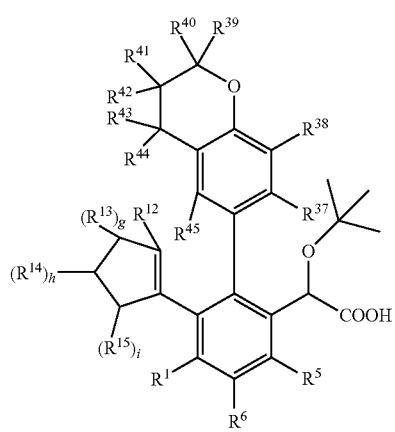
(B15c)
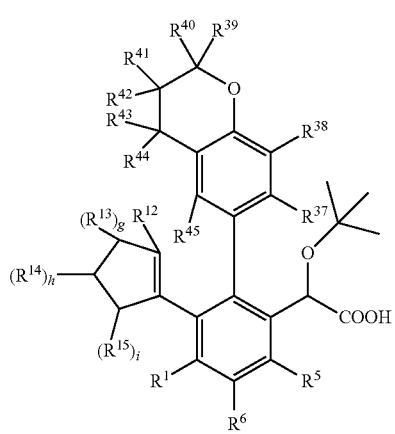
(B15d)
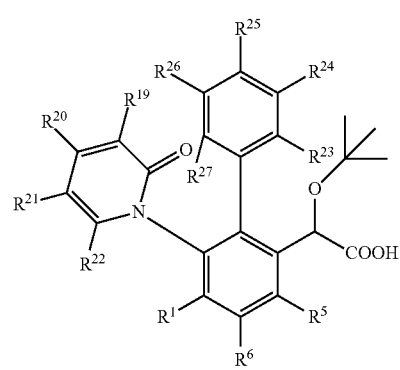
(C1a)
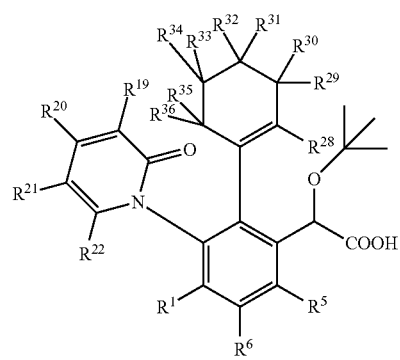
(C1b)
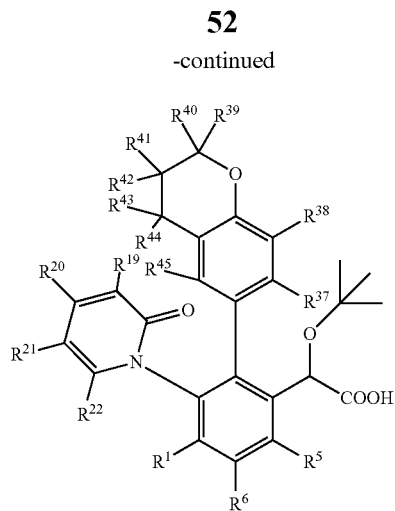
(C1c)
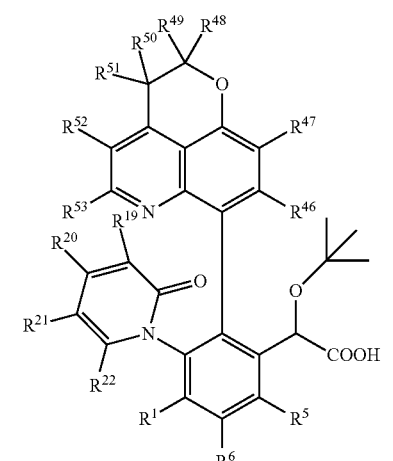
(C1d)
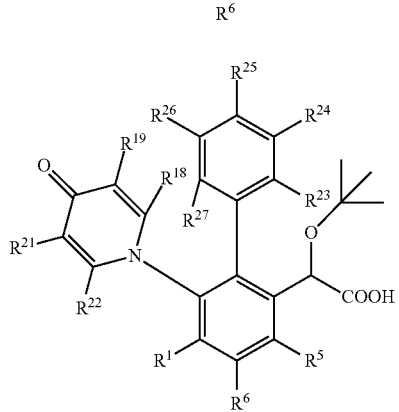
(C2a)
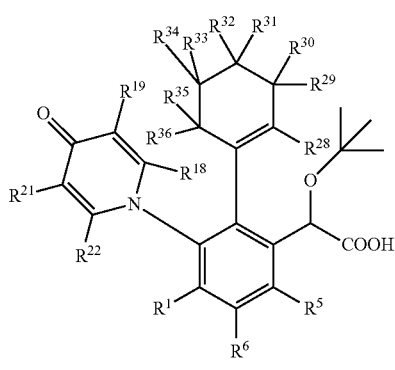
(C2b)

-continued
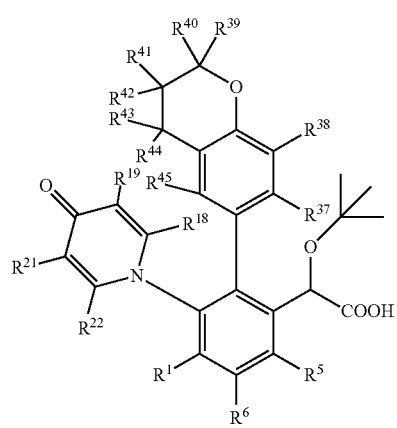
(C2c)
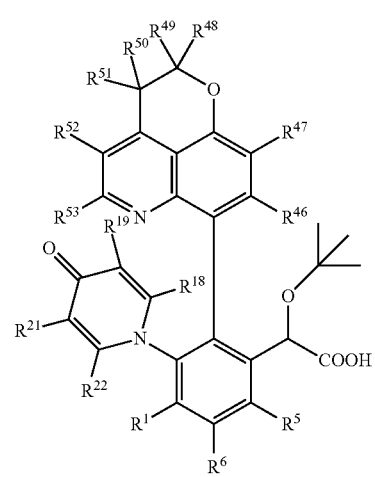
(C2d)
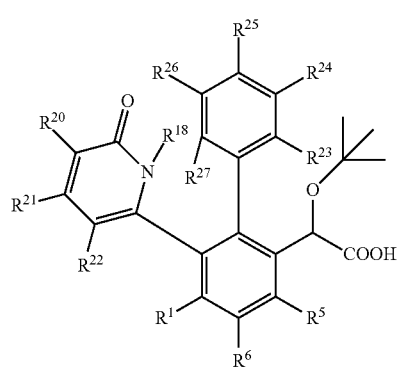
(C3a)
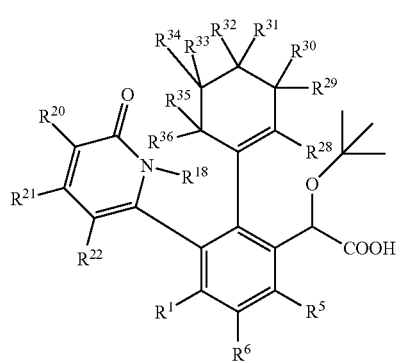
(C3b)
-continued
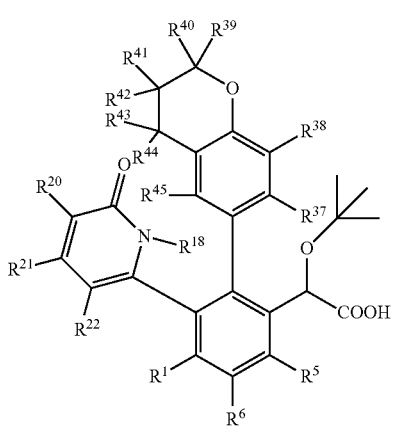
(C3c)
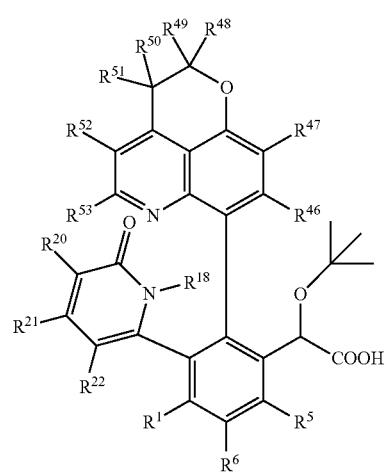
(C3d)
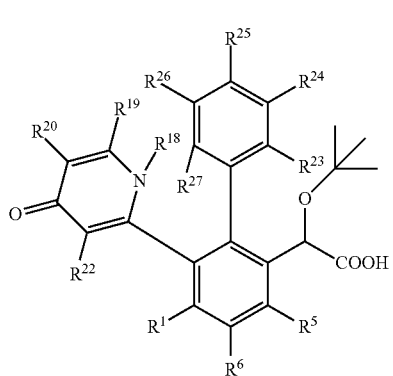
(C4a)
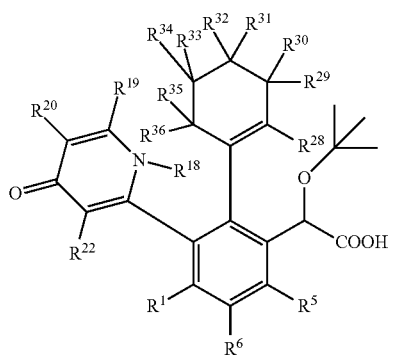
(C4b)

-continued
(C4c)
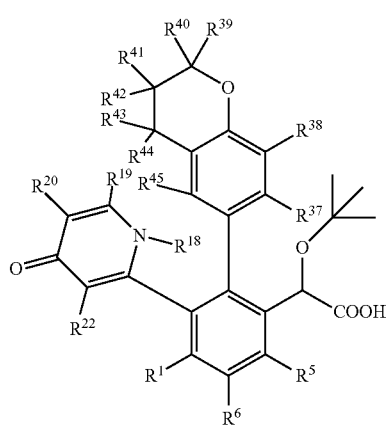
(C4d)
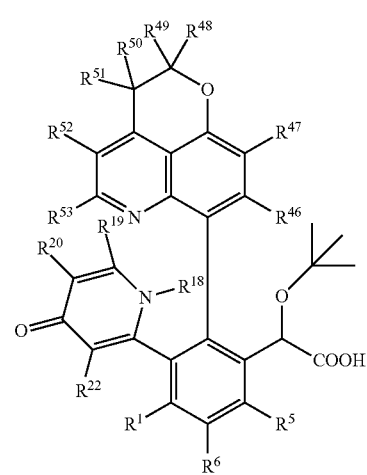
(C5a)
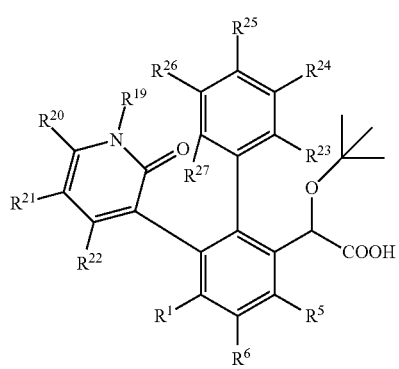
(C5b)
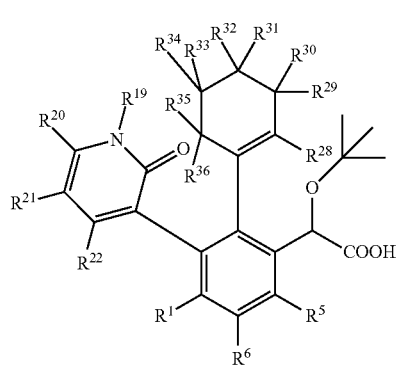
(C5c)
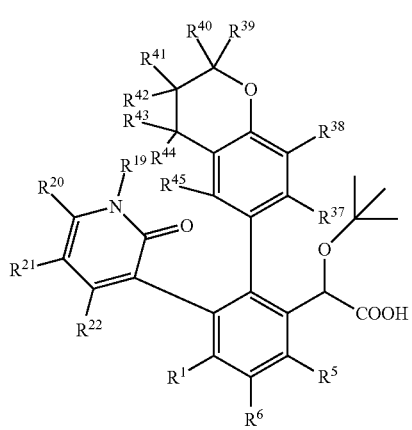
(C5d)
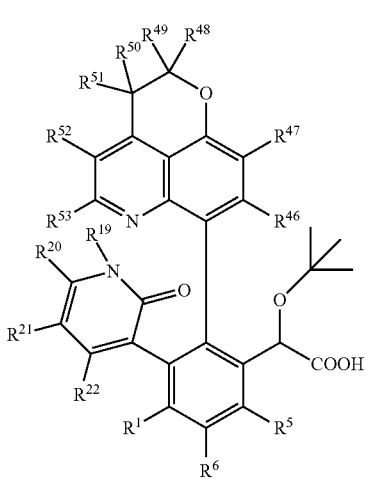
(C6a)
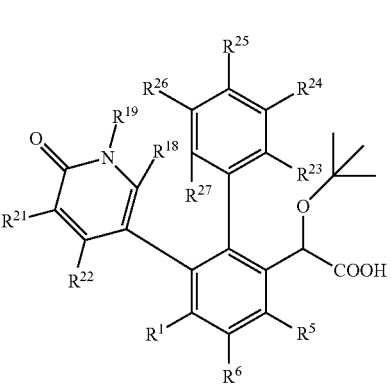
(C6b)
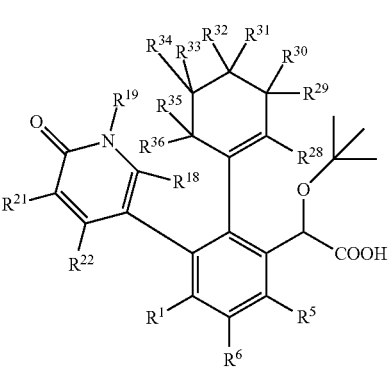

-continued
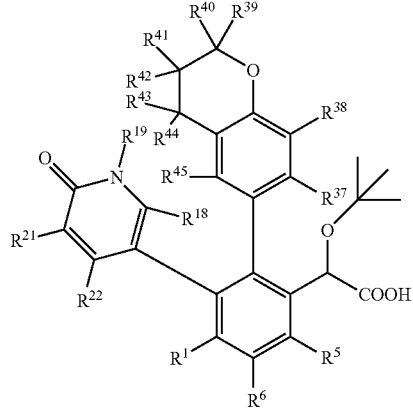
(C6c)
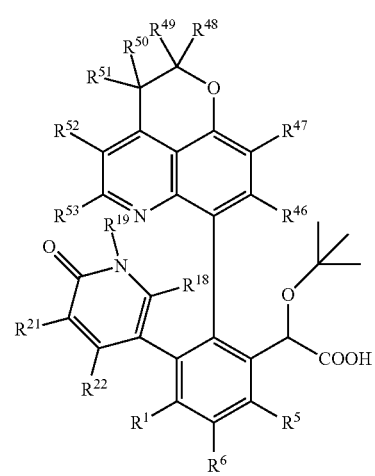
(C6d)
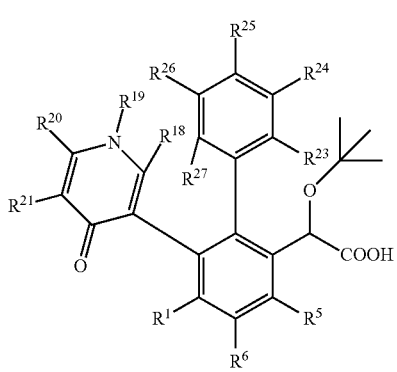
(C7a)
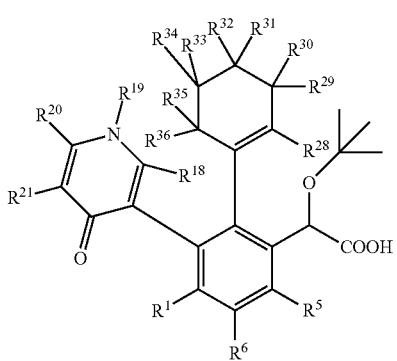
(C7b)
-continued
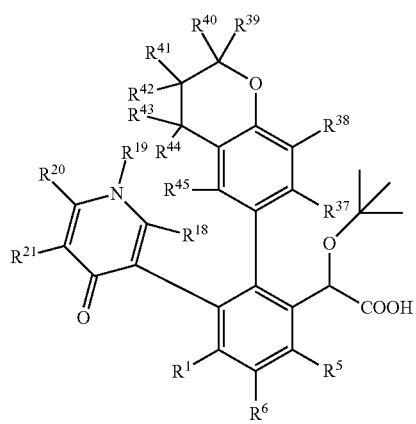
(C7c)
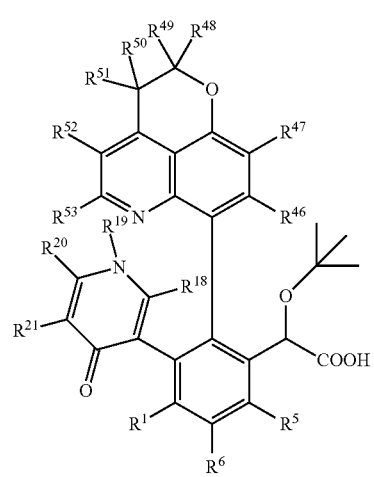
(C7d)
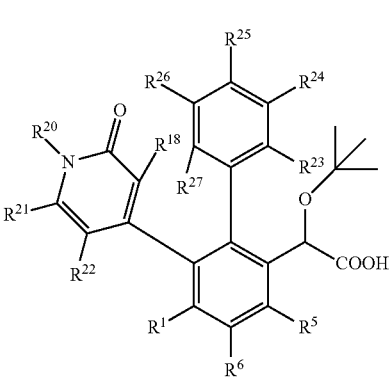
(C8a)
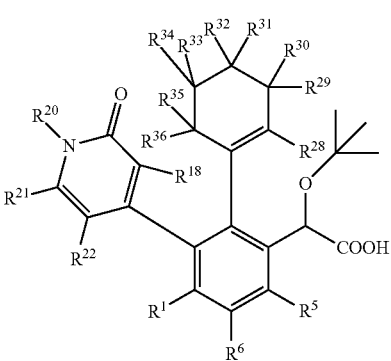
(C8b)

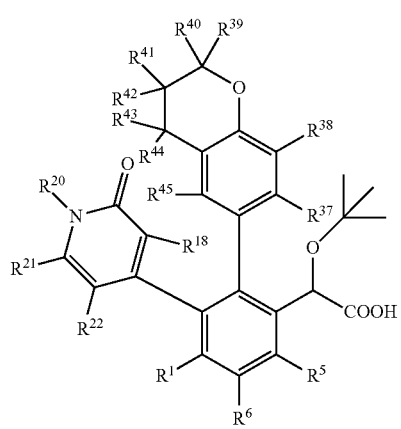
(C8c)
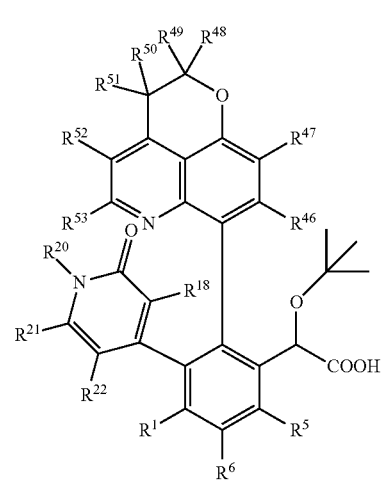
(C8d)
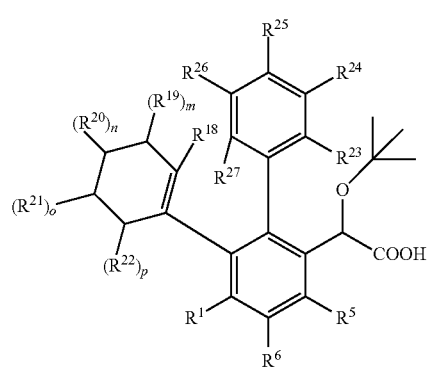
(C9a)
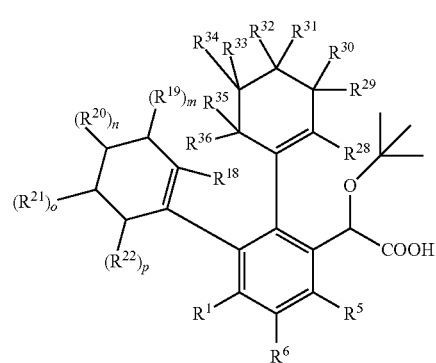
(C9b)
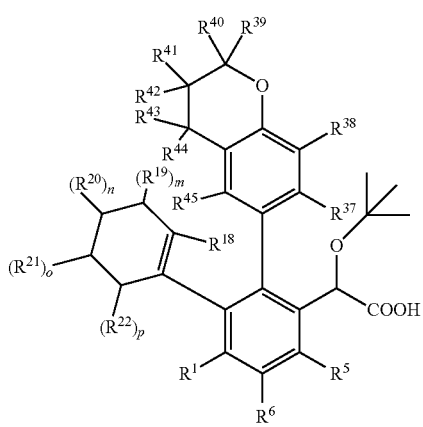
(C9c)
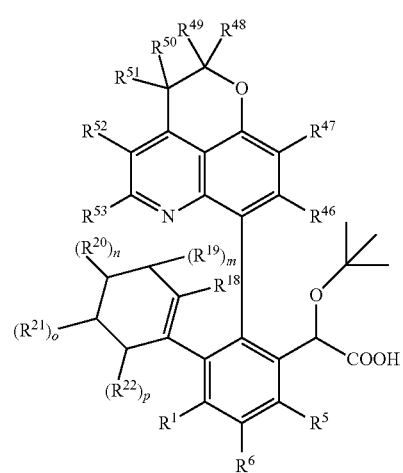
(C9d)
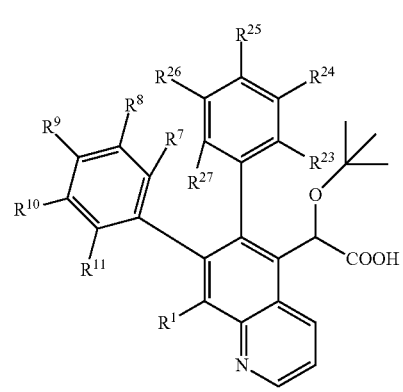
(D1a)
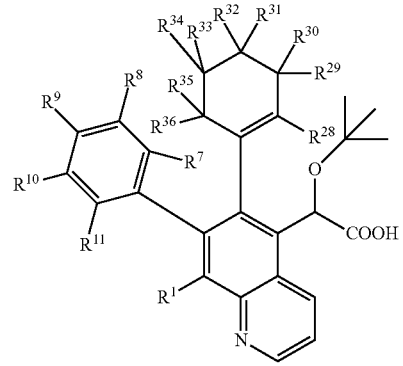
(D1b)

-continued
(D1c) 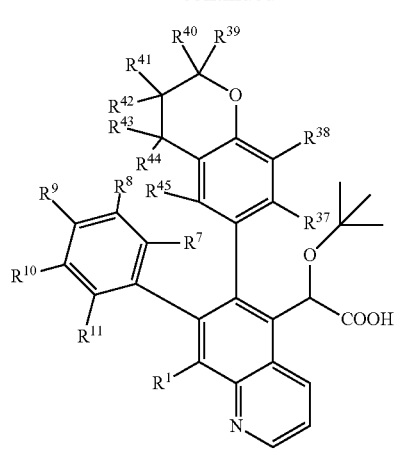
(D1d) 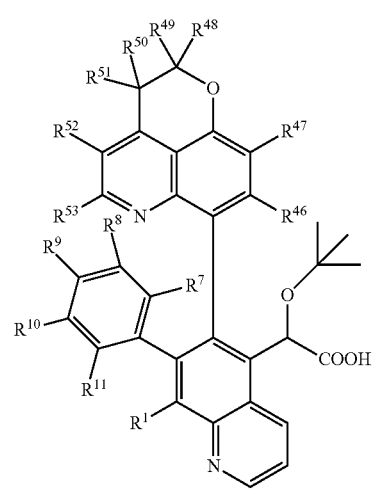
(D2a) 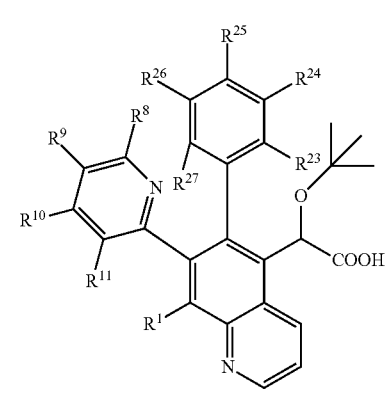
(D2b) 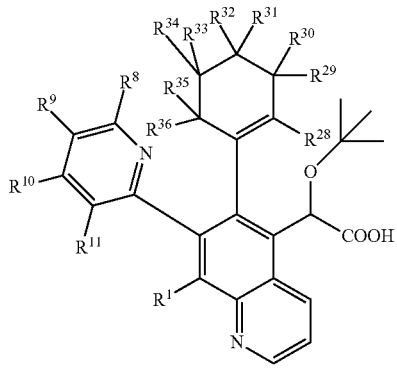
(D2c) 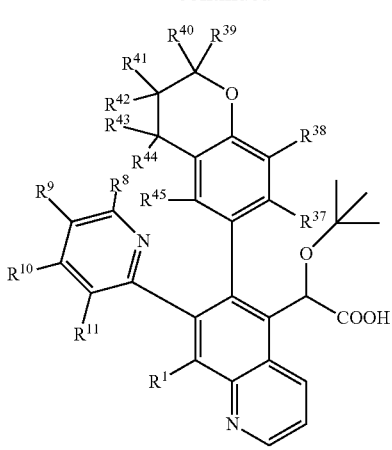
(D2d) 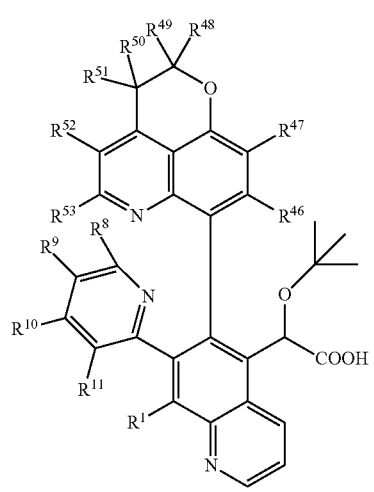
(D3a) 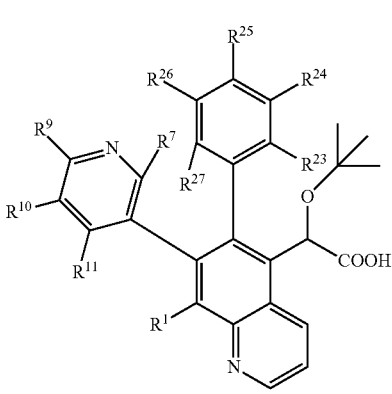
(D3b)

-continued
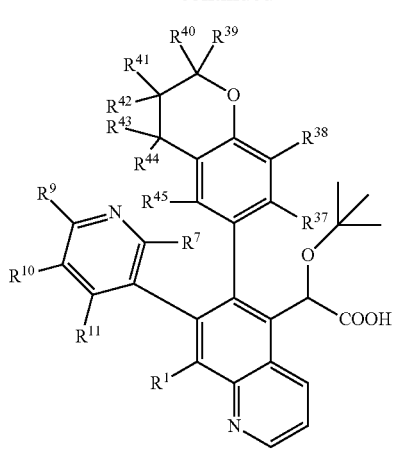
(D3c)
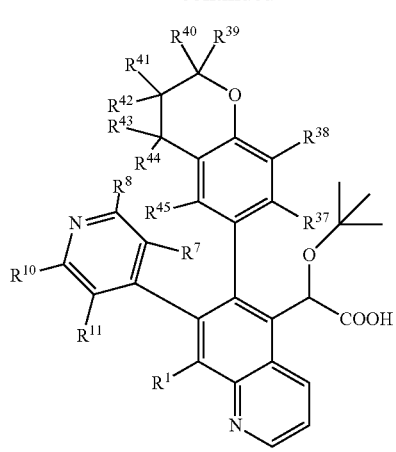
(D4c)
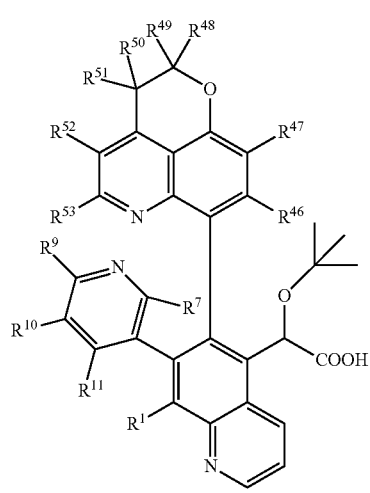
(D3d)
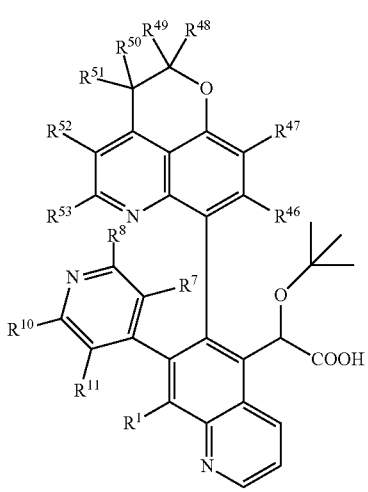
(D4d)
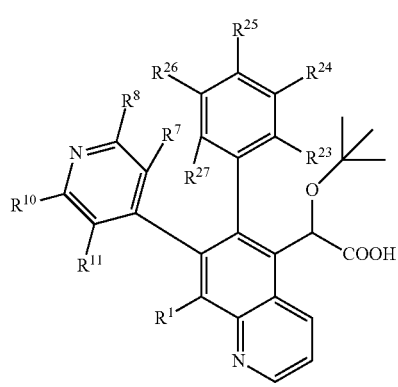
(D4a)
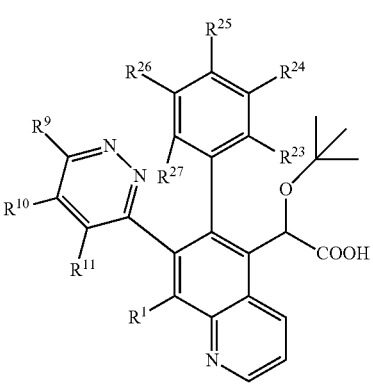
(D5a)
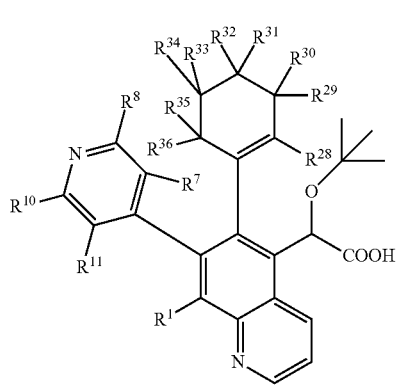
(D4b)
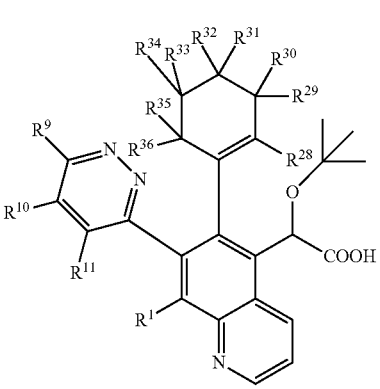
(D5b)

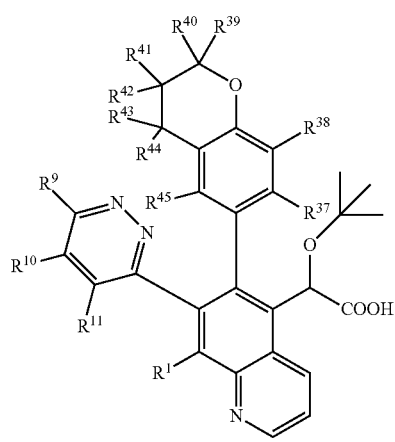
(D5c)
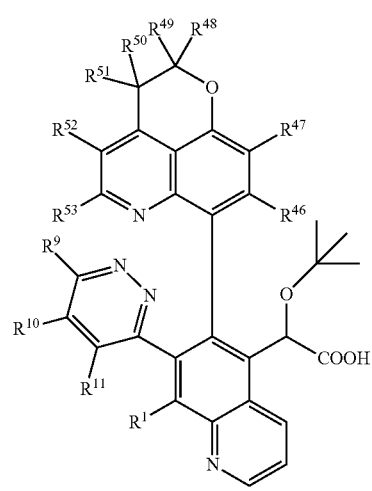
(D5d)
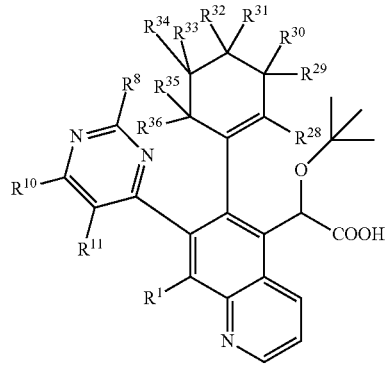
(D6b)
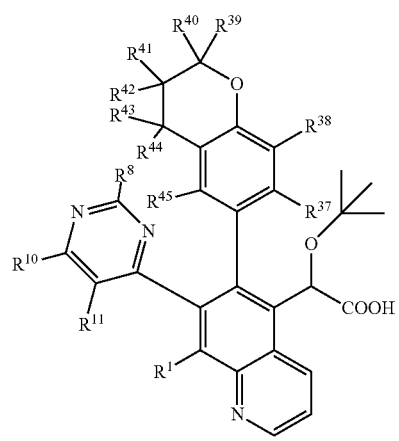
(D6c)
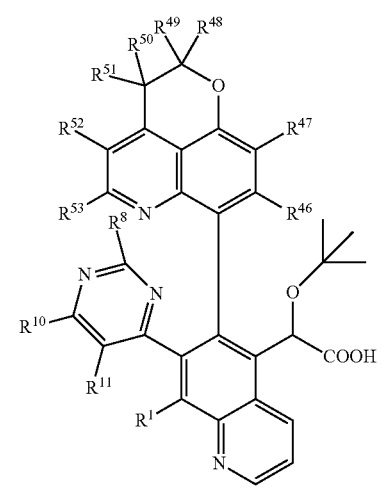
(D6d)
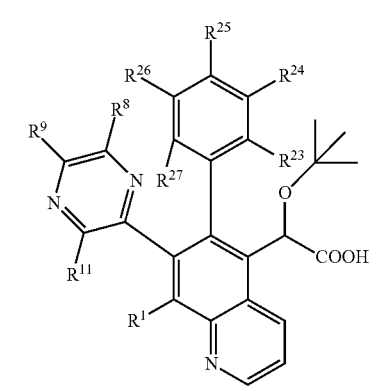
(D7a)

-continued
(D7b)
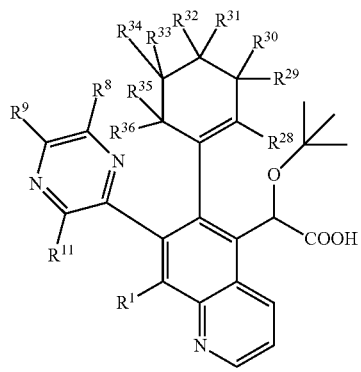
(D7c)
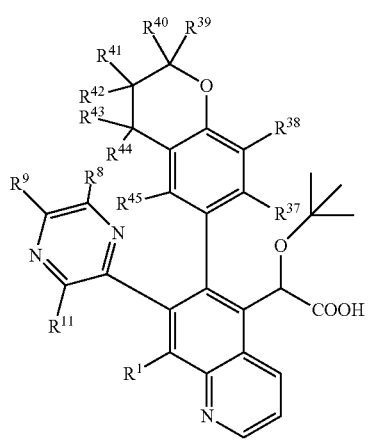
(D7d)
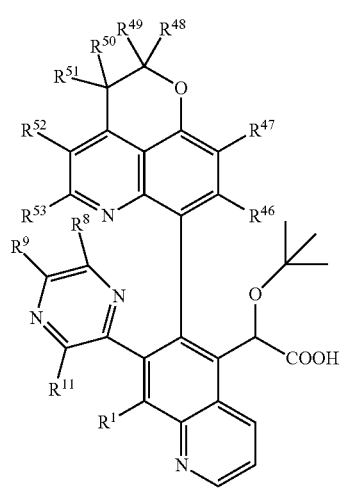
(D8a)
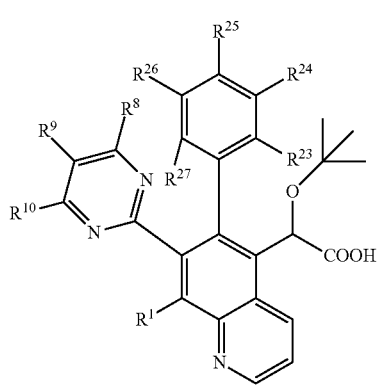
-continued
(D8b)
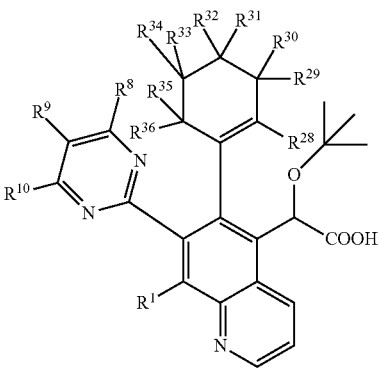
(D8c)
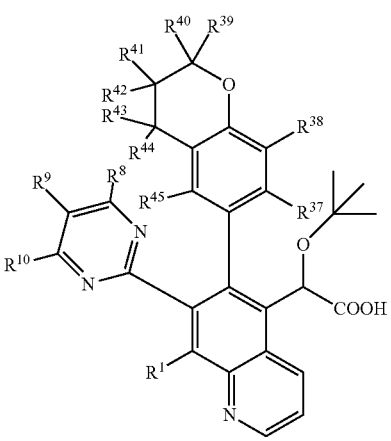
(D8d)
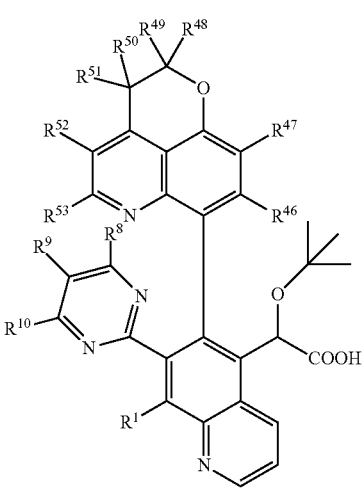
(D9a)
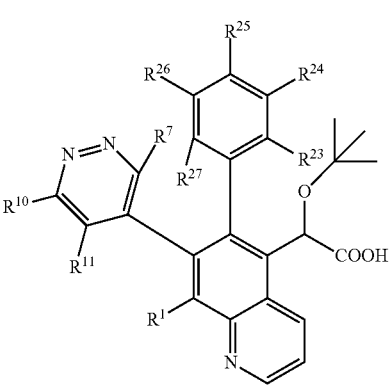

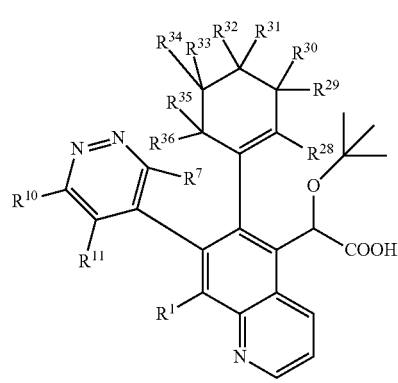 (D9b)
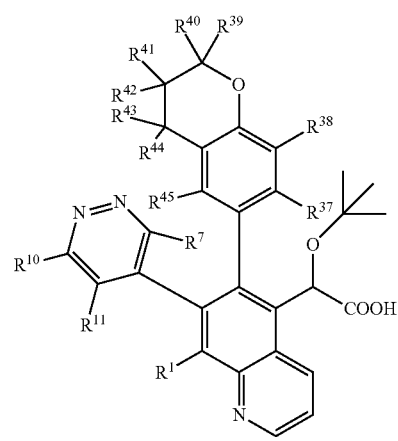 (D9c)
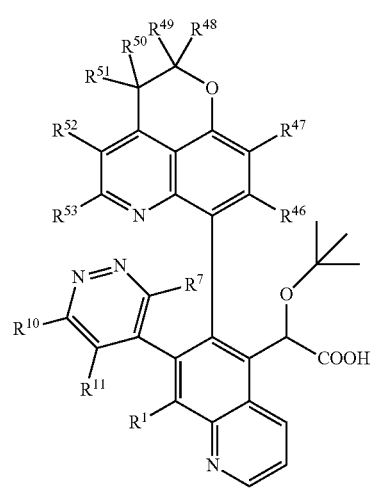 (D9d)
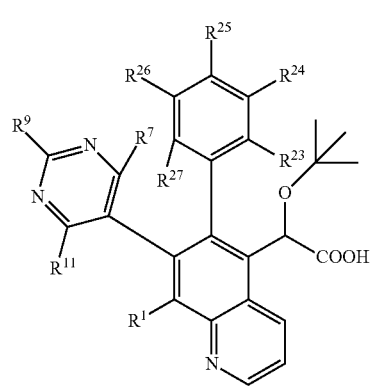 (D10a)
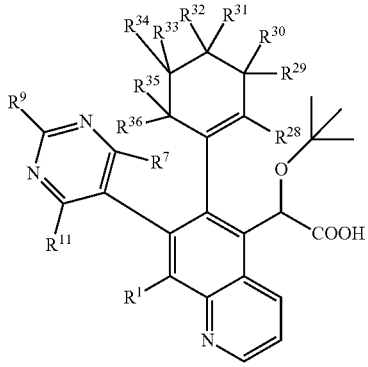 (D10b)
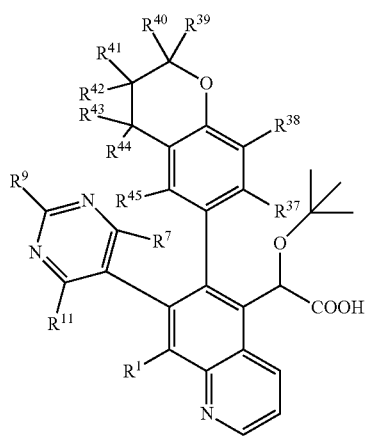 (D10c)
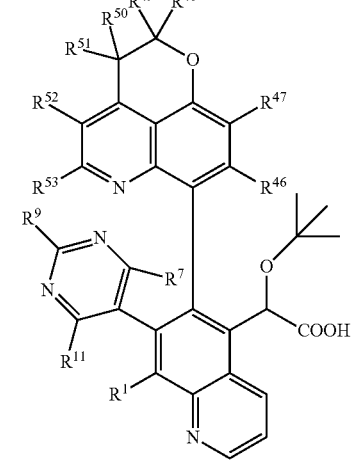 (D10d)
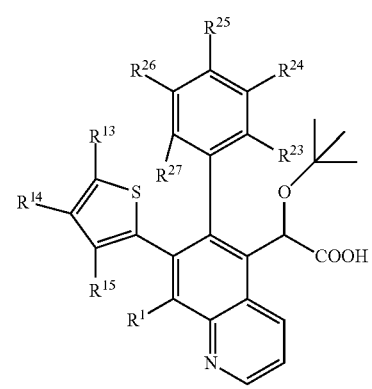 (E1a)

-continued
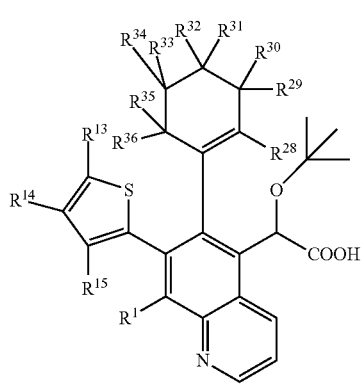
(E1b)
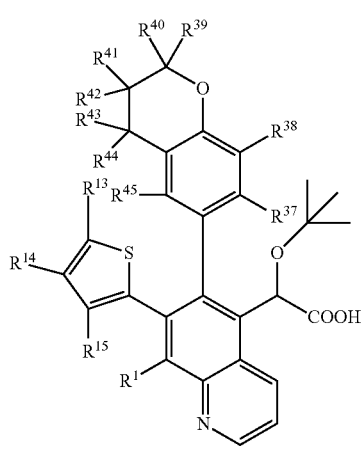
(E1c)
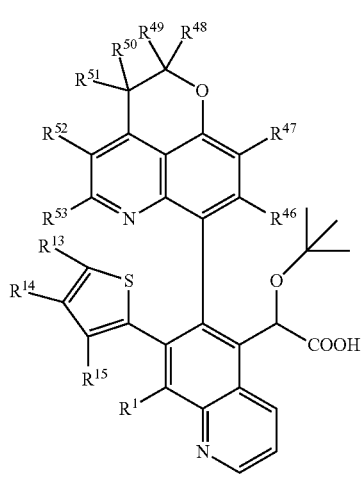
(E1d)
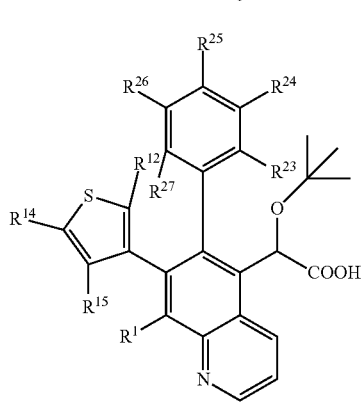
(E2a)
-continued
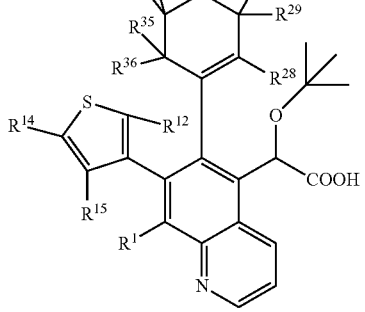
(E2b)
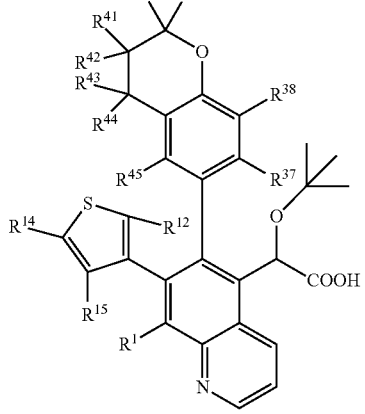
(E2c)
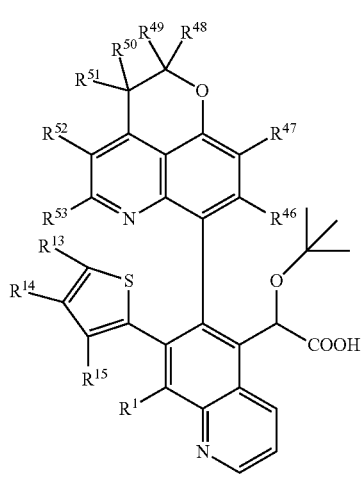
(E2d)
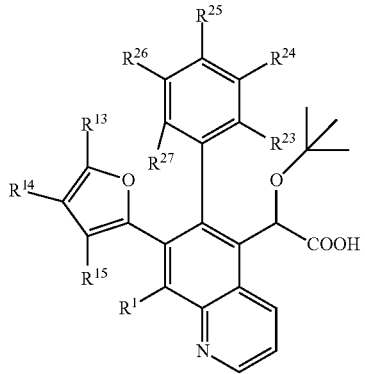
(E3a)

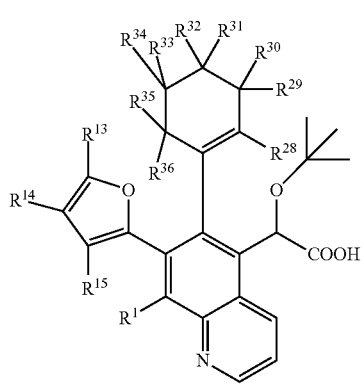
(E3b)
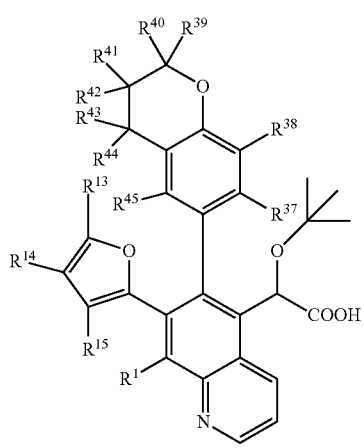
(E3c)
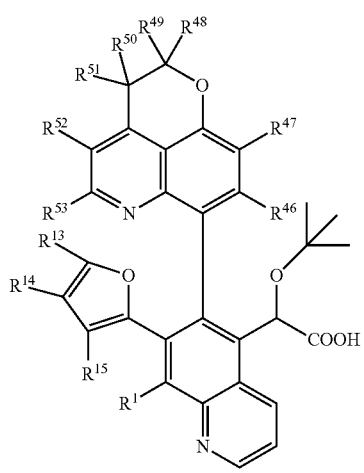
(E3d)
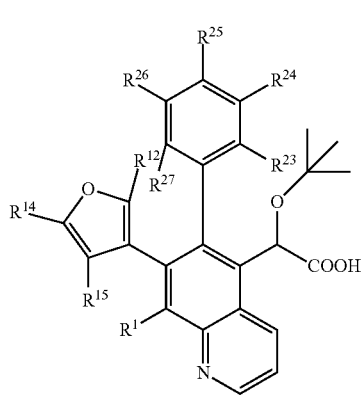
(E4a)
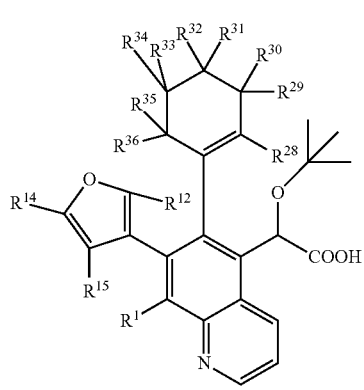
(E4b)
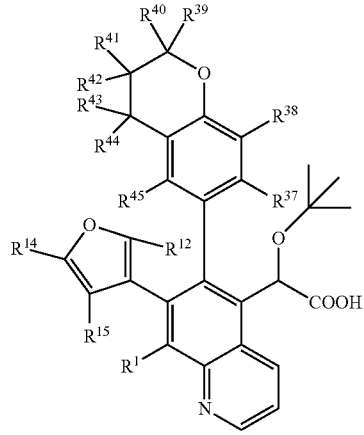
(E4c)
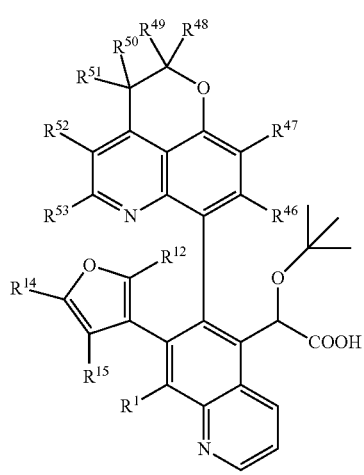
(E4d)
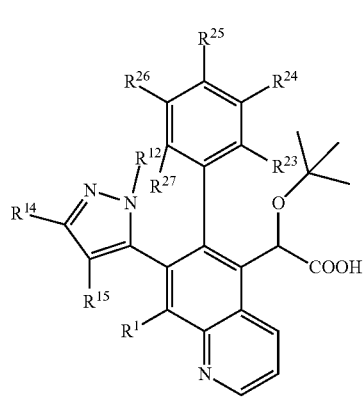
(E5a)

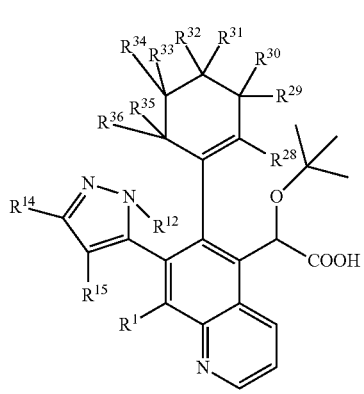
(E5b)
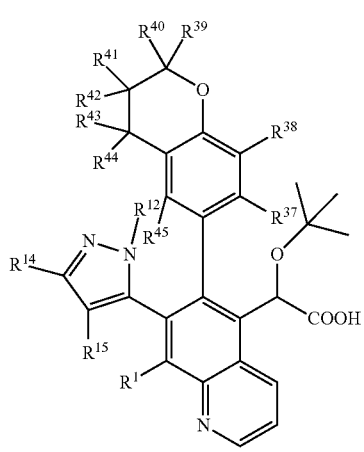
(E5c)
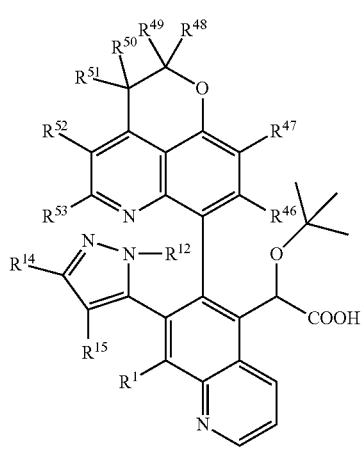
(E5d)
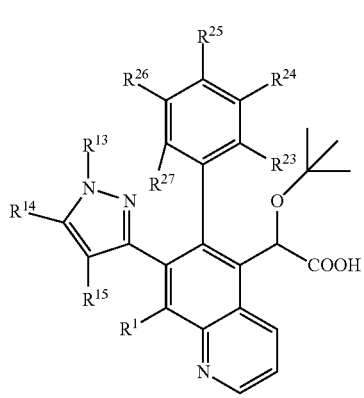
(E6a)
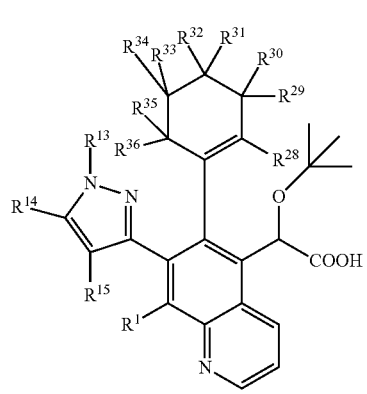
(E6b)
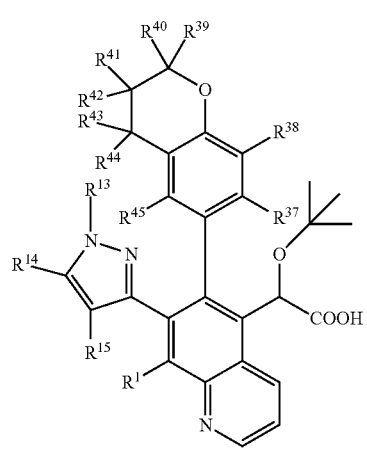
(E6c)
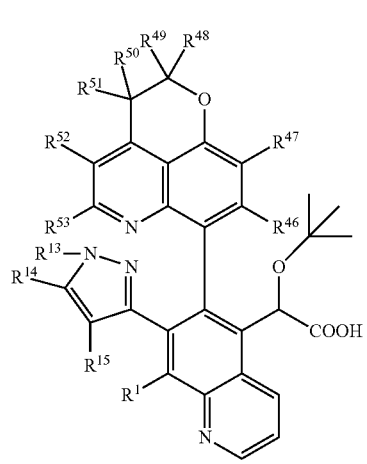
(E6d)
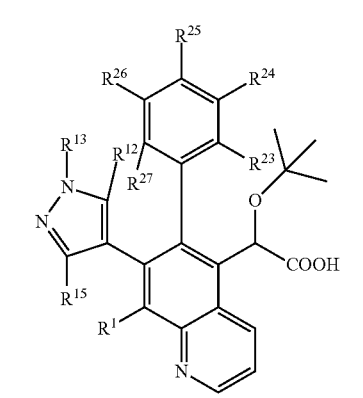
(E7a)

(E7b) 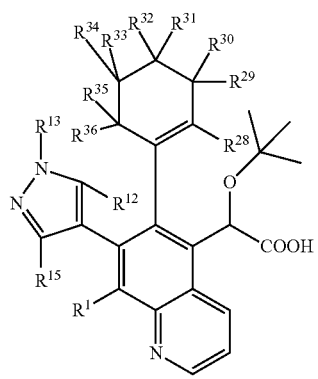
(E7c) 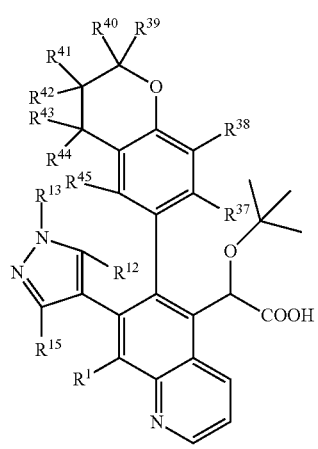
(E7d) 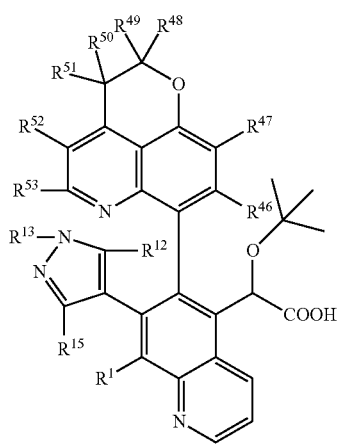
(F1a) 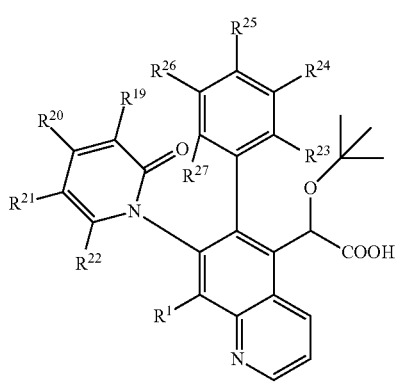
(F1b) 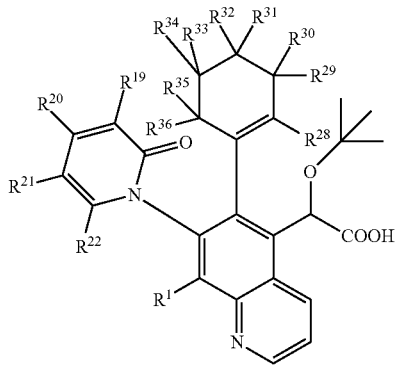
(F1c) 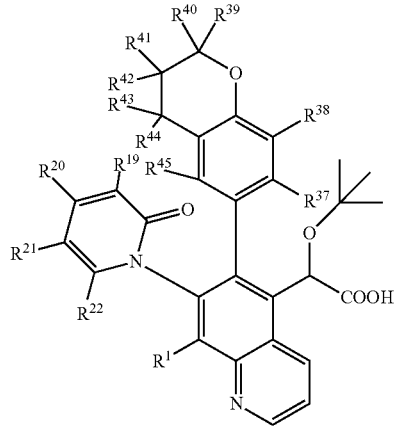
(F1d) 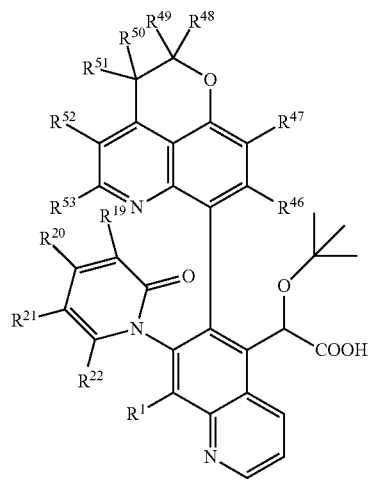
(F2a) 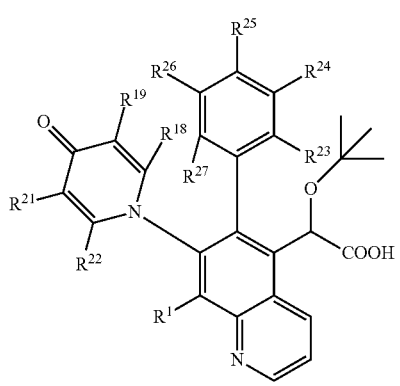

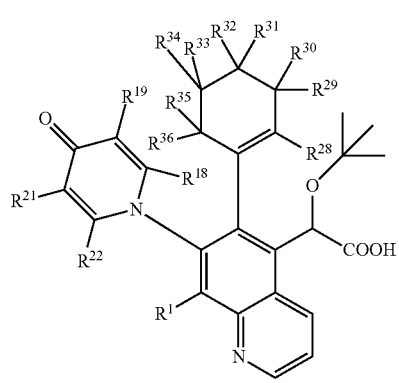
(F2b)
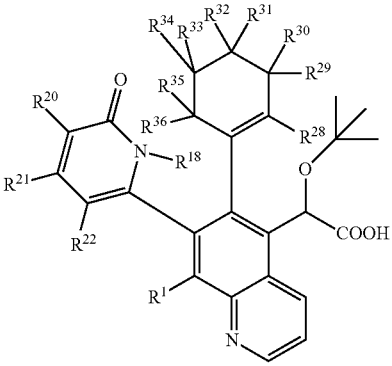
(F3b)
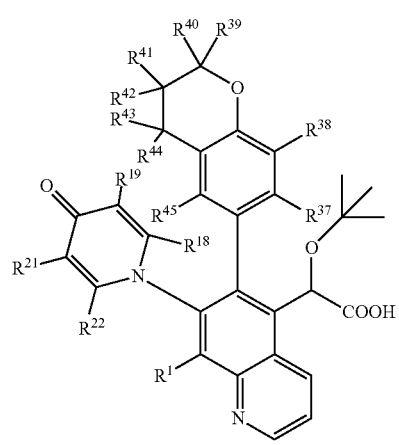
(F2c)
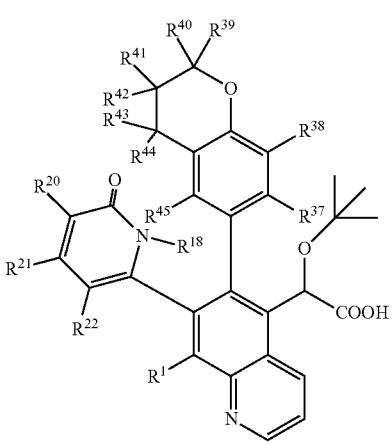
(F3c)
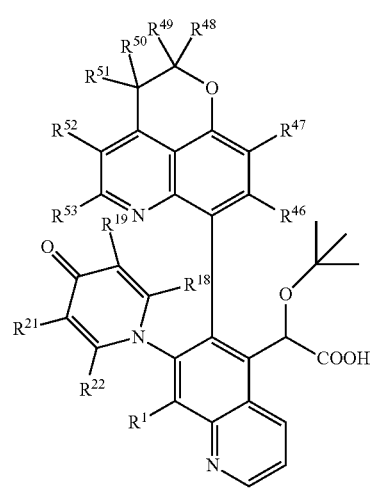
(F2d)
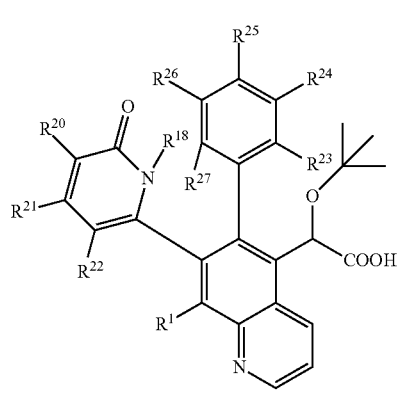
(F3a)
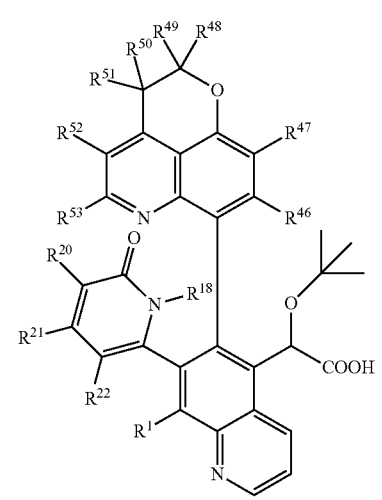
(F3d)

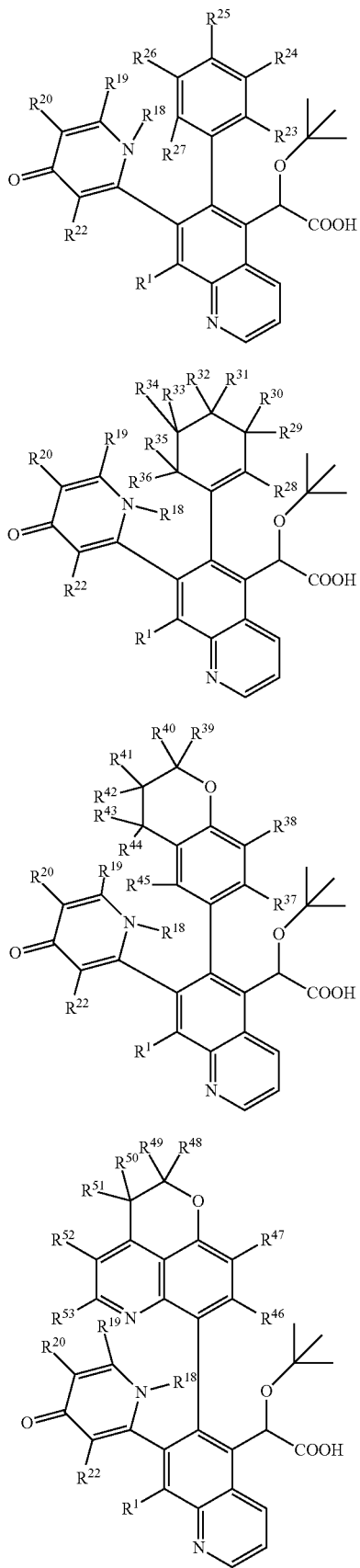
(F4a)
(F4b)
(F4c)
(F4d)
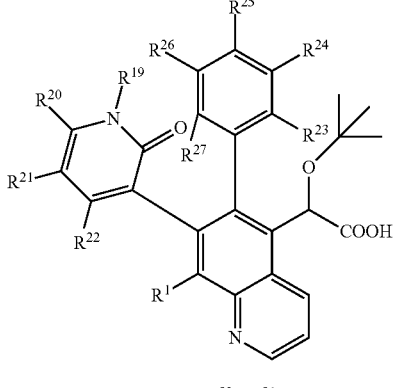
(F5a)
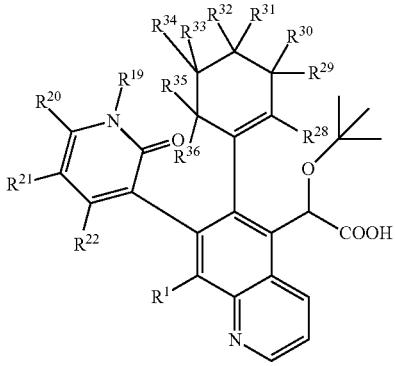
(F5b)
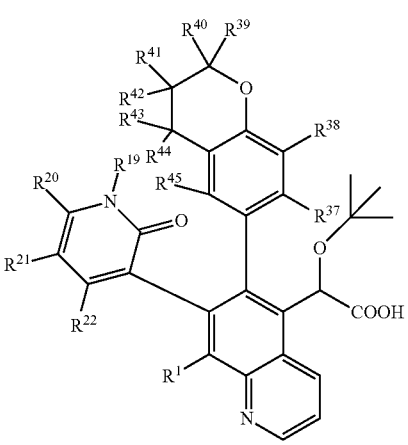
(F5c)
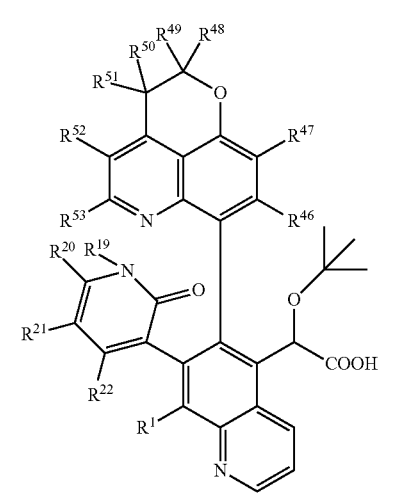
(F5d)

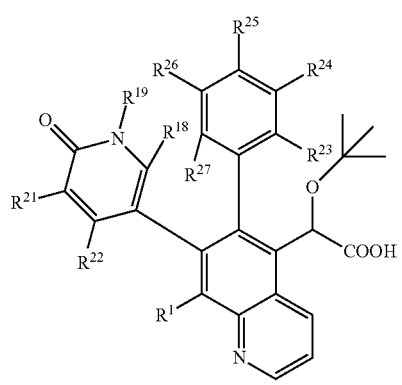
(F6a)
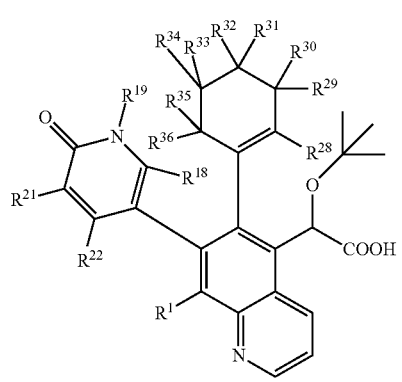
(F6b)
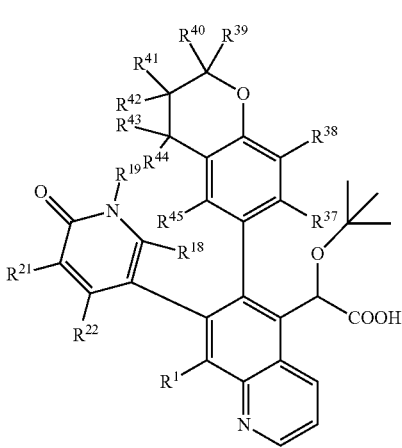
(F6c)
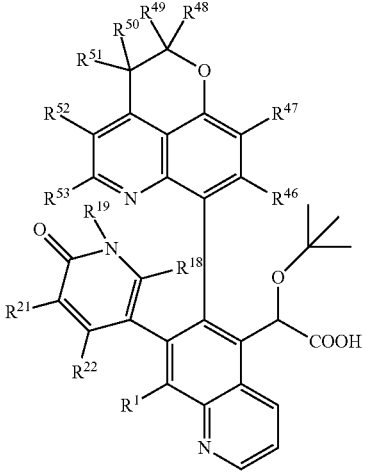
(F6d)
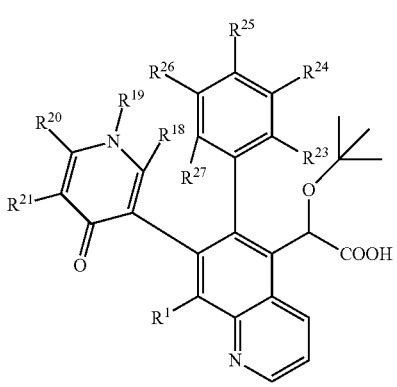
(F7a)
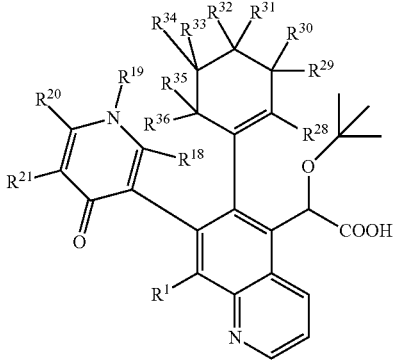
(F7b)
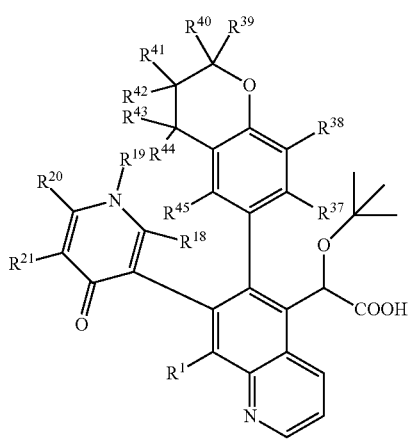
(F7c)

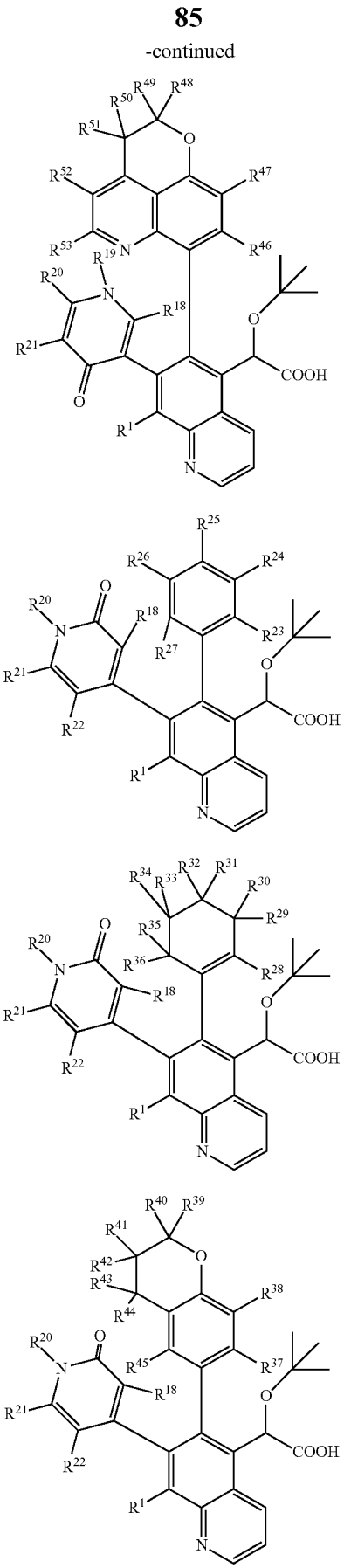

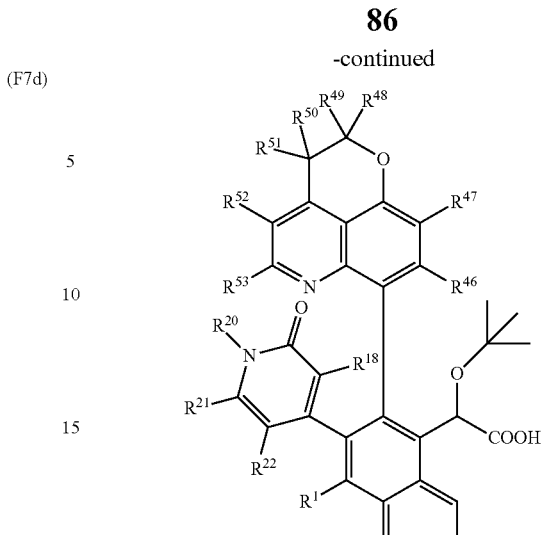

wherein $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ identical or different, independently represent a hydrogen atom; a halogen atom; —CH$_3$; —CH$_2$CH$_3$; —(CH$_2$)$_2$CH$_3$; —CH(CH$_3$)$_2$; —CH$_2$CF$_3$; —OCH$_3$; —NH$_2$; —N(CH$_3$)$_2$; —CH$_2$F; —CHF$_2$; —CF$_3$; —OCH$_2$F; —OCHF$_2$; —OCF$_3$; —(X)$_x$—C$_3$-C$_6$ cycloalkyl; —(X)$_x$—(CT$^5$T$^6$)$_y$cycloalkyl; —(X)$_x$—(CT$^5$T$^6$)$_y$-aryl; —(X)$_x$—(CT$^5$T$^6$)$_y$CN; —(X)$_x$—(CT$^5$T$^6$)$_y$OT$^3$; —(X)$_x$—(CT$^5$T$^6$)$_y$ST$^3$; —(X)$_x$—(CT$^5$T$^6$)$_y$S(O)T$^3$; —(X)$_x$—(CT$^5$T$^6$)$_y$S(O)$_2$T$^3$; —(X)$_x$—(CT$^5$T$^6$)$_y$NT$^3$T$^4$; —(X)$_x$—(CT$^5$T$^6$)$_y$C(O)T$^3$; —(X)$_x$—(CT$^5$T$^6$)$_y$C(O)OT$^3$; —(X)$_x$—(CT$^5$T$^6$)$_y$C(O)NT$^3$T$^4$; —(X)$_x$—(CT$^5$T$^6$)$_y$NT$^3$C(O)NT$^3$T$^4$; —(X)$_x$—(CT$^5$T$^6$)$_y$NT$^3$C(O)T$^4$; —(X)$_x$—(CT$^5$T$^6$)$_y$NT$^3$C(O)OT$^4$; —(X)$_x$—(CT$^5$T$^6$)$_y$OC(O)NT$^3$T$^4$; —(X)$_x$—(CT$^5$T$^6$) S(O)$_2$NT$^3$T$^4$ or —(X)$_x$—(CT$^5$T$^6$)$_y$NT$^3$S(O)$_2$T$^4$;

$R^1$, $R^5$, $R^6$, X, x, y and T$^3$ to T$^6$ are independently defined as for the compounds of formula (I), (A), (B), (C), (D), (E), (F), (A1) to (A10), (B1) to (B15), (C1) to (C9), (D1) to (D10), (E1) to (E7) or (F1) to (F8).

The invention also provides compounds of formula (A1a) to (A10a), (A1b) to (A10b), (A1c) to (A10c), (A1d) to (A10d), (B1a) to (B15a), (B1b) to (B15b), (B1c) to (B15c), (B1d) to (B15d), (C1a) to (C9a), (C1b) to (C9b), (C1c) to (C9c), (C1d) to (C9d), (D1a) to (D10a), (D1b) to (D10b), (D1c) to (D10c), (D1d) to (D10d), (E1a) to (E7a), (E1b) to (E7b), (E1c) to (E7c), (E1d) to (E7d), (F1a) to (F8a), (F1b) to (F8b), (F1c) to (F8c) or (F1d) to (F8d), wherein:

$R^7$, $R^8$ and the carbon atoms to which they are bonded form a saturated, partially or totally unsaturated 6-membered carbo- or heterocycle;

$R^8$, $R^9$ and the carbon atoms to which they are bonded form a saturated, partially or totally unsaturated 6-membered carbo- or heterocycle;

$R^9$, $R^{10}$ and the carbon atoms to which they are bonded form a saturated, partially or totally unsaturated 6-membered carbo- or heterocycle;

$R^{10}$, $R^{11}$ and the carbon atoms to which they are bonded form a saturated, partially or totally unsaturated 6-membered carbo- or heterocycle;

$R^{12}$, $R^{13}$ and the carbon or nitrogen atoms to which they are bonded form a saturated, partially or totally unsaturated 6-membered carbo- or heterocycle;

R$^{13}$, R$^{14}$ and the carbon or nitrogen atoms to which they are bonded form a saturated, partially or totally unsaturated 6-membered carbo- or heterocycle; or R$^{14}$, R$^{15}$ and the carbon atoms to which they are bonded form a saturated, partially or totally unsaturated 6-membered carbo- or heterocycle.

The invention also provides compounds of formula (A1a) to (A10a), (A1b) to (A10b), (A1c) to (A10c), (A1d) to (A10d), (B1a) to (B15a), (B1b) to (B15b), (B1c) to (B15c), (B1d) to (B15d), (C1a) to (C9a), (C1b) to (C9b), (C1c) to (C9c), (C1d) to (C9d), (D1a) to (D10a), (D1b) to (D10b), (D1c) to (D10c), (D1d) to (D10d), (E1a) to (E7a), (E1b) to (E7b), (E1c) to (E7c), (E1d) to (E7d), (F1a) to (F8a), (F1b) to (F8b), (F1c) to (F8c) or (F1d) to (F8d), wherein:

R$^{23}$, R$^{24}$, R$^{25}$, R$^{26}$, R$^{27}$, R$^{28}$, R$^{29}$, R$^{30}$, R$^{31}$, R$^{32}$, R$^{33}$, R$^{34}$, R$^{35}$, R$^{36}$, R$^{37}$, R$^{38}$, R$^{39}$, R$^{40}$, R$^{41}$, R$^{42}$, R$^{43}$, R$^{44}$, R$^{45}$, R$^{46}$, R$^{47}$, R$^{48}$, R$^{49}$, R$^{50}$, R$^{51}$, R$^{52}$ and R$^{53}$, identical or different, independently represent a hydrogen atom or a linear or branched C1-C$_6$ alkyl;

R$^{24}$, R$^{25}$ and the carbon atoms to which they are bonded form a saturated, partially or totally unsaturated 6-membered carbo- or heterocycle;

R$^{25}$, R$^{26}$ and the carbon atoms to which they are bonded form a saturated, partially or totally unsaturated 6-membered carbo- or heterocycle; or R$^{31}$, R$^{32}$ and the carbon atom to which they are bounded form a saturated 3-, 4-, 5- or 6-membered carbocycle.

Advantageously, the invention also provides compounds of formulae (A1a) to (A10a), (A1b) to (A10b), (A1c) to (A10c), (A1d) to (A10d), (B1a) to (B15a), (B1b) to (B15b), (B1c) to (B15c), (B1d) to (B15d), (C1a) to (C9a), (C1b) to (C9b), (C1c) to (C9c), (C1d) to (C9d), (D1a) to (D10a), (D1b) to (D10b), (D1c) to (D10c), (D1d) to (D10d), (E1a) to (E7a), (E1b) to (E7b), (E1c) to (E7c), (E1d) to (E7d), (F1a) to (F8a), (F1b) to (F8b), (F1c) to (F8c) or (F1d) to (F8d), wherein R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$ and R$^{22}$, identical or different, independently represent a hydrogen atom; a halogen atom; a linear or branched C$_1$-C$_6$ alkyl; a linear or branched —O—C$_1$-C$_6$ alkyl; a linear or branched —O—C$_1$-C$_{10}$ alkylaryl; —C(O)OH; —C(O)NH$_2$; —C(O)NH(CH$_3$); or —NHC(O)CH$_3$.

As examples of compounds of formula (A1c), the invention provides:
2-(tert-butoxy)-2-[2-(3,4-dihydro-2H-1-benzopyran-6-yl)-3-phenyl-6-(trifluoromethyl)phenyl]acetic acid;
2-(tert-butoxy)-2-[2-(3,4-dihydro-2H-1-benzopyran-6-yl)-3-(4-methoxyphenyl)-6-(trifluoromethyl)phenyl]acetic acid;
2-(tert-butoxy)-2-[3-(4-carbamoylphenyl)-2-(3,4-dihydro-2H-1-benzopyran-6-yl)-6-(trifluoromethyl)phenyl]acetic acid;
2-(tert-butoxy)-2-[3-(3-carbamoylphenyl)-2-(3,4-dihydro-2H-1-benzopyran-6-yl)-6-(trifluoromethyl)phenyl]acetic acid;
2-(tert-butoxy)-2-[2-(3,4-dihydro-2H-1-benzopyran-6-yl)-3[4(methylcarbamoyl)phenyl]-6-(trifluoromethyl)phenyl]acetic acid;
2-[3-(4-aminophenyl)-2-(3,4-dihydro-2H-1-benzopyran-6-yl)-6-(trifluoromethyl)phenyl]-2-(tert-butoxy)acetic acid;
2-(tert-butoxy)-2-[3-(4-acetamidophenyl)-2-(3,4-dihydro-2H-1-benzopyran-6-yl)-6-(trifluoromethyl)phenyl]acetic acid;
2-[3-(3-aminophenyl)-2-(3,4-dihydro-2H-1-benzopyran-6-yl)-6-(trifluoromethyl)phenyl]-2-(tert-butoxy)acetic acid;
2-(tert-butoxy)-2-[3-(3-acetamidophenyl)-2-(3,4-dihydro-2H-1-benzopyran-6-yl)-6-(trifluoromethyl)phenyl]acetic acid;
2-(tert-butoxy)-2-[2-(3,4-dihydro-2H-1-benzopyran-6-yl)-3-(3-propylphenyl)-6-(trifluoromethyl)phenyl]acetic acid;
4-{3-[(tert-butoxy)(carboxy)methyl]-2-(3,4-dihydro-2H-1-benzopyran-6-yl)-4-(trifluoromethyl)phenyl}benzoic acid;
3-{3-[(tert-butoxy)(carboxy)methyl]-2-(3,4-dihydro-2H-1-benzopyran-6-yl)-4-(trifluoromethyl)phenyl}benzoic acid.

As examples of compounds of formula (A2c), the invention provides:
2-(tert-butoxy)-2-[2-(3,4-dihydro-2H-1-benzopyran-6-yl)-3-(6-propylpyridin-2-yl)-6-(trifluoromethyl)phenyl]acetic acid;
2-(tert-butoxy)-2-[2-(3,4-dihydro-2H-1-benzopyran-6-yl)-3-(4-propylpyridin-2-yl)-6-(trifluoromethyl)phenyl]acetic acid;
2-(tert-butoxy)-2-[2-(3,4-dihydro-2H-1-benzopyran-6-yl)-3-(pyridin-2-yl)-6-(trifluoromethyl)phenyl]acetic acid.

As an example of compounds of formula (A4b), the invention provides 2-(tert-butoxy)-2-[2-(4,4-dimethylcyclohex-1-en-1-yl)-3-(pyridin-4-yl)-6-(trifluoromethyl)phenyl]acetic acid.

As examples of compounds of formula (A4c), the invention provides:
2-{3-[2-(benzyloxy)pyridin-4-yl]-2-(3,4-dihydro-2H-1-benzopyran-6-yl)-6-(trifluoromethyl)phenyl}-2-(tert-butoxy)acetic acid;
2-(tert-butoxy)-2-[2-(3,4-dihydro-2H-1-benzopyran-6-yl)-3-(3-fluoropyridin-4-yl)-6-(trifluoromethyl)phenyl]acetic acid;
2-(tert-butoxy)-2-[2-(3,4-dihydro-2H-1-benzopyran-6-yl)-3-(2-propylpyridin-4-yl)-6-(trifluoromethyl)phenyl]acetic acid;
2-(tert-butoxy)-2-[2-(3,4-dihydro-2H-1-benzopyran-6-yl)-3-(pyridin-4-yl)-6-(trifluoromethyl)phenyl]acetic acid.

As an example of compounds of formula (A3c), the invention provides 2-(tert-butoxy)-2-[2-(3,4-dihydro-2H-1-benzopyran-6-yl)-3-(pyridin-3-yl)-6-(trifluoromethyl)phenyl]acetic acid.

As an example of compounds of formula (A6c), the invention provides 2-(tert-butoxy)-2-[2-(3,4-dihydro-2H-1-benzopyran-6-yl)-3-(pyrimidin-4-yl)-6-(trifluoromethyl)phenyl]acetic acid.

As an example of compounds of formula (A9c), the invention provides 2-(tert-butoxy)-2-[2-(3,4-dihydro-2H-1-benzopyran-6-yl)-3-(pyridazin-4-yl)-6-(trifluoromethyl)phenyl]acetic acid.

As an example of compounds of formula (B1c), the invention provides 2-(tert-butoxy)-2-[2-(3,4-dihydro-2H-1-benzopyran-6-yl)-3-(thiophen-2-yl)-6-(trifluoromethyl)phenyl]acetic acid.

As an example of compounds of formula (B2c), the invention provides 2-(tert-butoxy)-2-[2-(3,4-dihydro-2H-1-benzopyran-6-yl)-3-(2,5-dimethyl-thiophen-3-yl)-6-(trifluoromethyl)phenyl]acetic acid.

As examples of compounds of formula (B5c), the invention provides:
2-(tert-butoxy)-2-[2-(3,4-dihydro-2H-1-benzopyran-6-yl)-3-(1-methyl-1H-pyrazol-5-yl)-6-(trifluoromethyl)phenyl]acetic acid;
2-(tert-butoxy)-2-[2-(3,4-dihydro-2H-1-benzopyran-6-yl)-3-[1-methyl-3-(trifluoromethyl)-1H-pyrazol-5-yl]-6-(trifluoromethyl)phenyl]acetic acid.

As an example of compounds of formula (B6c), the invention provides:

2-(tert-butoxy)-2-[2-(3,4-dihydro-2H-1-benzopyran-6-yl)-3-(1-methyl-1H-pyrazol-3-yl)-6-(trifluoromethyl)phenyl] acetic acid.

As an example of compounds of formula (B7b), the invention provides:

2-(tert-butoxy)-2-[2-(4,4-dimethylcyclohex-1-en-1-yl)-3-(1-methyl-1H-pyrazol-4-yl)-6-(trifluoromethyl)phenyl] acetic acid.

As examples of compounds of formula (B7c), the invention provides:

2-(tert-butoxy)-2-[2-(3,4-dihydro-2H-1-benzopyran-6-yl)-3-(1-methyl-1H-pyrazol-4-yl)-6-(trifluoromethyl)phenyl] acetic acid;

2-(tert-butoxy)-2-{2-(3,4-dihydro-2H-1-benzopyran-6-yl)-3-[1-(2,2,2-trifluoroethyl)-1H-pyrazol-4-yl]-6-(trifluoromethyl)phenyl}acetic.

As an example of compounds of formula (B8b), the invention provides 2-(tert-butoxy)-2-[2-(4,4-dimethylcyclohex-1-en-1-yl)-3-(1H-pyrazol-1-yl)-6-(trifluoromethyl)phenyl]acetic acid.

As examples of compounds of formula (B8c), the invention provides:

2-(tert-butoxy)-2-[2-(3,4-dihydro-2H-1-benzopyran-6-yl)-3-(3-phenyl-1H-pyrazol-1-yl)-6-(trifluoromethyl)phenyl] acetic acid;

2-[3-(4-bromo-1H-pyrazol-1-yl)-2-(3,4-dihydro-2H-1-benzopyran-6-yl)-6-(trifluoromethyl)phenyl]-2-(tert-butoxy) acetic acid;

2-[3-(4-chloro-1H-pyrazol-1-yl)-2-(3,4-dihydro-2H-1-benzopyran-6-yl)-6-(trifluoromethyl)phenyl]-2-(tert-butoxy) acetic acid;

2-(tert-butoxy)-2-[2-(3,4-dihydro-2H-1-benzopyran-6-yl)-3-[3-(dimethylamino)-1H-pyrazol-1-yl]-6-(trifluoromethyl)phenyl]acetic acid;

2-(tert-butoxy)-2-[2-(3,4-dihydro-2H-1-benzopyran-6-yl)-3-[4-(dimethylamino)-1H-pyrazol-1-yl]-6-(trifluoromethyl)phenyl]acetic acid;

2-(tert-butoxy)-2-[2-(3,4-dihydro-2H-1-benzopyran-6-yl)-3-(5-methyl-1H-pyrazol-1-yl)-6-(trifluoromethyl)phenyl] acetic acid;

2-(tert-butoxy)-2-[2-(3,4-dihydro-2H-1-benzopyran-6-yl)-3-(1H-pyrazol-1-yl)-6-(trifluoromethyl)phenyl]acetic acid;

2-(tert-butoxy)-2-[2-(3,4-dihydro-2H-1-benzopyran-6-yl)-3-(3-methyl-1H-pyrazol-1-yl)-6-(trifluoromethyl)phenyl] acetic acid;

2-(tert-butoxy)-2-[2-(3,4-dihydro-2H-1-benzopyran-6-yl)-3-(4-methyl-1H-pyrazol-1-yl)-6-(trifluoromethyl)phenyl] acetic acid.

As an example of compounds of formula (B9c), the invention provides 2-(tert-butoxy)-2-[2-(3,4-dihydro-2H-1-benzopyran-6-yl)-3-(1H-imidazol-1-yl)-6-(trifluoromethyl) phenyl]acetic acid.

As examples of compounds of formula (B10c), the invention provides:

2-[3-(1,3-benzothiazol-2-yl)-2-(3,4-dihydro-2H-1-benzopyran-6-yl)-6-(trifluoromethyl)phenyl]-2-(tert-butoxy)acetic acid;

2-(tert-butoxy)-2-[2-(3,4-dihydro-2H-1-benzopyran-6-yl)-3-(1,3-thiazol-2-yl)-6-(trifluoromethyl)phenyl]acetic acid.

As an example of compounds of formula (B11c), the invention provides 2-(tert-butoxy)-2-[2-(3,4-dihydro-2H-1-benzopyran-6-yl)-3-(1,2-thiazol-4-yl)-6-(trifluoromethyl) phenyl]acetic acid.

As an example of compounds of formula (B12c), the invention provides 2-(tert-butoxy)-2-[2-(3,4-dihydro-2H-1-benzopyran-6-yl)-3-(1-methyl-1H-imidazol-4-yl)-6-(trifluoromethyl)phenyl]acetic acid.

As example of compounds of formula (B13c), the invention provides 2-(tert-butoxy)-2-[2-(3,4-dihydro-2H-1-benzopyran-6-yl)-3-{pyrazolo[1,5-a]pyridin-3-yl}-6-(trifluoromethyl)phenyl]acetic acid.

As an example of compounds of formula (B14c), the invention provides 2-(tert-butoxy)-2-[2-(3,4-dihydro-2H-1-benzopyran-6-yl)-3-(1-methyl-1H-pyrrol-3-yl)-6-(trifluoromethyl)phenyl]acetic acid.

As an example of compounds of formula (B15c), the invention provides 2-(tert-butoxy)-2-[3-(cyclopent-1-en-1-yl)-2-(3,4-dihydro-2H-1-benzopyran-6-yl)-6-(trifluoromethyl)phenyl]acetic acid.

As an example of compounds of formula (C3c), the invention provides 2-(tert-butoxy)-2-{3-[1-(cyclobutylmethyl)-6-oxo-1,6-dihydropyridin-2-yl]-2-(3,4-dihydro-2H-1-benzopyran-6-yl)-6-(trifluoromethyl)phenyl}acetic acid.

As an example of compounds of formula (C5c), the invention provides 2-(tert-butoxy)-2-{3-[1-(cyclobutylmethyl)-2-oxo-1,2-dihydropyridin-3-yl]-2-(3,4-dihydro-2H-1-benzopyran-6-yl)-6-(trifluoromethyl)phenyl}acetic acid.

As examples of compounds of formula (C6c), the invention provides:

2-(tert-butoxy)-2-[2-(3,4-dihydro-2H-1-benzopyran-6-yl)-3-(1-methyl-1H-pyridin-2-one-5-yl)-6-(trifluoromethyl) phenyl]acetic acid;

2-(tert-butoxy)-2-[2-(3,4-dihydro-2H-1-benzopyran-6-yl)-3-(6-oxo-1-propyl-1,6-dihydropyridin-3-yl)-6-(trifluoromethyl)phenyl]acetic;

2-[3-(1-benzyl-6-oxo-1,6-dihydropyridin-3-yl)-2-(3,4-dihydro-2H-1-benzopyran-6-yl)-6-(trifluoromethyl)phenyl]-2-(tert-butoxy)acetic;

2-(tert-butoxy)-2-{3-[1-(cyclopropylmethyl)-6-oxo-1,6-dihydropyridin-3-yl]-2-(3,4-dihydro-2H-1-benzopyran-6-yl)-6-(trifluoromethyl)phenyl}acetic acid;

2-(tert-butoxy)-2-{3-[1-(cyclobutylmethyl)-6-oxo-1,6-dihydropyridin-3-yl]-2-(3,4-dihydro-2H-1-benzopyran-6-yl)-6-(trifluoromethyl)phenyl}acetic acid;

2-(tert-butoxy)-2-{3-[1-(2-cyclopropylethyl)-6-oxo-1,6-dihydropyridin-3-yl]-2-(3,4-dihydro-2H-1-benzopyran-6-yl)-6-(trifluoro methyl)phenyl}acetic acid;

2-(tert-butoxy)-2-[2-(3,4-dihydro-2H-1-benzopyran-6-yl)-3-[1-(2-methylpropyl)-6-oxo-1,6-dihydropyridin-3-yl]-6-(trifluoromethyl)phenyl]acetic acid;

2-(tert-butoxy)-2-[3-(1-cyclobutylmethyl-6-oxo-1,6-dihydro-pyridin-3-yl)-2-(3,4-dihydro-2H-1-benzopyran-6-yl)-6-methylphenyl]acetic acid;

2-(tert-butoxy)-2-[3-(1-cyclobutylmethyl-6-oxo-1,6-dihydro-pyridin-3-yl)-6-methyl-2-[5-methyl-(3,4-dihydro-2H-1-benzopyran-6-yl)]phenyl]acetic acid; or 2-(tert-butoxy)-2-[3-(1-cyclopropyl-6-oxo-1,6-dihydropyridin-3-yl)-2-(3,4-dihydro-2H-1-benzopyran-6-yl)-6-(trifluoromethyl)phenyl]acetic acid.

As an example of compounds of formula (C8c), the invention provides 2-(tert-butoxy)-2-[2-(3,4-dihydro-2H-1-benzopyran-6-yl)-3-(1-ethyl-2-oxo-1,2-dihydropyridin-4-yl)-6-(trifluoromethyl)phenyl]acetic.

As an example of compounds of formula (C9c), the invention provides 2-(tert-butoxy)-2-[3-(cyclohex-1-en-1-yl)-2-(3,4-dihydro-2H-1-benzopyran-6-yl)-6-(trifluoromethyl)phenyl]acetic acid.

EXAMPLES

The following examples are provided for the purpose of illustrating the present invention and by no means should be interpreted to limit the scope of the present invention.

The first part represents the preparation of the compounds (intermediates and final compounds) whereas the second part describes the evaluation of antiviral activity of compounds according to the invention.

Preparation of the Compounds

Abbreviations or symbols used herein include:
DMSO: dimethylsulfoxide
MS: Mass Spectrometry
NMR: Nuclear Magnetic Resonance Spectroscopy
s: singlet
bs: broad singlet
d: doublet
t: triplet
q: quadruplet
dd: doubled doublet
ddd: doubled doubled doublet
dt: doubled triplet
m: massif
TLC: Thin Layer Chromatography Example 1

Synthesis of 2-(tert-butoxy)-2-[2-(3,4-dihydro-2H-1-benzopyran-6-yl)-3-phenyl-6-(trifluoromethyl)phenyl]acetic acid

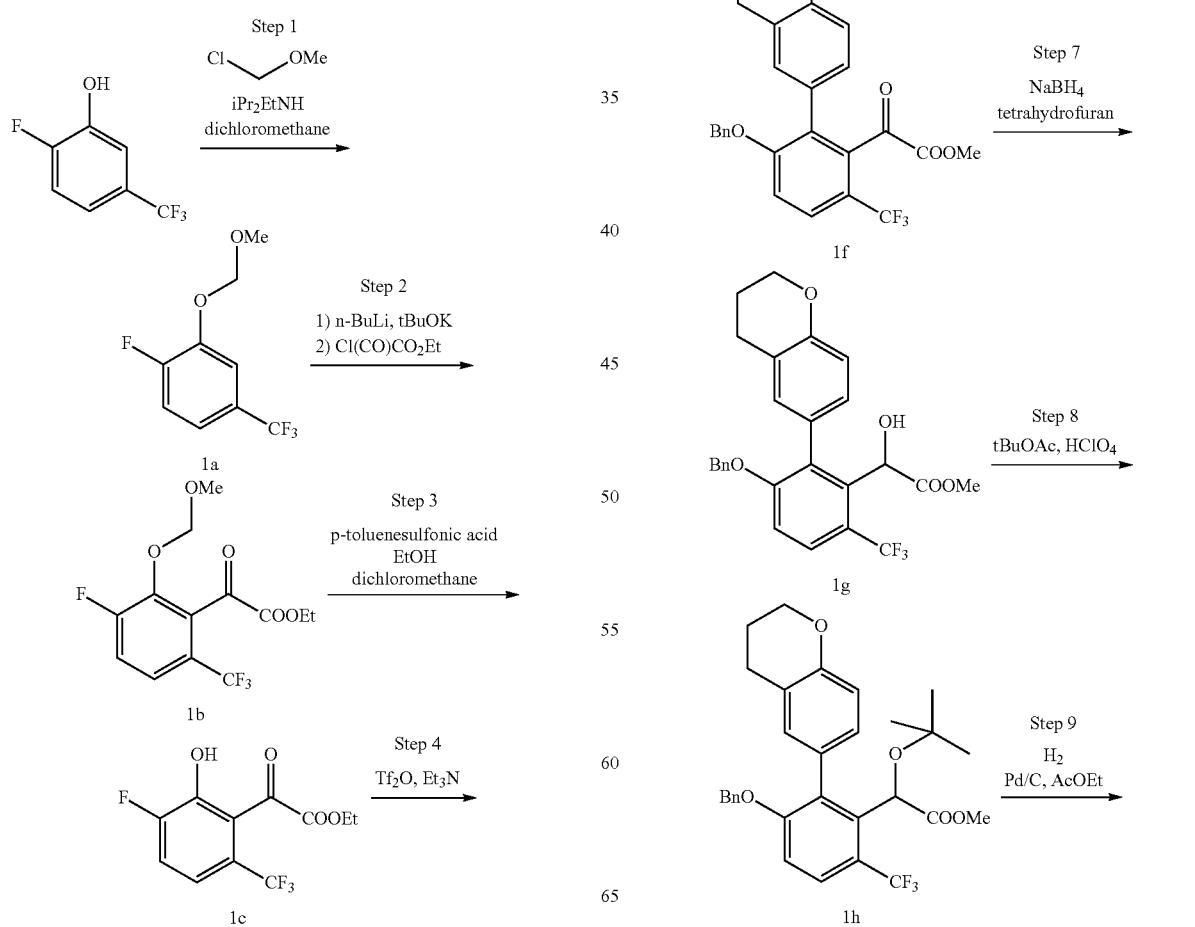

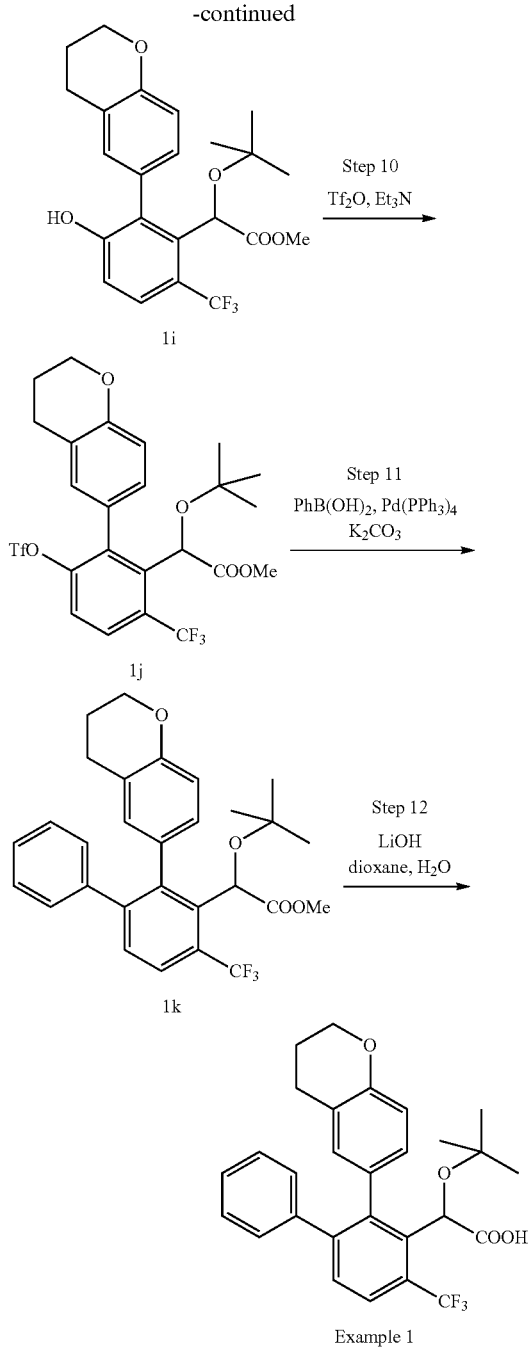

Example 1

Step 1: Preparation of Intermediate 1-fluoro-2-(methoxymethoxy)-4-(trifluoro methyl)benzene (1a)

To a solution of 2-fluoro-5-(trifluoromethyl)phenol (2.0 g, 11.1 mmol) in anhydrous dichloromethane (20 mL) under nitrogen atmosphere at 0° C. were successively added diisopropylethylamine (3.87 mL, 22.2 mmol) and chloromethyl methyl ether (1.26 mL, 16.6 mmol). The mixture was stirred at 0° C. for 45 minutes before adding water (20 mL). Layers were separated and the aqueous one was extracted with dichloromethane (30 mL). The combined organic layers were washed with a 2 M sodium hydroxide solution (20 mL), dried over sodium sulfate and concentrated in vacuo to provide 1-fluoro-2-(methoxymethoxy)-4-(trifluoromethyl)benzene (1a) (2.49 g, 11.1 mmol, 100%) as a lightly yellow oil.

$^1$H NMR (400 MHz, CDCl$_3$) δ 3.53 (s, 3H), 5.25 (s, 2H), 7.16-7.20 (m, 1H), 7.24-7.27 (m, 1H), 7.46 (dd, J=1.8 Hz, J=7.4 Hz, 1H).

Step 2: Preparation of Intermediate ethyl 2-[3-fluoro-2-(methoxymethoxy)-6-(trifluoromethyl)phenyl]-2-oxoacetate (1b)

Under nitrogen atmosphere, a 1.6 M n-butyllithium solution in hexanes (3.5 mL, 5.6 mmol) and a 1 M potassium tert-butoxide solution in tetrahydrofuran (5.6 mL, 5.6 mmol) were added to anhydrous tetrahydrofuran (30 mL) at −78° C. The mixture was stirred for 15 minutes before adding dropwise a solution of 1-fluoro-2-(methoxymethoxy)-4-(trifluoromethyl)benzene (1a) (1.0 g, 4.46 mmol) in tetrahydrofuran (10 mL). The mixture was stirred at −78° C. for 2 hours and was added via cannulation to a solution of ethyl oxalyl chloride (1.4 mL, 9.0 mmol) in tetrahydrofuran (20 mL) at −78° C. The mixture was stirred at −78° C. for 45 minutes and water (50 mL) was added. Layers were separated and the aqueous layer was extracted with ethyl acetate (2×30 mL). The combined organic layers were washed with a saturated solution of sodium hydrogenocarbonate (30 mL), brine (30 mL), dried over sodium sulfate and concentrated in vacuo. The residue was purified by flash chromatography on silica gel (cyclohexane/ethyl acetate 90/10) to provide ethyl 2-[3-fluoro-2-(methoxymethoxy)-6-(trifluoromethyl)phenyl]-2-oxoacetate (840 mg, 2.59 mmol, 58%) (1b) as a yellow oil.

$^1$H NMR (300 MHz, CDCl$_3$) δ 1.36 (t, J=7.2 Hz, 3H), 3.45 (s, 3H), 4.38 (q, J=7.2 Hz, 2H), 5.16 (s, 2H), 7.28-7.34 (m, 1H), 7.43 (dd, J=4.4 Hz, J=8.8 Hz, 1H).

Step 3: Preparation of Intermediate ethyl 2-[3-fluoro-2-hydroxy-6-(trifluoromethyl)phenyl]-2-oxoacetate (1c)

To a solution of ethyl 2-[3-fluoro-2-(methoxymethoxy)-6-(trifluoromethyl)phenyl]-2-oxoacetate (1b) (500 mg, 1.54 mmol) and p-toluenesulfonic acid (59 mg, 0.31 mmol) in dichloromethane (7.5 mL) and ethanol (1.5 mL) was heated at 50° C. overnight. The mixture was concentrated in vacuo. The residue was purified by flash chromatography on silica gel (cyclohexane/ethyl acetate 60/40) to provide ethyl 2-[3-fluoro-2-hydroxy-6-(trifluoromethyl)phenyl]-2-oxoacetate (1c) (394 mg, 1.40 mmol, 91%) as a yellow oil.

$^1$H NMR (300 MHz, CDCl$_3$) δ 1.38 (t, J=7.2 Hz, 3H), 4.38 (q, J=7.2 Hz, 2H), 6.91 (d, J=2.7 Hz), 7.26-7.35 (m, 2H).

Step 4: Preparation of Intermediate ethyl 2-{3-fluoro-2-[(trifluoromethane) sulfonyloxy]-6-(trifluoromethyl)phenyl}-2-oxoacetate (1d)

To a solution of ethyl 2-[3-fluoro-2-hydroxy-6-(trifluoromethyl)phenyl]-2-oxoacetate (394 mg, 1.41 mmol) (1c) in anhydrous dichloromethane (5 mL) under nitrogen atmosphere at −78° C. were successively added triethylamine (0.24 mL, 1.69 mmol) and triflic anhydride (0.26 mL, 1.55 mmol). The mixture was stirred at −78° C. for 45 minutes before adding water (10 mL). Layers were separated. The aqueous layer was extracted with dichloromethane (10 mL). The combined organic layers were washed with a saturated solution of sodium hydrogenocarbonate (10 mL), dried over sodium sulfate and concentrated in vacuo to ethyl 2-{3-fluoro-2-[(trifluoromethane)sulfonyloxy]-6-(trifluoromethyl)phenyl}-2-oxoacetate (1d) (548 mg, 1.32 mmol, 94%) as a yellow oil which was used without further purification.

$^1$H NMR (300 MHz, CDCl$_3$) δ 1.37 (t, J=7.2 Hz, 3H), 4.42 (q, J=7.2 Hz, 2H), 7.55 (t, J=8.7 Hz), 7.78 (dd, J=4.5 Hz, J=8.7 Hz, 1H).

Step 5: Preparation of Intermediate 2-[2-(3,4-dihydro-2H-1-benzopyran-6-yl)-3-fluoro-6-(trifluoromethyl)phenyl]-2-oxoacetic acid (1e)

A degassed solution of ethyl 2-{3-fluoro-2-[(trifluoromethane)sulfonyloxy]-6-(trifluoromethyl)phenyl}-2-oxoacetate (1d) (8.0 g, 19.41 mmol), potassium carbonate (10.73 g, 77.63 mmol), 6-(4,4,5,5-tetramethyl-1,3,2-dioxaborolan-2-yl)chroman (6.56 g, 25.23 mmol) and palladium tetrakis(triphenylphosphine) (2.24 g, 1.94 mmol) in dioxane (167 mL) and water (33.5 mL) was heated at 85° C. for 20 hours. Water (30 mL) was added and the reaction mixture was heated at 85° C. for 1 h more. Water (170 mL) was added and dioxane was evaporated in vacuo. Diethyl ether (2×80 mL) was added and the layers were separated. The organic layer was washed with a saturated solution of sodium hydrogenocarbonate (170 mL). The combined aqueous layers were acidified with 2N hydrochloric acid until pH 2 then extracted with diethyl ether (2×170 mL). The organic layer was dried over sodium sulfate and concentrated in vacuo to provide 2-[2-(3,4-dihydro-2H-1-benzopyran-6-yl)-3-fluoro-6-(trifluoromethyl)phenyl]-2-oxoacetic acid (1e) (6.09 g, 16.54 mmol, 85%) as a orange oil which was used without further purification.

$^1$H NMR (300 MHz, CDCl$_3$) δ1.97-2.04 (m, 2H), 2.77 (t, J=6.5 Hz, 2H), 4.21 (t, J=5.2 Hz, 2H), 6.81 (s, 1H), 6.92 (m, 2H), 7.39 (t, J=8.6 Hz, 1H), 7.73 (dd, J=8.6, 4.8 Hz, 1H).

Step 6: Preparation of Intermediate methyl 2-[3-(benzyloxy)-2-(3,4-dihydro-2H-1-benzopyran-6-yl)-6-(trifluoromethyl)phenyl]-2-oxoacetate (1f)

To a suspension of sodium hydride 60% in oil (340 mg, 14.2 mmol) in anhydrous N,N-dimethylformamide (14 mL) at 0° C. under nitrogen atmosphere, was dropwise added anhydrous benzyl alcohol (1.47 mL, 14.2 mmol). The mixture was stirred at room temperature for 30 minutes before adding dropwise a solution of 2-[2-(3,4-dihydro-2H-1-benzopyran-6-yl)-3-fluoro-6-(trifluoromethyl)phenyl]-2-oxoacetic acid (1e) (1.306 g, 3.55 mmol) in anhydrous N,N-dimethylformamide (13 mL) at 0° C. The dark red mixture was stirred at 60° C. for 3 hours. The dark green solution was cooled at 0° C. and water (80 mL) was added cautiously. The resulting basic solution was extracted with diethyl ether (2×70 mL). The aqueous phase was acidified with 1 M hydrochloric acid until pH 2, then extracted with AcOEt (3×70 mL). The combined organic layers were washed with brine (50 mL), dried over sodium sulfate and concentrated in vacuo. The residue was dissolved in toluene and concentrated. The residue was dissolved in cyclohexane (41.0 mL) and methanol (20.5 mL) at 0° C. and a 2 M solution of trimethylsilyldiazomethane in diethyl ether (4.4 mL, 8.87 mmol) was added. The mixture was stirred at room temperature for 30 minutes before adding acetic acid (0.5 mL). The mixture was concentrated in vacuo. The residue was dissolved in ethyl acetate (120 mL), washed with a saturated solution of sodium hydrogenocarbonate (120 mL), brine (120 mL), dried over sodium sulfate, concentrated in vacuo an then co-evaporated with toluene to provide methyl 2-[3-(benzyloxy)-2-(3,4-dihydro-2H-1-benzopyran-6-yl)-6-(trifluoromethyl)phenyl]-2-oxo acetate (1f) (1.31 g, 2.78 mmol, 78%) as a orange oil that was used without further purification.

$^1$H NMR (300 MHz, CDCl$_3$) δ 1.97-2.05 (m, 2H), 2.75 (t, J=6.4 Hz, 2H), 3.55 (s, 3H), 4.19-4.22 (m, 2H), 5.15 (s, 2H), 6.80 (d, J=8.4 Hz, 1H), 6.85 (d, J=2.1 Hz, 1H), 6.99 (dd, J=2.1 Hz, J=8.4 Hz, 1H), 7.11 (d, J=8.7 Hz, 1H), 7.23-7.36 (m, 5H), 7.65 (d, J=8.7 Hz, 1H).

Step 7: Preparation of Intermediate methyl 2-[3-(benzyloxy)-2-(3,4-dihydro-2H-1-benzopyran-6-yl)-6-(trifluoromethyl)phenyl]-2-hydroxyacetate (1g)

To a solution of methyl 2-[3-(benzyloxy)-2-(3,4-dihydro-2H-1-benzopyran-6-yl)-6-(trifluoromethyl)phenyl]-2-oxoacetate (1f) (1.32 g, 2.81 mmol) in tetrahydrofurane (44 mL) at 0° C. was added portion-wise sodium borohydride (159 mg, 4.21 mmol). The mixture was stirred at 0° C. for 90 minutes. Acetic acid (0.5 mL) was added, followed by water (60 mL). The resulting solution was extracted with ethyl acetate (3×50 mL). The organic layer was washed with brine (30 mL) and dried over sodium sulfate. The residue was purified by flash chromatography on silica gel (cyclohexane/ethyl acetate 80/20) to provide methyl 2-[3-(benzyloxy)-2-(3,4-dihydro-2H-1-benzopyran-6-yl)-6-(trifluoromethyl)phenyl]-2-hydroxyacetate (1g) (1.04 g, 2.20 mmol, 78%).

$^1$H NMR (300 MHz, CDCl$_3$) δ 2.01-2.09 (m, 2H), 2.75-2.82 (m, 2H), 3.57 and 3.60 (2 s, 3H), 4.24 (t, J=5.1 Hz, 2H), 5.07 (s, 2H), 5.38 (bs, 1H), 6.79-6.85 (m, 2H), 6.97-7.14 (m, 4H), 7.24-7.31 (m, 3H), 7.65 (d, J=8.7 Hz, 1H).

Step 8: Preparation of Intermediate methyl 2-[3-(benzyloxy)-2-(3,4-dihydro-2H-1-benzopyran-6-yl)-6-(trifluoromethyl)phenyl]-2-(tert-butoxy)acetate (1h)

Under nitrogen, methyl 2-[3-(benzyloxy)-2-(3,4-dihydro-2H-1-benzopyran-6-yl)-6-(trifluoromethyl)phenyl]-2-hydroxyacetate (1g) (5.36 g, 11.35 mmol) was dissolved in tert-butyl acetate (142 mL), cooled at 0° C. and 70% perchloric acid (2.94 mL, 34.04 mmol) was added. The reaction mixture was stirred at room temperature for 2 hours. Then the reaction mixture was poured into a saturated solution of sodium hydrogenocarbonate. The mixture was extracted with ethyl acetate. The resulting organic layer was washed with brine, dried over sodium sulfate and concentrated in vacuo. The crude mixture was purified by DCVC (Dry Column Vacuum Chromatography, using 250 mL Silicagel, cyclohexane/ethyl acetate 100/0 to 60/40) to provide methyl 2-[3-(benzyloxy)-2-(3,4-dihydro-2H-1-benzopyran-6-yl)-6-(trifluoromethyl)phenyl]-2-(tert-butoxy)acetate (1h) (3.58 g, 6.77 mmol, 58%) as a yellow oil.

$^1$H NMR (300 MHz, CDCl$_3$) δ 0.99 and 1.36 and 1.37 (s, 9H), 2.00-2.09 (m, 2H), 2.70-2.85 (m, 2H), 3.59 and 3.61 and 3.69 and 3.70 (s, 3H), 4.22-4.27 (m, 2H), 5.00-5.41 (m, 3H), 6.81-7.32 (m, 9H), 7.63-7.70 (m, 1H).

Step 9: Preparation of Intermediate methyl 2-(tert-butoxy)-2-[2-(3,4-dihydro-2H-1-benzopyran-6-yl)-3-hydroxy-6-(trifluoromethyl)phenyl]acetate (1i)

A solution of methyl 2-[3-(benzyloxy)-2-(3,4-dihydro-2H-1-benzopyran-6-yl)-6-(trifluoromethyl)phenyl]-2-(tert-butoxy)acetate (1h) (3.48g, 6.57 mmol) in ethyl acetate (130 mL) was passed through the H-Cube (0.8 mL/min, full H$_2$ mode, 40° C.). The resulting solution was concentrated in vacuo to provide methyl 2-(tert-butoxy)-2-[2-(3,4-dihydro-2H-1-benzopyran-6-yl)-3-hydroxy-6-(trifluoromethyl)phenyl]acetate (1i) (2.62 g, 5.97 mmol, 91%) as a white solid.

$^1$H NMR (300 MHz, CDCl$_3$) δ 1.00 and 1.01 (s, 9H), 2.05 (m, 2H), 2.78 (m, 2H), 3.66 (s, 3H), 4.25 (m, 2H), 5.04 and 5.05 (s, 1H), 5.10 and 5.13 (s, 1H), 6.89-6.93 (m, 2H), 6.99 (d, J=10.0 Hz, 1H), 7.08-7.11 (m, 1H), 7.62 (d, J=8.7 Hz, 1H).

MS m/z ([M−H]$^-$) 437.

Step 10: Preparation of Intermediate methyl 2-(tert-butoxy)-2-[2-(3,4-dihydro-2H-1-benzopyran-6-yl)-3-[(trifluoromethane)sulfonyloxy]-6-(trifluoromethyl)phenyl]acetate (1j)

To a solution of methyl 2-(tert-butoxy)-2-[2-(3,4-dihydro-2H-1-benzopyran-6-yl)-3-hydroxy-6-(trifluoromethyl)phenyl]acetate (1i) (1.00 g, 2.28 mmol) in anhydrous dichloromethane (16 mL) under nitrogen atmosphere at −78° C. were successively added triethylamine (0.95 mL, 6.84 mmol) and triflic anhydride (0.48 mL, 2.85 mmol). The colorless solution was stirred at −78° C. for 45 minutes before adding water (30 mL). The layers were separated. The aqueous layer was extracted with dichloromethane (30 mL). The combined organic layers were washed with a saturated solution of sodium hydrogenocarbonate (30 mL), dried over sodium sulfate and concentrated in vacuo to provide methyl 2-(tert-butoxy)-2-[2-(3,4-dihydro-2H-1-benzopyran-6-yl)-3-[(trifluoromethane)sulfonyloxy]-6-(trifluoromethyl)phenyl]acetate (1j) (1.30 g, 2.28 mmol, 100%) as a orange oil.

$^1$H NMR (300 MHz, CDCl$_3$) δ 0.98 and 0.99 (s, 9H), 1.98-2.10 (m, 2H), 2.65-2.85 (m, 2H), 3.70 (s, 3H), 4.20-4.28 (m, 2H), 5.12 (s, 1H), 6.80-7.05 (m, 3H), 7.42 (d, J=8.7 Hz, 1H), 7.80 (d, J=8.7 Hz, 1H).

Step 11: Preparation of Intermediate methyl 2-(tert-butoxy)-2-[2-(3,4-dihydro-2H-1-benzopyran-6-yl)-3-phenyl-6-(trifluoromethyl)phenyl]acetate (1k)

A degassed solution of methyl 2-(tert-butoxy)-2-[2-(3,4-dihydro-2H-1-benzopyran-6-yl)-3-[(trifluoromethane)sulfonyloxy]-6-(trifluoromethyl)phenyl]acetate (1j) (200 mg, 0.351 mmol), potassium carbonate (194 mg, 1.40 mmol), phenylboronic acid (52.3 mg, 0.421 mmol) and palladium tetrakis(triphenylphosphine) (40.5 mg, 0.035 mmol) in dioxane (3 mL) and water (0.6 mL) was heated at 85° C. overnight. Water (2 mL) was added and dioxane was evaporated in vacuo. The aqueous residue was extracted with ethyl acetate (3×4 mL). The combined organics were washed with a saturated solution of sodium hydrogenocarbonate (4 mL), dried over sodium sulfate and concentrated in vacuo. The residue was purified by preparative TLC (cyclohexane/ethyl acetate 90/10) to provide methyl 2-(tert-butoxy)-2-[2-(3,4-dihydro-2H-1-benzopyran-6-yl)-3-phenyl-6-(trifluoromethyl)phenyl]acetate (1k) (128 mg, 0.264 mmol, 73%) as a white solid.

$^1$H NMR (300 MHz, CDCl$_3$) δ 0.95 (s, 9H), 1.84-1.89 (m, 1H), 1.98-2.04 (m, 1H), 2.30-2.54 (m, 1H), 2.66-2.80 (m, 1H), 3.74 (s, 3H), 4.08-4.18 (m, 2H), 5.17 and 5.19 (s, 1H), 6.39-6.72 (m, 2H), 7.0-7.03 (m, 2H), 7.10-7.16 (m, 4H), 7.43 (bs, 1H), 7.75 (d, J=8.1 Hz, 1H).

Step 12: Preparation of 2-(tert-butoxy)-2-[2-(3,4-dihydro-2H-1-benzopyran-6-yl)-3-phenyl-6-(trifluoromethyl)phenyl]acetic acid (Example 1)

A lithium hydroxide aqueous solution (2N, 257 μL, 0.513 mmol) was added to a solution of methyl 2-(tert-butoxy)-2-[2-(3,4-dihydro-2H-1-benzopyran-6-yl)-3-phenyl-6-trifluoromethyl)phenyl]acetate (1k) (128 mg, 0.256 mmol) in a mixture of tetrahydrofurane (1.5 mL) and methanol (1.5 mL). The mixture was then heated at 60° C. for 4 hours. The mixture was cooled at room temperature, a lithium hydroxide aqueous solution (2N, 257 μL, 0.513 mmol) was added and the resulting solution was further stirred at 70° C. for 3 hours. A lithium hydroxide aqueous solution (2N, 257 μL, 513 μmol) was added and the solution was further stirred at 50° C. The organics were removed in vacuo then dioxane was added (1.5 mL). The resulting solution was heated at 100° C. under stirring for 6 hours, then placed at 4° C. for 3 days. The solution was then further heated at 100° C. under stirring for 6 hours. The solvents were removed and the residue partially dissolved in water (10 mL). The solution was washed with diethyl ether. The aqueous phase was acidified with HCl 1N until pH 2 and then extracted with ethyl acetate. The combined organic layers (diethyl ether and ethyl acetate) were dried over sodium sulfate and concentrated in vacuo. The residue was purified by preparative TLC (pentane/ethyl acetate/acetic acid 70/30/0.07) to provide 2-(tert-butoxy)-2-[2-(3,4-dihydro-2H-1-benzopyran-6-yl)-3-phenyl-6-(trifluoro methyl)phenyl]acetic acid (example 1) (85 mg, 0.175 mmol, 68%) as a white foam.

$^1$H NMR (300 MHz, CDCl$_3$) δ 0.97 (s, 9H), 1.80-2.05 (m, 2H), 2.20-2.60 and 2.75-2.85 (2 m, 2H), 4.12 and 4.17 (2 t, J=10.5 Hz, 2H), 5.33 and 5.38 (2 s, 1H), 6.30-6.50 and and 6.70-6.85 (2 m, 2H), 6.98-7.08 (m, 2H), 7.12-7.20 (m, 3H), 7.45-7.55 (m, 2H), 7.76 (d, J=8.1 Hz, 1H), 9.60 (bs, 1H).

MS m/z ([M−H]$^-$) 483.

Example 2

Synthesis of 2-(tert-butoxy)-2-[2-(3,4-dihydro-2H-1-benzopyran-6-yl)-3-(pyridin-4-yl)-6-(trifluoromethyl)phenyl]acetic acid

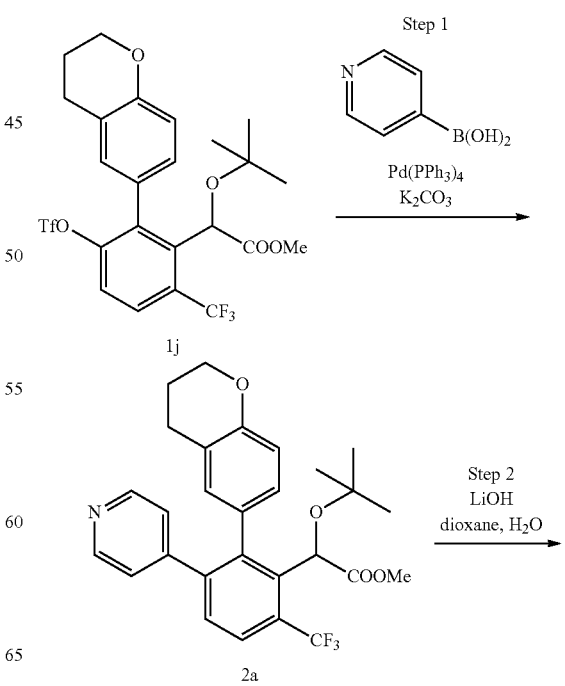

99

-continued

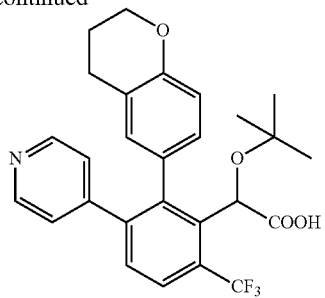

Example 2

Step 1: Preparation of Intermediate methyl 2-(tert-butoxy)-2-[2-(3,4-dihydro-2H-1-benzopyran-6-yl)-3-(pyridin-4-yl)-6-(trifluoromethyl)phenyl]acetate (2a)

Using the procedure described in example 1, step 11, the intermediate methyl 2-(tert-butoxy)-2-[2-(3,4-dihydro-2H-1-benzopyran-6-yl)-3-[(trifluoromethane)sulfonyloxy]-6-(trifluoromethyl)phenyl]acetate (1j) (95 mg, 0.166 mmol) is converted by reaction with pyridin-4-ylboronic acid (26 mg, 0.2 mmol) into methyl 2-(tert-butoxy)-2-[2-(3,4-dihydro-2H-1-benzopyran-6-yl)-3-(pyridin-4-yl)-6-(trifluoromethyl)phenyl]acetate (2a) (57 mg, 0.114 mmol, 69%) as a white solid, after purification by preparative TLC (cyclohexane/ethyl acetate 70/30).

$^1$H NMR (300 MHz, CDCl$_3$) δ 0.94 and 0.96 (s, 9H), 1.87-1.92 (m, 1H), 1.98-2.04 (m, 1H), 2.34-2.57 (m, 1H), 2.69-2.76 (m, 1H), 3.74 (s, 3H), 4.11-4.20 (m, 2H), 5.18 (bs, 1H), 6.37-6.74 (m, 2H), 6.96 (d, J=6.3 Hz, 2H), 7.09-7.16 (m, 1H), 7.41 and 7.42 (d, J=8.2 Hz, 1H), 7.80 (d, J=8.2 Hz, 1H), 8.40 (d, J=6.3 Hz, 2H).

Step 2: Preparation of 2-(tert-butoxy)-2-[2-(3,4-dihydro-2H-1-benzopyran-6-yl)-3-(pyridin-4-yl)-6-(trifluoromethyl)phenyl]acetic acid (Example 2)

To a solution of methyl 2-(tert-butoxy)-2-[2-(3,4-dihydro-2H-1-benzopyran-6-yl)-3-(pyridin-4-yl)-6-(trifluoromethyl)phenyl]acetate (2a) (57 mg, 0.114 mmol) in a mixture of dioxane (1 mL) and water (0.5 mL) was added lithium hydroxide (14 mg, 0.333 mmol). The reaction mixture was heated at 95° C. overnight. Dioxane (0.5 mL) and water (0.2 mL) were added and the mixture was stirred at 100° C. for 9 hours. Further lithium hydroxide (5 mg, 0.111 mmol) was added and the mixture was stirred at 100° C. for 3 hours. The reaction mixture was cooled to room temperature and concentrated in vacuo. Water (4 mL) was added to the residue and the solution was acidified with a 1 M hydrochloric acid solution until pH 5 followed by extraction with ethyl acetate (4×5 mL). The combined organic layers were dried over sodium sulfate and concentrated in vacuo. The residue was purified by preparative TLC (cyclohexane/ethyl acetate/acetic acid 20/80/0.1) to provide 2-(tert-butoxy)-2-[2-(3,4-dihydro-2H-1-benzopyran-6-yl)-3-(pyridin-4-yl)-6-(trifluoromethyl)phenyl]acetic acid (example 2) (43 mg, 0.088 mmol, 78%) as a beige solid.

$^1$H NMR (300 MHz, CDCl$_3$) δ 0.97 (s, 9H), 1.80-2.10 (m, 2H), 2.30-2.90 (m, 2H), 4.10-4.25 (m, 2H), 5.32 and 5.35 (s, 1H), 6.30-6.90 (m, 2H), 6.98 (d, J=5.7 Hz, 2H), 7.40-7.60 (m, 2H), 7.81 (d, J=8.1 Hz, 1H), 8.42 (d, J=5.7 Hz, 2H).
MS m/z ([M+H]$^+$) 486.
MS m/z ([M−H]$^−$) 484.

100

Example 3

Synthesis of 2-(tert-butoxy)-2-[3-(cyclopent-1-en-1-yl)-2-(3,4-dihydro-2H-1-benzopyran-6-yl)-6-(trifluoromethyl)phenyl]acetic acid

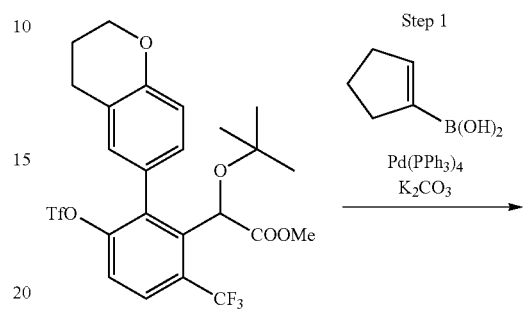

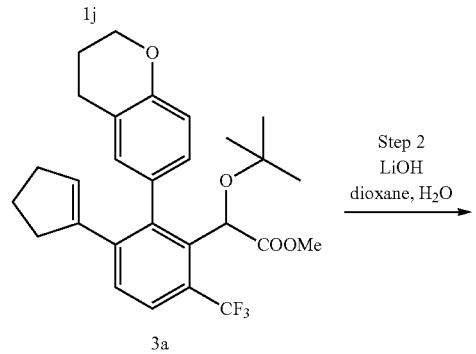

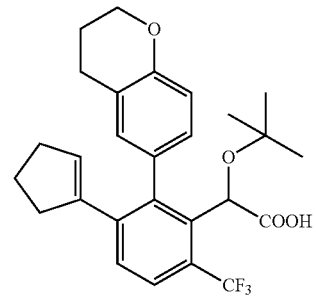

Example 3

Step 1: Preparation of Intermediate methyl 2-(tert-butoxy)-2-[3-(cyclopent-1-en-1-yl)-2-(3,4-dihydro-2H-1-benzopyran-6-yl)-6-(trifluoromethyl)phenyl]acetate (3a)

Using the procedure described in example 1, step 11, the intermediate methyl 2-(tert-butoxy)-2-[2-(3,4-dihydro-2H-1-benzopyran-6-yl)-3-[(trifluoromethane)sulfonyloxy]-6-(trifluoromethyl)phenyl]acetate (1j) (120 mg, 0.210 mmol) is converted by reaction with 1-cyclopentenyl boronic acid (28 mg, 0.252 mmol) into methyl 2-(tert-butoxy)-2-[3-(cyclopent-1-en-1-yl)-2-(3,4-dihydro-2H-1-benzopyran-6-yl)-6-(trifluoromethyl)phenyl]acetate (3a) (69 mg, 0.141 mmol, 67%) as a colourless oil, after purification by preparative TLC (cyclohexane/ethyl acetate 90/10).

$^1$H NMR (300 MHz, CDCl$_3$) δ 0.95 (s, 9H), 1.61-1.92 (m, 3H), 1.95-2.13 (m, 3H), 2.18-2.33 (m, 2H), 2.64-2.84 (m,

2H), 3.69 (s, 3H), 4.23 (t, J=5.2 Hz, 2H), 5.14 and 5.16 (s, 1H), 5.48-5.57 (m, 1H), 6.71-6.85 (m, 2H), 7.00-7.10 (m, 1H), 7.34 (d, J=8.2 Hz, 1H), 7.61 (d, J=8.2 Hz, 1H).

Step 2: Preparation of 2-(tert-butoxy)-2-[3-(cyclopent-1-en-1-yl)-2-(3,4-dihydro-2H-1-benzopyran-6-yl)-6-(trifluoromethyl)phenyl]acetic acid (Example 3)

Using the procedure described in example 2, step 2, the intermediate methyl 2-(tert-butoxy)-2-[3-(cyclopent-1-en-1-yl)-2-(3,4-dihydro-2H-1-benzopyran-6-yl)-6-(trifluoromethyl)phenyl]acetate (3a) (69 mg, 0.141 mmol) is converted into 2-(tert-butoxy)-2-[3-(cyclopent-1-en-1-yl)-2-(3,4-dihydro-2H-1-benzopyran-6-yl)-6-(trifluoromethyl)phenyl]acetic acid (example 3) (40 mg, 0.084 mmol, 59%) as a white solid.

$^1$H NMR (300 MHz, CDCl$_3$) δ 0.96 (s, 9H), 1.45-1.90 (m, 4H), 1.92-2.12 (m, 2H), 2.12-2.36 (m, 2H), 2.60-2.91 (m, 2H), 4.12-4.32 (t, J=4.6 Hz, 2H), 5.28 and 5.32 (s, 1H), 5.54 (s, 1H), 6.67-6.87 (m, 2H), 7.30-7.50 (m, 2H), 7.61 (d, J=8.2 Hz, 1H), 9.59 (bs, 1H).

MS m/z ([M−H]$^-$) 473.

Example 4

Synthesis of 2-(tert-butoxy)-2-[2-(3,4-dihydro-2H-1-benzopyran-6-yl)-3-(1-methyl-1H-pyrazol-4-yl)-6-(trifluoromethyl)phenyl]acetic acid

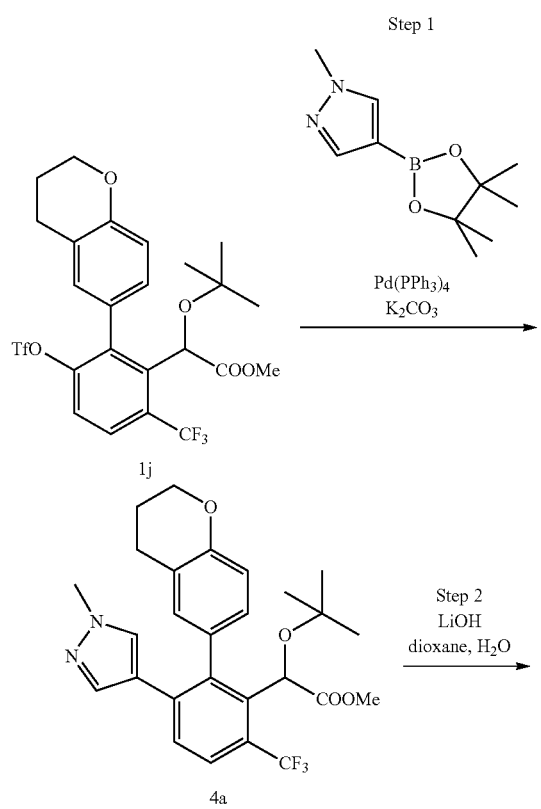

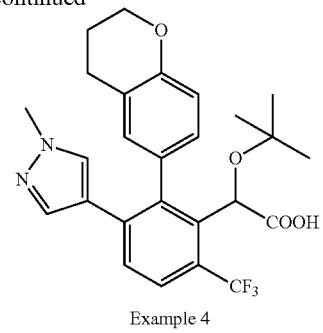

Example 4

Step 1: Preparation of Intermediate methyl 2-(tert-butoxy)-2-[2-(3,4-dihydro-2H-1-benzopyran-6-yl)-3-(1-methyl-1H-pyrazol-4-yl)-6-(trifluoromethyl)phenyl]acetate (4a)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (100 mg, 0.175 mmol) is converted by reaction with 1-methylpyrazole-4-boronic acid pinacol ester (43 mg, 0.210 mmol) into methyl 2-(tert-butoxy)-2-[2-(3,4-dihydro-2H-1-benzopyran-6-yl)-3-(1-methyl-1H-pyrazol-4-yl)-6-(trifluoromethyl)phenyl]acetate (4a) (44 mg, 0.087 mmol, 50%) as a yellow oil, after purification by preparative TLC (cyclohexane/ethyl acetate 25/75).

$^1$H NMR (300 MHz, CDCl$_3$) δ 0.97 (s, 9H), 2.04 (m, 2H), 2.67 (m, 2H), 2.76 (m, 2H), 3.68 (s, 3H), 3.74 (s, 3H), 5.14 (s, 1H), 6.62-6.85 (m, 3H), 7.04 (m, 1H), 7.09 (s, 1H), 7.54 (d, J=8.4 Hz, 1H), 7.69 (d, J=8.4 Hz, 1H).

MS m/z ([M+H]$^+$) 503.

Step 2: Preparation of 2-(tert-butoxy)-2-[2-(3,4-dihydro-2H-1-benzopyran-6-yl)-3-(1-methyl-1H-pyrazol-4-yl)-6-(trifluoromethyl)phenyl]acetic acid (Example 4)

Using the procedure described in example 2, step 2, the intermediate methyl 2-(tert-butoxy)-2-[2-(3,4-dihydro-2H-1-benzopyran-6-yl)-3-(1-methyl-1H-pyrazol-4-yl)-6-(trifluoromethyl)phenyl]acetate (4a) (44 mg, 0.087 mmol) is converted into 2-(tert-butoxy)-2-[2-(3,4-dihydro-2H-1-benzopyran-6-yl)-3-(1-methyl-1H-pyrazol-4-yl)-6-(trifluoromethyl)phenyl]acetic acid (example 4) (30 mg, 0.061 mmol, 70%) as a white solid.

$^1$H NMR (300 MHz, CDCl$_3$) δ 1.01 (s, 9H), 1.98-2.08 (m, 2H), 2.65-2.83 (m, 2H), 3.74 (s, 3H), 4.21 and 4.25 (t, J=6.0 Hz, 2H), 5.26 (s, 1H), 6.61-6.73 (m, 3H), 7.11 and 7.19 (s, 1H), 7.40 (m, 1H), 7.57 (d, J=8.4 Hz, 1H), 7.60 (d, J=8.4 Hz, 1H), 9.59 (bs, 1H).

MS m/z ([M+H]$^+$) 489.
MS m/z ([M−H]$^-$) 487.

Example 5

Synthesis of 2-(tert-butoxy)-2-[2-(3,4-dihydro-2H-1-benzopyran-6-yl)-3-(3-phenyl-1H-pyrazol-1-yl)-6-(trifluoromethyl)phenyl]acetic acid

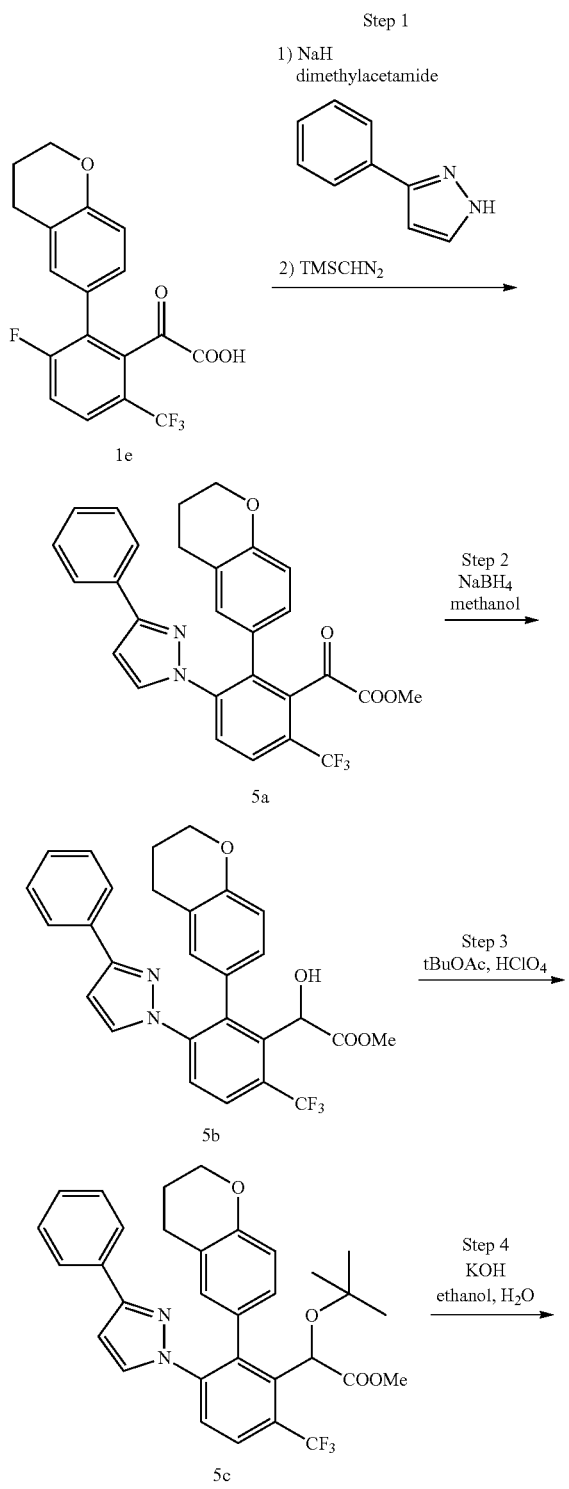

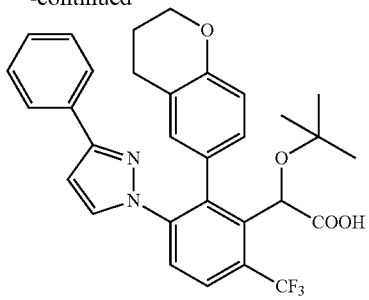

Example 5

Step 1: Preparation of Intermediate methyl 2-[2-(3,4-dihydro-2H-1-benzopyran-6-yl)-3-(3-phenyl-1H-pyrazol-1-yl)-6-(trifluoromethyl)phenyl]-2-oxoacetate (5a)

To a solution of 2-[2-(3,4-dihydro-2H-1-benzopyran-6-yl)-3-fluoro-6-(trifluoromethyl)phenyl]-2-oxoacetic acid (1e) (124 mg, 0.34 mmol) and 3-phenyl-1H-pyrazole (97 mg, 0.67 mmol) in anhydrous dimethylacetamide (2 mL) at room temperature under nitrogen atmosphere, was added sodium hydride 60% in oil (40 mg, 1.01 mmol). The reaction mixture was heated at 90° C. overnight then poured in water (10 mL). The mixture was acidified with 1 M hydrochloric acid until pH 2 and extracted with ethyl acetate (2×10 mL). The organic layer was washed with brine (10 mL), dried over sodium sulfate and concentrated in vacuo. The residue was dissolved in a mixture of methanol (2 mL) and cyclohexane (4 mL) and a 2 M solution of trimethylsilyldiazomethane in diethyl ether (0.5 mL, 1 mmol) was added. The mixture was stirred at 0° C. for 30 minutes and a few drops of acetic acid was added. The mixture was concentrated in vacuo. The residue was dissolved in ethyl acetate (10 mL) and washed with a saturated solution of sodium hydrogenocarbonate (10 mL). The organic layer was dried over sodium sulfate and concentrated in vacuo. The residue was purified by preparative TLC (cyclohexane/ethyl acetate 75/25) to provide methyl 2-[2-(3,4-dihydro-2H-1-benzopyran-6-yl)-3-(3-phenyl-1H-pyrazol-1-yl)-6-(trifluoromethyl)phenyl]-2-oxoacetate (5a) (42 mg, 0.082 mmol, 24%) as a white solid.

$^1$H NMR (300 MHz, CDCl$_3$) δ 1.94-2.02 (m, 2H), 2.62-2.77 (m, 2H), 3.55 (s, 3H), 4.17-4.21 (m, 2H), 6.49 (d, J=2.5 Hz, 1H), 6.70-6.78 (m, 3H), 6.98 (d, J=2.5 Hz, 1H), 7.34-7.44 (m, 3H), 7.81-7.87 (m, 3H), 8.08 (d, J=8.5 Hz, 1H). MS m/z ([M+H]$^+$) 507.

Step 2: Preparation of Intermediate methyl 2-[2-(3,4-dihydro-2H-1-benzopyran-6-yl)-3-(3-phenyl-1H-pyrazol-1-yl)-6-(trifluoromethyl)phenyl]-2-hydroxyacetate (5b)

To a solution of methyl 2-[2-(3,4-dihydro-2H-1-benzopyran-6-yl)-3-(3-phenyl-1H-pyrazol-1-yl)-6-(trifluoromethyl)phenyl]-2-oxoacetate (5a) (42 mg, 0.082 mmol) in anhydrous methanol (3 mL) at 0° C. was added sodium borohydride (6.1 mg, 0.153 mmol). The mixture was stirred at room temperature for 45 minutes before adding water (2 mL). Methanol was evaporated in vacuo. The resulting solution was extracted with ethyl acetate (2×5 mL). The organic layer was washed with brine (5 mL) and dried over sodium sulfate to provide methyl 2-[2-(3,4-dihydro-2H-1- benzopyran-6-yl)-3-(3-phenyl-1H-pyrazol-1-yl)-6-(trifluoromethyl)phenyl]-2-hydroxy acetate (5b) (42 mg, 0.082 mmol, 100%) as a white solid.

$^1$H NMR (300 MHz, CDCl$_3$) δ 1.90-2.07 (m, 2H), 2.50-2.67 (m, 1H), 2.69-2.84 (m, 1H), 3.23 (bs, 1H), 3.51 and 3.54 (s, 3H), 4.16-4.23 (m, 2H), 5.46 and 5.47 (s, 1H), 6.40-6.42 (m, 1H), 6.57-6.80 (m, 2H), 6.91-6.92 (m, 1H), 7.17-7.20 (m, 1H), 7.31-7.42 (m, 3H), 7.77-7.81 (m, 2H), 7.85-7.92 (m, 2H).

MS m/z ([M+H]$^+$) 509.

Step 3: Preparation of Intermediate methyl 2-(tert-butoxy)-2-[2-(3,4-dihydro-2H-1-benzopyran-6-yl)-3-(3-phenyl-1H-pyrazol-1-yl)-6-(trifluoromethyl)phenyl]acetate (5c)

Using the procedure described in example 1, step 8, the intermediate methyl 2-[2-(3,4-dihydro-2H-1-benzopyran-6-yl)-3-(3-phenyl-1H-pyrazol-1-yl)-6-(trifluoromethyl)phenyl]-2-hydroxy acetate (5b) (42 mg, 0.082 mmol) is converted into methyl 2-(tert-butoxy)-2-[2-(3,4-dihydro-2H-1-benzopyran-6-yl)-3-(3-phenyl-1H-pyrazol-1-yl)-6-(trifluoromethyl)phenyl]acetate (5c) (21 mg, 0.037 mmol, 44%) as a colorless oil, after purification by preparative TLC (cyclohexane/ethyl acetate 80/20).

$^1$H NMR (400 MHz, CDCl$_3$) δ 0.95 and 0.96 (s, 9H), 1.89-1.95 (m, 1H), 2.01-2.07 (m, 1H), 2.46-2.62 (m, 1H), 2.71-2.85 (m, 1H), 3.74 (s, 3H), 4.16-4.23 (m, 2H), 5.21 (s, 1H), 6.41 and 6.42 (d, J=2.5 Hz, 1H), 6.64-6.84 (m, 2H), 6.90 and 6.93 (d, J=2.5 Hz, 1H), 7.18-7.23 (m, 1H), 7.31-7.42 (m, 3H), 7.79-7.85 (m, 4H).

Step 4: Preparation of 2-(tert-butoxy)-2-[2-(3,4-dihydro-2H-1-benzopyran-6-yl)-3-(3-phenyl-1H-pyrazol-1-yl)-6-(trifluoromethyl)phenyl]acetic acid (Example 5)

A solution of 2-(tert-butoxy)-2-[2-(3,4-dihydro-2H-1-benzopyran-6-yl)-3-(3-phenyl-1H-pyrazol-1-yl)-6-(trifluoromethyl)phenyl]acetate (5c) (21 mg, 0.037 mmol) and potassium hydroxide (21 mg, 0.37 mmol) in a mixture of ethanol (3 mL) and water (1 mL) was stirred at 100° C. for 18 hours. Ethanol was evaporated in vacuo. The residue was diluted with water (2 mL) and washed with pentane (5 mL). The aqueous layer was acidified with 1M hydrochloric acid was added until pH 1 and extracted with diethyl ether (2×5 mL). The organic layer was dried over sodium sulfate and concentrated in vacuo. The residue was purified by preparative TLC (dichloromethane/methanol 95/5) to provide 2-(tert-butoxy)-2-[2-(3,4-dihydro-2H-1-benzopyran-6-yl)-3-(3-phenyl-1H-pyrazol-1-yl)-6-(trifluoromethyl)phenyl] acetic acid (example 5) (11 mg, 0.020 mmol, 55%) as a white solid.

$^1$H NMR (300 MHz, CDCl$_3$) δ 0.96 (s, 9H), 1.88-1.94 (m, 1H), 2.01-2.07 (m, 1H), 2.44-2.65 (m, 1H), 2.84-2.86 (m, 1H), 3.74 (s, 3H), 4.16-4.25 (m, 2H), 5.33 and 5.37 (s, 1H), 6.41 and 6.43 (d, J=2.5 Hz, 1H), 6.63-6.90 (m, 3H), 7.31-7.43 (m, 3H), 7.58 (bs, 1H), 7.80-7.93 (m, 4H).

MS m/z ([M+H]$^+$) 551.

Example 6

Synthesis of 2-{3-[2-(benzyloxy)pyridin-4-yl]-2-(3,4-dihydro-2H-1-benzopyran-6-yl)-6-(trifluoromethyl)phenyl}-2-(tert-butoxy)acetic acid

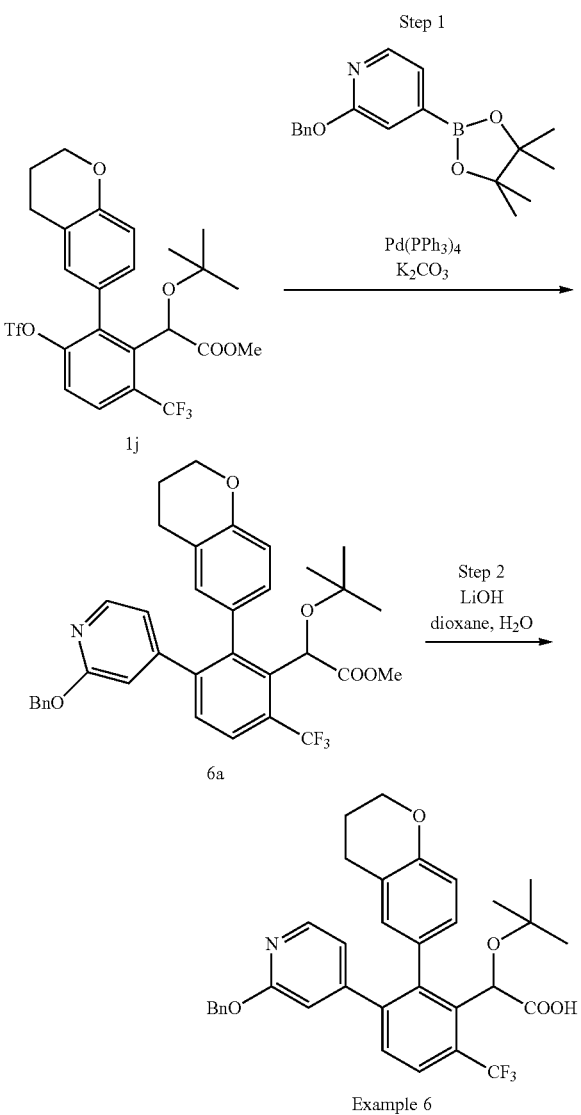

Step 1: preparation of intermediate methyl 2-{3-[2-(benzyloxy)pyridin-4-yl]-2-(3,4-dihydro-2H-1-benzopyran-6-yl)-6-(trifluoromethyl)phenyl}-2-(tert-butoxy)acetate (6a)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (120 mg, 0.210 mmol) is converted by reaction with 2-(benzyloxy)-4-(tetramethyl-1,3,2-dioxaborolan-2-yl)pyridine (78 mg, 0.252 mmol) into methyl 2-{3-[2-(benzyloxy)pyridin-4-yl]-2-(3,4-dihydro-2H-1-benzopyran-6-yl)-6-(trifluoromethyl)phenyl}-2-(tert-butoxy)acetate (6a) (74 mg, 0.122 mmol, 58%) as a light yellow oil after purification by preparative TLC (cyclohexane/ethyl acetate 85/15).

$^1$H NMR (300 MHz, CDCl$_3$) δ 0.95 (s, 9H), 1.82-2.02 (m, 2H), 2.34-2.83 (m, 2H), 3.73 (s, 3H), 4.05-4.26 (m, 2H), 5.19 (s, 1H), 5.24-5.41 (m, 2H), 6.40-6.84 (m, 4H), 7.05-7.18 (m, 1H), 7.29-7.52 (m, 6H), 7.76 (d, J=8.2 Hz, 1H), 7.91 (m, 1H)

Step 2: Preparation of 2-{3-[2-(benzyloxy)pyridin-4-yl]-2-(3,4-dihydro-2H-1-benzo pyran-6-yl)-6-(trifluoromethyl)phenyl}-2-(tert-butoxy)acetic acid (Example 6)

Using the procedure described in example 2, step 2, the methyl 2-{3-[2-(benzyloxy)pyridin-4-yl]-2-(3,4-dihydro-2H-1-benzopyran-6-yl)-6-(trifluoro methyl)phenyl}-2-(tert-butoxy)acetate (6a) (74 mg, 0.122 mmol) is converted into 2-{3-[2-(benzyloxy)pyridin-4-yl]-2-(3,4-dihydro-2H-1-benzopyran-6-yl)-6-(trifluoromethyl)phenyl}-2-(tert-butoxy)acetic acid (example 6) (68 mg, 0.115 mmol, 94%) as a white solid.

$^1$H NMR (300 MHz, CDCl$_3$) δ 0.95 (s, 9H), 1.75-2.09 (m, 2H), 2.22-2.93 (m, 2H), 3.93-4.28 (m, 2H), 5.21-5.46 (m, 3H), 6.35-6.89 (m, 4H), 7.29-7.57 (m, 7H), 7.77 (d, J=8.2 Hz, 1H), 7.86-7.99 (m, 1H), 9.64 (bs, 1H).

MS m/z ([M+H]$^+$) 592.

Example 7

Synthesis of 2-(tert-butoxy)-2-[2-(3,4-dihydro-2H-1-benzopyran-6-yl)-3-(thiophen-2-yl)-6-(trifluoromethyl)phenyl]acetic acid

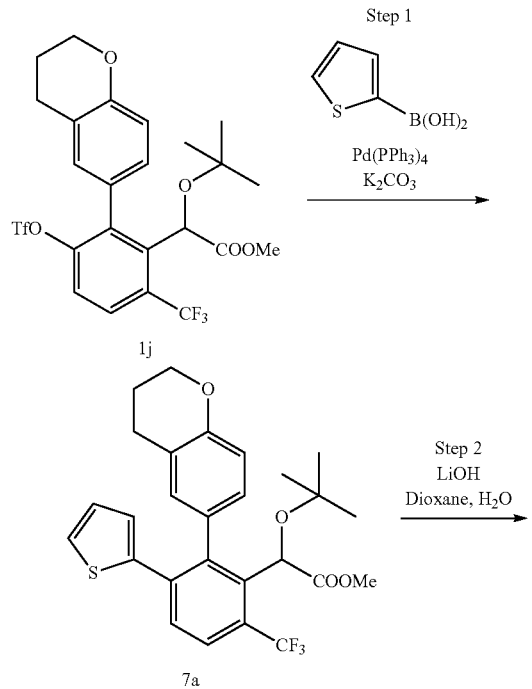

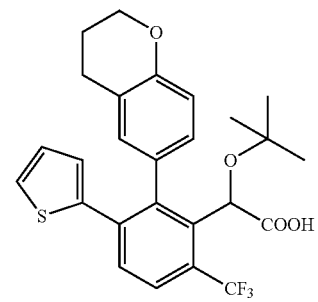

Example 7

Step 1: Preparation of Intermediate methyl 2-(tert-butoxy)-2-[2-(3,4-dihydro-2H-1-benzopyran-6-yl)-3-(thiophen-2-yl)-6-(trifluoromethyl)phenyl]acetate (7a)

Using the procedure described in example 1, step 11, the intermediate methyl 2-(tert-butoxy)-2-[2-(3,4-dihydro-2H-1-benzopyran-6-yl)-3-[(trifluoromethane)sulfonyloxy]-6-(trifluoromethyl)phenyl]acetate (1j) (120 mg, 0.210 mmol) is converted by reaction with (thiophen-2-yl)boronic acid (32 mg, 0.252 mmol) into methyl 2-(tert-butoxy)-2-[2-(3,4-dihydro-2H-1-benzopyran-6-yl)-3-(thiophen-2-yl)-6-(trifluoromethyl)phenyl]acetate (7a) (71 mg, 0.141 mmol, 67%) as a colourless oil after purification by preparative TLC (cyclohexane/ethyl acetate 85/15).

$^1$H NMR (300 MHz, CDCl$_3$) δ 0.99 (s, 9H), 1.90-2.11 (m, 2H), 2.53-2.83 (m, 2H), 3.70 and 3.71 (s, 3H), 4.16-4.28 (m, 2H), 5.16 (s, 1H), 6.64-6.70 (m, 4H), 7.07-7.13 (m, 1H), 7.13-7.23 (m, 1H), 7.58-7.76 (m, 2H).

Step 2: Preparation of 2-(tert-butoxy)-2-[2-(3,4-dihydro-2H-1-benzopyran-6-yl)-3-(thiophen-2-yl)-6-(trifluoromethyl)phenyl]acetic acid (Example 7)

Using the procedure described in example 2, step 2, the methyl 2-(tert-butoxy)-2-[2-(3,4-dihydro-2H-1-benzopyran-6-yl)-3-(thiophen-2-yl)-6-(trifluoromethyl)phenyl]acetate (7a) (65 mg, 0.128 mmol) is converted into 2-(tert-butoxy)-2-[2-(3,4-dihydro-2H-1-benzopyran-6-yl)-3-(thiophen-2-yl)-6-(trifluoromethyl)phenyl]acetic acid (example 7) (62 mg, 0.126 mmol, 98%) as a white solid.

$^1$H NMR (300 MHz, CDCl$_3$) δ 1.00 (s, 9H), 1.87-2.16 (m, 2H), 2.41-2.93 (m, 2H), 4.02-4.39 (m, 2H), 5.30 (bs, 1H), 6.61-6.78 (m, 4H), 6.79-6.93 (m, 1H), 7.37-7.53 (m, 1H), 7.62-7.78 (m, 2H), 9.57 (bs, 1H).

MS m/z ([M−H]$^−$) 489.

Example 8

Synthesis of 2-(tert-butoxy)-2-[2-(3,4-dihydro-2H-1-benzopyran-6-yl)-3-(4-methoxyphenyl)-6-(trifluoromethyl)phenyl]acetic acid

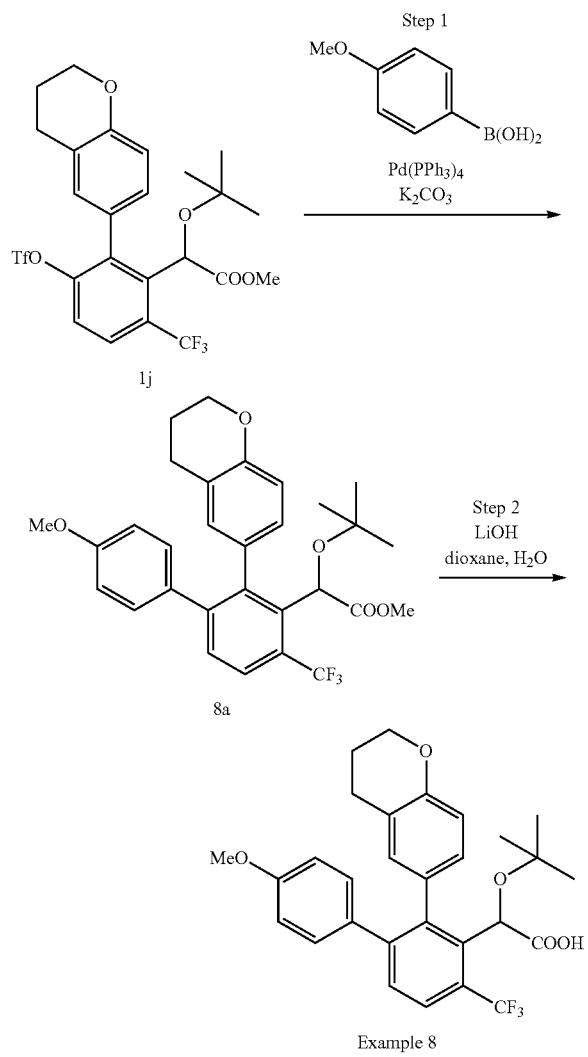

Step 1: Preparation of Intermediate methyl 2-(tert-butoxy)-2-[2-(3,4-dihydro-2H-1-benzopyran-6-yl)-3-(4-methoxyphenyl)-6-(trifluoromethyl)phenyl]acetate (8a)

Using the procedure described in example 1, step 11, the intermediate methyl 2-(tert-butoxy)-2-[2-(3,4-dihydro-2H-1-benzopyran-6-yl)-3-[(trifluoromethane)sulfonyloxy]-6-(trifluoromethyl)phenyl]acetate (1j) (100 mg, 0.175 mmol) is converted by reaction with (4-methoxyphenyl)boronic acid (32 mg, 0.210 mmol) into methyl 2-(tert-butoxy)-2-[2-(3,4-dihydro-2H-1-benzopyran-6-yl)-3-(4-methoxyphenyl)-6-(trifluoromethyl)phenyl]acetate (8a) (71 mg, 0.134 mmol, 76%) as a colourless oil, after purification by preparative TLC (cyclohexane/ethyl acetate 80/20).

$^1$H NMR (300 MHz, CDCl$_3$) δ 0.94 (s, 9H), 1.90-2.04 (m, 2H), 2.45-2.72 (m, 2H), 3.73 (s, 3H), 3.75 (s, 3H), 4.12-4.18 (m, 2H), 5.17 (bs, 1H), 6.42-6.68 (m, 4H), 6.94 (m, 2H), 7.10 (m, 1H), 7.25-7.50 (m, 1H), 7.71-7.74 (m, 1H).

MS m/z ([M+Na]$^+$) 551.

Step 2: Preparation of 2-(tert-butoxy)-2-[2-(3,4-dihydro-2H-1-benzopyran-6-yl)-3-(4-methoxyphenyl)-6-(trifluoromethyl)phenyl]acetic acid (Example 8)

Using the procedure described in example 2, step 2, the methyl 2-(tert-butoxy)-2-[2-(3,4-dihydro-2H-1-benzopyran-6-yl)-3-(4-methoxyphenyl)-6-(trifluoromethyl)phenyl]acetate (8a) (71 mg, 0.134 mmol) is converted into 2-(tert-butoxy)-2-[2-(3,4-dihydro-2H-1-benzopyran-6-yl)-3-(4-methoxyphenyl)-6-(trifluoromethyl)phenyl]acetic acid (example 8) (65 mg, 0.126 mmol, 94%) as a white solid.

$^1$H NMR (300 MHz, CDCl$_3$) δ 0.96 (s, 9H), 1.87-1.91 (m, 1H), 1.98-2.01 (m, 1H), 2.43-2.50 (m, 1H), 2.79-2.81 (m, 1H), 3.76 (s, 3H), 4.12-4.20 (m, 2H), 5.32 and 5.35 (s, 1H), 6.40-6.75 (m, 4H), 6.95 (d, J=8.7 Hz, 2H), 7.42-7.44 (m, 2H), 7.74 (d, J=8.1 Hz, 1H), 9.60 (bs, 1H).

MS m/z ([M+Na]$^+$) 537.

MS m/z ([M−H]$^−$) 513.

Example 9

Synthesis of 2-[3-(4-bromo-1H-pyrazol-1-yl)-2-(3,4-dihydro-2H-1-benzopyran-6-yl)-6-(trifluoromethyl)phenyl]-2-(tert-butoxy)acetic acid

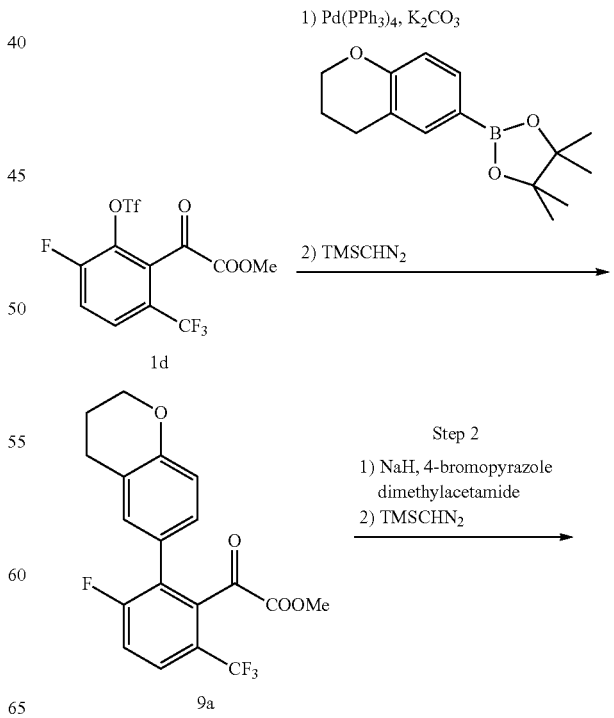

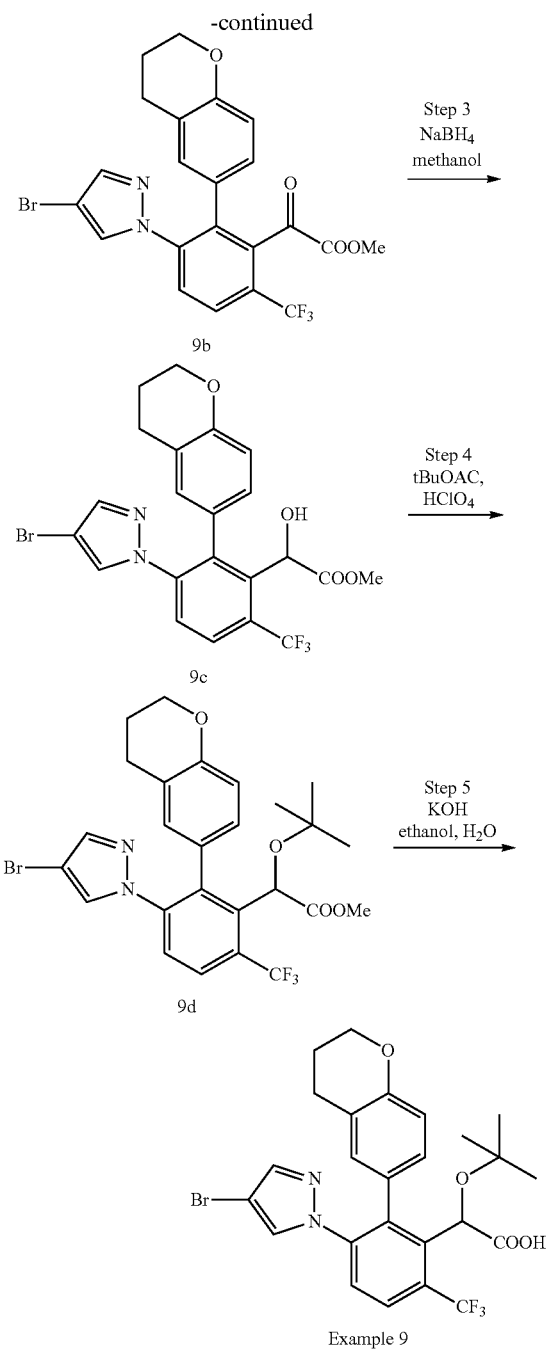

Example 9

Step 1: Preparation of Intermediate methyl 2-[2-(3,4-dihydro-2H-1-benzopyran-6-yl)-3-fluoro-6-(trifluoromethyl)phenyl]-2-oxoacetate (9a)

A degassed solution of ethyl 2-{3-fluoro-2-[(trifluoromethane)sulfonyloxy]-6-(trifluoromethyl)phenyl}-2-oxoacetate (1d) (478 mg, 1.16 mmol), potassium carbonate (641 mg, 4.64 mmol), 6-(4,4,5,5-tetramethyl-1,3,2-dioxaborolan-2-yl)chroman (392 mg, 1.51 mmol) and palladium tetrakis(triphenylphosphine) (134 mg, 0.12 mmol) in dioxane (10 mL) and water (2 mL) was heated at 85° C. overnight. Water (10 mL) was added and dioxane was evaporated in vacuo. Diethyl ether (10 mL) was added and the layers were separated. The organic layer was washed with a saturated solution of sodium hydrogenocarbonate (10 mL). The combined aqueous layers were acidified with 37% hydrochloric acid until pH 2 then extracted with diethyl ether (2×20 mL). The organic layer was dried over sodium sulfate and concentrated in vacuo. The residue was dissolved in cyclohexane (5 mL) and methanol (2.5 mL) at 0° C. and a 2M solution of trimethylsilyldiazomethane in diethyl ether (4 mL, 8 mmol) was added. The reaction mixture was stirred at room temperature for 15 minutes, cooled at 0° C. and acetic acid was added until the end of bubbling. The reaction mixture was concentrated in vacuo. The residue was dissolved in ethyl acetate (10 mL), washed with a saturated solution of sodium hydrogenocarbonate (10 mL), brine (10 mL), dried over sodium sulfate and concentrated in vacuo to provide methyl 2-[2-(3,4-dihydro-2H-1-benzopyran-6-yl)-3-fluoro-6-(trifluoromethyl)phenyl]-2-oxoacetate (9a) (343 mg, 0.90 mmol, 77%) as a yellow solid which was used without further purification.

$^1$H NMR (400 MHz, CDCl$_3$) δ 1.98-2.04 (m, 2H), 2.77 (t, J=6.4 Hz, 2H), 3.57 (s, 3H), 4.19-4.22 (m, 2H), 6.81 (d, J=8.4 Hz, 1H), 6.86 (d, J=1.0 Hz, 1H), 6.95 (dd, J=1.0 Hz, J=8.4 Hz, 1H), 7.35 (t, J=8.6 Hz, 1H), 7.73 (dd, J=4.8 Hz, J=8.6 Hz, 1H).

Step 2: Preparation of Intermediate methyl 2-[3-(4-bromo-1H-pyrazol-1-yl)-2-(3,4-dihydro-2H-1-benzopyran-6-yl)-6-(trifluoromethyl)phenyl]-2-oxoacetate (9b)

To a solution of methyl 2-[2-(3,4-dihydro-2H-1-benzopyran-6-yl)-3-fluoro-6-(trifluoromethyl)phenyl]-2-oxoacetate (9a) (300 mg, 0.78 mmol) and 4-bromo-1H-pyrazole (231 mg, 1.57 mmol) in anhydrous dimethylacetamide (3 mL), under nitrogen atmosphere, was added sodium hydride 60% in oil (94 mg, 2.35 mmol). The mixture was heated at 70° C. for 1 hour then at 100° C. for 4 hours. The mixture was then poured in water (10 mL) and 1 M hydrochloric acid was added until pH 2. The reaction mixture was extracted with ethyl acetate (2×10 mL). The organic layer was washed with brine (5 mL), dried over sodium sulfate and concentrated in vacuo. The residue was dissolved in a mixture of cyclohexane (6 mL) and methanol (3 mL) at 0° C. and a 2 M solution of trimethylsilyldiazomethane in diethyl ether (1 mL, 2.0 mmol) was added. The mixture was stirred at room temperature for 30 minutes before adding a few drops of acetic acid. The mixture was concentrated in vacuo. The residue was dissolved in ethyl acetate (10 mL), washed with a saturated solution of sodium hydrogenocarbonate (10 mL), brine (10 mL), dried over sodium sulfate and concentrated in vacuo The residue was purified by flash chromatography on silica gel (cyclohexane/ethyl acetate 85/15) to provide methyl 2-[3-(4-bromo-1H-pyrazol-1-yl)-2-(3,4-dihydro-2H-1-benzopyran-6-yl)-6-(trifluoromethyl)phenyl]-2-oxoacetate (9b) (200 mg, 0.39 mmol, 50%).

$^1$H NMR (400 MHz, CDCl$_3$) δ 1.96-2.03 (m, 2H), 2.67-2.71 (m, 2H), 3.55 (s, 3H), 4.19-4.22 (m, 2H), 6.67-6.74 (m, 3H), 6.98 (s, 1H), 7.59 (s, 1H), 7.84 (d, J=8.6 Hz, 1H), 7.90 (d, J=8.6 Hz, 1H).

MS m/z ([M+H]$^+$) 509/511.

Step 3: Preparation of Intermediate methyl 2-[3-(4-bromo-1H-pyrazol-1-yl)-2-(3,4-dihydro-2H-1-benzopyran-6-yl)-6-(trifluoromethyl)phenyl]-2-hydroxyacetate (9c)

Using the procedure described in example 5, step 2, the intermediate methyl 2-[3-(4-bromo-1H-pyrazol-1-yl)-2-(3, 4-dihydro-2H-1-benzopyran-6-yl)-6-(trifluoromethyl)phenyl]-2-oxoacetate (9b) (200 mg, 0.39 mmol) is converted into methyl 2-[2-(3,4-dihydro-2H-1-benzopyran-6-yl)-3-(4-bromo-1H-pyrazol-1-yl)-6-(trifluoromethyl)phenyl]-2-hydroxyacetate (9c) (196 mg, 0.38 mmol, 97%).

$^1$H NMR (300 MHz, CDCl$_3$) δ 1.94-2.07 (m, 2H), 2.60 (t, J=6.6 Hz, 1H), 2.76 (t, J=6.6 Hz, 1H), 3.52 and 3.55 (s, 3H), 4.18-4.24 (m, 2H), 5.44 and 5.45 (s, 1H), 6.47-6.55 (m, 1H), 6.66 and 6.80 (d, J=8.4 Hz, 1H), 6.87 and 6.90 (s, 1H), 7.09-7.16 (m, 1H), 7.49 and 7.50 (s, 1H), 7.71 and 7.73 (d, J=8.5 Hz, 1H), 7.85 (d, J=8.5 Hz, 1H).

MS m/z ([M+H]$^+$) 511/513.

Step 4: Preparation of Intermediate methyl 2-[3-(4-bromo-1H-pyrazol-1-yl)-2-(3,4-dihydro-2H-1-benzopyran-6-yl)-6-(trifluoromethyl)phenyl]-2-(tert-butoxy)acetate (9d)

To a solution of methyl 2-[3-(4-bromo-1H-pyrazol-1-yl)-2-(3,4-dihydro-2H-1-benzopyran-6-yl)-6-(trifluoromethyl)phenyl]-2-hydroxyacetate (9c) (196 mg, 0.38 mmol) in tert-butyl acetate (2 mL) at 0° C. was added perchloric acid (0.25 mL). The mixture was stirred at 0° C. for 2 hours and 30 minutes before being poured into a saturated aqueous solution of sodium hydrogenocarbonate (15 mL). The layers were separated and the aqueous layer was extracted with ethyl acetate (2×10 mL). The organic layers were washed with brine, dried over sodium sulfate and concentrated in vacuo. The residue was purified by preparative TLC (cyclohexane/ethyl acetate 80/20) to provide methyl 2-[3-(4-bromo-1H-pyrazol-1-yl)-2-(3,4-dihydro-2H-1-benzopyran-6-yl)-6-(trifluoromethyl)phenyl]-2-(tert-butoxy)acetate (9d) (115 mg, 0.20 mmol, 53%) as a colorless oil.

$^1$H NMR (400 MHz, CDCl$_3$) δ 0.94 and 0.95 (s, 9H), 1.94-2.07 (m, 2H), 2.50-2.65 (m, 1H), 2.67-2.84 (m, 1H), 3.73 and 3.74 (s, 3H), 4.19-4.24 (m, 2H), 5.17 and 5.20 (s, 1H), 6.49-6.94 (m, 3H), 7.10-7.18 (m, 1H), 7.50 and 7.52 (s, 1H), 7.64-7.69 (m, 1H), 7.82 and 7.83 (d, J=8.5 Hz, 1H).

MS m/z ([M+H]$^+$) 567/569.

Step 5: Preparation of 2-[3-(4-bromo-1H-pyrazol-1-yl)-2-(3,4-dihydro-2H-1-benzopyran-6-yl)-6-(trifluoromethyl)phenyl]-2-(tert-butoxy)acetic acid Example 9

Using the procedure described in example 5, step 4, methyl 2-[3-(4-bromo-1H-pyrazol-1-yl)-2-(3,4-dihydro-2H-1-benzopyran-6-yl)-6-(trifluoromethyl)phenyl]-2-(tert-butoxy)acetate (9d) (85 mg, 0.15 mmol) is converted into 2-[3-(4-bromo-1H-pyrazol-1-yl)-2-(3,4-dihydro-2H-1-benzopyran-6-yl)-6-(trifluoro methyl)phenyl]-2-(tert-butoxy) acetic acid (example 9) (63 mg, 0.11 mmol, 76%) as a white solid.

$^1$H NMR (400 MHz, CDCl$_3$) δ 0.96 (s, 9H), 1.95-2.07 (m, 2H), 2.56 (bs, 1H), 2.83 (bs, 1H), 4.19-4.25 (m, 2H), 5.30 and 5.37 (s, 1H), 6.47-6.93 (m, 3H), 7.50-7.57 (m, 2H), 7.71-7.76 (m, 1H), 7.84-7.87 (m, 1H).

MS m/z ([M+H]$^+$) 553/555.

Example 10

Synthesis of 2-[3-(4-chloro-1H-pyrazol-1-yl)-2-(3,4-dihydro-2H-1-benzopyran-6-yl)-6-(trifluoromethyl)phenyl]-2-(tert-butoxy)acetic acid

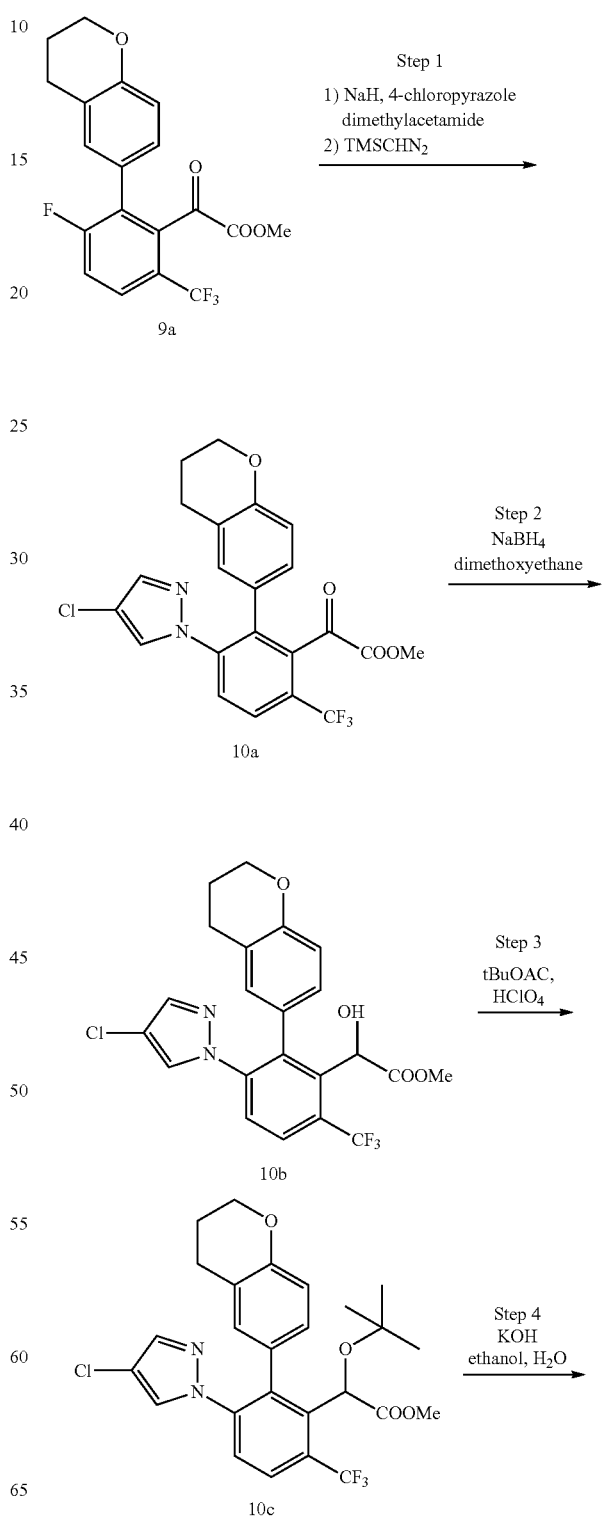

-continued

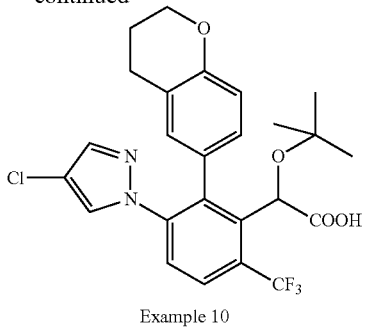

Example 10

Step 1: Preparation of Intermediate methyl 2-[3-(4-chloro-1H-pyrazol-1-yl)-2-(3,4-dihydro-2H-1-benzopyran-6-yl)-6-(trifluoromethyl)phenyl]-2-oxoacetate (10a)

To a solution of methyl 2-[2-(3,4-dihydro-2H-1-benzopyran-6-yl)-3-fluoro-6-(trifluoromethyl)phenyl]-2-oxoacetate (9a) (201 mg, 0.53 mmol) and 4-chloro-1H-pyrazole (108 mg, 1.05 mmol) in anhydrous dimethylacetamide (2 mL), under nitrogen atmosphere, was added sodium hydride 60% in oil (63 mg, 1.58 mmol). The mixture was heated at 100° C. for 90 minutes. The reaction mixture was cooled at room temperature and dimethyl sulfate (149 µL, 1.58 mmol) was added. The mixture was stirred at room temperature for 1 hour then poured in water (10 mL) and extracted with ethyl acetate (2×10 mL). The organic layer was washed with a 2 M sodium hydroxide solution (10 mL), brine (2×10 mL), dried over sodium sulfate and concentrated in vacuo The residue was purified by flash chromatography on silica gel (cyclohexane/ethyl acetate 85/15) to provide methyl 2-[3-(4-chloro-1H-pyrazol-1-yl)-2-(3,4-dihydro-2H-1-benzopyran-6-yl)-6-(trifluoromethyl)phenyl]-2-oxoacetate (10a) (130 mg, 0.28 mmol, 53%) as a white solid.

$^1$H NMR (400 MHz, CDCl$_3$) δ 1.97-2.04 (m, 2H), 2.68-2.72 (m, 2H), 3.55 (s, 3H), 4.19-4.22 (m, 2H), 6.67-6.74 (m, 3H), 6.96 (s, 1H), 7.56 (s, 1H), 7.84 (d, J=8.6 Hz, 1H), 7.91 (d, J=8.6 Hz, 1H).

MS m/z ([M+H]$^+$) 465/467.

Step 2: Preparation of Intermediate methyl 2-[3-(4-chloro-1H-pyrazol-1-yl)-2-(3,4-dihydro-2H-1-benzopyran-6-yl)-6-(trifluoromethyl)phenyl]-2-hydroxyacetate (10b)

To a solution of methyl 2-[3-(4-chloro-1H-pyrazol-1-yl)-2-(3,4-dihydro-2H-1-benzopyran-6-yl)-6-(trifluoromethyl)phenyl]-2-oxoacetate (10a) (130 mg, 0.28 mmol) in anhydrous dimethyl ethylene glycol (3 mL) at 0° C. was added sodium borohydride (21 mg, 0.56 mmol). The mixture was stirred at 0° C. for 45 minutes before adding water (2 mL). The resulting solution was extracted with ethyl acetate (2×10 mL). The organic layer was washed with brine (5 mL) and dried over sodium sulfate to provide methyl 2-[3-(4-chloro-1H-pyrazol-1-yl)-2-(3,4-dihydro-2H-1-benzopyran-6-yl)-6-(trifluoromethyl)phenyl]-2-hydroxyacetate (10b) (131 mg, 0.28 mmol, 100%) as a white solid.

$^1$H NMR (300 MHz, CDCl$_3$) δ 1.94-2.07 (m, 2H), 2.61 (t, J=6.6 Hz, 1H), 2.77 (t, J=6.6 Hz, 1H), 3.52 and 3.55 (s, 3H), 4.18-4.24 (m, 2H), 5.44 and 5.45 (s, 1H), 6.49-6.55 (m, 1H), 6.66 and 6.80 (d, J=8.4 Hz, 1H), 6.85 and 6.87 (s, 1H), 7.10-7.16 (m, 1H), 7.47 (s, 1H), 7.72 and 7.73 (d, J=8.4 Hz, 1H), 7.85 (d, J=8.4 Hz, 1H).

MS m/z ([M+H]$^+$) 467/469.

Step 3: Preparation of Intermediate methyl 2-[3-(4-chloro-1H-pyrazol-1-yl)-2-(3,4-dihydro-2H-1-benzopyran-6-yl)-6-(trifluoromethyl)phenyl]-2-(tert-butoxy)acetate (10c)

Using the procedure described in example 9, step 4, the intermediate methyl 2-[3-(4-chloro-1H-pyrazol-1-yl)-2-(3,4-dihydro-2H-1-benzopyran-6-yl)-6-(trifluoromethyl)phenyl]-2-hydroxyacetate (10b) (131 mg, 0.28 mmol) is converted, after purification by preparative TLC (cyclohexane/ethyl acetate 80/20) into methyl 2-[3-(4-chloro-1H-pyrazol-1-yl)-2-(3,4-dihydro-2H-1-benzopyran-6-yl)-6-(trifluoromethyl)phenyl]-2-(tert-butoxy)acetate (10c) (70 mg, 0.13 mmol, 47%) as a colorless oil.

$^1$H NMR (300 MHz, CDCl$_3$) δ 0.93 and 0.94 (s, 9H), 1.93-2.08 (m, 2H), 2.50-2.67 (m, 1H), 2.69-2.86 (m, 1H), 3.73 and 3.74 (s, 3H), 4.18-4.24 (m, 2H), 5.16 and 5.19 (s, 1H), 6.51-6.90 (m, 3H), 7.10-7.18 (m, 1H), 7.48 and 7.49 (s, 1H), 7.66-7.67 (d, J=8.5 Hz, 1H), 7.83 (d, J=8.5 Hz, 1H).

Step 4: Preparation of 2-[3-(4-chloro-1H-pyrazol-1-yl)-2-(3,4-dihydro-2H-1-benzopyran-6-yl)-6-(trifluoromethyl)phenyl]-2-(tert-butoxy)acetic acid (Example 10)

Using the procedure described in example 5, step 4, the intermediate methyl 2-[3-(4-chloro-1H-pyrazol-1-yl)-2-(3,4-dihydro-2H-1-benzopyran-6-yl)-6-(trifluoromethyl)phenyl]-2-(tert-butoxy)acetate (10c) (70 mg, 0.13 mmol) is converted, after purification by preparative TLC (dichloromethane/methanol 97/3) into 2-[3-(4-chloro-1H-pyrazol-1-yl)-2-(3,4-dihydro-2H-1-benzopyran-6-yl)-6-(trifluoromethyl)phenyl]-2-(tert-butoxy)acetic acid (example 10) (36 mg, 0.07 mmol, 53%) as a white solid.

$^1$H NMR (400 MHz, CDCl$_3$) δ 0.95 (s, 9H), 1.94-2.04 (m, 2H), 2.56 (bs, 1H), 2.82 (bs, 1H), 4.18-4.24 (m, 2H), 5.28 and 5.34 (s, 1H), 6.49-6.87 (m, 3H), 7.49-7.51 (m, 2H), 7.70-7.75 (m, 1H), 7.84 (d, J=8.4 Hz, 1H).

MS m/z ([M+H]$^+$) 509/511.

Example 11

Synthesis of 2-(tert-butoxy)-2-[2-(4,4-dimethylcyclohex-1-en-1-yl)-3-(pyridin-4-yl)-6-(trifluoromethyl)phenyl]acetic acid

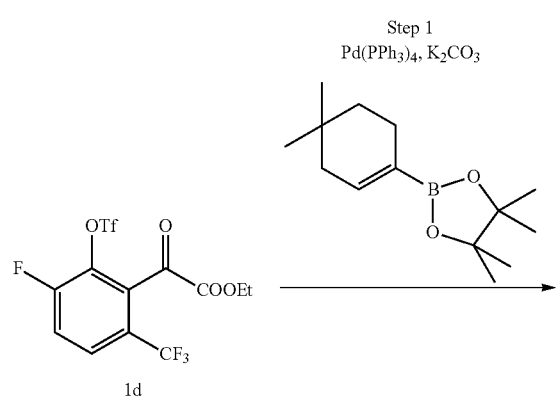

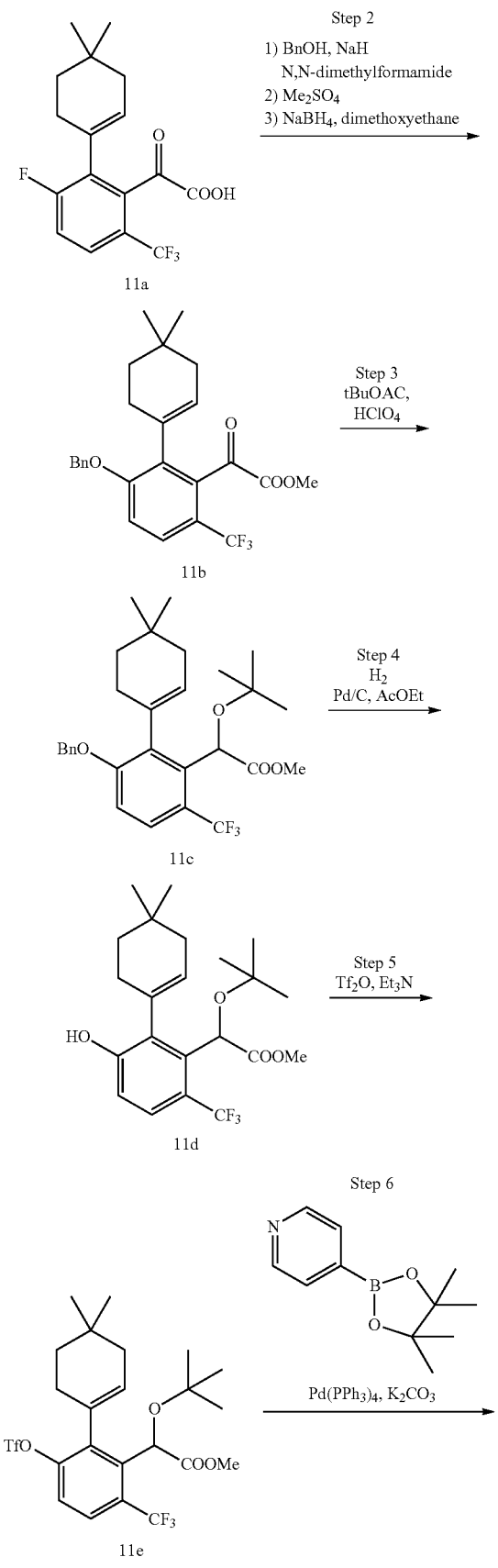
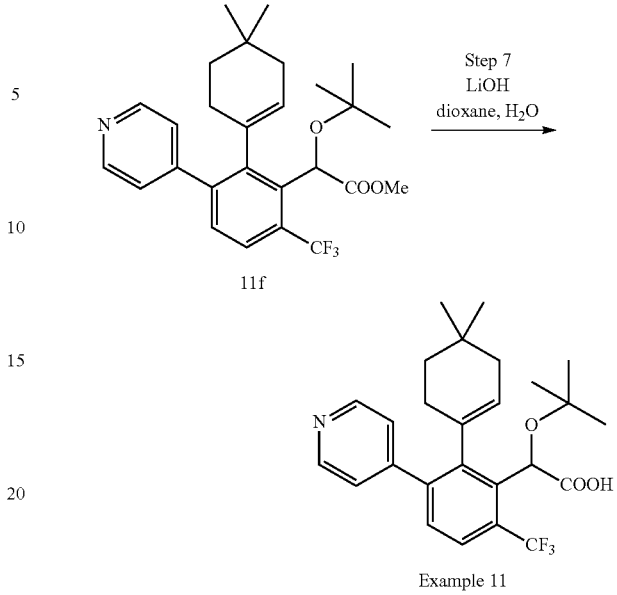

Example 11

Step 1: Preparation of Intermediate ethyl 2-[2-(4,4-dimethylcyclohex-1-en-1-yl)-3-fluoro-6-(trifluoromethyl)phenyl]-2-oxoacetate (11a)

A degassed solution of ethyl 2-{3-fluoro-2-[(trifluoromethane)sulfonyloxy]-6-(trifluoromethyl)phenyl}-2-oxoacetate (1d) (2.1 g, 5.09 mmol), potassium carbonate (2.11 g, 15.28 mmol), 2-(4,4-dimethyl-1-cyclohexen-1-yl)-4,4,5,5-tetramethyl-1,3,2-dioxaborolane (1.99 g, 7.64 mmol) and palladium tetrakis(triphenylphosphine) (589 mg, 0.51 mmol) in tetrahydrofurane (20 mL) and water (5 mL) was heated at 65° C. for 2 hours. The mixture was poured in water (30 mL) and extracted with ethyl acetate (2×20 mL). The organic layer was washed with a saturated solution of sodium hydrogenocarbonate (20 mL), brine (20 mL), dried over sodium sulfate and concentrated in vacuo. The residue was purified by flash chromatography on silica gel (cyclohexane/ethyl acetate 95/5) to provide ethyl 2-[2-(4,4-dimethylcyclohex-1-en-1-yl)-3-fluoro-6-(trifluoromethyl)phenyl]-2-oxoacetate (11a) (712 mg, 1.91 mmol, 37%) as a colorless oil.

$^1$H NMR (300 MHz, CDCl$_3$) δ 0.94 (s, 6H), 1.33-1.43 (m, 5H), 1.88-1.91 (m, 2H), 2.24-2.29 (m, 2H), 4.31 (q, J=7.2 Hz, 2H), 5.55-5.58 (m, 1H), 7.23 (t, J=8.7 Hz, 1H), 7.63 (dd, J=4.8 Hz, J=8.7 Hz, 1H).

Step 2: Preparation of Intermediate methyl 2-[3-(benzyloxy)-2-(4,4-dimethylcyclohex-1-en-1-yl)-6-(trifluoromethyl)phenyl]-2-hydroxyacetate (11 b)

To a solution of ethyl 2-[2-(4,4-dimethylcyclohex-1-en-1-yl)-3-fluoro-6-(trifluoromethyl)phenyl]-2-oxoacetate (11a) (712 mg, 1.91 mmol) and anhydrous benzyl alcohol (0.40 mL, 3.86 mmol) in anhydrous N,N-dimethylformamide (7 mL) at 0° C. under nitrogen atmosphere was portion wise added sodium hydride 60% in oil (229 mg, 5.74 mmol). The reaction mixture was stirred at 60° C. for 1 hour. The mixture was cooled to room temperature before adding dimethyl sulfate (0.54 mL, 5.74 mmol). The mixture was stirred at room temperature for 30 minutes and poured in water (40 mL). The resulting solution was extracted with ethyl acetate (2×20 mL). The organic layer was washed with a saturated solution of sodium hydrogenocarbonate (20 mL), brine (20 mL), dried over sodium sulfate and concentrated in vacuo. The residue was dissolved in anhydrous dimethoxyethane (7 mL) and sodium borohydride (145 mg, 3.82 mmol) was portion wise added at 0° C. The mixture was stirred at 0° C. for 1 hour. Water (10 mL). The layers were separated and the aqueous layer was extracted with ethyl acetate (2×10 mL). The unified organic layers were washed with brine (10 mL), dried over sodium sulfate and concentrated in vacuo. The residue was purified by flash chromatography on silica gel (cyclohexane/ethyl acetate 90/10) to provide intermediate methyl 2-[3-(benzyloxy)-2-(4,4-dimethylcyclohex-1-en-1-yl)-6-(trifluoromethyl)phenyl]-2-hydroxy acetate (11b) (566 mg, 1.26 mmol, 66%).

$^1$H NMR (400 MHz, CDCl$_3$) δ 0.77 and 0.81 (s, 3H), 0.95 and 0.96 (s, 3H), 1.38-1.45 (m, 2H), 1.76-1.99 (m, 2H), 2.16-2.45 (m, 2H), 3.71 and 3.75 (s, 3H), 5.03-5.71 (m, 4H), 6.94 (d, J=8.7 Hz, 1H), 7.33-7.37 (m, 5H), 7.58 and 7.59 (d, J=8.7 Hz, 1H).

Step 3: Preparation of Intermediate methyl 2-[3-(benzyloxy)-2-(4,4-dimethylcyclohex-1-en-1-yl)-6-(trifluoromethyl)phenyl]-2-(tert-butoxy)acetate (11c)

To a solution of methyl 2-[3-(benzyloxy)-2-(4,4-dimethylcyclohex-1-en-1-yl)-6-(trifluoromethyl)phenyl]-2-hydroxyacetate (11b) (377 mg, 0.84 mmol) in tert-butyl acetate (6 mL) at 0° C. was added 70% perchloric acid (0.75 mL). The reaction mixture was stirred at 0° C. for 1 hour then poured into a saturated solution of sodium hydrogenocarbonate (50 mL). The mixture was extracted with ethyl acetate (2×20 mL). The resulting organic layer was washed with brine, dried over sodium sulfate and concentrated in vacuo. The residue was purified by flash chromatography on silica gel (cyclohexane/ethyl acetate 95/5) to provide methyl 2-[3-(benzyloxy)-2-(4,4-dimethylcyclohex-1-en-1-yl)-6-(trifluoromethyl)phenyl]-2-(tert-butoxy)acetate (11c) (130 mg, 0.257 mmol, 30%) as a colorless oil.

$^1$H NMR (400 MHz, CDCl$_3$) δ 0.84 and 0.85 (s, 3H), 0.99 and 1.00 (s, 3H), 1.15 and 1.18 (s, 9H), 1.35-1.48 (m, 2H), 1.83-1.91 (m, 2H), 2.27-2.70 (m, 2H), 3.63 and 3.68 (s, 3H), 5.05-5.63 (m, 4H), 6.83-6.93 (m, 1H), 7.29-7.42 (m, 5H), 7.55 and 7.59 (d, J=8.8 Hz, 1H).

Step 4: Preparation of Intermediate methyl 2-(tert-butoxy)-2-[2-(4,4-dimethylcyclohex-1-en-1-yl)-3-hydroxy-6-(trifluoromethyl)phenyl]acetate (11d)

A solution of methyl 2-[3-(benzyloxy)-2-(4,4-dimethylcyclohex-1-en-1-yl)-6-(trifluoromethyl)phenyl]-2-(tert-butoxy)acetate (11c) (225 mg, 0.446 mmol) in ethyl acetate (5 mL) was stirred under hydrogen atmosphere for 48 hours. The reaction mixture was filtered over Millipore and the filtrate concentrated in vacuo. The residue was purified by flash chromatography on silica gel (cyclohexane/ethyl acetate 90/10) to provide methyl 2-(tert-butoxy)-2-[2-(4,4-dimethylcyclohex-1-en-1-yl)-3-hydroxy-6-(trifluoromethyl) phenyl]acetate (11d) (111 mg, 0.267 mmol, 60%) as a lightly yellow oil.

$^1$H NMR (400 MHz, CDCl$_3$) δ 1.02-1.06 (m, 6H), 1.16 and 1.19 (s, 9H), 1.42-1.60 (m, 2H), 1.96-2.59 (m, 4H), 3.63 and 3.67 (s, 3H), 5.35-5.76 (m, 2H), 6.95 (d, J=8.7 Hz, 1H), 7.22 (d, J=8.7 Hz, 1H).
MS m/z ([M−H]$^-$) 413.

Step 5: Preparation of Intermediate methyl 2-(tert-butoxy)-2-[2-(4,4-dimethylcyclohex-1-en-1-yl)-3-[(trifluoromethane)sulfonyloxy]-6-(trifluoromethyl)phenyl]acetate (11e)

To a solution of methyl 2-(tert-butoxy)-2-[2-(4,4-dimethylcyclohex-1-en-1-yl)-3-hydroxy-6-(trifluoromethyl)phenyl]acetate (11d) (111 mg, 0.267 mmol) in anhydrous dichloromethane (3 mL) under nitrogen atmosphere at −78° C. were successively added triethylamine (45 µL, 0.330 mmol) and triflic anhydride (50 µL, 0.297 mmol). The mixture was stirred at −78° C. for 1 hour before adding water (5 mL). The layers were separated. The aqueous layer was extracted with dichloromethane (10 mL). The combined organic layers were washed with a saturated solution of sodium hydrogenocarbonate (10 mL), dried over sodium sulfate and concentrated in vacuo to provide methyl 2-(tert-butoxy)-2-[2-(4,4-dimethylcyclohex-1-en-1-yl)-3-[(trifluoromethane)sulfonyloxy]-6-(trifluoromethyl)phenyl]acetate (11e) (137 mg, 0.250 mmol, 94%) as a colorless oil.

$^1$H NMR (400 MHz, CDCl$_3$) δ 1.01 and 1.04 (s, 6H), 1.15 and 1.18 (s, 9H), 1.48-1.53 (m, 2H), 1.59-2.47 (m, 4H), 3.65 and 3.69 (s, 3H), 5.29-5.77 (m, 2H), 7.33 (d, J=8.8 Hz, 1H), 7.69 and 7.72 (d, J=8.8 Hz, 1H).

Step 6: Preparation of Intermediate methyl 2-(tert-butoxy)-2-[2-(4,4-dimethylcyclohex-1-en-1-yl)-3-(pyridin-4-yl)-6-(trifluoromethyl)phenyl]acetate (11f)

A degassed solution of methyl 2-(tert-butoxy)-2-[2-(4,4-dimethylcyclohex-1-en-1-yl)-3-[(trifluoromethane)sulfonyloxy]-6-(trifluoromethyl)phenyl]acetate (11e) (67 mg, 0.122 mmol), potassium carbonate (51 mg, 0.369 mmol), 4-pyridine boronic acid pinacol ester (38 mg, 0.185 mmol) and palladium tetrakis(triphenylphosphine) (14 mg, 0.012 mmol) in dioxane (1 mL) and water (0.25 mL) was heated at 85° C. overnight. Water (5 mL) was added. The aqueous layer was extracted with ethyl acetate (2×5 mL). The combined organics were washed with brine (5 mL), dried over sodium sulfate and concentrated in vacuo. The residue was purified by preparative TLC (cyclohexane/ethyl acetate 60/40) to provide methyl 2-(tert-butoxy)-2-[2-(4,4-dimethylcyclohex-1-en-1-yl)-3-(pyridin-4-yl)-6-(trifluoromethyl) phenyl]acetate (11f) (40 mg, 0.084 mmol, 69%).

$^1$H NMR (400 MHz, CDCl$_3$) δ 0.57 and 0.64 (s, 3H), 0.91 (s, 3H), 1.13 and 1.17 (s, 9H), 1.22-1.32 (m, 2H), 1.48-2.27 (m, 4H), 3.67 and 3.72 (s, 3H), 5.29-5.83 (m, 2H), 7.20-7.30 (m, 3H), 7.65 and 7.69 (d, J=8.1 Hz, 1H), 8.57-8.61 (m, 2H).

Step 7: Preparation of 2-(tert-butoxy)-2-[2-(4,4-dimethylcyclohex-1-en-1-yl)-3-(pyridin-4-yl)-6-(trifluoromethyl)phenyl]acetic acid (Example 11)

Using the procedure described in example 2, step 2, the methyl 2-(tert-butoxy)-2-[2-(4,4-dimethylcyclohex-1-en-1-yl)-3-(pyridin-4-yl)-6-(trifluoro methyl)phenyl]acetate (11f) (40 mg, 0.084 mmol) is converted into 2-(tert-butoxy)-2-[2-(4,4-dimethylcyclohex-1-en-1-yl)-3-(pyridin-4-yl)-6-(trifluoromethyl)phenyl]acetic acid (example 11) (33 mg, 0.071 mmol, 84%) as a white solid.

$^1$H NMR (400 MHz, CDCl$_3$) δ 0.55 and 0.65 (s, 3H), 0.90 (s, 3H), 1.18 and 1.29 (m, 11H), 1.65-2.45 (m, 4H), 5.48-6.25 (m, 2H), 7.22-7.34 (m, 3H), 7.71 (d, J=8.1 Hz, 1H), 8.61-8.64 (m, 2H).
MS m/z ([M+H]$^+$) 462
MS m/z ([M−H]$^-$) 460. .

Example 12

Synthesis of 2-(tert-butoxy)-2-[2-(3,4-dihydro-2H-1-benzopyran-6-yl)-3-{pyrazolo[1,5-a]pyridin-3-yl}-6-(trifluoromethyl)phenyl]acetic acid

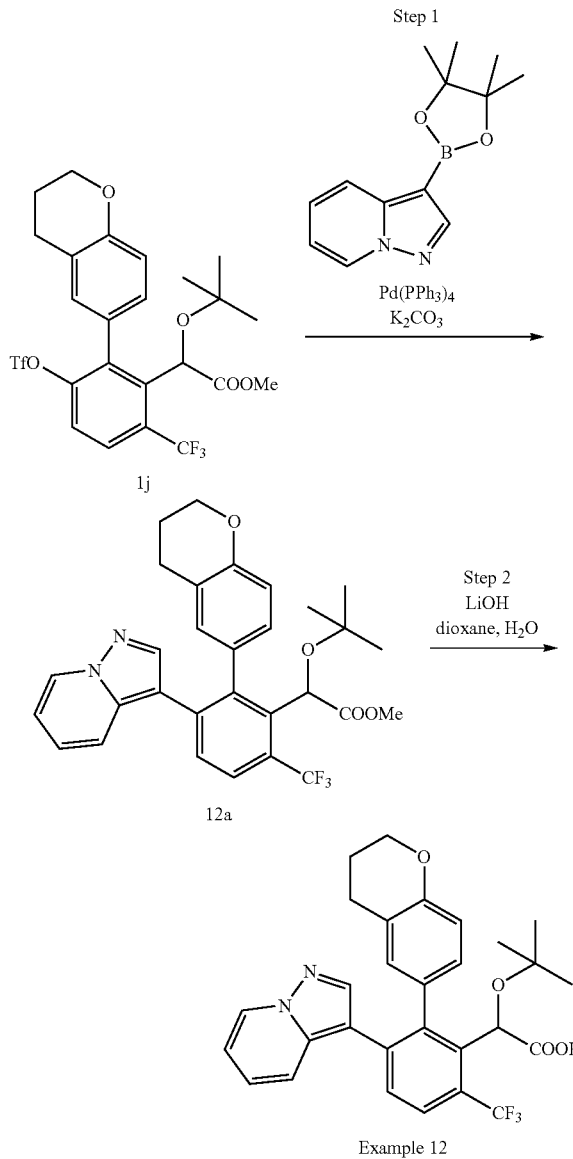

Example 12

Step 1: Preparation of Intermediate methyl 2-(tert-butoxy)-2-[2-(3,4-dihydro-2H-1-benzopyran-6-yl)-3-{pyrazolo[1,5-a]pyridin-3-yl}-6-(trifluoromethyl)phenyl]acetate (12a)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (100 mg, 0.175 mmol) is converted by reaction with 3-(tetramethyl-1,3,2-dioxaborolan-2-yl)pyrazolo[1,5-a]pyridine (64 mg, 0.263 mmol, prepared using the procedure described in Tetrahedron, 2012, 68, 5434-5444), after purification by preparative TLC (cyclohexane/ethyl acetate 50/50), into methyl 2-(tert-butoxy)-2-[2-(3,4-dihydro-2H-1-benzopyran-6-yl)-3-{pyrazolo[1,5-a]pyridin-3-yl}-6-(trifluoro methyl)phenyl]acetate (12a) (83 mg, 0.154 mmol, 88%).

$^1$H NMR (400 MHz, CDCl$_3$) δ 0.99 (s, 9H), 1.87-1.95 (m, 1H), 1.97-2.07 (m, 1H), 2.42-2.60 (m, 1H), 2.66-2.83 (m, 1H), 3.72 and 3.73 (s, 3H), 4.10-4.24 (m, 2H), 5.18 and 5.19 (s, 1H), 6.52-6.76 (m, 3H), 7.08-7.14 (m, 2H), 7.18 and 7.25 (s, 1H), 7.56-7.59 (m, 2H), 7.76 (d, J=8.3 Hz, 1H), 8.36 (d, J=6.9 Hz, 1H).

MS m/z ([M+H]$^+$) 539.

Step 2: Preparation of 2-(tert-butoxy)-2-[2-(3,4-dihydro-2H-1-benzopyran-6-yl)-3-{pyrazolo[1,5-a]pyridin-3-yl}-6-(trifluoromethyl)phenyl]acetic acid (Example 12)

Using the procedure described in example 2, step 2, methyl 2-(tert-butoxy)-2-[2-(3,4-dihydro-2H-1-benzopyran-6-yl)-3-{pyrazolo[1,5-a]pyridin-3-yl}-6-(trifluoromethyl)phenyl]acetate (12a) (83 mg, 0.154 mmol) is converted into 2-(tert-butoxy)-2-[2-(3,4-dihydro-2H-1-benzopyran-6-yl)-3-{pyrazolo[1,5-a]pyridine-3-yl}-6-(trifluoromethyl)phenyl]acetic acid (example 12) (65 mg, 0.124 mmol, 81%).

$^1$H NMR (300 MHz, CDCl$_3$) δ 1.00 (bs, 9H), 1.83-1.95 (m, 1H), 1.95-2.07 (m, 1H), 2.38-2.61 (m, 1H), 2.72-2.87 (m, 1H), 4.06-4.25 (m, 2H), 5.34 and 5.35 (s, 1H), 6.49-6.79 (m, 3H), 7.06-7.10 (m, 1H), 7.21-7.33 (m, 1H), 7.45-7.58 (m, 2H), 7.62 (d, J=8.2 Hz, 1H), 7.78 (d, J=8.2 Hz, 1H), 8.35 and 8.36 (d, J=7.0 Hz, 1H).

MS m/z ([M+H]$^+$) 525.

Example 13

Synthesis of 2-(tert-butoxy)-2-[3-(4-carbamoylphenyl)-2-(34-dihydro-2H-1-benzopyran-6-yl)-6-(trifluoromethyl)phenyl]acetic acid

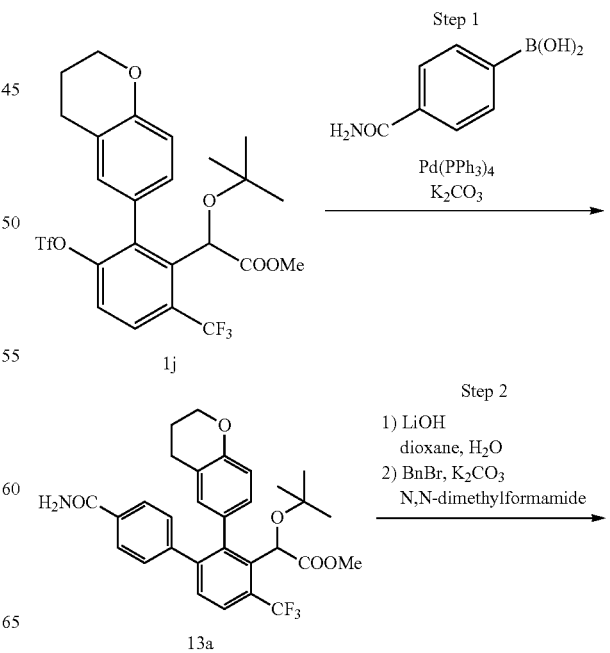

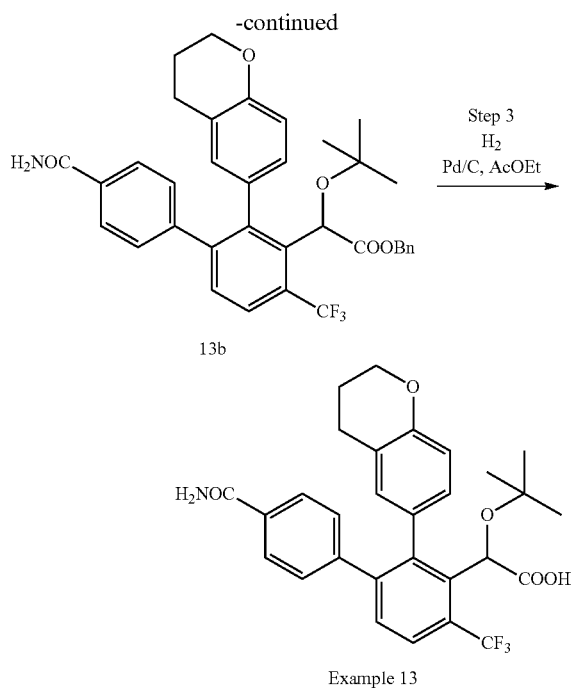

13b

Example 13

Step 1: Preparation of Intermediate methyl 2-(tert-butoxy)-2-[3-(4-carbamoylphenyl)-2-(3,4-dihydro-2H-1-benzopyran-6-yl)-6-(trifluoromethyl)phenyl]acetate (13a)

Using the procedure described in example 1, step 11, the intermediate methyl 2-(tert-butoxy)-2-[2-(3,4-dihydro-2H-1-benzopyran-6-yl)-3-[(trifluoromethane)sulfonyloxy]-6-(trifluoromethyl)phenyl]acetate (1j) (75 mg, 0.131 mmol) is converted by reaction with (4-carbamoylphenyl)boronic acid (32.5 mg, 0.197 mmol), after purification by preparative TLC (cyclohexane/ethyl acetate 50/50) into methyl 2-(tert-butoxy)-2-[3-(4-carbamoylphenyl)-2-(3,4-dihydro-2H-1-benzopyran-6-yl)-6-(trifluoromethyl)phenyl]acetate (13a) (58.8 mg, 0.108 mmol, 82%).

$^1$H NMR (400 MHz, CDCl$_3$) δ 0.95 (s, 9H), 1.81-1.96 (m, 1H), 1.95-2.07 (m, 1H), 2.30-2.59 (m, 1H), 2.59-2.83 (m, 1H), 3.73 (s, 3H), 4.07-4.22 (m, 2H), 5.17 (s, 1H), 5.66 (bs, 1H), 6.02 (bs, 1H), 6.35-6.75 (m, 2H), 7.07-7.18 (m, 3H), 7.42 (d, J=8.1 Hz, 1H), 7.62 (d, J=7.9 Hz, 2H), 7.77 (d, J=8.1 Hz, 1H).

MS m/z ([M+H]$^+$) 542.

Step 2: Preparation of Intermediate benzyl 2-(tert-butoxy)-2-[3-(4-carbamoylphenyl)-2-(3,4-dihydro-2H-1-benzopyran-6-yl)-6-(trifluoromethyl)phenyl]acetate (13b)

To a solution of methyl 2-(tert-butoxy)-2-[3-(4-carbamoylphenyl)-2-(3,4-dihydro-2H-1-benzopyran-6-yl)-6-(trifluoromethyl)phenyl]acetate (13a) (58.8 mg, 0.108 mmol) in a mixture of dioxane (1.8 mL) and water (0.9 mL) was added lithium hydroxide (29.5 mg, 0.869 mmol). The mixture was heated at 90° C. overnight. The reaction mixture was cooled to room temperature and concentrated in vacuo. Water (2 mL) was added to the residue and the aqueous layer was washed with diethyl ether (2 mL), acidified with 1M hydrochloric acid until pH 3 and extracted with diethyl ether (2×3 mL). The organic layer was dried over sodium sulfate and concentrated in vacuo. The residue was dissolved in anhydrous N,N-dimethylformamide (2 mL). Benzyl bromide (39 μL, 0.326 mmol) and potassium carbonate (45 mg, 0.326 mmol) were added, and the reaction mixture was stirred at room temperature for 5 hours. Water (3 mL) was added and the mixture was extracted with ethyl acetate (2×5 mL). The organic layer was washed with brine (5 mL), dried over sodium sulfate and concentrated in vacuo. The residue was purified by preparative TLC (dichloromethane/methanol: 97/3) to provide benzyl 2-(tert-butoxy)-2-[3-(4-carbamoylphenyl)-2-(3,4-dihydro-2H-1-benzopyran-6-yl)-6-(trifluoromethyl)phenyl]acetate (13b) (27.8 mg, 0.045 mmol, 41%).

$^1$H NMR (300 MHz, CDCl$_3$) δ 0.94 (s, 9H), 1.80-1.96 (m, 2H), 2.26-2.42 (m, 1H), 2.42-2.59 (m, 1H), 4.05-4.18 (m, 2H), 5.09-5.27 (m, 3H), 5.70 (bs, 1H), 6.03 (bs, 1H), 6.34-6.58 (m, 2H), 6.94-7.01 (m, 1H), 7.06-7.14 (m, 2H), 7.25-7.38 (m, 5H), 7.41 (d, J=8.2 Hz, 1H), 7.60 (dd, J=8.4 Hz, J=2.3 Hz, 2H), 7.78 (d, J=8.2 Hz, 1H).

Step 3: Preparation of 2-(tert-butoxy)-2-[3-(4-carbamoylphenyl)-2-(3,4-dihydro-2H-1-benzopyran-6-yl)-6-(trifluoromethyl)phenyl]acetic acid (Example 13)

A mixture of benzyl 2-(tert-butoxy)-2-[3-(4-carbamoylphenyl)-2-(3,4-dihydro-2H-1-benzopyran-6-yl)-6-(trifluoromethyl)phenyl]acetate (13b) (27.8 mg, 0.045 mmol) and palladium on carbon (7 mg) in ethyl acetate (3 mL) was stirred under hydrogen atmosphere for 3 hours. The mixture was filtered over Millipore and the filtrate concentrated in vacuo to provide 2-(tert-butoxy)-2-[3-(4-carbamoylphenyl)-2-(3,4-dihydro-2H-1-benzopyran-6-yl)-6-(trifluoromethyl)phenyl]acetic acid (example 13) (20 mg, 0.038 mmol, 84%).

$^1$H NMR (400 MHz, CDCl$_3$) δ 0.97 (s, 9H), 1.79-1.92 (m, 1H), 1.94-2.06 (m, 1H), 2.28-2.57 (m, 1H), 2.68-2.85 (m, 1H), 4.06-4.24 (m, 2H), 5.31 and 5.34 (s, 1H), 6.00 (bs, 2H), 6.31-6.83 (m, 2H), 7.12 and 7.13 (d, J=8.4 Hz, 2H), 7.41-7.50 (m, 2H), 7.62 and 7.63 (d, J=8.4 Hz, 2H), 7.78 (d, J=8.2 Hz, 1H).

MS m/z ([M+H]$^+$) 528.

Example 14

Synthesis of 2-(tert-butoxy)-2-[3-(3-carbamoylphenyl)-2-(3,4-dihydro-2H-1-benzopyran-6-yl)-6-(trifluoromethyl)phenyl]acetic acid

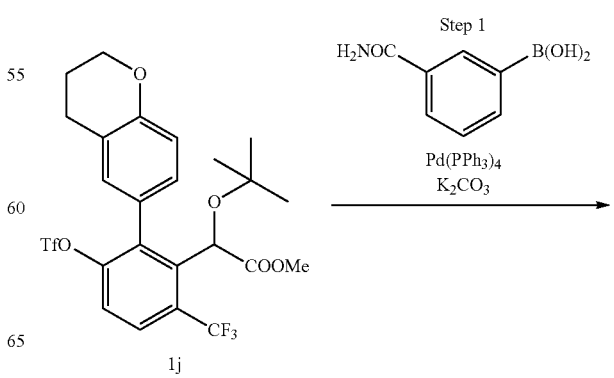

1j

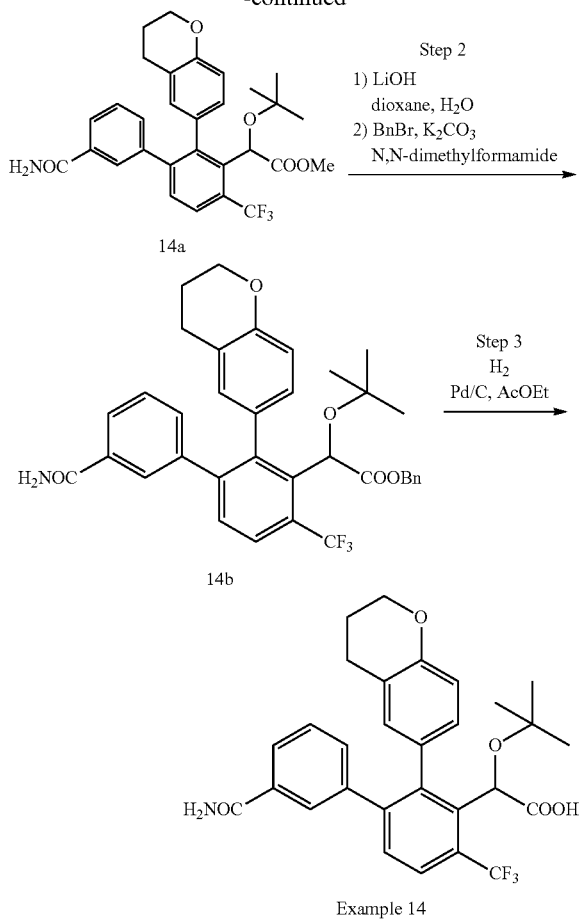

Example 14

Step 1: Preparation of Intermediate methyl 2-(tert-butoxy)-2-[3-(3-carbamoylphenyl)-2-(3,4-dihydro-2H-1-benzopyran-6-yl)-6-(trifluoromethyl)phenyl]acetate (14a)

Using the procedure described in example 1, step 11, the intermediate methyl 2-(tert-butoxy)-2-[2-(3,4-dihydro-2H-1-benzopyran-6-yl)-3-[(trifluoromethane)sulfonyloxy]-6-(trifluoromethyl)phenyl]acetate (1j) (79 mg, 0.138 mmol) is converted by reaction with (3-carbamoylphenyl)boronic acid (34 mg, 0.206 mmol), after purification by preparative TLC (cyclohexane/ethyl acetate 20/80) into methyl 2-(tert-butoxy)-2-[3-(3-carbamoylphenyl)-2-(3,4-dihydro-2H-1-benzopyran-6-yl)-6-(trifluoromethyl)phenyl]acetate (14a) (54 mg, 0.099 mmol, 72%).

$^1$H NMR (400 MHz, CDCl$_3$) δ 0.95 and 0.96 (s, 9H), 1.83-2.04 (m, 2H), 2.30-2.55 (m, 1H), 2.66-2.79 (m, 1H), 3.74 (s, 3H), 4.09-4.18 (m, 2H), 5.19 and 5.20 (s, 1H), 5.75 (bs, 2H), 6.39-6.75 (m, 2H), 7.13-7.30 (m, 3H), 7.39-7.49 (m, 2H), 7.59 and 7.64 (dt, J=7.4 Hz, J=1.6 Hz, 1H), 7.77 and 7.78 (d, J=8.2 Hz, 1H).

Step 2: Preparation of Intermediate benzyl 2-(tert-butoxy)-2-[3-(3-carbamoylphenyl)-2-(3,4-dihydro-2H-1-benzopyran-6-yl)-6-(trifluoromethyl)phenyl]acetate (14b)

Using the procedure described in example 13, step 2, the intermediate methyl 2-(tert-butoxy)-2-[3-(3-carbamoylphenyl)-2-(3,4-dihydro-2H-1-benzopyran-6-yl)-6-(trifluoromethyl)phenyl]acetate (14a) (54 mg, 0.099 mmol) is converted, after purification by preparative TLC (cyclohexane/ethyl acetate 40/60) into benzyl 2-(tert-butoxy)-2-[3-(3-carbamoylphenyl)-2-(3,4-dihydro-2H-1-benzo pyran-6-yl)-6-(trifluoromethyl)phenyl]acetate (14b) (20 mg, 0.032 mmol, 32%).

$^1$H NMR (300 MHz, CDCl$_3$) δ 0.94 and 0.95 (s, 9H), 1.80-1.92 (m, 2H), 2.27-2.39 (m, 1H), 2.45-2.55 (m, 1H), 4.06-4.12 (m, 2H), 5.13-5.23 (m, 3H), 5.75 (bs, 2H), 6.37-6.57 (m, 2H), 7.00-7.04 (m, 1H), 7.16-7.25 (m, 2H), 7.28-7.48 (m, 7H), 7.58 and 7.63 (dt, J=7.7 Hz, J=1.5 Hz, 1H), 7.78 (d, J=8.2 Hz, 1H).

Step 3: Preparation of 2-(tert-butoxy)-2-[3-(3-carbamoylphenyl)-2-(3,4-dihydro-2H-1-benzopyran-6-yl)-6-(trifluoromethyl)phenyl]acetic acid (Example 14)

Using the procedure described in example 13, step 3, the intermediate benzyl 2-(tert-butoxy)-2-[3-(3-carbamoylphenyl)-2-(3,4-dihydro-2H-1-benzopyran-6-yl)-6-(trifluoromethyl)phenyl]acetate (14b) (20 mg, 0.032 mmol) is converted into 2-(tert-butoxy)-2-[3-(3-carbamoylphenyl)-2-(3,4-dihydro-2H-1-benzopyran-6-yl)-6-(trifluoromethyl)phenyl]acetic acid (example 14) (13 mg, 0.024 mmol, 77%).

$^1$H NMR (400 MHz, CDCl$_3$) δ 0.97 (s, 9H), 1.81-1.91 (m, 1H), 1.93-2.04 (m, 1H), 2.22-2.53 (m, 1H), 2.78 (bs, 1H), 4.10-4.18 (m, 2H), 5.33 and 5.36 (s, 1H), 5.90 and 5.96 (bs, 2H), 6.38-6.80 (m, 2H), 7.18-7.30 (m, 2H), 7.42-7.65 (m, 4H), 7.78 and 7.79 (d, J=8.2 Hz, 1H).

MS m/z ([M+H]$^+$) 528.

Example 15

Synthesis of 2-(tert-butoxy)-2-[2-(4,4-dimethylcyclohex-1-en-1-yl)-3-(1-methyl-1H-pyrazol-4-yl)-6-(trifluoromethyl)phenyl]acetic acid -continued

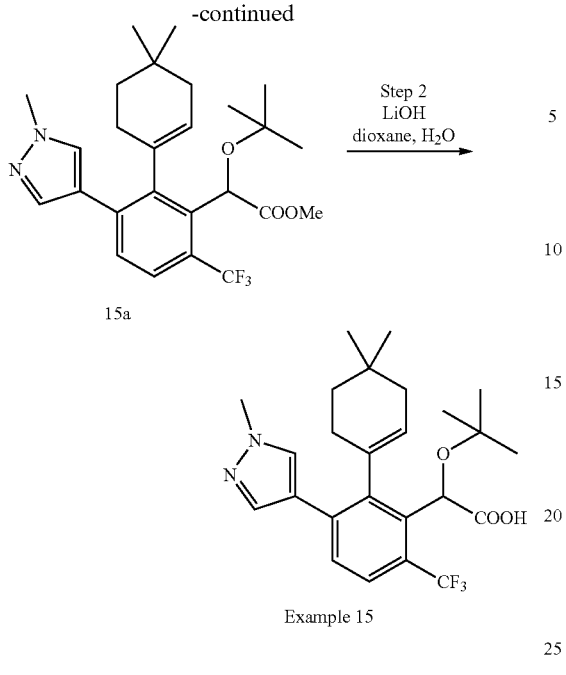

Example 16

Synthesis of 2-(tert-butoxy)-2-[2-(3,4-dihydro-2H-1-benzopyran-6-yl)-3-(pyrimidin-4-yl)-6-(trifluoromethyl)phenyl]acetic acid

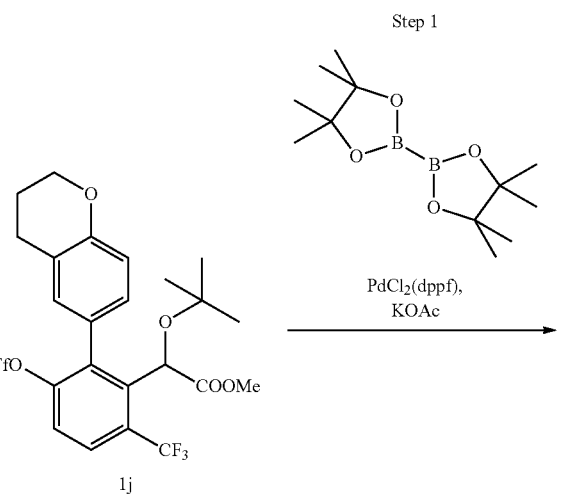

Step 1: Preparation of Intermediate methyl 2-(tert-butoxy)-2-[2-(4,4-dimethylcyclohex-1-en-1-yl)-3-(1-methyl-1H-pyrazol-4-yl)-6-(trifluoromethyl)phenyl]acetate (15a)

Using the procedure described in example 11, step 6, methyl 2-(tert-butoxy)-2-[2-(4,4-dimethylcyclohex-1-en-1-yl)-3-[(trifluoromethane)sulfonyloxy]-6-(trifluoromethyl)phenyl]acetate (11e) (80 mg, 0.146 mmol) is converted by reaction with 1-methylpyrazole-4-boronic acid pinacol ester (46 mg, 0.22 mmol) after purification by preparative TLC (cyclohexane/ethyl acetate 60/40) into methyl 2-(tert-butoxy)-2-[2-(4,4-dimethylcyclohex-1-en-1-yl)-3-(1-methyl-1H-pyrazol-4-yl)-6-(trifluoromethyl)phenyl]acetate (15a) (44 mg, 0.092 mmol, 63%) as a white solid.

$^1$H NMR (400 MHz, CDCl$_3$) δ 0.86 and 0.90 (s, 3H), 1.00 and 1.02 (s, 3H), 1.14 and 1.18 (s, 9H), 1.35-1.68 (m, 2H), 1.61-1.89 (m, 2H), 2.36 (bs, 2H), 3.66 and 3.71 (s, 3H), 3.94 (s, 3H), 5.30-5.80 (m, 2H), 7.33 and 7.34 (d, J=8.1 Hz, 1H), 7.46 and 7.48 (s, 1H), 7.58-7.63 (m, 2H).
MS m/z ([M+H]$^+$) 479.

Step 2: Preparation of 2-(tert-butoxy)-2-[2-(4,4-dimethylcyclohex-1-en-1-yl)-3-(1-methyl-1H-pyrazol-4-yl)-6-(trifluoromethyl)phenyl]acetic acid (Example 15)

Using the procedure described in example 2, step 2, the methyl 2-(tert-butoxy)-2-[2-(4,4-dimethylcyclohex-1-en-1-yl)-3-(1-methyl-1H-pyrazol-4-yl)-6-(trifluoromethyl)phenyl]acetate (15a) (44 mg, 0.092 mmol) is converted into 2-(tert-butoxy)-2-[2-(4,4-dimethylcyclohex-1-en-1-yl)-3-(1-methyl-1H-pyrazol-4-yl)-6-(trifluoromethyl)phenyl]acetic acid (example 15) (26 mg, 0.056 mmol, 60%) as a white solid.

$^1$H NMR (400 MHz, CDCl$_3$) δ 0.86 and 0.90 (s, 3H), 0.98 (s, 3H), 1.18 and 1.23 (s, 9H), 1.29-1.37 (m, 1H), 1.60-2.18 (m, 5H), 3.92 and 3.93 (s, 3H), 5.46-6.23 (m, 2H), 7.35-7.64 (m, 4H).
MS m/z ([M+H]$^+$) 465.
MS m/z ([M−H]$^−$) 463.

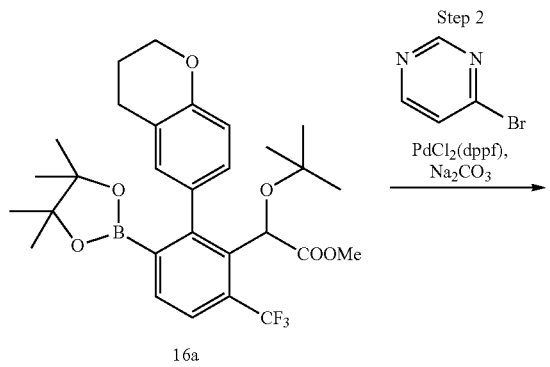

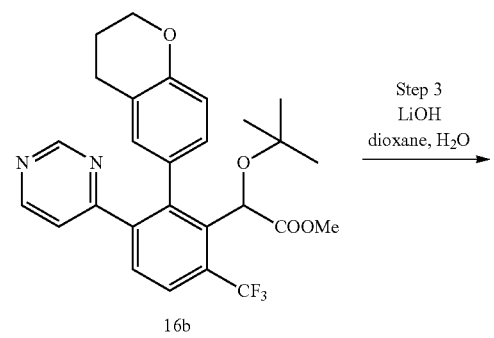

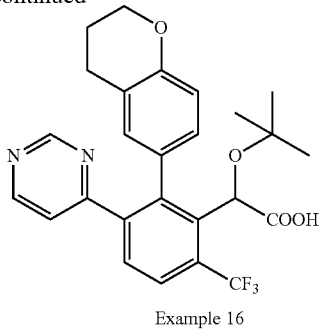

Example 16

Step 1: Preparation of Intermediate methyl 2-(tert-butoxy)-2-[2-(3,4-dihydro-2H-1-benzopyran-6-yl)-3-(tetramethyl-1,3,2-dioxaborolan-2-yl)-6-(trifluoromethyl)phenyl]acetate (16a)

A flame-dried vial containing methyl 2-(tert-butoxy)-2-[2-(3,4-dihydro-2H-1-benzopyran-6-yl)-3-[(trifluoromethane)sulfonyloxy]-6-(trifluoromethyl)phenyl]acetate (1j) (437 mg, 0.766 mmol), [1,1'-bis(diphenylphosphino) ferrocene]dichloropalladium(II), complex with dichloromethane (125 mg, 0.153 mmol), bis[pinacolato]diboron (389 mg, 1.53 mmol) and potassium acetate (225 mg, 2.30 mmol) was purged with argon for 10 minutes and then degassed anhydrous dioxane (5 mL) was added. The resulting mixture was placed in a preheated oil bath (80° C.) and stirred for 22 hours. LCMS showed remaining starting triflate and the mixture was cooled to room temperature, anhydrous dioxane (2 mL) was added and the mixture was purged with argon (10 min) followed by addition of bis[pinacolato]diboron (194 mg, 0.765 mmol), potassium acetate (113 mg, 1.15 mmol) and [1,1'-bis(diphenylphosphino) ferrocene]dichloropalladium(II), complex with dichloromethane (62 mg, 0.076 mmol), further purged with argon and then stirred at 80° C. for further 24 hours. The mixture was cooled to room temperature and diluted in ethyl acetate (100 mL) and washed with water (2×15 mL) and brine (15 mL), dried over sodium sulfate, filtered and concentrated in vacuo. The residue was purified by Dry Column Vacuum Chromatography on Silicagel (30 mL) (cyclohexane/ethyl acetate 100/0 up to 70/30) to provide methyl 2-(tert-butoxy)-2-[2-(3,4-dihydro-2H-1-benzopyran-6-yl)-3-(tetramethyl-1,3,2-dioxaborolan-2-yl)-6-(trifluoromethyl)phenyl]acetate (16a) (520 mg, quantitative yield) as a yellow oil.

$^1$H NMR (300 MHz, CDCl$_3$) δ 0.92 and 0.95 (s, 9H), 1.06 (s, 6H), 1.13 (s, 6H), 2.04 (m, 2H), 2.75 (m, 2H), 3.67 (s, 3H), 4.21 (m, 2H), 5.18 (s, 1H), 6.74-6.93 (m, 2H), 7.05-7.10 (m, 1H), 7.26-7.67 (m, 2H).

Step 2: Preparation of Intermediate methyl 2-(tert-butoxy)-2-[2-(3,4-dihydro-2H-1-benzopyran-6-yl)-3-(pyrimidin-4-yl)-6-(trifluoromethyl)phenyl]acetate (16b)

To a solution of methyl 2-(tert-butoxy)-2-[2-(3,4-dihydro-2H-1-benzopyran-6-yl)-3-(tetramethyl-1,3,2-dioxaborolan-2-yl)-6-(trifluoromethyl)phenyl]acetate (16a) (120 mg, 0.218 mmol) in dioxane (1.5 mL) was added 4-bromopyrimidine hydrochloride (57 mg, 0.291 mmol) and sodium carbonate saturated aqueous solution (1.5 mL). This mixture was stirred at room temperature for 20 minutes while passing a stream of argon. [1,1'-bis(diphenylphosphino) ferrocene]dichloropalladium(II), complex with dichloromethane (14 mg, 0.018 mmol) was added and the resulting mixture was stirred at 80° C. for 72 hours. The reaction mixture was cooled to room temperature and diluted with ethyl acetate (70 mL). The organic phase were washed with water (2×15 mL) and brine (15 mL), dried over sodium sulfate and concentrated in vacuo. The crude residue was purified on preparative TLC (cyclohexane/ethyl acetate 70/30) to provide methyl 2-(tert-butoxy)-2-[2-(3,4-dihydro-2H-1-benzopyran-6-yl)-3-(1,3-thiazol-2-yl)-6-(trifluoromethyl)phenyl]acetate (16b) (38 mg, 0.075 mmol, 35%).

$^1$H NMR (400 MHz, CDCl$_3$) δ 0.91 and 0.92 (s, 9H), 1.89-1.92 (m, 1H), 2.00-2.05 (m, 1H), 2.37-2.58 (m, 1H), 2.68-2.80 (m, 1H), 3.74 (s, 3H), 4.13-4.21 (m, 2H), 5.20 (s, 1H), 6.46-6.80 (m, 3H), 7.18-7.25 (m, 1H), 7.73-7.77 (m, 1H), 7.85 (d, J=8.2 Hz, 1H), 8.38 and 8.39 (d, J=5.8 Hz, 1H), 9.18 and 9.20 (d, J=1.1 Hz, 1H).

MS m/z ([M+H]$^+$) 501.

Step 3: Preparation of 2-(tert-butoxy)-2-[2-(3,4-dihydro-2H-1-benzopyran-6-yl)-3-(pyrimidin-4-yl)-6-(trifluoromethyl)phenyl]acetic acid (Example 16)

Using the procedure described in example 2, step 2, the methyl 2-(tert-butoxy)-2-[2-(3,4-dihydro-2H-1-benzopyran-6-yl)-3-(pyrimidin-4-yl)-6-(trifluoro methyl)phenyl]acetate (16b) (50 mg, 0.100 mmol) is converted into 2-(tert-butoxy)-2-[2-(3,4-dihydro-2H-1-benzopyran-6-yl)-3-(pyrimidin-4-yl)-6-(trifluoromethyl)phenyl]acetic acid (example 16) (46 mg, 0.094 mmol, 94%) as a white solid.

$^1$H NMR (400 MHz, CDCl$_3$) δ 0.94 (s, 9H), 1.87-1.94 (m, 1H), 2.00-2.08 (m, 1H), 2.39-2.53 (m, 1H), 2.80-2.85 (m, 1H), 4.14-4.23 (m, 2H), 5.34 and 5.37 (s, 1H), 6.43-6.88 (m, 3H), 7.59-7.65 (m, 1H), 7.79-7.84 (m, 1H), 7.88 (d, J=7.8 Hz, 1H), 8.40 and 8.41 (d, J=4.7 Hz, 1H), 9.22 and 9.23 (d, J=0.9 Hz, 1H).

MS m/z ([M+H]$^+$) 487.

MS m/z ([M+H]$^+$) 485.

Example 17

Synthesis of 2-(tert-butoxy)-2-[2-(3,4-dihydro-2H-1-benzopyran-6-yl)-3-(3-fluoropyridin-4-yl)-6-(trifluoromethyl)phenyl]acetic acid

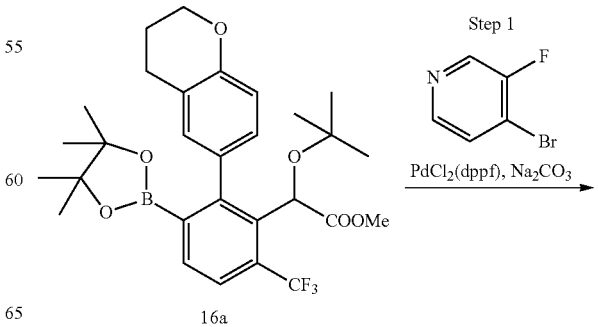

131

-continued

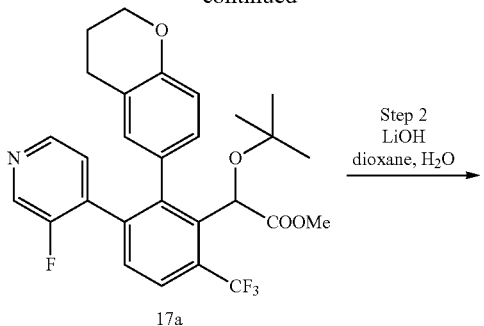

17a

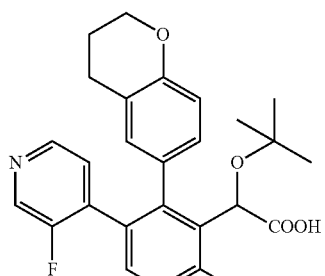

Example 17

Step 1: Preparation of Intermediate methyl 2-(tert-butoxy)-2-[2-(3,4-dihydro-2H-1-benzopyran-6-yl)-3-(3-fluoropyridin-4-yl)-6-(trifluoromethyl)phenyl]acetate (17a)

Using the procedure described in example 16, step 2, the methyl 2-(tert-butoxy)-2-[2-(3,4-dihydro-2H-1-benzopyran-6-yl)-3-(tetramethyl-1,3,2-dioxaborolan-2-yl)-6-(trifluoromethyl)phenyl]acetate (16a) (48 mg, 0.087 mmol) is converted by reaction with 4-bromo-3-fluoro-pyridine hydrochloride (37 mg, 0.174 mmol) into methyl 2-(tert-butoxy)-2-[2-(3,4-dihydro-2H-1-benzopyran-6-yl)-3-(3-fluoropyridin-4-yl)-6-(trifluoromethyl)phenyl]acetate (17a) (37 mg, 0.071 mmol, 82%), after purification by preparative TLC (dichloromethane/ethyl acetate 80/20).

$^1$H NMR (400 MHz, CDCl$_3$) δ 0.96 and 0.97 (s, 9H), 1.88-2.00 (m, 2H), 2.37-2.61 (m, 1H), 2.69 (t, J=6.3 Hz, 1H), 3.71 (s, 3H), 4.10-4.17 (m, 2H), 5.17 (s, 1H), 6.48-6.69 (m, 2H), 6.91-6.97 (m, 1H), 7.03-7.09 (m, 1H), 7.39 and 7.41 (d, J=8.1 Hz, 1H), 7.80 (d, J=8.1 Hz, 1H), 8.20-8.23 (m, 1H), 8.32 and 8.33 (d, J=4.4 Hz, 1H).

MS m/z ([M+H]$^+$) 518.

Step 2: Preparation of 2-(tert-butoxy)-2-[2-(3,4-dihydro-2H-1-benzopyran-6-yl)-3-(3-fluoropyridin-4-yl)-6-(trifluoromethyl)phenyl]acetic acid (Example 17)

Using the procedure described in example 2, step 2, the methyl 2-(tert-butoxy)-2-[2-(3,4-dihydro-2H-1-benzopyran-6-yl)-3-(3-fluoropyridin-4-yl)-6-(trifluoromethyl)phenyl]acetate (17a) (36 mg, 0.069 mmol) is converted into 2-(tert-butoxy)-2-[2-(3,4-dihydro-2H-1-benzopyran-6-yl)-3-(3-fluoropyridin-4-yl)-6-(trifluoromethyl)phenyl]acetic acid (example 17) (26 mg, 0.051 mmol, 74%) as a white solid.

$^1$H NMR (400 MHz, CDCl$_3$) δ 0.99 (s, 9H), 1.87-2.02 (m, 2H), 2.34-2.59 (m, 1H), 2.68-2.81 (m, 1H), 4.10-4.18 (m, 2H), 5.29 and 5.32 (s, 1H), 6.47-6.75 (m, 2H), 6.93-6.98 (m, 1H), 7.37-7.47 (m, 2H), 7.82 (d, J=8.1 Hz, 1H), 8.21-8.24 (m, 1H), 8.37-8.38 (m, 1H).

132

MS m/z ([M+H]$^+$) 504.

Example 18

Synthesis of 2-(tert-butoxy)-2-[2-(3,4-dihydro-2H-1-benzopyran-6-yl)-3-(1-methyl-1H-pyridin-2-one-5-yl)-6-(trifluoromethyl)phenyl]acetic acid

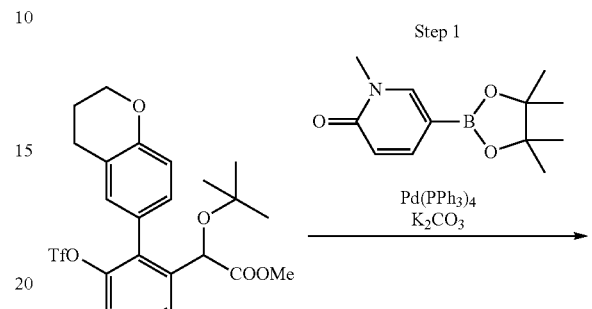

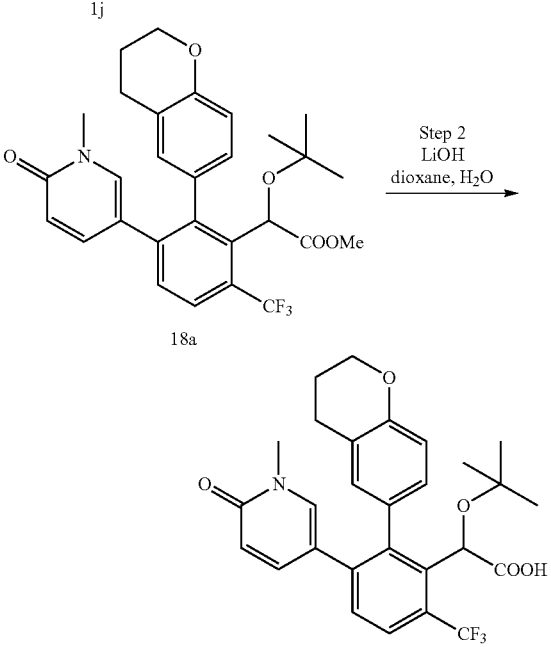

Example 18

Step 1: Preparation of Intermediate methyl 2-(tert-butoxy)-2-[2-(3,4-dihydro-2H-1-benzopyran-6-yl)-3-(1-methyl-1H-pyridin-2-one-5-yl)-6-(trifluoromethyl)phenyl]acetate (18a)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (70 mg, 0.122 mmol) is converted, by reaction with N-methyl-1H-pyridin-2-one-5-boronic acid, pinacol ester (43 mg, 0.183 mmol) into methyl 2-(tert-butoxy)-2-[2-(3,4-dihydro-2H-1-benzopyran-6-yl)-3-(1-methyl-1H-pyridin-2-one-5-yl)-6-(trifluoromethyl) phenyl]acetate (18a) (35 mg, 0.066 mmol, 54%), after purification by preparative TLC (ethyl acetate).

$^1$H NMR (400 MHz, CDCl$_3$) δ 0.94 and 0.96 (s, 9H), 1.91-2.03 (m, 2H), 2.53-2.65 (m, 1H), 2.67-2.81 (m, 1H), 3.42 and 3.43 (s, 3H), 3.71 (s, 3H), 4.16-4.22 (m, 2H), 5.15 and 5.17 (s, 1H), 6.34 and 6.37 (d, J=9.5 Hz, 1H), 6.52-6.79 (m, 2H), 6.96-7.12 (m, 3H), 7.37 and 7.38 (d, J=8.1 Hz, 1H), 7.74 (d, J=8.1 Hz, 1H).

MS m/z ([M+H]$^+$) 530.

Step 2: Preparation 2-(tert-butoxy)-2-[2-(3,4-dihydro-2H-1-benzopyran-6-yl)-3-(1-methyl-1H-pyridin-2-one-5-yl)-6-(trifluoromethyl)phenyl]acetic acid (Example 18)

Using the procedure described in example 2, step 2, the methyl 2-(tert-butoxy)-2-[2-(3,4-dihydro-2H-1-benzopyran-6-yl)-3-(1-methyl-1H-pyridin-2-one-5-yl)-6-(trifluoromethyl)phenyl]acetate (18a) (35 mg, 0.066 mmol) is converted into 2-(tert-butoxy)-2-[2-(3,4-dihydro-2H-1-benzopyran-6-yl)-3-(1-methyl-1H-pyridin-2-one-5-yl)-6-(trifluoromethyl)phenyl]acetic acid (example 18) (25 mg, 0.048 mmol, 73%) as a white solid.

$^1$H NMR (400 MHz, CDCl$_3$) δ 0.97 (s, 9H), 1.95-2.03 (m, 2H), 2.59 (bs, 1H), 2.79 (bs, 1H), 3.42 and 3.43 (s, 3H), 4.16-4.21 (m, 2H), 5.30 (bs, 1H), 6.40-6.45 (m, 1H), 6.51-6.84 (m, 2H), 7.00-7.08 (m, 2H), 7.40-7.48 (m, 2H), 7.75 (d, J=8.0 Hz, 1H).

MS m/z ([M+H]$^+$) 516.

Example 19

Synthesis of 2-(tert-butoxy)-2-[2-(3,4-dihydro-2H-1-benzopyran-6-yl)-3-[4-(methylcarbamoyl)phenyl]-6-(trifluoromethyl)phenyl]acetic acid

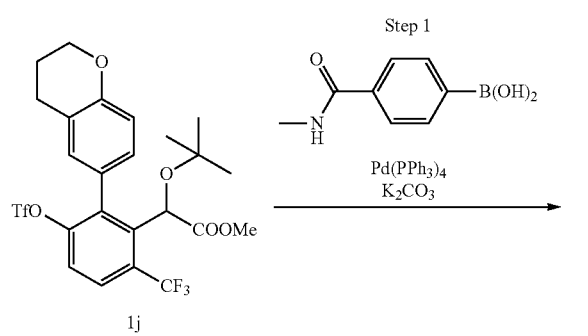

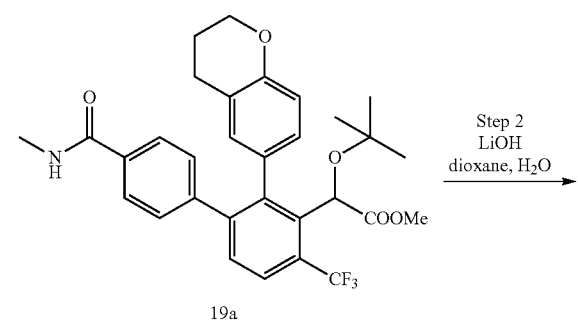

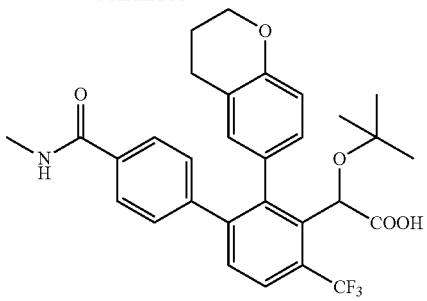

Example 19

Step 1: preparation of intermediate methyl 2-(tert-butoxy)-2-[2-(3,4-dihydro-2H-1-benzopyran-6-yl)-3-[4-(methylcarbamoyl)phenyl]-6-(trifluoromethyl)phenyl]acetate (19a)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (70 mg, 0.123 mmol) is converted by reaction with [4-(methylcarbamoyl)phenyl] boronic acid (33 mg, 0.184 mmol) into the methyl 2-(tert-butoxy)-2-[2-(3,4-dihydro-2H-1-benzo pyran-6-yl)-3-[4-(methylcarbamoyl)phenyl]-6-(trifluoromethyl)phenyl] acetate (19a) (65 mg, 0.117 mmol, 95%) after purification by preparative TLC (cyclohexane/ethyl acetate 30/70).

$^1$H NMR (400 MHz, CDCl$_3$) δ 0.94 (s, 9H), 1.82-1.93 (m, 1H), 1.94-2.07 (m, 1H), 2.29-2.58 (m, 1H), 2.65-2.80 (m, 1H), 2.98-3.03 (m, 3H), 3.73 and 3.74 (s, 3H), 4.08-4.21 (m, 2H), 5.17 (s, 1H), 6.10 (bs, 1H), 6.37-6.44 (m, 1H), 6.46 and 6.70 (d, J=8.3 Hz, 1H), 7.06-7.14 (m, 2H), 7.38-7.46 (m, 1H), 7.53-7.60 (m, 2H), 7.72-7.80 (m, 2H).

MS m/z ([M+H]$^+$) 556.

Step 2: Preparation of 2-(tert-butoxy)-2-[2-(3,4-dihydro-2H-1-benzopyran-6-yl)-3-[4-(methylcarbamoyl)phenyl]-6-(trifluoromethyl)phenyl]acetic acid (Example 19)

Using the procedure described in example 2, step 2, methyl 2-(tert-butoxy)-2-[2-(3,4-dihydro-2H-1-benzopyran-6-yl)-3-[4-(methylcarbamoyl)phenyl]-6-(trifluoromethyl) phenyl]acetate (19a) (65 mg, 0.117 mmol) is converted into 2-(tert-butoxy)-2-[2-(3,4-dihydro-2H-1-benzopyran-6-yl)-3-[4-(methylcarbamoyl)phenyl]-6-(trifluoromethyl)phenyl] acetic acid (32.5 mg, 0.060 mmol, 51%) after purification by preparative TLC (cyclohexane/ethyl acetate 20/80).

$^1$H NMR (300 MHz, CDCl$_3$) δ 0.96 (s, 9H), 1.78-1.94 (m, 1H), 1.94-2.09 (m, 1H), 2.28-2.58 (m, 1H), 2.68-2.86 (m, 1H), 2.98 and 3.00 (s, 3H), 4.07-4.22 (m, 2H), 5.31 and 5.34 (s, 1H), 6.00-6.18 (m, 1H), 6.29-6.84 (m, 2H), 7.06-7.15 (m, 2H), 7.41-7.53 (m, 2H), 7.53-7.62 (m, 2H), 7.77 (d, J=8.2 Hz, 1H).

MS m/z ([M+H]$^+$) 542.

Example 20

Synthesis of 2-[3-(4-aminophenyl)-2-(3,4-dihydro-2H-1-benzo pyran-6-yl)-6-(trifluoromethyl)phenyl]-2-(tert-butoxy)acetic acid

Example 21

Synthesis of 2-(tert-butoxy)-2-[3-(4-acetamidophenyl)-2-(3,4-dihydro-2H-1-benzopyran-6-yl)-6-(trifluoromethyl)phenyl]acetic acid

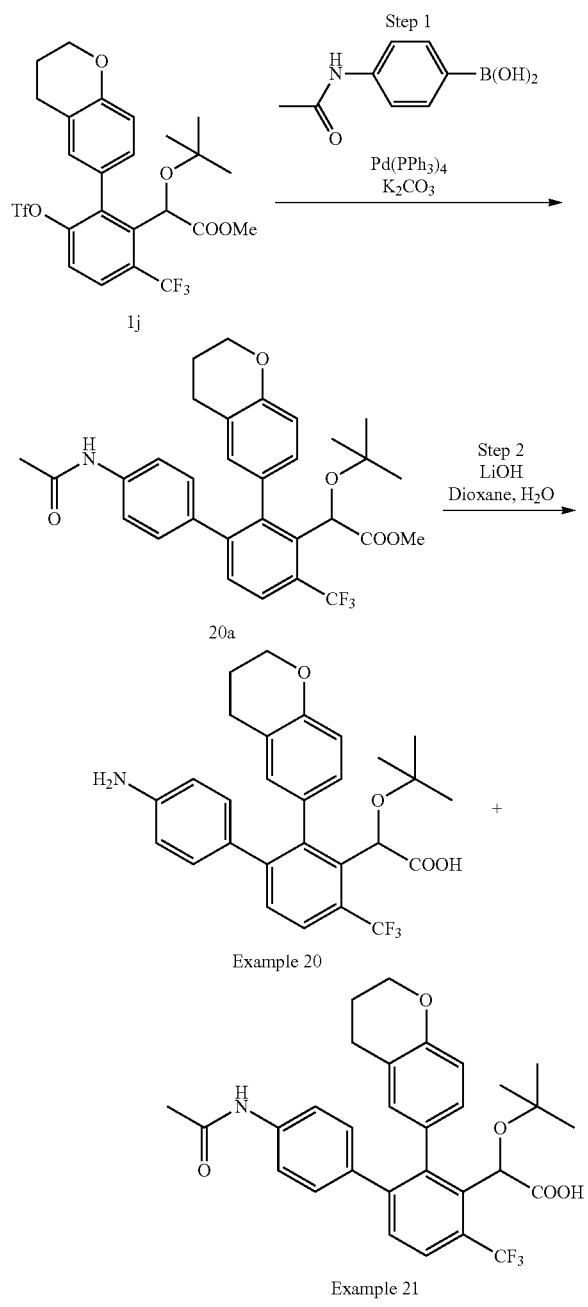

Example 20

Example 21

Step 1: Preparation of Intermediate methyl 2-(tert-butoxy)-2-[3-(4-acetamidophenyl)-2-(3,4-dihydro-2H-1-benzopyran-6-yl)-6-(trifluoromethyl)phenyl] acetate (20a)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (70 mg, 0.123 mmol) is converted by reaction with (4-acetamidophenyl)boronic acid (33 mg, 0.184 mmol) into the methyl 2-(tert-butoxy)-2-[3-(4-acetamidophenyl)-2-(3,4-dihydro-2H-1-benzopyran-6-yl)-6—(trifluoromethyl)phenyl]acetate (20a) (63 mg, 0.113 mmol, 92%) after purification by preparative TLC (cyclohexane/ethyl acetate 50/50).

$^1$H NMR (400 MHz, CDCl$_3$) δ 0.94 (s, 9H), 1.82-2.07 (m, 2H), 2.15 (s, 3H), 2.37-2.61 (m, 1H), 2.61-2.85 (m, 1H), 3.72 and 3.73 (s, 3H), 4.09-4.21 (m, 2H), 5.16 (s, 1H), 6.40-6.74 (m, 2H), 6.94-7.16 (m, 2H), 7.22 (bs, 1H), 7.26-7.53 (m, 4H), 7.69-7.80 (m, 1H).

MS m/z ([M+H]$^+$) 556.

Step 2: Preparation of 2-[3-(4-aminophenyl)-2-(3,4-dihydro-2H-1-benzopyran-6-yl)-6-(trifluoromethyl) phenyl]-2-(tert-butoxy)acetic acid (Example 20) and 2-(tert-butoxy)-2-[3-(4-acetamidophenyl)-2-(3,4-dihydro-2H-1-benzopyran-6-yl)-6-(trifluoromethyl) phenyl]acetic acid (Example 21)

To a solution of methyl 2-(tert-butoxy)-2-[3-(4-acetamidophenyl)-2-(3,4-dihydro-2H-1-benzopyran-6-yl)-6-(trifluoromethyl)phenyl]acetate (20a) (63 mg, 0.113 mmol) in a mixture of dioxane (1.9 mL) and water (1.0 mL) was added lithium hydroxide (22 mg, 0.91 mmol). The mixture was stirred at 90° C. for 16 hours, followed by 5 hours at 105° C. The mixture was concentrated in vacuo. The residue was dissolved in water (2 mL) and extracted with diethyl ether (2×2 mL). The aqueous layer was acidified with a 1 M hydrochloric acid solution until pH 3 followed by extraction with diethyl ether (2×2 mL). The combined organic layers were dried over sodium sulfate and concentrated in vacuo. The residue was purified by preparative TLC (cyclohexane/ethyl acetate 20/80) to provide 2-[3-(4-aminophenyl)-2-(3,4-dihydro-2H-1-benzopyran-6-yl)-6-(trifluoromethyl)phenyl]-2-(tert-butoxy)acetic acid (example 20) (15 mg, 0.03 mmol, 26%) and 2-(tert-butoxy)-2-[3-(4-acetamidophenyl)-2-(3,4-dihydro-2H-1-benzopyran-6-yl)-6-(trifluoromethyl) phenyl]acetic acid (example 21) (16.4 mg, 0.030 mmol, 27%).

$^1$H NMR (300 MHz, CDCl$_3$) (example 20) δ 0.96 (s, 9H), 1.83-2.07 (m, 2H), 2.38-2.60 (m, 1H), 2.72-2.85 (m, 1H), 4.08-4.24 (m, 2H), 5.30 and 5.33 (s, 1H), 6.33-6.57 (m, 2H), 6.71-7.04 (m, 4H), 7.38-7.56 (m, 2H), 7.69-7.80 (m, 1H).

MS m/z ([M+H]$^+$) 500.

MS m/z ([M−H]$^−$) 498.

$^1$H NMR (300 MHz, CDCl$_3$) (example 21) δ 0.95 (s, 9H), 1.82-1.95 (m, 1H), 1.95-2.06 (m, 1H), 2.15 (s, 3H), 2.35-2.59 (m, 1H), 2.71-2.86 (m, 1H), 4.09-4.22 (m, 2H), 5.31 and 5.34 (s, 1H), 6.35-6.81 (m, 2H), 6.93-7.03 (m, 2H), 7.12 (bs, 1H), 7.27-7.35 (m, 2H), 7.40-7.53 (m, 2H), 7.70-7.80 (m, 1H).

MS m/z ([M+H]$^+$) 542.

MS m/z ([M−H]$^−$) 540.

Example 22

Synthesis of 2-(tert-butoxy)-2-{2-(3,4-dihydro-2H-1-benzopyran-6-yl)-3-[1-(2,2,2-trifluoroethyl)-1H-pyrazol-4-yl]-6-(trifluoromethyl)phenyl}acetic acid

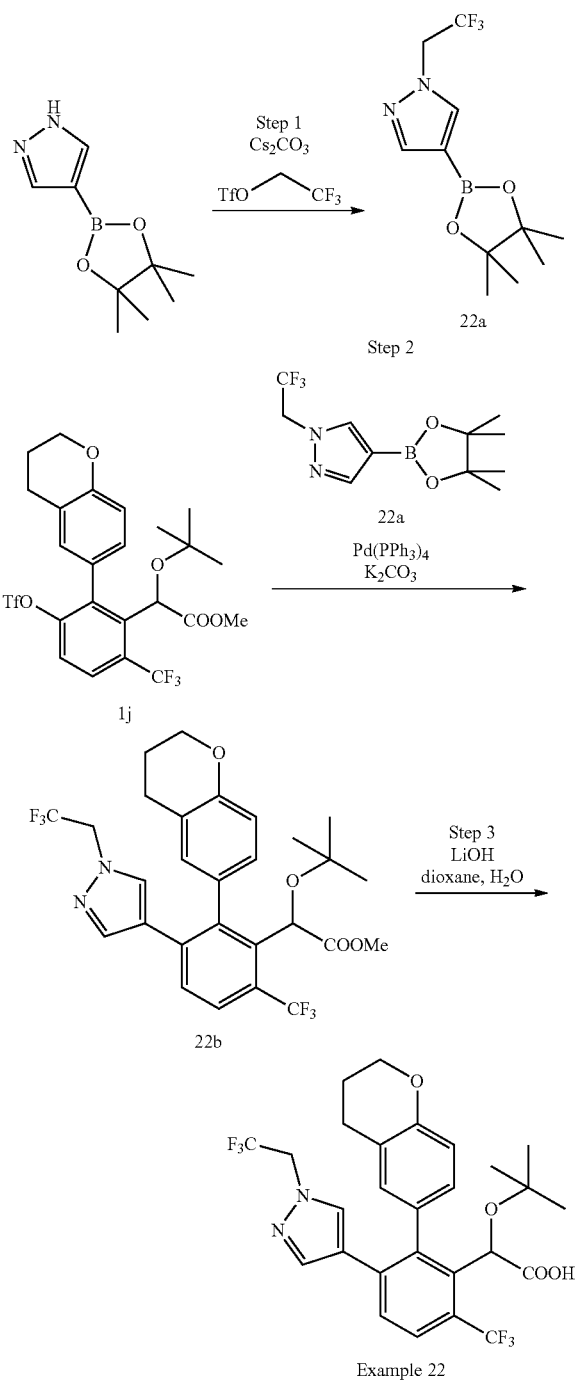

Example 22

Step 1: Preparation of Intermediate 4-(4,4,5,5,-tetramethyl-1,3,2-dioxaborolan-2-yl)-1-(2,2,2-trifluoroethyl)-1H-pyrazole (22a)

To a solution of 4-(4,4,5,5,-tetramethyl-1,3,2-dioxaborolan-2-yl)-1H-pyrazole (250 mg, 1.29 mmol) in N,N-dimethylformamide (4 mL) were added cesium carbonate (630 mg, 1.93 mmol) and 2,2,2-trifluoroethyl trifluoro methanesulfonate (0.37 mL, 2.58 mmol). The mixture was stirred at 100° C. for 50 minutes. The mixture was then poured in water (15 mL) and extracted with ethyl acetate (2×10 mL). The organic layer was washed with a saturated solution of sodium hydrogenocarbonate (10 mL), brine (10 mL), dried over sodium sulfate and concentrated in vacuo to provide 4-(4,4,5,5,-tetramethyl-1,3,2-dioxaborolan-2-yl)-1-(2,2,2-trifluoroethyl)-1H-pyrazole (22a) (271 mg, 0.98 mmol, 76%) which was used without further purification.

$^1$H NMR (300 MHz, CDCl$_3$) δ 1.32 (s, 12H), 4.71 (q, J=8.4 Hz, 2H), 7.80 (s, 1H), 7.84 (s, 1H).

Step 2: Preparation of Intermediate methyl 2-(tert-butoxy)-2-{2-(3,4-dihydro-2H-1-benzopyran-6-yl)-3-[1-(2,2,2-trifluoroethyl)-1H-pyrazol-4-yl]-6-(trifluoro methyl)phenyl}acetate (22b)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (62 mg, 0.108 mmol) is converted by reaction with 4-(4,4,5,5,-tetramethyl-1,3,2-dioxaborolan-2-yl)-1-(2,2,2-trifluoroethyl)-1H-pyrazole (22a) (45 mg, 0.163 mmol) into methyl 2-(tert-butoxy)-2-{2-(3,4-dihydro-2H-1-benzopyran-6-yl)-3-[1-(2,2,2-trifluoroethyl)-1H-pyrazol-4-yl]-6-(trifluoromethyl)phenyl}acetate (22b) (51 mg, 0.089 mmol, 82%), after purification by preparative TLC (cyclohexane/ethyl acetate 60/40).

$^1$H NMR (400 MHz, CDCl$_3$) δ 0.98 and 1.00 (s, 9H), 1.95-2.07 (m, 2H), 2.55-2.79 (m, 2H), 3.68-3.69 (m, 3H), 4.18-4.27 (m, 2H), 4.39-4.63 (m, 2H), 5.16 and 5.19 (s, 1H), 6.55-6.85 (m, 3H), 7.01-7.11 (m, 1H), 7.33 and 7.45 (s, 1H), 7.55 (d, J=8.2 Hz, 1H), 7.72 (d, J=8.2 Hz, 1H).

MS m/z ([M+H]$^+$) 571.

Step 3: Preparation of 2-(tert-butoxy)-2-{2-(3,4-dihydro-2H-1-benzopyran-6-yl)-3-[1-(2,2,2-trifluoroethyl)-1H-pyrazol-4-yl]-6-(trifluoromethyl)phenyl}acetic acid (Example 22)

Using the procedure described in example 2, step 2, the methyl 2-(tert-butoxy)-2-{2-(3,4-dihydro-2H-1-benzopyran-6-yl)-3-[1-(2,2,2-trifluoroethyl)-1H-pyrazol-4-yl]-6-(trifluoromethyl)phenyl}acetate (22b) (59 mg, 0.101 mmol) is converted into 2-(tert-butoxy)-2-{2-(3,4-dihydro-2H-1-benzopyran-6-yl)-3-[1-(2,2,2-trifluoroethyl)-1H-pyrazol-4-yl]-6-(trifluoromethyl)phenyl}acetic acid (10 mg, 0.018 mmol, 18%) (example 22) as a white solid after purification by preparative TLC (dichloromethane/methanol 90/10).

$^1$H NMR (300 MHz, CDCl$_3$) b 1.01 and 1.03 (s, 9H), 1.96-2.05 (m, 2H), 2.58-2.62 (m, 1H), 2.78-2.82 (m, 1H), 4.18-4.26 (m, 2H), 4.40-4.64 (m, 2H), 5.31 (bs, 1H), 6.55-6.91 (m, 3H), 7.34-7.49 (m, 2H), 7.59 and 7.60 (d, J=8.3 Hz, 1H), 7.73 (d, J=8.2 Hz, 1H).

MS m/z ([M+H]$^+$) 557.

Example 23

Synthesis of 2-[3-(3-aminophenyl)-2-(3,4-dihydro-2H-1-benzopyran-6-yl)-6-(trifluoromethyl)phenyl]-2-(tert-butoxy)acetic acid

Example 24

Synthesis of 2-(tert-butoxy)-2-[3-(3-acetamidophenyl)-2-(3,4-dihydro-2H-1-benzopyran-6-yl)-6-(trifluoromethyl)phenyl]acetic acid

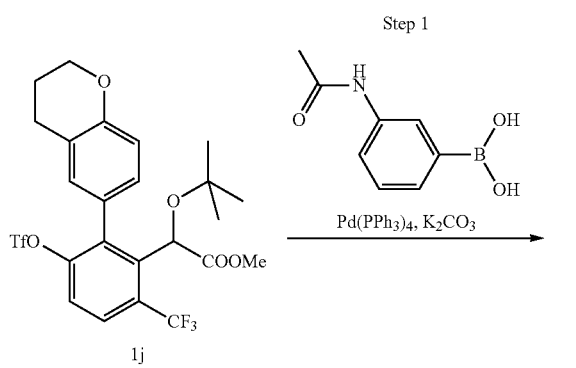

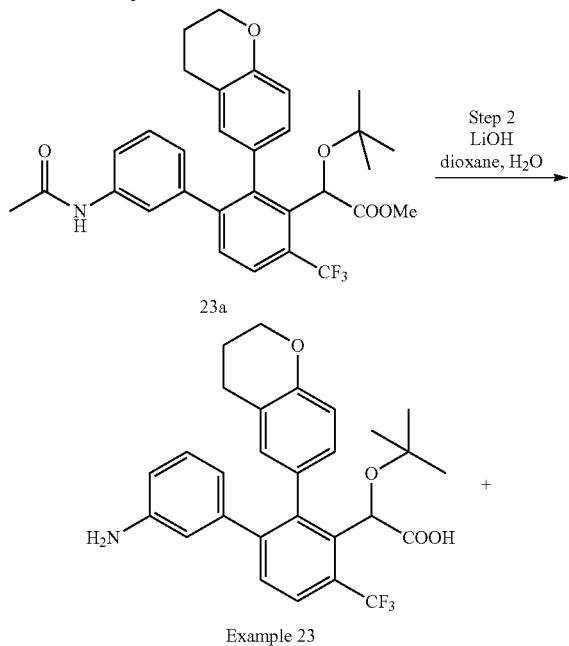

Step 1: Preparation of Intermediate methyl 2-(tert-butoxy)-2-[3-(3-acetamidophenyl)-2-(3,4-dihydro-2H-1-benzopyran-6-yl)-6-(trifluoromethyl)phenyl]acetate (23a)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (70 mg, 0.123 mmol) is converted by reaction with (3-acetamidophenyl)boronic acid (33 mg, 0.184 mmol), after purification by preparative TLC (dichloromethane/ethyl acetate 70/30) into methyl 2-(tert-butoxy)-2-[3-(3-acetamidophenyl)-2-(3,4-dihydro-2H-1-benzopyran-6-yl)-6-(trifluoromethyl)phenyl]acetate (23a) (46 mg, 0.082 mmol, 67%).

$^1$H NMR (300 MHz, CDCl$_3$) δ 0.94 and 0.95 (s, 9H), 1.82-1.94 (m, 1H), 1.94-2.04 (m, 1H), 2.13 and 2.14 (s, 3H), 2.32-2.61 (m, 1H), 2.61-2.84 (m, 1H), 3.73 (s, 3H), 4.10-4.18 (m, 2H), 5.17 (s, 1H), 6.42-6.77 (m, 3H), 6.99-7.15 (m, 3H), 7.15-7.24 (m, 1H), 7.31-7.38 (m, 1H), 7.42 (d, J=8.1 Hz, 1H), 7.74 (d, J=8.1 Hz, 1H).
MS m/z ([M+H]$^+$) 556.

Step 2: Preparation of 2-[3-(3-aminophenyl)-2-(3,4-dihydro-2H-1-benzopyran-6-yl)-6-(trifluoromethyl)phenyl]-2-(tert-butoxy)acetic acid (Example 23) and 2-(tert-butoxy)-2-[3-(3-acetamidophenyl)-2-(3,4-dihydro-2H-1-benzopyran-6-yl)-6-(trifluoromethyl)phenyl]acetic acid (Example 24)

Using the procedure described in example 2, step 2, methyl 2-(tert-butoxy)-2-[3-(3-acetamidophenyl)-2-(3,4-dihydro-2H-1-benzopyran-6-yl)-6-(trifluoromethyl)phenyl]acetate (46 mg, 0.082 mmol) is converted, after purification by preparative TLC (cyclohexane/ethyl acetate 20/80), into 2-[3-(3-aminophenyl)-2-(3,4-dihydro-2H-1-benzopyran-6-yl)-6-(trifluoromethyl)phenyl]-2-(tert-butoxy)acetic acid (example 23) (18 mg, 0.036 mmol, 43%) and 2-(tert-butoxy)-2-[3-(3-acetamidophenyl)-2-(3,4-dihydro-2H-1-benzopyran-6-yl)-6-(trifluoromethyl)phenyl]acetic acid (example 24) (14 mg, 0.026 mmol, 31%)

$^1$H NMR (300 MHz, CDCl$_3$) (example 23) δ 0.96 (s, 9H), 1.81-2.09 (m, 2H), 2.32-2.62 (m, 1H), 2.66-2.87 (m, 1H), 4.02-4.26 (m, 2H), 5.32 and 5.36 (s, 1H), 6.33-6.60 (m, 4H), 6.67-7.02 (m, 2H), 7.36-7.57 (m, 2H), 7.68-7.80 (m, 1H).
MS m/z ([M−H]$^−$) 498.

$^1$H NMR (300 MHz, CDCl$_3$) (example 24) δ 0.95 (s, 9H), 1.80-2.06 (m, 2H), 2.13 (s, 3H), 2.30-2.61 (m, 1H), 2.67-2.82 (m, 1H), 4.06-4.22 (m, 2H), 5.32 and 5.35 (s, 1H), 6.36-6.80 (m, 3H), 7.00-7.26 (m, 3H), 7.36 (bs, 1H), 7.40-7.53 (m, 2H), 7.74 (d, J=8.2 Hz, 1H).
MS m/z ([M+H]$^+$) 542.

Example 25

Synthesis of 2-(tert-butoxy)-2-[2-(3,4-dihydro-2H-1-benzopyran-6-yl)-3-(6-oxo-1-propyl-1,6-dihydropyridin-3-yl)-6-(trifluoromethyl)phenyl]acetic acid

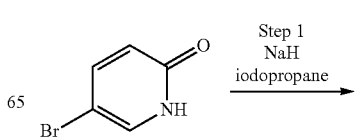

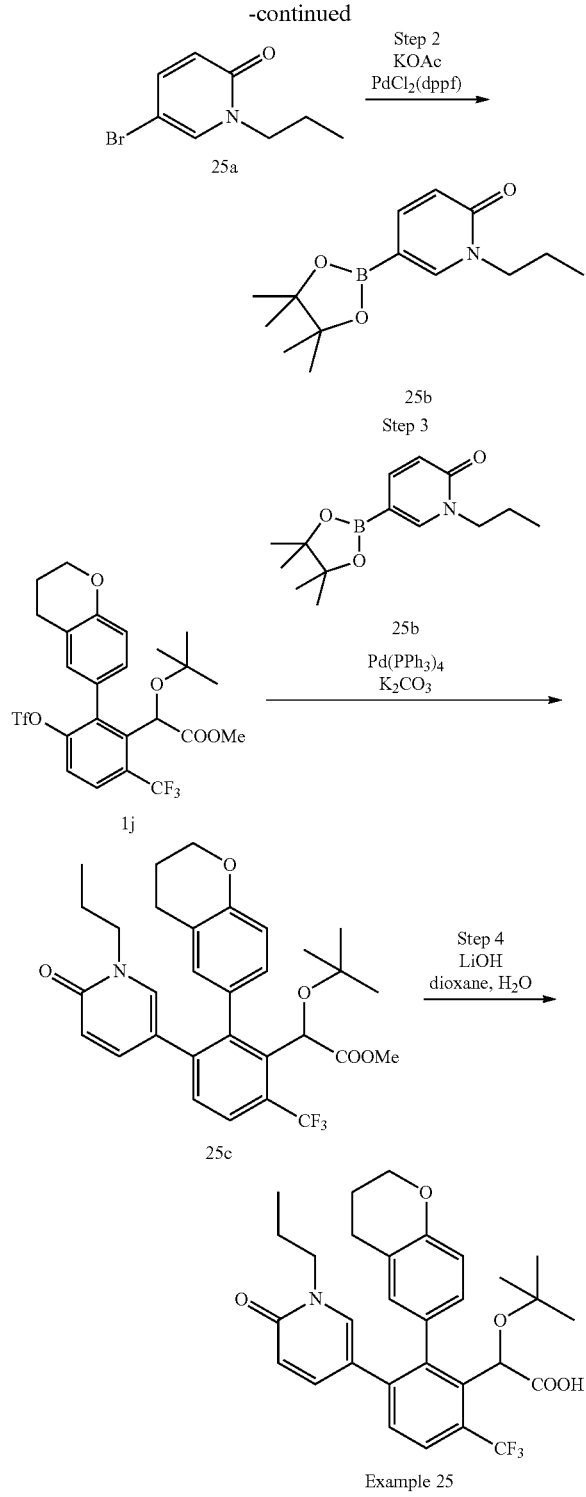

was stirred at 50° C. for 40 hours. Water (10 mL) was added and the mixture was extracted with ethyl acetate (2×15 mL). The organic layer was washed with brine (2×10 mL), dried over sodium sulfate and concentrated in vacuo. The residue was purified by flash chromatography on silica gel (dichloromethane/ethyl acetate 100/0 to 80/20) to provide 5-bromo-1-propyl-1,2-dihydropyridin-2-one (25a) (776 mg, 3.59 mmol, 62%).

$^1$H NMR (400 MHz, CDCl$_3$) 0.96 (t, J=7.4 Hz, 3H), 1.77 (sext, J=7.4 Hz, 2H), 3.85 (t, J=7.4 Hz, 2H), 6.48 (d, J=9.6 Hz, 1H), 7.32 (dd, J=2.7 Hz, J=9.6 Hz, 1H), 7.37 (d, J=2.7 Hz, 1H).

MS m/z ([M+H]$^+$) 216/218.

Step 2: Preparation of Intermediate 1-propyl-5-(tetramethyl-1,3,2-dioxaborolan-2-yl)-1,2-dihydropyridin-2-one (25b)

[1,1'-Bis(diphenylphosphino)ferrocene]dichloropalladium(II) (293 mg, 0.36 mmol) was added to a previously degassed with argon solution of 5-bromo-1-propyl-1,2-dihydropyridin-2-one (25a) (776 mg, 3.59 mmol), bis(pinacolato)diboron (1.37 g, 5.39 mmol) and potassium acetate (1.23 g, 12.57 mmol) in anhydrous N,N-dimethylformamide (20 mL). The reaction mixture was heated at 95° C. for 16 hours. Water (50 mL) was added and the reaction mixture was concentrated in vacuo. Water (50 mL) was added to the residue and the mixture was extracted with ethyl acetate (2×50 mL). The organic layer was washed with brine (40 mL), dried over sodium sulfate, concentrated in vacuo, and co-evaporated with toluene. The residue was purified by flash chromatography on silica gel (dichloromethane/methanol 100/0 to 95/5) then by preparative TLC (dichloromethane/ethyl acetate 60/40) to provide 1-propyl-5-(tetramethyl-1,3,2-dioxaborolan-2-yl)-1,2-dihydropyridin-2-one (25b) (467 mg, 1.77 mmol, 49%).

$^1$H NMR (300 MHz, CDCl$_3$) δ 0.95 (t, J=7.3 Hz, 3H), 1.30 (s, 12H), 1.68-1.87 (m, 2H), 3.98 (t, J=7.3 Hz, 2H), 6.50 (d, J=8.9 Hz, 1H), 7.58 (d, J=8.1 Hz, 1H), 7.72 (s, 1H).

MS m/z ([M+H]$^+$) 264.

Step 3: Preparation of Intermediate methyl 2-(tert-butoxy)-2-[2-(3,4-dihydro-2H-1-benzopyran-6-yl)-3-(6-oxo-1-propyl-1,6-dihydropyridin-3-yl)-6-(trifluoromethyl)phenyl]acetate (25c)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (70 mg, 0.123 mmol) is converted by reaction with 1-propyl-5-(tetramethyl-1,3,2-dioxaborolan-2-yl)-1,2-dihydropyridin-2-one (25b) (64 mg, 0.245 mmol), after purification by preparative TLC (dichloromethane/ethyl acetate 50/50) to methyl 2-(tert-butoxy)-2-[2-(3,4-dihydro-2H-1-benzopyran-6-yl)-3-(6-oxo-1-propyl-1,6-dihydropyridin-3-yl)-6-(trifluoromethyl)phenyl]acetate (25c) (43 mg, 0.077 mmol, 63%).

$^1$H NMR (300 MHz, CDCl$_3$) δ 0.83 and 0.84 (t, J=7.3 Hz, 3H), 0.94 and 0.95 (s, 9H), 1.46-1.64 (m, 2H), 1.89-2.08 (m, 2H), 2.48-2.67 (m, 1H), 2.69-2.77 (m, 1H), 3.49-3.68 (m, 1H), 3.72 (s, 3H), 3.80-3.98 (m, 1H), 4.10-4.27 (m, 2H), 5.15 and 5.16 (s, 1H), 6.40 and 6.42 (d, J=9.3 Hz, 1H), 6.51-6.57 (m, 1H), 6.64 and 6.78 (d, J=8.3 Hz, 1H), 6.85-6.91 (m, 1H), 7.07-7.14 (m, 2H), 7.34-7.43 (m, 1H), 7.74 (d, J=8.2 Hz, 1H).

MS m/z ([M+H]$^+$) 558.

Step 1: Preparation of Intermediate 5-bromo-1-propyl-1,2-dihydropyridin-2-one (25a)

Under a nitrogen atmosphere, sodium hydride 60% in oil (0.23 g, 5.75 mmol) was added portionwise to a solution of 5-bromo-2(1H)-pyridone (1.00 g, 5.75 mmol) in dry tetrahydrofuran (20 mL). After 10 minutes stirring, iodopropane (1.68 mL, 17.24 mmol) was added and the reaction mixture

Step 4: Preparation of 2-(tert-butoxy)-2-[2-(3,4-dihydro-2H-1-benzopyran-6-yl)-3-(6-oxo-1-propyl-1,6-dihydropyridin-3-yl)-6-(trifluoromethyl)phenyl]acetic acid (Example 25)

To a solution of methyl 2-(tert-butoxy)-2-[2-(3,4-dihydro-2H-1-benzopyran-6-yl)-3-(6-oxo-1-propyl-1,6-dihydropyridin-3-yl)-6-(trifluoromethyl)phenyl]acetate (25c) (43 mg, 0.077 mmol) in a mixture of dioxane (1.0 mL) and water (0.5 mL) was added lithium hydroxide (15 mg, 0.62 mmol). The mixture was heated at 110° C. for 80 hours. The reaction mixture was cooled to room temperature and concentrated in vacuo. Water (2 mL) was added to the residue and the aqueous layer was washed with diethyl ether (2 mL), acidified with 1M hydrochloric acid until pH 3 and extracted with diethyl ether (2×3 mL). The organic layer was dried over sodium sulfate and concentrated in vacuo to provide 2-(tert-butoxy)-2-[2-(3,4-dihydro-2H-1-benzopyran-6-yl)-3-(6-oxo-1-propyl-1,6-dihydropyridin-3-yl)-6-(trifluoromethyl)phenyl]acetic acid (example 25) (37 mg, 0.068 mmol, 88%).

$^1$H NMR (300 MHz, CDCl$_3$) δ 0.82 and 0.83 (t, J=7.5 Hz, 3H), 0.97 (s, 9H), 1.44-1.68 (m, 2H), 1.85-2.12 (m, 2H), 2.45-2.66 (m, 1H), 2.66-2.94 (m, 1H), 3.38-3.72 (m, 1H), 3.77-4.01 (m, 1H), 4.08-4.30 (m, 2H), 5.29 and 5.32 (s, 1H), 6.38-6.48 (m, 1H), 6.48-6.60 (m, 1H), 6.61-6.91 (m, 2H), 7.07-7.18 (m, 1H), 7.38-7.55 (m, 2H), 7.76 (d, J=8.2 Hz, 1H).

MS m/z ([M+H]$^+$) 544.

Example 26

Synthesis of 2-[3-(1-benzyl-6-oxo-1,6-dihydropyridin-3-yl)-2-(3,4-dihydro-2H-1-benzopyran-6-yl)-6-(trifluoromethyl)phenyl]-2-(tert-butoxy)acetic acid

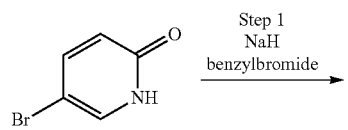

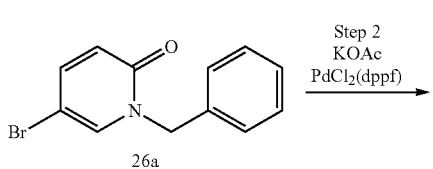

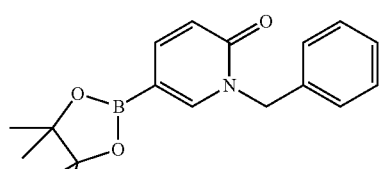

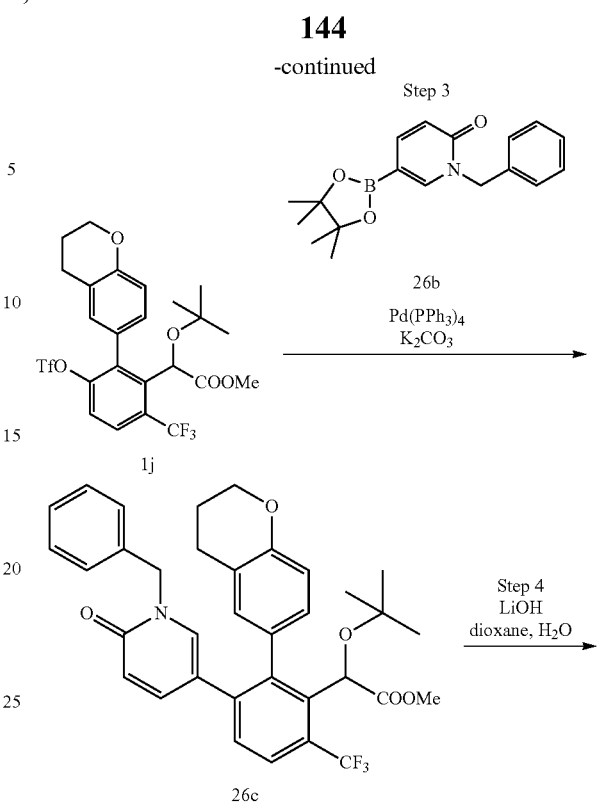

Step 1: Preparation of Intermediate 1-benzyl-5-bromo-1,2-dihydropyridin-2-one (26a)

Under a nitrogen atmosphere, sodium hydride 60% in oil (0.23 g, 5.75 mmol) was added portionwise to a solution of 5-bromo-2(1H)-pyridone (1.00 g, 5.75 mmol) in anhydrous tetrahydrofuran (20 mL). After 10 minutes stirring, benzyl bromide (2.05 mL, 17.24 mmol) was added and the reaction mixture was stirred at 50° C. for 5 hours. Water (10 mL) was added and the mixture was extracted with ethyl acetate (2×15 mL). The organic layer was washed with brine (2×10 mL), dried over sodium sulfate and concentrated in vacuo. The residue was purified by flash chromatography on silica gel (dichloromethane/ethyl acetate 100/0 to 85/15) to provide 1-benzyl-5-bromo-1,2-dihydropyridin-2-one (26a) (1.47 g, 5.57 mmol, 97%).

$^1$H NMR (300 MHz, CDCl$_3$) δ 5.09 (s, 2H), 6.53 (d, J=9.5 Hz, 1H), 7.27-7.41 (m, 7H).

MS m/z ([M+H]$^+$) 264/266.

Step 2: Preparation of Intermediate 1-benzyl-5-(tetramethyl-1,3,2-dioxaborolan-2-yl)-1,2-dihydropyridin-2-one (26b)

Using the procedure described in example 25, step 2, the intermediate 1-benzyl-5-bromo-1,2-dihydropyridin-2-one (26a) (1.45 g, 5.49 mmol) is converted, after purification by flash chromatography on silica gel (dichloromethane/ethyl acetate 100/0 to 80/20), and trituration in diethyl ether, to 1-benzyl-5-(tetramethyl-1,3,2-dioxaborolan-2-yl)-1,2-dihydropyridin-2-one (26b) (734 mg, 2.36 mmol, 43%).

$^1$H NMR (300 MHz, CDCl$_3$) δ 1.29 (s, 12H), 5.15 (s, 2H), 6.57 (d, J=9.1 Hz, 1H), 7.26-7.38 (m, 5H), 7.60 (dd, J=1.9 Hz, J=9.1 Hz, 1H), 7.78 (d, J=1.9 Hz, 1H).

MS m/z ([M+H]$^+$) 312.

Step 3: Preparation of Intermediate methyl 2-[3-(1-benzyl-6-oxo-1,6-dihydropyridin-3-yl)-2-(3,4-dihydro-2H-1-benzopyran-6-yl)-6-(trifluoromethyl)phenyl]-2-(tert-butoxy)acetate (26c)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (70 mg, 0.123 mmol) is converted by reaction with 1-benzyl-5-(tetramethyl-1,3,2-dioxaborolan-2-yl)-1,2-dihydropyridin-2-one (26b) (76 mg, 0.245 mmol), after purification by preparative TLC (dichloromethane/ethyl acetate 50/50) to methyl 2-[3-(1-benzyl-6-oxo-1,6-dihydropyridin-3-yl)-2-(3,4-dihydro-2H-1-benzopyran-6-yl)-6-(trifluoromethyl)phenyl]-2-(tert-butoxy)acetate (26c) (48 mg, 0.079 mmol, 65%).

$^1$H NMR (300 MHz, CDCl$_3$) δ 0.93 and 0.95 (s, 9H), 1.88-2.06 (m, 2H), 2.43-2.62 (m, 1H), 2.65-2.74 (m, 1H), 3.71 (s, 3H), 4.12-4.27 (m, 2H), 4.88-5.09 (m, 2H), 5.12 and 5.13 (s, 1H), 6.41-6.55 (m, 2H), 6.65 and 6.74 (d, J=8.3 Hz, 1H), 6.96-7.14 (m, 5H), 7.27-7.37 (m, 4H), 7.72 (d, J=8.2 Hz, 1H).

MS m/z ([M+H]$^+$) 606.

Step 4: Preparation of 2-[3-(1-benzyl-6-oxo-1,6-dihydropyridin-3-yl)-2-(3,4-dihydro-2H-1-benzopyran-6-yl)-6-(trifluoromethyl)phenyl]-2-(tert-butoxy)acetic acid (Example 26)

Using the procedure described in example 25, step 4, the intermediate methyl 2-[3-(1-benzyl-6-oxo-1,6-dihydropyridin-3-yl)-2-(3,4-dihydro-2H-1-benzopyran-6-yl)-6-(trifluoromethyl)phenyl]-2-(tert-butoxy)acetate (26c) (48 mg, 0.079 mmol) is converted to 2-[3-(1-benzyl-6-oxo-1,6-dihydropyridin-3-yl)-2-(3,4-dihydro-2H-1-benzopyran-6-yl)-6-(trifluoromethyl)phenyl]-2-(tert-butoxy)acetic acid (example 26) (43 mg, 0.073 mmol, 62%).

$^1$H NMR (300 MHz, CDCl$_3$) δ 0.96 (s, 9H), 1.88-2.05 (m, 2H), 2.41-2.62 (m, 1H), 2.62-2.85 (m, 1H), 4.10-4.26 (m, 2H), 4.93 (d, J=14.2 Hz, 1H), 5.02 (d, J=14.2 Hz, 1H), 5.26 and 5.28 (s, 1H), 6.40-6.55 (m, 2H), 6.65 and 6.79 (d, J=8.3 Hz, 1H), 6.95-6.99 (m, 1H), 7.04-7.13 (m, 3H), 7.27-7.47 (m, 5H), 7.73 (d, J=8.2 Hz, 1H).

MS m/z ([M+H]$^+$) 592.

Example 27

Synthesis of 2-(tert-butoxy)-2-{3-[1-(cyclopropylmethyl)-6-oxo-1,6-dihydropyridin-3-yl]-2-(3,4-dihydro-2H-1-benzopyran-6-yl)-6-(trifluoromethyl)phenyl}acetic acid

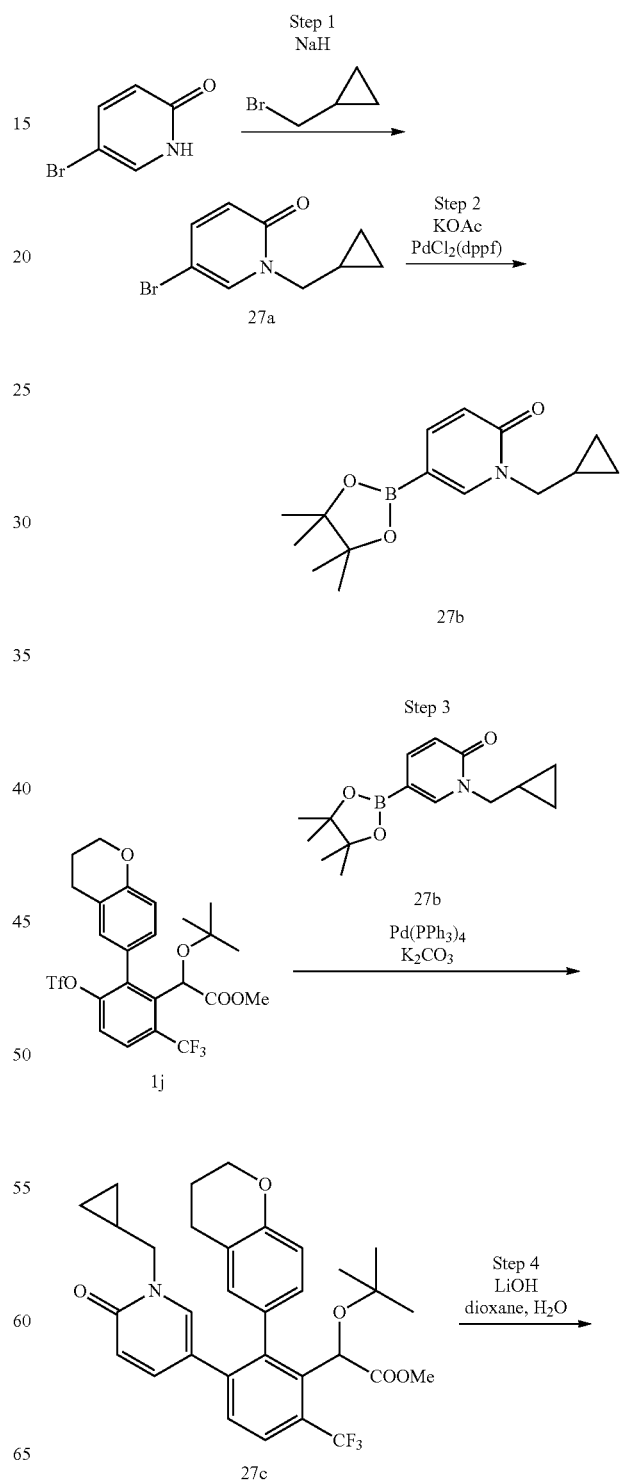

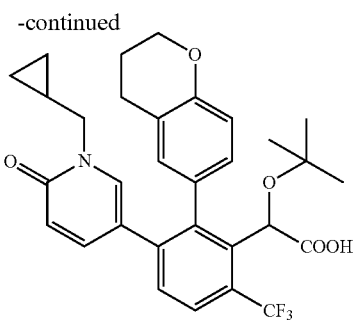

Example 27

Step 1: Preparation of Intermediate 5-bromo-1-(cyclopropylmethyl)-1,2-dihydropyridin-2-one (27a)

Under a nitrogen atmosphere, sodium hydride 60% in oil (0.41 g, 10.34 mmol) was added portionwise to a solution of 5-bromo-2(1H)-pyridone (1.50 g, 8.62 mmol) in dry tetrahydrofuran (25 mL). After 10 minutes stirring, (bromomethyl)cyclopropane (1.25 mL, 12.93 mmol) was added and the reaction mixture was stirred at 50° C. for 7 days. Water (10 mL) was added and the mixture was extracted with ethyl acetate (2×15 mL). The organic layer was washed with brine (2×10 mL), dried over sodium sulfate and concentrated in vacuo. The residue was purified by flash chromatography on silica gel (dichloromethane/ethyl acetate 100/0 to 85/15) to provide 5-bromo-1-(cyclopropylmethyl)-1,2-dihydropyridin-2-one (27a) (1.45 g, 6.36 mmol, 74%).

$^1$H NMR (300 MHz, CDCl$_3$) δ 0.35-0.42 (m, 2H), 0.59-0.68 (m, 2H), 1.15-1.29 (m, 1H), 3.76 (d, J=7.2 Hz, 2H), 6.49 (d, J=9.6 Hz, 1H), 7.34 (dd, J=2.7 Hz, J=9.6 Hz, 1H), 7.50 (d, J=2.7 Hz, 1H),

MS m/z ([M+H]$^+$) 228/230.

Step 2: Preparation of Intermediate 1-(cyclopropylmethyl)-5-(tetramethyl-1,3,2-dioxaborolan-2-yl)-1,2-dihydropyridin-2-one (27b)

Using the procedure described in example 25, step 2, the intermediate 5-bromo-1-(cyclopropylmethyl)-1,2-dihydropyridin-2-one (27a) (0.70 g, 3.07 mmol) is converted, after purification by flash chromatography on silica gel (dichloromethane/ethyl acetate 100/0 to 80/20), into 1-(cyclopropylmethyl)-5-(tetramethyl-1,3,2-dioxaborolan-2-yl)-1,2-dihydropyridin-2-one (27b) (384 mg, 1.40 mmol, 45%).

$^1$H NMR (300 MHz, CDCl$_3$) δ 0.36-0.42 (m, 2H), 0.54-0.62 (m, 2H), 1.26-1.35 (m, 1H), 1.31 (s, 12H), 3.80 (d, J=7.2 Hz, 2H), 6.52 (d, J=9.1 Hz, 1H), 7.59 (dd, J=2.0 Hz, J=9.1 Hz, 1H), 7.78 (d, J=2.0 Hz, 1H),

MS m/z ([M+H]$^+$) 276.

Step 3: Preparation of Intermediate methyl 2-(tert-butoxy)-2-{3-[1-(cyclopropylmethyl)-6-oxo-1,6-dihydropyridin-3-yl]-2-(3,4-dihydro-2H-1-benzopyran-6-yl)-6-(trifluoromethyl)phenyl}acetate (27c)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (70 mg, 0.123 mmol) is converted by reaction with 1-(cyclopropylmethyl)-5-(tetramethyl-1,3,2-dioxaborolan-2-yl)-1,2-dihydropyridin-2-one (27b) (68 mg, 0.245 mmol), after purification by preparative TLC (dichloromethane/ethyl acetate 50/50) to methyl 2-(tert-butoxy)-2-{3-[1-(cyclopropylmethyl)-6-oxo-1,6-dihydropyridin-3-yl]-2-(3,4-dihydro-2H-1-benzopyran-6-yl)-6-(trifluoromethyl)phenyl}acetate (27c) (42 mg, 0.074 mmol, 60%).

$^1$H NMR (400 MHz, CDCl$_3$) δ 0.19-0.30 (m, 2H), 0.47-0.58 (m, 2H), 0.94-1.07 (m, 10H), 1.90-2.07 (m, 2H), 2.52-2.66 (m, 1H), 2.68-2.76 (m, 1H), 3.48-3.61 (m, 1H), 3.67-3.79 (m, 4H), 4.12-4.24 (m, 2H), 5.15 and 5.16 (s, 1H), 6.41 and 6.42 (d, J=9.3 Hz, 1H), 6.50-6.60 (m, 1H), 6.65 and 6.77 (d, J=8.3 Hz, 1H), 6.98-7.02 (m, 1H), 7.07-7.15 (m, 2H), 7.39 (d, J=8.2 Hz, 1H), 7.75 (d, J=8.2 Hz, 1H).

MS m/z ([M+H]$^+$) 570.

Step 4: Preparation of 2-(tert-butoxy)-2-{3-[1-(cyclopropylmethyl)-6-oxo-1,6-dihydropyridin-3-yl]-2-(3,4-dihydro-2H-1-benzopyran-6-yl)-6-(trifluoromethyl)phenyl}acetic acid (Example 27)

Using the procedure described in example 25, step 4, the intermediate methyl 2-(tert-butoxy)-2-{3-[1-(cyclopropylmethyl)-6-oxo-1,6-dihydropyridin-3-yl]-2-(3,4-dihydro-2H-1-benzopyran-6-yl)-6-(trifluoromethyl)phenyl}acetate (27c) (42 mg, 0.074 mmol) is converted into 2-(tert-butoxy)-2-{3-[1-(cyclopropylmethyl)-6-oxo-1,6-dihydropyridin-3-yl]-2-(3,4-dihydro-2H-1-benzopyran-6-yl)-6-(trifluoromethyl)phenyl}acetic acid (example 27) (39 mg, 0.070 mmol, 95%).

$^1$H NMR (400 MHz, CDCl$_3$) δ 0.17-0.31 (m, 2H), 0.47-0.59 (m, 2H), 0.97 (s, 10H), 1.89-2.10 (m, 2H), 2.51-2.65 (m, 1H), 2.70-2.90 (m, 1H), 3.45-3.62 (m, 1H), 3.64-3.82 (m, 1H), 4.10-4.25 (m, 2H), 5.29 and 5.31 (s, 1H), 6.44 and 6.45 (d, J=9.3 Hz, 1H), 6.50-6.59 (m, 1H), 6.66 and 6.83 (d, J=8.3 Hz, 1H), 6.97-7.04 (m, 1H), 7.10-7.18 (m, 1H), 7.39-7.57 (m, 2H), 7.76 (d, J=8.2 Hz, 1H).

MS m/z ([M+H]$^+$) 556.

Example 28

Synthesis of 2-(tert-butoxy)-2-[2-(3,4-dihydro-2H-1-benzopyran-6-yl)-3-(2-propylpyridin-4-yl)-6-(trifluoromethyl)phenyl]acetic acid

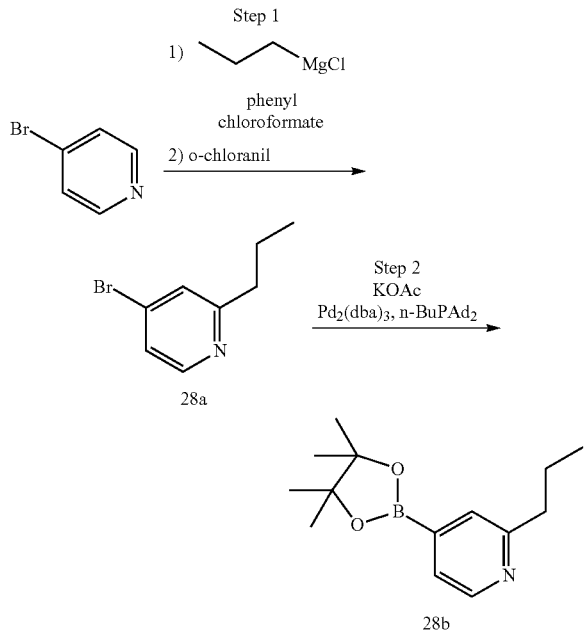

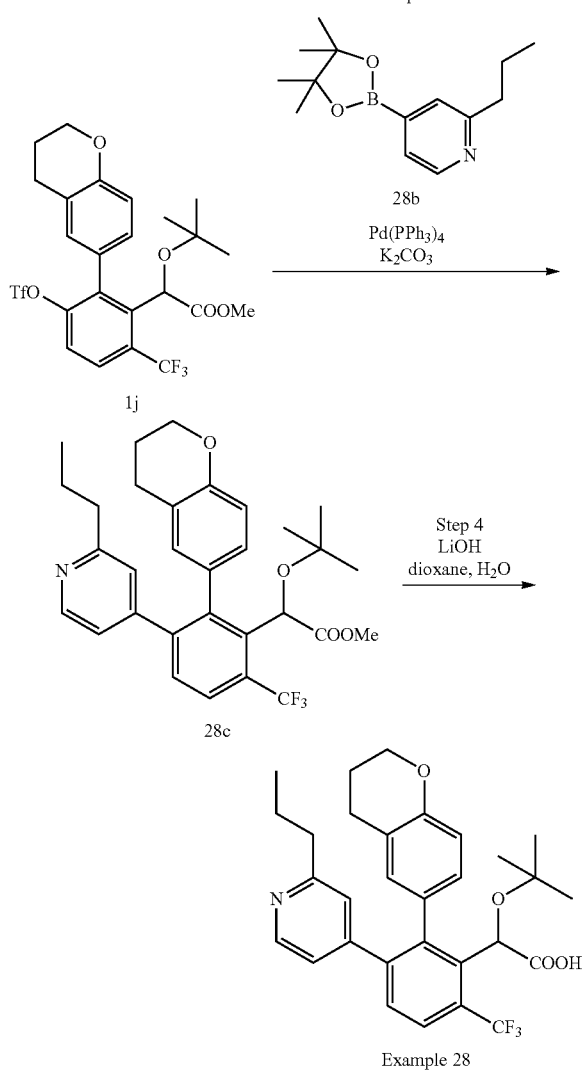

Step 1: Preparation of Intermediate 4-bromo-2-propylpyridine (28a)

Under a nitrogen atmosphere, a suspension of 4-bromopyridine hydrochloride (1.0 g, 5.14 mmol) in anhydrous tetrahydrofuran (20 mL) was cooled to −78° C. Propylmagnesium chloride 2.0M in diethyl ether (5.66 mL, 11.31 mmol) was dropwise added, followed by phenyl chloroformate (0.77 mL, 6.17 mmol) 5 minutes later. The mixture was stirred at −78° C. for 15 minutes, then allowed to reach 10° C. to be quenched by adding a saturated solution of ammonium chloride (20 mL). Diethyl ether (10 mL) was added, and the organic layer was successively washed with 1N hydrochloric acid (20 mL), water (20 mL) and brine (20 mL). The organic layer was dried over sodium sulfate and concentrated in vacuo. The residue was dissolved in anhydrous toluene (20 mL). To this solution was dropwise added a solution of o-chloranil (1.39 g, 5.66 mmol) in glacial acetic acid (15 mL). The mixture was stirred at room temperature for 16 hours, then cooled to 0° C., and basified with 1N sodium hydroxide until pH 10. The mixture was extracted with ethyl acetate (2×10 mL). The organic layer was extracted with 1N hydrochloric acid (2×10 mL). The acidic aqueous layer was washed with ethyl acetate (2×10 mL), basified with 1N sodium hydroxide until pH 10, and extracted with ethyl acetate (2×10 mL). The combined organic layers were dried over sodium sulfate and concentrated in vacuo. The residue was purified by flash chromatography on silica gel (cyclohexane/ethyl acetate 100/0 to 95/5) to provide 4-bromo-2-propylpyridine (28a) (649 mg, 3.24 mmol, 63%) as a colorless oil.

$^{1}$H NMR (400 MHz, CDCl$_3$) δ 0.97 (t, J=7.4 Hz, 3H), 1.45 (sext, J=7.4 Hz, 2H), 2.74 (t, J=7.4 Hz, 2H), 7.27 (dd, J=5.3 Hz, J=1.8 Hz, 1H), 7.33 (d, J=1.8 Hz, 1H), 8.33 (d, J=5.3 Hz, 1H).

Step 2: Preparation of Intermediate 2-propyl-4-(tetramethyl-1,3,2-dioxaborolan-2-yl)pyridine (28b)

Di(1-adamantyl)-n-butylphosphine (8.1 mg, 0.022 mmol) and tris(dibenzylideneacetone)dipalladium(0) (6.8 mg, 0.007 mmol) were added to a previously degassed solution of 4-bromo-2-propylpyridine (28a) (150 mg, 0.75 mmol), bis(pinacolato)diboron (228 mg, 0.90 mmol) and potassium acetate (221 mg, 2.25 mmol) in anhydrous dimethylacetamide (0.5 mL). The reaction mixture was heated at 90° C. for 16 hours. Water (5 mL) was added and the precipitate was filtrated and rinsed with water (2 mL). The filtrated was extracted with ethyl acetate (2×8 mL). The organic layer was washed with brine (10 mL), dried over sodium sulfate, concentrated in vacuo and co-evaporated with toluene to provide 2-propyl-4-(tetramethyl-1,3,2-dioxaborolan-2-yl) pyridine (28b) (126 mg, 0.51 mmol, 68%) which was used without further purification.

$^{1}$H NMR (300 MHz, CDCl$_3$) δ 0.96 (t, J=7.4 Hz, 3H), 1.35 (s, 12H), 1.76 (sext, J=7.4 Hz, 2H), 2.77 (m, 2H), 7.43 (d, J=4.7 Hz, 1H), 4.49 (s, 1H), 8.54 (d, J=4.7 Hz, 1H).

Step 3: Preparation of Intermediate methyl 2-(tert-butoxy)-2-[2-(3,4-dihydro-2H-1-benzopyran-6-yl)-3-(2-propylpyridin-4-yl)-6-(trifluoromethyl)phenyl] acetate (28c)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (80 mg, 0.140 mmol) is converted by reaction with 2-propyl-4-(tetramethyl-1,3,2-dioxaborolan-2-yl)pyridine (28b) (69 mg, 0.280 mmol), after purification by preparative TLC (dichloromethane/ethyl acetate 80/20) to methyl 2-(tert-butoxy)-2-[2-(3,4-dihydro-2H-1-benzopyran-6-yl)-3-(2-propylpyridin-4-yl)-6-(trifluoromethyl)phenyl]acetate (28c) (45 mg, 0.083 mmol, 59%).

$^{1}$H NMR (400 MHz, CDCl$_3$) δ 0.82 and 0.83 (t, J=7.4 Hz, 3H), 0.95 and 0.96 (s, 9H), 1.51-1.62 (m, 2H), 1.84-1.92 (m, 1H), 1.94-2.04 (m, 1H), 2.34-2.57 (m, 1H), 2.58-2.65 (m, 2H), 2.70-2.75 (m, 1H), 3.74 (s, 3H), 4.06-4.22 (m, 2H), 5.20 (s, 1H), 6.37-6.47 (m, 1H), 6.48-6.78 (m, 2H), 6.81-6.87 (m, 1H), 7.08-7.17 (m, 1H), 7.41 and 7.42 (d, J=8.1 Hz, 1H), 7.78 (d, J=8.1 Hz, 1H), 8.35 (d, J=5.1 Hz, 1H).

MS m/z ([M+H]$^+$) 542.

Step 4: Preparation of 2-(tert-butoxy)-2-[2-(3,4-dihydro-2H-1-benzopyran-6-yl)-3-(2-propylpyridin-4-yl)-6-(trifluoromethyl)phenyl]acetic acid (Example 28)

Using the procedure described in example 2, step 2, methyl 2-(tert-butoxy)-2-[2-(3,4-dihydro-2H-1-benzopyran- 6-yl)-3-(2-propylpyridin-4-yl)-6-(trifluoromethyl)phenyl]acetate (28c) (45 mg, 0.083 mmol) is converted into 2-(tert-butoxy)-2-[2-(3,4-dihydro-2H-1-benzopyran-6-yl)-3-(2-propylpyridin-4-yl)-6-(trifluoromethyl)phenyl]acetic acid (example 28) (35 mg, 0.066 mmol, 80%).

$^1$H NMR (400 MHz, CDCl$_3$) δ 0.82 (t, J=7.4 Hz, 3H), 0.98 (s, 9H), 1.49-1.63 (m, 2H), 1.82-1.94 (m, 1H), 1.94-2.08 (m, 1H), 2.29-2.89 (m, 4H), 4.05-4.23 (m, 2H), 5.33 and 5.37 (s, 1H), 6.29-6.47 (m, 1H), 6.48-6.82 (m, 2H), 6.84-6.89 (m, 1H), 7.42-7.57 (m, 2H), 7.80 (d, J=8.2 Hz, 1H), 8.37 (d, J=5.0 Hz, 1H).

MS m/z ([M+H]$^+$) 528.

Example 29

Synthesis of 2-(tert-butoxy)-2-[2-(3,4-dihydro-2H-1-benzopyran-6-yl)-3-(3-propylphenyl)-6-(trifluoromethyl)phenyl]acetic acid

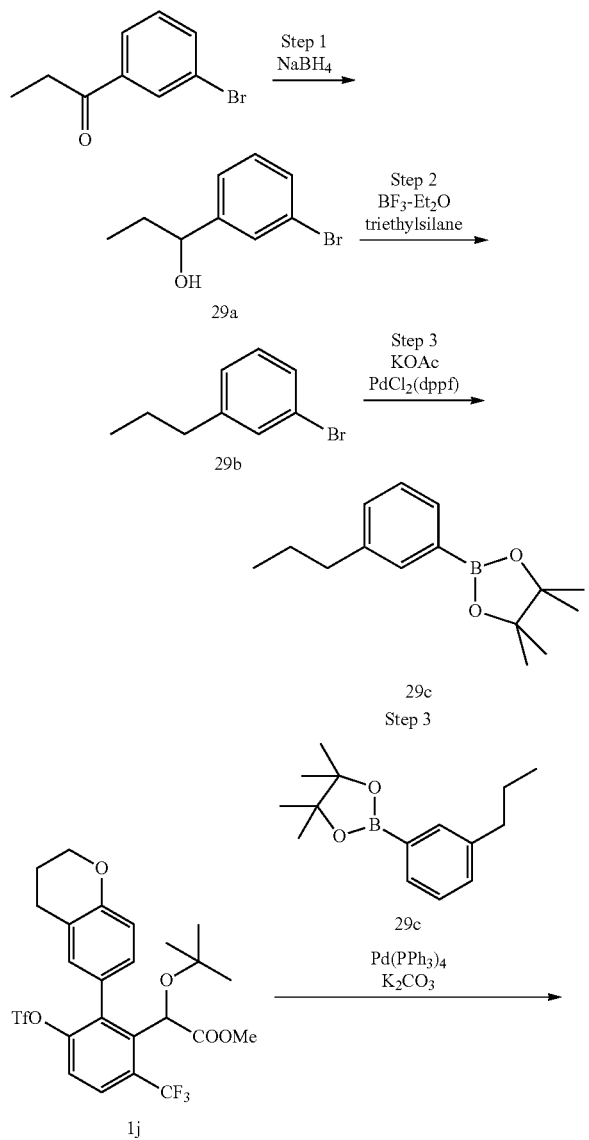

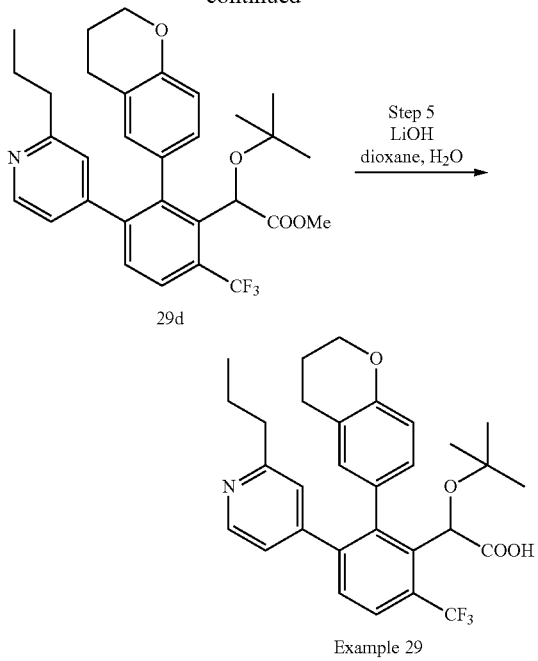

Step 1: Preparation of Intermediate 1-(3-bromophenyl)propan-1-ol (29a)

Under a nitrogen atmosphere, sodium borohydride (106 mg, 2.82 mmol) was portionwise added to a solution of 3'-bromopropiophenone (500 mg, 2.35 mmol) in anhydrous methanol (20 mL). The mixture was stirred for 3 hours and water was added (5 mL). The methanol was removed in vacuo, and the aqueous layer was extracted with ethyl acetate (2×6 mL). The organic layer was successively washed with water (3 mL) and brine (3 mL), before being dried over sodium sulfate and concentrated in vacuo to provide 1-(3-bromophenyl)propan-1-ol (29a) (502 mg, 2.33 mmol, 99%) which was used without further purification.

$^1$H NMR (300 MHz, CDCl$_3$) δ 0.92 (t, J=7.4 Hz, 3H), 1.68-1.85 (m, 2H), 4.58 (t, J=6.5 Hz, 1H), 7.18-7.28 (m, 2H), 7.37-7.43 (m, 1H), 7.49-7.52 (m, 1H).

Step 2: Preparation of Intermediate 1-bromo-3-propylbenzene (29b)

Under a nitrogen atmosphere, triethylsilane (4.46 mL, 27.90 mmol) and boron trifluoride ethyl etherate (0.92 mL, 7.44 mmol) were successively added to a solution of 1-(3-bromophenyl)propan-1-ol (29a) (400 mg, 1.86 mmol) in anhydrous dichloromethane (30 mL) at −78° C. The mixture was stirred at room temperature overnight. Water (15 mL) was added and layers were separated. The organic layer was washed with water (15 mL), dried over sodium sulfate and concentrated in vacuo to provide 1-bromo-3-propylbenzene (29b) (338 mg, 1.70 mmol, 91%) which was used without further purification.

$^1$H NMR (300 MHz, CDCl$_3$) δ 0.94 (t, J=7.4 Hz, 3H), 1.63 (sext, J=7.4 Hz, 2H), 2.53-2.58 (m, 2H), 7.07-7.17 (m, 2H), 7.28-7.34 (m, 2H).

Step 3: Preparation of Intermediate 4,4,5,5-tetramethyl-2-(3-propylphenyl)-1,3,2-dioxaborolane (29c)

Using the procedure described in example 25, step 2, the intermediate 1-bromo-3-propylbenzene (29b) (100 mg, 0.50 mmol) is converted, after purification by preparative TLC (cyclohexane/ethyl acetate 95/5) to 4,4,5,5-tetramethyl-2-(3-propylphenyl)-1,3,2-dioxaborolane (29c) (122 mg, 0.49 mmol, 99%).

$^1$H NMR (300 MHz, CDCl$_3$) δ 0.94 (t, J=7.4 Hz, 3H), 1.35 (s, 12H), 1.65 (sext, J=7.4 Hz, 2H), 2.56-2.62 (m, 2H), 7.27-7.32 (m, 2H), 7.59-7.67 (m, 2H).

MS m/z ([M+H]$^+$) 247.

Step 4: Preparation of Intermediate methyl 2-(tert-butoxy)-2-[2-(3,4-dihydro-2H-1-benzopyran-6-yl)-3-(3-propylphenyl)-6-(trifluoromethyl)phenyl]acetate (29d)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (80 mg, 0.140 mmol) is converted by reaction with 4,4,5,5-tetramethyl-2-(3-propylphenyl)-1,3,2-dioxaborolane (29c) (69 mg, 0.280 mmol), after purification by preparative TLC (cyclohexane/ethyl acetate 75/25) to methyl 2-(tert-butoxy)-2-[2-(3,4-dihydro-2H-1-benzopyran-6-yl)-3-(3-propylphenyl)-6-(trifluoromethyl)phenyl]acetate (29d) (62 mg, 0.11 mmol, 82%).

$^1$H NMR (400 MHz, CDCl$_3$) δ 0.78 (t, J=7.3 Hz, 3H), 0.95 and 0.96 (s, 9H), 1.35-1.48 (m, 2H), 1.83-1.92 (m, 1H), 1.94-2.03 (m, 1H), 2.32-2.57 (m, 3H), 2.71-2.77 (m, 1H), 3.73 and 3.74 (s, 3H), 4.07-4.21 (m, 2H), 5.19 and 5.21 (s, 1H), 6.37-6.79 (m, 3H), 6.88-7.19 (m, 4H), 7.42-7.46 (m, 1H), 7.74 (d, J=8.2 Hz, 1H).

Step 5: Preparation of 2-(tert-butoxy)-2-[2-(3,4-dihydro-2H-1-benzopyran-6-yl)-3-(3-propylphenyl)-6-(trifluoromethyl)phenyl]acetic acid (Example 29)

Using the procedure described in example 2, step 2, methyl 2-(tert-butoxy)-2-[2-(3,4-dihydro-2H-1-benzopyran-6-yl)-3-(3-propylphenyl)-6-(trifluoromethyl)phenyl]acetate (29d) (62 mg, 0.11 mmol) is converted, after purification by 2 preparative TLC (dichloromethane/methanol 98/2) and (cyclohexane/ethyl acetate 55/45) to 2-(tert-butoxy)-2-[2-(3,4-dihydro-2H-1-benzopyran-6-yl)-3-(3-propylphenyl)-6-(trifluoromethyl)phenyl]acetic acid (example 29) (20 mg, 0.038 mmol, 33%).

$^1$H NMR (400 MHz, CDCl$_3$) δ 0.78 (t, J=7.3 Hz, 3H), 0.97 (s, 9H), 1.34-1.50 (m, 2H), 1.77-1.90 (m, 1H), 1.94-2.04 (m, 1H), 2.26-2.60 (m, 3H), 2.72-2.86 (m, 1H), 4.03-4.21 (m, 2H), 5.35 and 5.40 (s, 1H), 6.31-6.82 (m, 3H), 6.87-6.99 (m, 2H), 7.04-7.17 (m, 1H), 7.42-7.55 (m, 2H), 7.78 (d, J=8.1 Hz, 1H).

MS m/z ([M−H]$^−$) 525.

Example 30

Synthesis of 2-(tert-butoxy)-2-{3-[1-(cyclobutylmethyl)-6-oxo-1,6-dihydropyridin-3-yl]-2-(3,4-dihydro-2H-1-benzopyran-6-yl)-6-(trifluoromethyl)phenyl}acetic acid

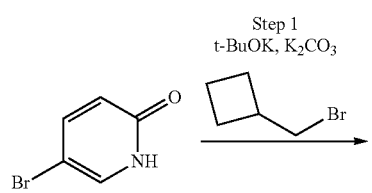

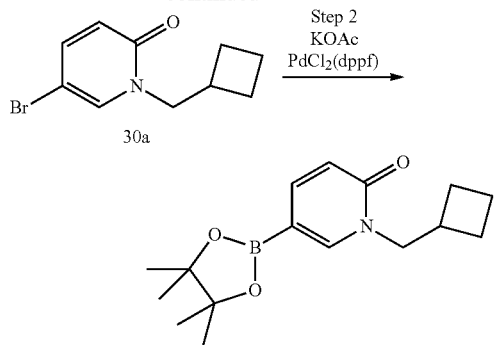

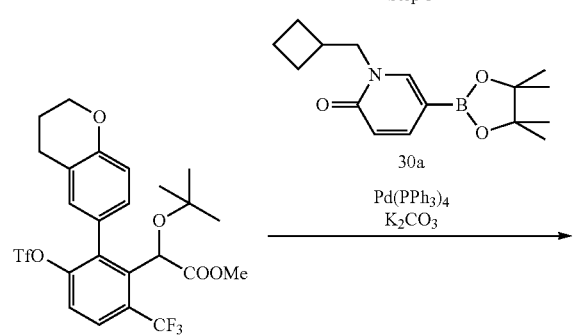

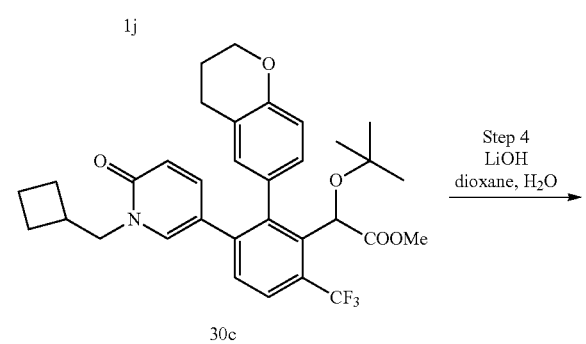

Example 30

Step 1: Preparation of Intermediate 5-bromo-1-(cyclobutylmethyl)-1,2-dihydropyridin-2-one (30a)

Potassium tert-butoxide 1N in tetrahydrofuran (5.75 mL, 5.75 mmol) was added to a suspension of 5-bromo-2(1H)-pyridone (1.00 g, 5.75 mmol) in dimethoxyethane (10 mL). After 30 minutes stirring at room temperature, potassium carbonate (0.56 g, 4.02 mmol) and (bromomethyl)cyclobutane (1.29 mL, 11.49 mmol) were added and the reaction mixture was refluxed for 24 hours. The resultant precipitate was filtered and rinsed with ethyl acetate (20 mL). The filtrate was successively washed with water (20 mL) and brine (20 mL), then dried over sodium sulfate and concentrated in vacuo. The residue was purified by flash chromatography on silica gel (dichloromethane/ethyl acetate: 100/0 to 80/20) to provide 5-bromo-1-(cyclobutylmethyl)-1,2-dihydropyridin-2-one (30a) (1.10 g, 4.54 mmol, 79%).

$^1$H NMR (400 MHz, CDCl$_3$) δ 1.72-1.85 (m, 2H), 1.85-1.97 (m, 2H), 2.01-2.12 (m, 2H), 2.77 (septuplet, J=7.5 Hz, 1H), 3.92 (d, J=7.5 Hz, 2H), 6.47 (d, J=9.5 Hz, 1H), 7.31 (dd, J=2.7 Hz, J=9.5 Hz, 1H), 7.34 (d, J=2.7 Hz, 1H).

MS m/z ([M+H]$^+$) 242/244.

Step 2: Preparation of Intermediate 1-(cyclobutylmethyl)-5-(tetramethyl-1,3,2-dioxaborolan-2-yl)-1,2-dihydropyridin-2-one (30b)

Using the procedure described in example 25, step 2, the intermediate 5-bromo-1-(cyclobutylmethyl)-1,2-dihydropyridin-2-one (30a) (1.0 g, 4.13 mmol) is converted into 1-(cyclobutylmethyl)-5-(tetramethyl-1,3,2-dioxaborolan-2-yl)-1,2-dihydropyridin-2-one (30b) (554 mg, 1.92 mmol, 46%), after purification by flash chromatography on silica gel (dichloromethane/ethyl acetate 100/0 to 80/20) and trituration in pentane.

$^1$H NMR (300 MHz, CDCl$_3$) δ 1.30 (s, 12H), 1.72-1.95 (m, 4H), 1.96-2.10 (m, 2H), 2.81 (septuplet, J=7.5 Hz, 1H), 3.96 (d, J=7.5 Hz, 2H), 6.49 (d, J=9.1 Hz, 1H), 7.55 (dd, J=2.0 Hz, J=9.1 Hz, 1H), 7.68 (d, J=2.0 Hz, 1H), MS m/z ([M+H]$^+$) 290.

Step 3: Preparation of Intermediate methyl 2-(tert-butoxy)-2-{3-[1-(cyclobutylmethyl)-6-oxo-1,6-dihydropyridin-3-yl]-2-(3,4-dihydro-2H-1-benzopyran-6-yl)-6-(trifluoromethyl)phenyl}acetate (30c)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (70 mg, 0.123 mmol) is converted by reaction with 1-(cyclobutylmethyl)-5-(tetramethyl-1,3,2-dioxaborolan-2-yl)-1,2-dihydropyridin-2-one (30b) (53 mg, 0.183 mmol) into methyl 2-(tert-butoxy)-2-{3-[1-(cyclobutylmethyl)-6-oxo-1,6-dihydropyridin-3-yl]-2-(3,4-dihydro-2H-1-benzopyran-6-yl)-6-(trifluoromethyl) phenyl}acetate (30c) (59 mg, 0.101 mmol, 81%), after purification by preparative TLC (dichloromethane/ethyl acetate 70/30).

$^1$H NMR (400 MHz, CDCl$_3$) δ 0.94 and 0.95 (s, 9H), 1.57-1.73 (m, 2H), 1.81-2.01 (m, 6H), 2.49-2.65 (m, 2H), 2.72-2.76 (m, 1H), 3.61-3.77 (m, 4H), 3.84-4.00 (m, 1H), 4.15-4.25 (m, 2H), 5.13 and 5.14 (s, 1H), 6.38 (d, J=9.4 Hz, 1H), 6.50-6.57 (m, 1H), 6.65 and 6.79 (d, J=8.3 Hz, 1H), 6.86 and 6.89 (d, J=2.4 Hz, 1H), 7.02-7.14 (m, 2H), 7.34-7.37 (m, 1H), 7.74 (d, J=8.2 Hz, 1H).

MS m/z ([M+H]$^+$) 584.

Step 4: Preparation of 2-(tert-butoxy)-2-{3-[1-(cyclobutylmethyl)-6-oxo-1,6-dihydropyridin-3-yl]-2-(3,4-dihydro-2H-1-benzopyran-6-yl)-6-(trifluoromethyl)phenyl}acetic acid (Example 30)

Using the procedure described in example 25, step 4, the intermediate methyl 2-(tert-butoxy)-2-{3-[1-(cyclobutylmethyl)-6-oxo-1,6-dihydropyridin-3-yl]-2-(3,4-dihydro-2H-1-benzopyran-6-yl)-6-(trifluoromethyl)phenyl}acetate (30c) (59 mg, 0.101 mmol) is converted into 2-(tert-butoxy)-2-{3-[1-(cyclobutylmethyl)-6-oxo-1,6-dihydropyridin-3-yl]-2-(3,4-dihydro-2H-1-benzopyran-6-yl)-6-(trifluoromethyl)phenyl}acetic acid (example 30) (37 mg, 0.065 mmol, 63%) as a white solid.

$^1$H NMR (400 MHz, CDCl$_3$) δ 0.96 (s, 9H), 1.58-1.71 (m, 2H), 1.82-2.04 (m, 6H), 2.49-2.60 (m, 2H), 2.73-2.84 (m, 1H), 3.58-3.72 (m, 1H), 3.85-4.00 (m, 1H), 4.15-4.22 (m, 2H), 5.27 (bs, 1H), 6.41 (d, J=9.3 Hz, 1H), 6.49-6.89 (m, 3H), 7.07-7.10 (m, 1H), 7.37-7.50 (m, 2H), 7.75 (d, J=8.2 Hz, 1H).

MS m/z ([M+H]$^+$) 570.

Example 31

Synthesis of 2-(tert-butoxy)-2-{3-[1-(2-cyclopropylethyl)-6-oxo-1,6-dihydropyridin-3-yl]-2-(3,4-dihydro-2H-1-benzopyran-6-yl)-6-(trifluoromethyl)phenyl}acetic acid

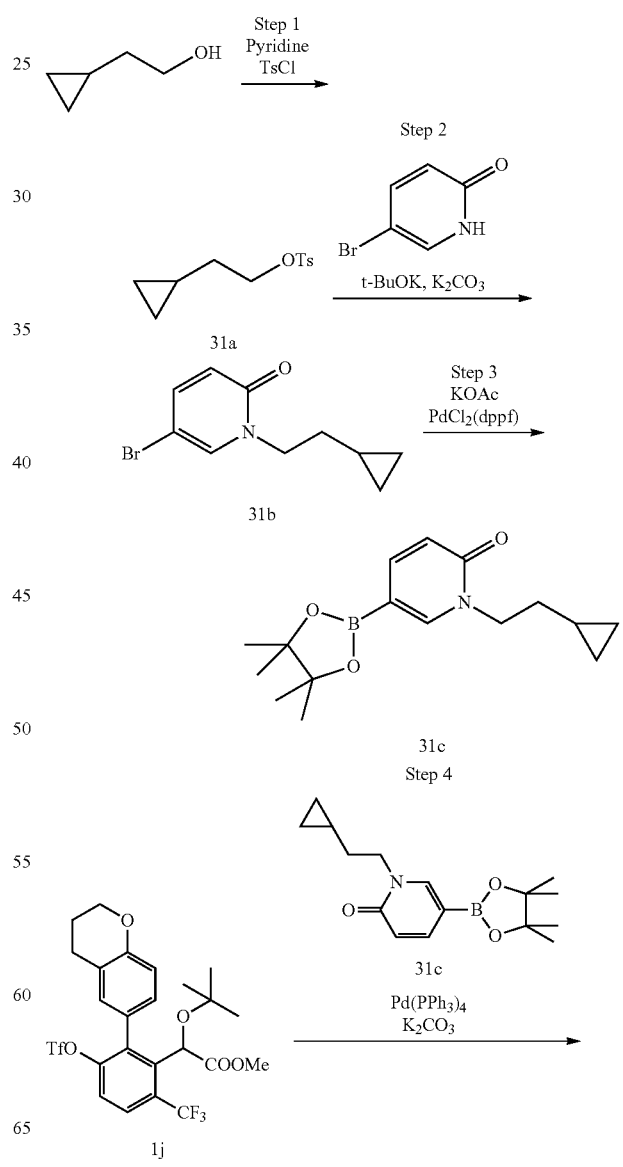

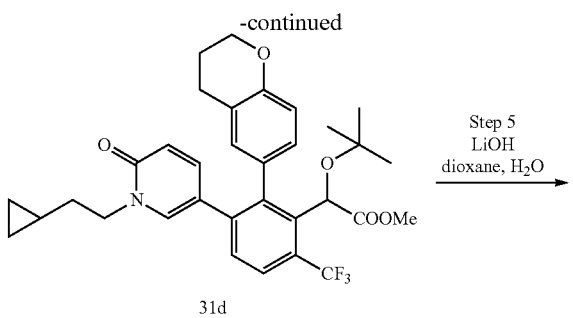

Step 5
LiOH
dioxane, H₂O

31d

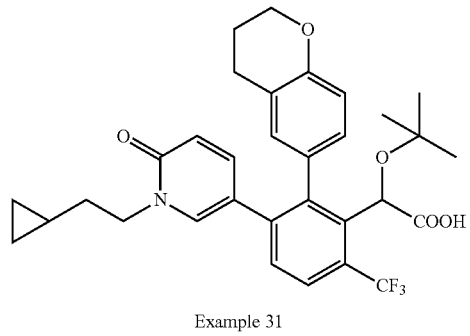

Example 31

Step 1: Preparation of Intermediate 2-cyclopropylethyl-4-methylbenzene-1-sulfonate (31a)

Pyridine (1.41 mL, 17.42 mmol) and p-Toluenesulfonyl chloride (2.10 g, 11.03 mmol) were added to a solution of 2-cyclopropylethanol (1.00 g, 11.61 mmol) in dichloromethane (10 mL). The reaction mixture was stirred at room temperature overnight. Water (20 mL) was added, and the mixture was extracted with dichloromethane (2×20 mL). The organic layer was successively washed with 10% aqueous hydrochloric acid (20 mL) and saturated solution of sodium bicarbonate (20 mL), then dried over sodium sulfate and concentrated in vacuo. The residue was purified by flash chromatography on silica gel (cyclohexane/ethyl acetate: 80/20) to provide 2-cyclopropylethyl 4-methylbenzene-1-sulfonate (31a) (2.10 g, 8.74 mmol, 75%) as a colorless oil.

$^1$H NMR (400 MHz, CDCl$_3$) δ −0.02-0.06 (m, 2H), 0.35-0.46 (m, 2H), 0.58-0.74 (m, 1H), 1.54 (q, J=6.7 Hz, 2H), 2.43 (s, 3H), 4.09 (t, J=6.7 Hz, 2H), 7.34 (d, J=8.1 Hz, 1H), 7.80 (d, J=8.1 Hz, 1H).

Step 2: Preparation of Intermediate 5-bromo-1-(2-cyclopropylethyl)-1,2-dihydropyridin-2-one (31b)

Using the procedure described in example 30, step 1, the intermediate 2-cyclopropylethyl 4-methylbenzene-1-sulfonate (31a) (2.02 g, 8.40 mmol) is converted by reaction with 5-bromo-2(1H)-pyridone (0.75 g, 4.31 mmol) into 5-bromo-1-(2-cyclopropylethyl)-1,2-dihydropyridin-2-one (31b) (743 mg, 3.07 mmol, 71%) after purification by flash chromatography on silica gel (dichloromethane/ethyl acetate 100/0 to 85/15).

$^1$H NMR (400 MHz, CDCl$_3$) δ −0.01-0.08 (m, 2H), 0.43-0.51 (m, 2H), 0.59-0.72 (m, 1H), 1.58-1.67 (m, 2H), 3.97 (t, J=7.0 Hz, 2H), 6.47 (d, J=9.6 Hz, 1H), 7.33 (dd, J=2.7 Hz, J=9.6 Hz, 1H), 7.41 (d, J=2.7 Hz, 1H).

MS m/z ([M+H]$^+$) 242/244.

Step 3: Preparation of Intermediate 1-(2-cyclopropylethyl)-5-(tetramethyl-1,3,2-dioxaborolan-2-yl)-1,2-dihydropyridin-2-one (31c)

Using the procedure described in example 25, step 2, the intermediate 5-bromo-1-(2-cyclopropylethyl)-1,2-dihydropyridin-2-one (31b) (800 mg, 3.31 mmol) is converted into 1-(2-cyclopropylethyl)-5-(tetramethyl-1,3,2-dioxaborolan-2-yl)-1,2-dihydropyridin-2-one (31c) (677 mg, 2.34 mmol, 71%) after purification by flash chromatography on silica gel (dichloromethane/ethyl acetate: 100/0 to 75/25).

$^1$H NMR (300 MHz, CDCl$_3$) δ −0.02-0.08 (m, 2H), 0.38-0.49 (m, 2H), 0.59-0.75 (m, 1H), 1.30 (s, 12H), 1.65 (q, J=7.1 Hz, 2H), 4.01 (t, J=7.1 Hz, 2H), 6.49 (d, J=9.1 Hz, 1H), 7.57 (dd, J=2.0 Hz, J=9.1 Hz, 1H), 7.74 (d, J=2.0 Hz, 1H).

MS m/z ([M+H]$^+$) 290.

Step 4: Preparation of Intermediate methyl 2-(tert-butoxy)-2-{3-[1-(2-cyclopropylethyl)-6-oxo-1,6-dihydropyridin-3-yl]-2-(3,4-dihydro-2H-1-benzopyran-6-yl)-6-(trifluoromethyl)phenyl}acetate (31d)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (70 mg, 0.123 mmol) is converted by reaction with 1-(cyclopropylethyl)-5-(tetramethyl-1,3,2-dioxaborolan-2-yl)-1,2-dihydropyridin-2-one (31c) (89 mg, 0.31 mmol) into methyl 2-(tert-butoxy)-2-{3-[1-(2-cyclopropylethyl)-6-oxo-1,6-dihydropyridin-3-yl]-2-(3,4-dihydro-2H-1-benzopyran-6-yl)-6-(trifluoromethyl)phenyl}acetate (31d) (54 mg, 0.092 mmol, 75%), after purification by preparative TLC (dichloromethane/ethyl acetate: 70/30).

$^1$H NMR (400 MHz, CDCl$_3$) δ −0.01-0.01 (m, 2H), 0.39-0.44 (m, 2H), 0.50-0.60 (m, 1H), 0.94 and 0.96 (s, 9H), 1.31-1.52 (m, 2H), 1.93-2.06 (m, 2H), 2.51-2.64 (m, 1H), 2.73 (t, J=6.3 Hz, 1H), 3.64-3.81 (m, 4H), 3.91-4.04 (m, 1H), 4.15-4.22 (m, 2H), 5.14 and 5.16 (s, 1H), 6.36 and 6.39 (d, J=9.4 Hz, 1H), 6.50-6.59 (m, 1H), 6.64 and 6.76 (d, J=8.3 Hz, 1H), 6.91 and 6.94 (d, J=2.4 Hz, 1H), 7.02-7.12 (m, 2H), 7.37 and 7.38 (d, J=8.2 Hz, 1H), 7.74 (d, J=8.2 Hz, 1H).

MS m/z ([M+H]$^+$) 584.

Step 5: Preparation of 2-(tert-butoxy)-2-{3-[1-(2-cyclopropylethyl)-6-oxo-1,6-dihydropyridin-3-yl]-2-(3,4-dihydro-2H-1-benzopyran-6-yl)-6-(trifluoromethyl)phenyl}acetic acid (Example 31)

Using the procedure described in example 25, step 4, the methyl 2-(tert-butoxy)-2-{3-[1-(2-cyclopropylethyl)-6-oxo-1,6-dihydropyridin-3-yl]-2-(3,4-dihydro-2H-1-benzopyran-6-yl)-6-(trifluoromethyl)phenyl}acetate (31d) (54 mg, 0.092 mmol) is converted into 2-(tert-butoxy)-2-{3-[1-(2-cyclopropylethyl)-6-oxo-1,6-dihydropyridin-3-yl]-2-(3,4-dihydro-2H-1-benzopyran-6-yl)-6-(trifluoro methyl)phenyl}acetic acid (example 31) (35 mg, 0.061 mmol, 66%) as a white solid.

$^1$H NMR (400 MHz, CDCl$_3$) δ −0.02 (s, 2H), 0.40-0.43 (m, 2H), 0.50-0.58 (m, 1H), 0.96 (s, 9H), 1.22-1.49 (m, 2H), 1.90-2.00 (m, 2H), 2.51-2.61 (m, 1H), 2.72-2.84 (m, 1H), 3.64-3.73 (m, 1H), 3.93-4.03 (m, 1H), 4.16-4.21 (m, 2H), 5.28 (s, 1H), 6.39 and 6.43 (d, J=9.4 Hz, 1H), 6.49-6.84 (m, 2H), 6.90-6.93 (m, 1H), 7.06-7.15 (m, 1H), 7.39-7.50 (m, 2H), 7.78 (d, J=8.2 Hz, 1H)

MS m/z ([M+H]$^+$) 570. .

Example 32

Synthesis of 2-(tert-butoxy)-2-[2-(3,4-dihydro-2H-1-benzopyran-6-yl)-3-[1-(2-methylpropyl)-6-oxo-1,6-dihydropyridin-3-yl]-6-(trifluoromethyl)phenyl]acetic acid

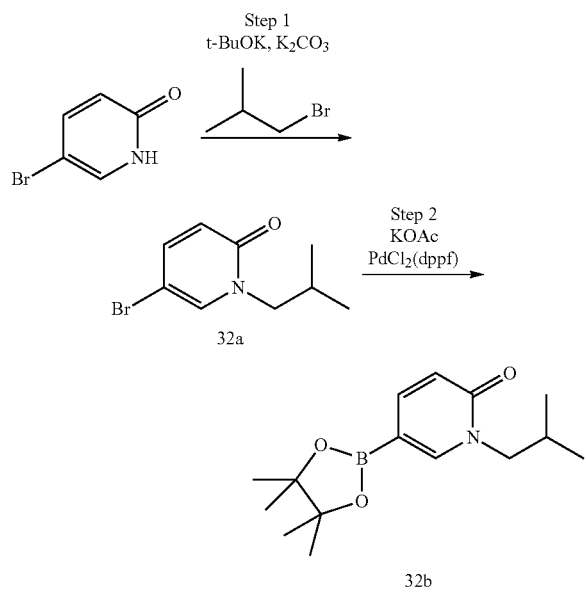

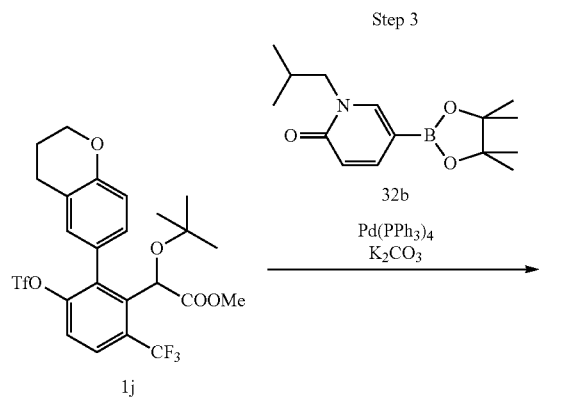

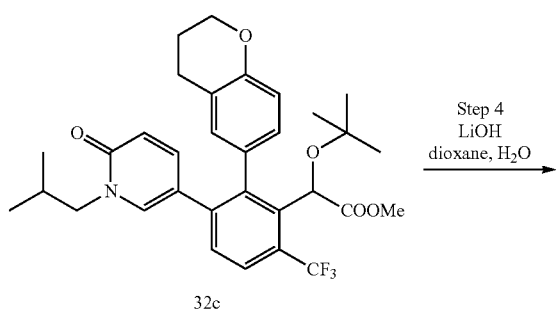

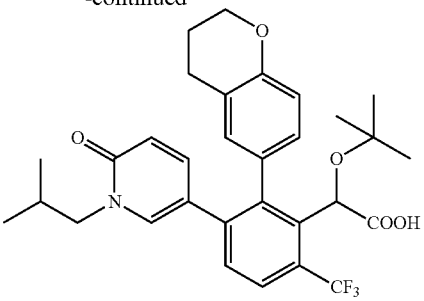

Example 32

Step 1: Preparation of Intermediate 5-bromo-1-(2-methylpropyl)-1,2-dihydropyridin-2-one (32a)

Using the procedure described in example 30, step 1, 5-bromo-2(1H)-pyridone (0.5 g, 2.87 mmol) is converted by reaction with 1-bromo-2-methylpropane (0.63 mL, 5.75 mmol), after purification by flash chromatography on silica gel (dichloromethane/ethyl acetate 100/0 to 80/20) to 5-bromo-1-(2-methylpropyl)-1,2-dihydropyridin-2-one (32a) (416 mg, 1.81 mmol, 63%).

$^1$H NMR (400 MHz, CDCl$_3$) δ 0.93 (d, J=6.7 Hz, 6H), 2.07-2.21 (m, 1H), 3.69 (d, J=7.6 Hz, 2H), 6.44-6.51 (m, 1H), 7.29-7.35 (m, 2H).

MS m/z ([M+H]$^+$) 230/232.

Step 2: Preparation of Intermediate 1-(2-methylpropyl)-5-(tetramethyl-1,3,2-dioxaborolan-2-yl)-1,2-dihydropyridin-2-one (32b)

Using the procedure described in example 25, step 2, the intermediate 5-bromo-1-(2-methylpropyl)-1,2-dihydropyridin-2-one (32a) (400 mg, 1.74 mmol) is converted, after purification by flash chromatography on silica gel (dichloromethane/ethyl acetate 100/0 to 90/10) and trituration in pentane, to 1-(2-methylpropyl)-5-(tetramethyl-1,3,2-dioxaborolan-2-yl)-1,2-dihydropyridin-2-one (32b) (250 mg, 0.90 mmol, 52%).

$^1$H NMR (400 MHz, CDCl$_3$) δ 0.93 (d, J=6.7 Hz, 6H), 1.31 (s, 12H), 2.14-2.26 (m, 1H), 3.75 (d, J=7.5 Hz, 1H), 6.50 (d, J=9.1 Hz, 1H), 7.57 (dd, J=2.0 Hz, J=9.1 Hz, 1H), 7.66 (d, J=2.0 Hz, 1H),

MS m/z ([M+H]$^+$) 278.

Step 3: Preparation of Intermediate methyl 2-(tert-butoxy)-2-[2-(3,4-dihydro-2H-1-benzopyran-6-yl)-3-[1-(2-methylpropyl)-6-oxo-1,6-dihydropyridin-3-yl]-6-(trifluoromethyl)phenyl]acetate (32c)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (70 mg, 0.123 mmol) is converted by reaction with 1-(2-methylpropyl)-5-(tetramethyl-1,3,2-dioxaborolan-2-yl)-1,2-dihydropyridin-2-one (32b) (85 mg, 0.307 mmol), after purification by preparative TLC (dichloromethane/ethyl acetate 60/40) to methyl 2-(tert-butoxy)-2-[2-(3,4-dihydro-2H-1-benzopyran-6-yl)-3-[1-(2-methylpropyl)-6-oxo-1,6-dihydropyridin-3-yl]-6-(trifluoromethyl)phenyl]acetate (32c) (58 mg, 0.101 mmol, 82%).

$^1$H NMR (300 MHz, CDCl$_3$) δ 0.76-0.86 (m, 6H), 0.94 and 0.95 (s, 9H), 1.81-2.07 (m, 3H), 2.46-2.66 (m, 1H), 2.68-2.76 (m, 1H), 3.38-3.53 (m, 1H), 3.62-3.82 (m, 4H), 4.10-4.26 (m, 2H), 5.13 and 5.15 (s, 1H), 6.38 and 6.39 (d, J=9.3 Hz, 1H), 6.48-6.60 (m, 1H), 6.64 and 6.77 (d, J=8.3 Hz, 1H), 6.84 and 6.87 (d, J=2.5 Hz, 1H), 7.02-7.16 (m, 2H), 7.36 (d, J=8.2 Hz, 1H), 7.74 (d, J=8.2 Hz, 1H).

MS m/z ([M+H]$^+$) 572.

Step 4: Preparation of 2-(tert-butoxy)-2-[2-(3,4-dihydro-2H-1-benzopyran-6-yl)-3-[1-(2-methylpropyl)-6-oxo-1,6-dihydropyridin-3-yl]-6-(trifluoromethyl)phenyl]acetic acid (Example 32)

Using the procedure described in example 25, step 4, methyl 2-(tert-butoxy)-2-[2-(3,4-dihydro-2H-1-benzopyran-6-yl)-3-[1-(2-methylpropyl)-6-oxo-1,6-dihydropyridin-3-yl]-6-(trifluoromethyl)phenyl]acetate (32c) (57 mg, 0.100 mmol) is converted to 2-(tert-butoxy)-2-[2-(3,4-dihydro-2H-1-benzopyran-6-yl)-3-[1-(2-methylpropyl)-6-oxo-1,6-dihydropyridin-3-yl]-6-(trifluoromethyl)phenyl]acetic acid (example 32) (45 mg, 0.081 mmol, 80%).

$^1$H NMR (300 MHz, CDCl$_3$) δ 0.77-0.83 (m, 6H), 0.97 (s, 9H), 1.83-2.08 (m, 3H), 2.50-2.65 (m, 1H), 2.66-2.86 (m, 1H), 3.31-3.53 (m, 1H), 3.61-3.86 (m, 1H), 4.10-4.26 (m, 2H), 5.28 and 5.30 (s, 1H), 6.41 and 6.42 (d, J=9.3 Hz, 1H), 6.47-6.59 (m, 1H), 6.61-6.89 (m, 2H), 7.05-7.15 (m, 1H), 7.36-7.56 (m, 2H), 7.75 (d, J=8.2 Hz, 1H).

MS m/z ([M+H]$^+$) 558.

Example 33

Synthesis of 2-(tert-butoxy)-2-[2-(3,4-dihydro-2H-1-benzopyran-6-yl)-3-(1-ethyl-2-oxo-1,2-dihydropyrindin-4-yl)-6-(trifluoromethyl)phenyl]acetic acid

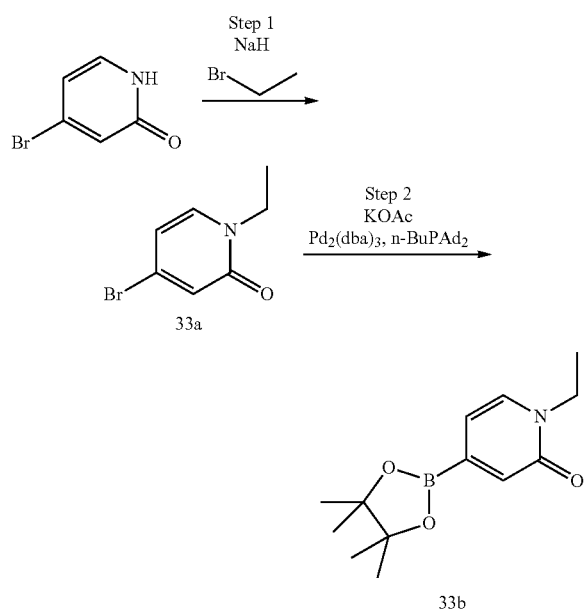

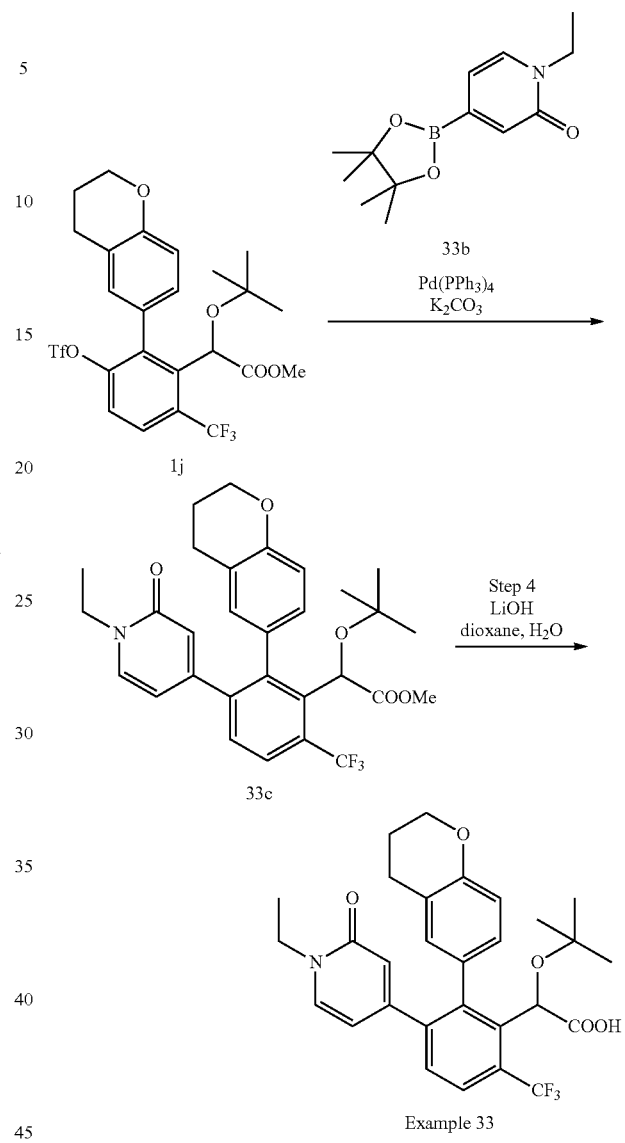

Example 33

Step 1: Preparation of Intermediate 4-bromo-1-ethyl-1,2-dihydropyridin-2-one (33a)

Using the procedure described in example 25, step 1,2-hydroxy-4-bromopyridine (1.00 g, 5.75 mmol) is converted by reaction with iodoethane (1.39 mL, 17.24 mmol), after purification by preparative TLC (dichloromethane/ethyl acetate 100/0 to 85/15) into 4-bromo-1-ethyl-1,2-dihydropyridin-2-one (33a) (981 mg, 4.86 mmol, 84%).

$^1$H NMR (300 MHz, CDCl$_3$) δ 1.34 (t, J=7.2 Hz, 3H), 3.94 (q, J=7.2 Hz, 2H), 6.33 (dd, J=2.1 Hz, J=7.2 Hz, 1H), 6.82 (d, J=2.1 Hz, 1H), 7.13 (d, J=7.2 Hz, 1H).

MS m/z ([M+H]$^+$) 202/204.

Step 2: Preparation of Intermediate 1-ethyl-4-(tetramethyl-1,3,2-dioxaborolan-2-yl)-1,2-dihydropyridin-2-one (33b)

Using the procedure described in example 28, step 2,4-bromo-1-ethyl-1,2-dihydropyridin-2-one (33a) (300 mg, 1.48 mmol) is converted, after purification by preparative TLC (dichloromethane/methanol 95/5), into 1-ethyl-4-(tetramethyl-1,3,2-dioxaborolan-2-yl)-1,2-dihydropyridin-2-one (33b) (70 mg, 0.28 mmol, 19%).

$^1$H NMR (300 MHz, CDCl$_3$) δ 1.31 (s, 12H), 1.33 (t, J=7.2 Hz, 3H), 3.97 (q, J=7.2 Hz, 2H), 6.40 (dd, J=1.2 Hz, J=6.7 Hz, 1H), 7.00 (bs, 1H), 7.22 (d, J=6.7 Hz, 1H).

Step 3: Preparation of Intermediate methyl 2-(tert-butoxy)-2-[2-(3,4-dihydro-2H-1-benzopyran-6-yl)-3-(1-ethyl-2-oxo-1,2-dihydropyridin-4-yl)-6-(trifluoromethyl)phenyl]acetate (33c)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (70 mg, 0.123 mmol) is converted by reaction with 1-ethyl-4-(tetramethyl-1,3,2-dioxaborolan-2-yl)-1,2-dihydropyridin-2-one (33b) (37 mg, 0.147 mmol), after purification by preparative TLC (dichloromethane/ethyl acetate 50/50) to methyl 2-(tert-butoxy)-2-[2-(3,4-dihydro-2H-1-benzopyran-6-yl)-3-(1-ethyl-2-oxo-1,2-dihydropyridin-4-yl)-6-(trifluoromethyl)phenyl]acetate (33c) (37 mg, 0.068 mmol, 55%).

$^1$H NMR (400 MHz, CDCl$_3$) δ 0.93 (s, 9H), 1.26-1.33 (m, 3H), 1.87-1.98 (m, 1H), 1.98-2.06 (m, 1H), 2.47-2.65 (m, 1H), 2.65-2.82 (m, 1H), 3.72 (s, 3H), 3.78-4.01 (m, 2H), 4.12-4.24 (m, 2H), 5.15 and 5.16 (s, 1H), 5.63 and 5.68 (dd, J=1.9 Hz, J=7.0 Hz, 1H), 6.42 and 6.49 (d, J=1.7 Hz, 1H), 6.53-6.76 (m, 2H), 6.92 and 6.95 (d, J=7.0 Hz, 1H), 7.05-7.15 (m, 1H), 7.36-7.43 (m, 1H), 7.75 and 7.76 (d, J=8.2 Hz, 1H).

MS m/z ([M+H]$^+$) 544.

Step 4: Preparation of 2-(tert-butoxy)-2-[2-(3,4-dihydro-2H-1-benzopyran-6-yl)-3-(1-ethyl-2-oxo-1,2-dihydropyridin-4-yl)-6-(trifluoromethyl)phenyl]acetic acid (Example 33)

Using the procedure described in example 25, step 4, methyl 2-(tert-butoxy)-2-[2-(3,4-dihydro-2H-1-benzopyran-6-yl)-3-(1-ethyl-2-oxo-1,2-dihydropyridin-4-yl)-6-(trifluoromethyl)phenyl]acetate (33c) (37 mg, 0.068 mmol) is converted into 2-(tert-butoxy)-2-[2-(3,4-dihydro-2H-1-benzopyran-6-yl)-3-(1-ethyl-2-oxo-1,2-dihydropyridin-4-yl)-6-(trifluoromethyl)phenyl]acetic acid (example 33) (25 mg, 0.047 mmol, 69%).

$^1$H NMR (400 MHz, CDCl$_3$) δ 0.94 (s, 9H), 1.25-1.35 (m, 3H), 1.87-1.97 (m, 1H), 1.97-2.07 (m, 1H), 2.47-2.67 (m, 1H), 2.67-2.86 (m, 1H), 3.76-4.05 (m, 2H), 4.17 and 4.20 (t, J=5.1 Hz, 2H), 5.29 and 5.33 (s, 1H), 5.62 and 5.67 (dd, J=1.6 Hz, J=7.0 Hz, 1H), 6.43-6.84 (m, 3H), 6.92 and 6.95 (d, J=7.0 Hz, 1H), 7.40-7.54 (m, 2H), 7.75 and 7.78 (d, J=8.2 Hz, 1H).

MS m/z ([M+H]$^+$) 530.

Example 34

Synthesis of 2-(tert-butoxy)-2-[3-(1-cyclobutylmethyl-6-oxo-1,6-dihydro-pyridin-3-yl)-2-(3,4-dihydro-2H-1-benzopyran-6-yl)-6-methylphenyl]acetic acid

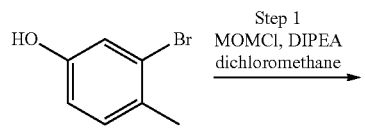
Step 1
MOMCl, DIPEA
dichloromethane

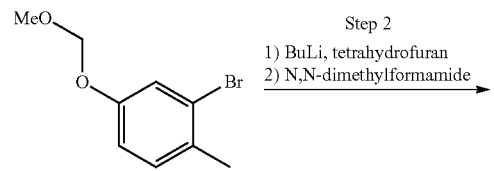
Step 2
1) BuLi, tetrahydrofuran
2) N,N-dimethylformamide

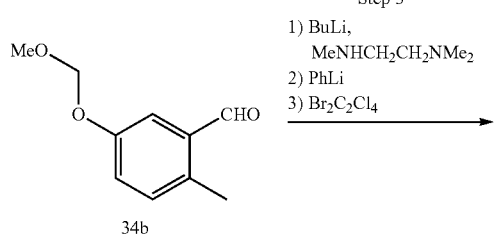
Step 3
1) BuLi, MeNHCH$_2$CH$_2$NMe$_2$
2) PhLi
3) Br$_2$C$_2$Cl$_4$

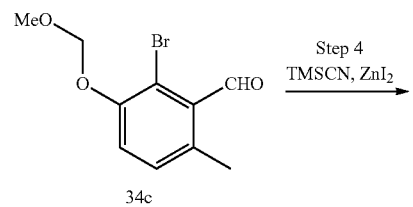
Step 4
TMSCN, ZnI$_2$

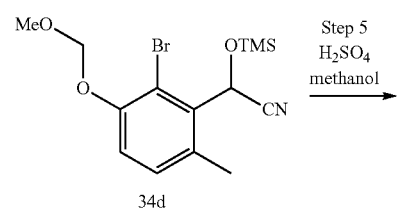
Step 5
H$_2$SO$_4$
methanol

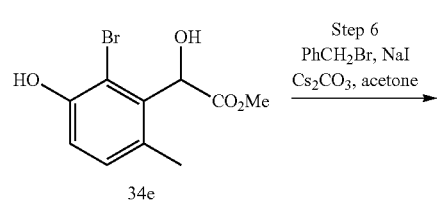
Step 6
PhCH$_2$Br, NaI
Cs$_2$CO$_3$, acetone

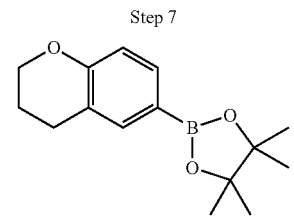

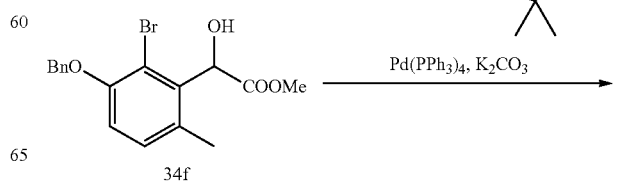
Step 7
Pd(PPh$_3$)$_4$, K$_2$CO$_3$

-continued

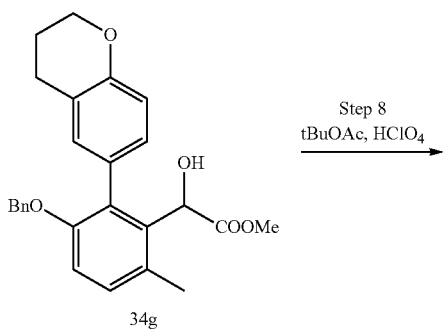

34g

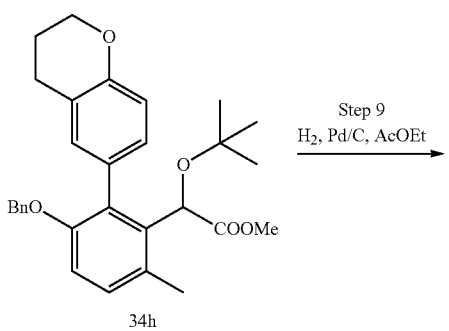

34h

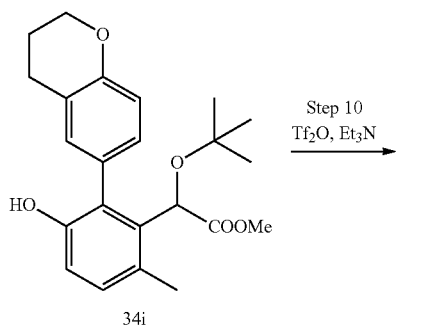

34i

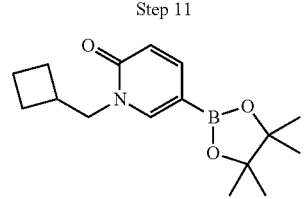

30b
Pd(PPh$_3$)$_4$, K$_2$CO$_3$
Dioxane, Eau

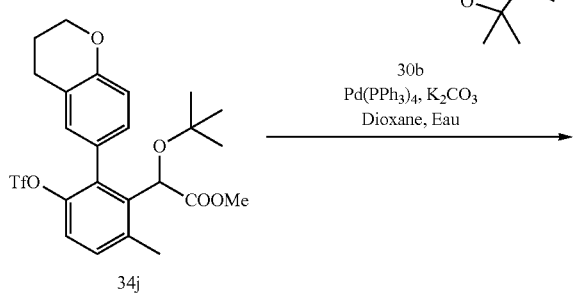

34j

-continued

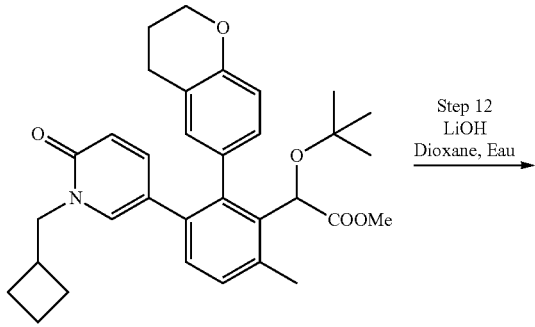

34k

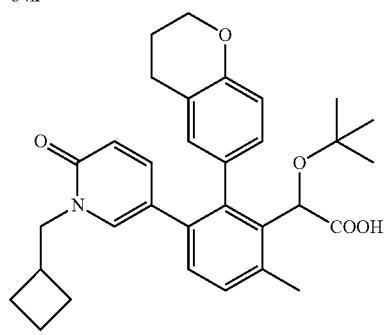

Example 34

Step 1: Preparation of Intermediate 2-bromo-4-methoxymethoxy-1-methyl-benzene (34a)

To a solution of 3-bromo-4-methylphenol (3.87 g, 20.7 mmol) in anhydrous dichloromethane (40 mL) under nitrogen atmosphere at 0° C. were successively added diisopropylethylamine (5.4 mL, 31.0 mmol) and chloromethyl methyl ether (2.0 mL, 26.9 mmol). The mixture was stirred at 0° C. for 3 hours before adding water (40 mL). Layers were separated and the aqueous one was extracted with dichloromethane (40 mL). The combined organic layers were washed with a 2 M sodium hydroxide solution (30 mL), dried over sodium sulfate and concentrated in vacuo to provide 2-bromo-4-methoxymethoxy-1-methyl-benzene (34a) (4.55 g, 19.7 mmol, 95%) as a yellow oil.

$^1$H NMR (400 MHz, CDCl$_3$) δ 2.33 (s, 3H), 3.46 (s, 3H), 5.13 (s, 2H), 6.89 (dd, J=2.4 Hz, J=8.4 Hz, 1H), 7.12 (d, J=8.4 Hz, 1H), 7.25 (d, J=2.4 Hz, 1H).

Step 2: Preparation of Intermediate 5-methoxymethox-2-methyl-benzaldehyde (34b)

To a solution of 2-bromo-4-methoxymethoxy-1-methyl-benzene (34a) (4.54 g, 19.6 mmol) in anhydrous tetrahydrofuran (100 mL) under nitrogen atmosphere at −78° C. was dropwise added a 1.6 M n-butyllithium solution in hexanes (15.3 mL, 24.5 mmol). The mixture was stirred at −78° C. for 30 minutes and N,N-dimethylformamide (2.3 mL, 29.7 mmol) was added. After 30 minutes at −78° C., water was added (100 mL). The layers were separated. The aqueous layer was extracted with ethyl acetate (2×50 mL). The combined organic layers were washed with brine (50 mL), dried over sodium sulfate and concentrated in vacuo to provide 5-methoxymethox-2-methyl-benzaldehyde (34b) (3.29 g, 18.2 mmol, 93%) as a yellow oil.

¹H NMR (300 MHz, CDCl₃) δ 2.60 (s, 3H), 3.48 (s, 3H), 5.20 (s, 2H), 7.14-7.20 (m, 2H), 7.47 (s, 1H), 10.24 (s, 1H).

Step 3: Preparation of Intermediate 2-bromo-3-methoxymethox-6-methyl-benzaldehyde (34c)

To a solution of N,N',N'-trimethylethylenediamine (2.6 mL, 20 mmol) in anhydrous toluene (30 mL) at 0° C. under nitrogen atmosphere was dropwise added a 1.6 M n-butyllithium solution in hexanes (12 mL, 19.2 mmol). The mixture was stirred at room temperature for 15 minutes before adding a solution of 5-methoxymethox-2-methyl-benzaldehyde (34b) (3.28 g, 18.2 mmol) in anhydrous toluene (10 mL). After 15 minutes at room temperature, the mixture was cooled with an ice bath and a 1.8 M phenyllithium solution in dibutyl ether (30 mL, 54 mmol) was dropwise added. The mixture was stirred at room temperature overnight. Anhydrous tetrahydrofuran (50 mL) was added to the resulting suspension and the mixture was cooled at −78° C. Dibromotetrachloroethane (17.8 g, 54.6 mmol) was portionwise added. The mixture was stirred at room temperature for 90 minutes before adding water (100 mL). The layers were separated. The aqueous layer was extracted with ethyl acetate (2×100 mL). The combined organic layers were washed with 1 M hydrochloric acid (100 mL), brine (100 mL), dried over sodium sulfate and concentrated in vacuo. The residue was purified by flash chromatography on silica gel (dichloromethane/ethyl acetate 30/70) to provide 2-bromo-3-methoxymethox-6-methyl-benzaldehyde (34c) (2.78 g, 10.7 mmol, 59%) as a yellow solid.

¹H NMR (300 MHz, CDCl₃) δ 2.50 (s, 3H), 3.53 (s, 3H), 5.25 (s, 2H), 7.13 (d, J=8.4 Hz, 1H), 7.23 (d, J=8.4 Hz, 1H), 10.55 (s, 1H).

MS m/z ([M+H]⁺) 259/261.

Step 4: Preparation of Intermediate 2-(2-bromo-3-methoxymethoxy-6-methylphenyl)-2-trimethylsilanyloxy-acetonitrile (34d)

To a solution of 2-bromo-3-methoxymethox-6-methyl-benzaldehyde (34c) (2.78 g, 10.7 mmol) in anhydrous dichloromethane (40 mL) at 0° C. under nitrogen atmosphere, were successively added zinc iodide (685 mg, 2.15 mmol) and trimethylsilylcyanide (2.04 mL, 16.1 mmol). The mixture was stirred at 0° C. for 90 minutes before adding a saturated solution of sodium hydrogenocarbonate (40 mL). The layers were separated. The aqueous layer was extracted with dichloromethane (40 mL). The combined organic layers were dried over sodium sulfate and concentrated in vacuo to provide 2-(2-bromo-3-methoxymethoxy-6-methyl-phenyl)-2-trimethylsilanyloxy-acetonitrile (34d) (3.78 g, 10.5 mmol, 98%) as a yellow oil.

¹H NMR (300 MHz, CDCl₃) δ 0.20 (s, 9H), 2.61 (s, 3H), 3.51 (s, 3H), 5.22 (s, 2H), 6.40 (s, 1H), 7.08 (d, J=8.4 Hz, 1H), 7.13 (d, J=8.4 Hz, 1H).

Step 5: Preparation of Intermediate methyl 2-(2-bromo-3-hydroxy-6-methylphenyl)-2-hydroxyacetate (34e)

To a solution of 2-(2-bromo-3-methoxymethoxy-6-methyl-phenyl)-2-trimethylsilanyloxy-acetonitrile (34d) (3.78 g, 10.5 mmol) in anhydrous methanol (50 mL) at 0° C. under nitrogen atmosphere was dropwise added sulfuric acid (23 mL). The mixture was refluxed overnight then cooled at room temperature and poured in water (150 mL). The aqueous layer was extracted with diethyl ether (2×50 mL) then with ethyl acetate (2×50 mL). The combined organic layers were washed with a saturated solution of sodium hydrogenocarbonate (100 mL), brine (100 mL), dried over sodium sulfate and concentrated in vacuo to provide methyl 2-(2-bromo-3-hydroxy-6-methyl-phenyl)-2-hydroxyacetate (34e) (2.58 g, 9.38 mmol, 89%) as a brown oil.

¹H NMR (300 MHz, CDCl₃) δ 2.33 (s, 3H), 3.43 (d, J=3.6 Hz, 1H), 3.79 (s, 3H), 5.56 (s, 1H), 5.72 (d, J=3.6 Hz, 1H), 6.93 (d, J=8.4 Hz, 1H), 7.04 (d, J=8.4 Hz, 1H).

Step 6: Preparation of Intermediate methyl 2-(3-benzyloxy-2-bromo-6-methylphenyl)-2-hydroxyacetate (34f)

To a solution of methyl 2-(2-bromo-3-hydroxy-6-methylphenyl)-2-hydroxyacetate (34e) (2.58 g, 9.38 mmol) in acetone (50 mL) were successively added cesium carbonate (3.67 g, 11.25 mmol) benzyl bromide (1.23 mL, 10.32 mmol) and sodium iodide (281 mg, 1.88 mmol). The mixture was refluxed for 45 minutes then concentrated in vacuo. Water (50 mL) was added to the residue. The aqueous layer was extracted with ethyl acetate (2×50 mL). The combined organic layers were washed with a 2M sodium hydroxide solution (30 mL), brine (30 mL), dried over sodium sulfate and concentrated in vacuo. The residue was purified by flash chromatography on silica gel (cyclohexane/ethyl acetate: 80/20) to provide methyl 2-(3-benzyloxy-2-bromo-6-methylphenyl)-2-hydroxyacetate (34f) (2.38 g, 6.51 mmol, 69%) as a white solid.

¹H NMR (300 MHz, CDCl₃) δ 2.34 (s, 3H), 3.49 (d, J=4.4 Hz, 1H), 3.78 (s, 3H), 5.13 (s, 2H), 5.86 (d, J=4.4 Hz, 1H), 6.84 (d, J=8.4 Hz, 1H), 7.06 (d, J=8.4 Hz, 1H), 7.30-7.34 (m, 1H), 7.37-7.41 (m, 2H), 7.47 (d, J=7.4 Hz, 2H).

MS m/z ([M+H−H₂O]⁺) 347/349.

Step 7: Preparation of Intermediate methyl 2-[3-benzyloxy-2-(3,4-dihydro-2H-1-benzopyran-6-yl)-6-methylphenyl]-2-hydroxyacetate (34g)

To a degassed mixture of methyl 2-(3-benzyloxy-2-bromo-6-methylphenyl)-2-hydroxyacetate (34f) (383 mg, 1.05 mmol), sodium carbonate (333 mg, 3.15 mmol), 6-(4,4,5,5-tetramethyl-1,3,2-dioxaborolan-2-yl)chroman (327 mg, 1.26 mmol) in dioxane (4 mL) and water (0.8 mL) was added palladium tetrakis(triphenylphosphine) (121 mg, 0.10 mmol). The mixture was heated at 120° C. overnight. Water (10 mL) was added. The aqueous layer was extracted with ethyl acetate (2×10 mL). The combined organic layers were washed with brine (10 mL), dried over sodium sulfate and concentrated in vacuo. The residue was purified by flash chromatography on silica gel (cyclohexane/ethyl acetate: 80/20) to provide methyl 2-[3-benzyloxy-2-(3,4-dihydro-2H-1-benzopyran-6-yl)-6-methylphenyl]-2-hydroxyacetate (34g) (347 mg, 0.83 mmol, 79%) as a yellow foam.

¹H NMR (300 MHz, CDCl₃) δ 2.01-2.08 (m, 2H), 2.26 and 2.28 (s, 3H), 2.78-2.82 (m, 2H), 3.09 and 3.11 (d, J=2.8 Hz, 1H), 3.70 and 3.72 (s, 3H), 4.21-4.26 (m, 2H), 4.97 (s, 2H), 5.26 (d, J=2.8 Hz, 1H), 6.81-6.89 (m, 2H), 6.98-7.16 (m, 5H), 7.22-7.30 (m, 3H).

MS m/z ([M+H−H₂O]⁺) 401.

Step 8: Preparation of Intermediate methyl 2-(tert-butoxy)-2-[3-benzyloxy-2-(3,4-dihydro-2H-1-benzopyran-6-yl)-6-methylphenyl]acetate (34h)

Using the procedure described in example 1, step 8, the intermediate methyl 2-[3-benzyloxy-2-(3,4-dihydro-2H-1- benzopyran-6-yl)-6-methylphenyl]-2-hydroxyacetate (34g) (347 mg, 0.83 mmol) is converted into the intermediate methyl 2-(tert-butoxy)-2-[3-benzyloxy-2-(3,4-dihydro-2H-1-benzopyran-6-yl)-6-methylphenyl]acetate (34h) (263 mg, 0.55 mmol, 66%) after purification by preparative TLC (cyclohexane/ethyl acetate 80/20).

$^1$H NMR (300 MHz, CDCl$_3$) δ 0.96 (s, 9H), 2.00-2.09 (m, 2H), 2.35 and 2.36 (s, 3H), 2.72-2.82 (m, 2H), 3.70 and 3.71 (s, 3H), 4.22-4.26 (m, 2H), 4.88-5.01 (m, 2H), 5.16 and 5.18 (s, 1H), 6.81-6.87 (m, 2H), 6.99-7.29 (m, 8H).

MS m/z ([M+Na]$^+$) 497.

Step 9: Preparation of Intermediate methyl 2-(tert-butoxy)-2-[2-(3,4-dihydro-2H-1-benzopyran-6-yl)-3-hydroxy-6-methylphenyl]acetate (34i)

A suspension of methyl 2-(tert-butoxy)-2-[3-benzyloxy-2-(3,4-dihydro-2H-1-benzopyran-6-yl)-6-methylphenyl]acetate (34h) (263 mg, 0.55 mmol) and palladium on carbon (30 mg) in ethyl acetate (5 mL) was stirred at room temperature under hydrogen atmosphere for 36 hours. The mixture was filtered over Millipore and concentrated in vacuo. The residue was purified by flash chromatography on silica gel (cyclohexane/ethyl acetate: 80/20) to provide methyl 2-(tert-butoxy)-2-[2-(3,4-dihydro-2H-1-benzopyran-6-yl)-3-hydroxy-6-methylphenyl]acetate (34i) (120 mg, 0.31 mmol, 56%).

$^1$H NMR (300 MHz, CDCl$_3$) δ 0.97 and 0.98 (s, 9H), 2.01-2.09 (m, 2H), 2.34 and 2.35 (s, 3H), 2.71-2.86 (m, 2H), 3.67 and 3.68 (s, 3H), 4.24-4.27 (m, 2H), 4.63 and 4.67 (s, 1H), 4.99 and 5.00 (s, 1H), 6.82-7.05 (m, 4H), 7.12-7.19 (m, 1H).

MS m/z ([M+Na]$^+$) 407.
MS m/z ([M−H]$^−$) 383.

Step 10: Preparation of Intermediate methyl 2-(tert-butoxy)-2-[2-(3,4-dihydro-2H-1-benzopyran-6-yl)-6-methyl-3-trifluoromethanesulfonyloxy-phenyl]acetate (34j)

A solution of methyl 2-(tert-butoxy)-2-[2-(3,4-dihydro-2H-1-benzopyran-6-yl)-3-hydroxy-6-methylphenyl]acetate (34i) (145 mg, 0.038 mmol) in anhydrous dichloromethane (5 mL) under nitrogen atmosphere at −78° C. were successively added triethylamine (158 μL, 1.136 mmol), and trifluoromethanesulfonic anhydride (79 μL, 0.47 mol). The mixture was stirred at this temperature for 1 hour before adding water (5 mL). Layers were separated. The aqueous layer was extracted with dichloromethane (5 mL). The combined organic layers were washed with a saturated solution of sodium hydrogenaocarbonate (5 mL), dried over sodium chloride and concentrated in vacuo to provide methyl 2-(tert-butoxy)-2-[2-(3,4-dihydro-2H-1-benzopyran-6-yl)-6-methyl-3-trifluoromethanesulfonyloxy-phenyl]acetate (34j) (193 mg, 0.37 mmol, 99%) as a colorless oil.

$^1$H NMR (300 MHz, CDCl$_3$) δ 0.95 and 0.96 (s, 9H), 2.00-2.09 (m, 2H), 2.43 and 2.45 (s, 3H), 2.68-2.87 (m, 2H), 3.70 and 3.71 (s, 3H), 4.22-4.26 (m, 2H), 5.11 and 5.13 (s, 1H), 6.82-6.87 (m, 1H), 6.94-7.11 (m, 2H), 7.15-7.21 (m, 2H).

MS m/z ([M−H]$^−$) 515.

Step 11: Preparation of Intermediate methyl 2-(tert-butoxy)-2-[3-(1-cyclobutylmethyl-6-oxo-1,6-dihydro-pyridin-3-yl)-2-(3,4-dihydro-2H-1-benzopyran-6-yl)-6-methylphenyl]acetate (34k)

A degassed solution of methyl 2-(tert-butoxy)-2-[2-(3,4-dihydro-2H-1-benzopyran-6-yl)-6-methyl-3-trifluorometh-anesulfonyloxy-phenyl]acetate (34j) (31 mg, 0.06 mmol), 1-cyclobutylmethyl-5-(4,4,5,5-tetramethyl-[1,3,2]dioxa-borolan-2-yl)-1H-pyridin-2-one (30b) (26 mg, 0.09 mmol), potassium carbonate (22 mg, 0.16 mmol) and palladium tetrakis(triphenylphosphine) (7 mg, 0.006 mmol) in dioxane (0.5 mL) and water (0.125 mL) was heated in microwaves at 110° C. for 1 hour. Water (5 mL) was added. The aqueous layer was extracted with ethyl acetate (2×5 mL). The combined organic layers were washed with brine (5 mL), dried over sodium sulfate and concentrated in vacuo. The residue was purified by preparative TLC (cyclohexane/ethyl acetate: 50/50) to provide methyl 2-(tert-butoxy)-2-[3-(1-cyclobu-tylmethyl-6-oxo-1,6-dihydro-pyridin-3-yl)-2-(3,4-dihydro-2H-1-benzopyran-6-yl)-6-methylphenyl]acetate (34k) (21 mg, 0.039 mmol, 65%) as a yellow oil.

$^1$H NMR (300 MHz, CDCl$_3$) δ 0.92 and 0.93 (s, 9H), 1.60-1.73 (m, 2H), 1.80-2.05 (m, 6H), 2.44 and 2.45 (s, 3H), 2.53-2.61 (m, 2H), 2.76 (t, J=6.4 Hz, 1H), 3.60-3.99 (m, 5H), 4.13-4.23 (m, 2H), 5.20 (s, 1H), 6.34 (d, J=9.3 Hz, 1H), 6.53-6.86 (m, 3H), 7.00-7.05 (m, 1H), 7-10-7.18 (m, 3H).

Step 12: Preparation of 2-(tert-butoxy)-2-[3-(1-cy-clobutylmethyl-6-oxo-1,6-dihydro-pyridin-3-yl)-2-(3,4-dihydro-2H-1-benzopyran-6-yl)-6-methylphe-nyl]acetic acid (Example 34)

Using the procedure described in example 25, step 4, the methyl 2-(tert-butoxy)-2-[3-(1-cyclobutylmethyl-6-oxo-1,6-dihydro-pyridin-3-yl)-2-(3,4-dihydro-2H-1-benzopyran-6-yl)-6-methylphenyl]acetate (34k) (21 mg, 0.039 mmol) is converted into 2-(tert-butoxy)-2-[3-(1-cyclobutylmethyl-6-oxo-1,6-dihydro-pyridin-3-yl)-2-(3,4-dihydro-2H-1-benzo-pyran-6-yl)-6-methylphenyl]acetic acid (example 34) (9 mg, 0.017 mmol, 45%) as a white solid.

$^1$H NMR (400 MHz, CDCl$_3$) δ 0.95 (s, 9H), 1.56-1.72 (m, 2H), 1.78-2.07 (m, 6H), 2.43 (s, 3H), 2.47-2.58 (m, 2H), 2.75-2.85 (m, 1H), 3.54-3.72 (m, 1H), 3.85-4.03 (m, 1H), 4.11-4.25 (m, 2H), 5.33 and 5.34 (s, 1H), 6.39 and 6.40 (d, J=9.3 Hz, 1H), 6.50-6.84 (m, 3H), 7.05-7.10 (m, 1H), 7-13-7.19 (m, 2H), 7.36 (bs, 1H).

MS m/z ([M+H]$^+$) 516.
MS m/z ([M−H]$^−$) 514.

Example 35

Synthesis of 2-(tert-butoxy)-2-[2-(3,4-dihydro-2H-1-benzopyran-6-yl)-3-(6-propylpyridin-2-yl)-6-(trif-luoromethyl)phenyl]acetic acid

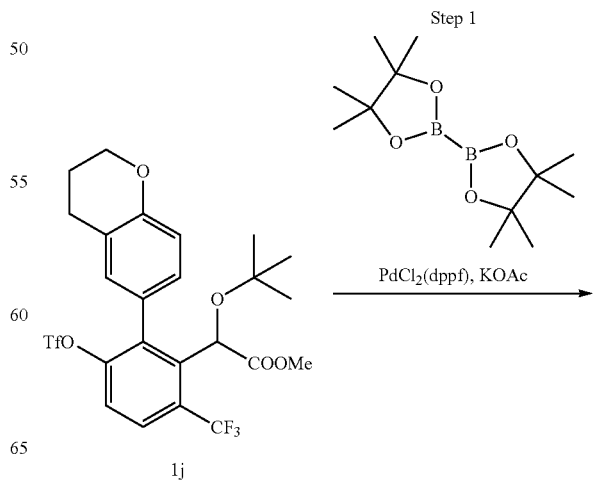

-continued

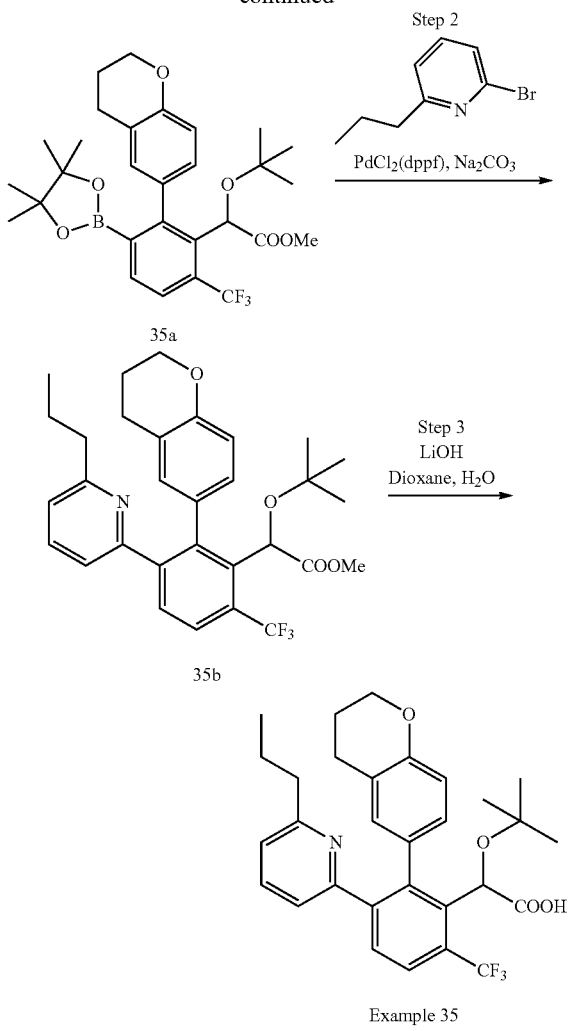

Example 35

Step 1: Preparation of intermediate methyl 2-(tert-butoxy)-2-[2-(3,4-dihydro-2H-1-benzopyran-6-yl)-3-(tetramethyl-1,3,2-dioxaborolan-2-yl)-6-(trifluoromethyl)phenyl]acetate (35a)

A flame-dried vial containing methyl 2-(tert-butoxy)-2-[2-(3,4-dihydro-2H-1-benzopyran-6-yl)-3-[(trifluoromethane)sulfonyloxy]-6-(trifluoromethyl)phenyl]acetate (1j) (437 mg, 0.766 mmol), [1,1'-Bis(diphenylphosphino)ferrocene]dichloropalladium(II), complex with dichloromethane (125 mg, 0.153 mmol), bis[pinacolato]diboron (389 mg, 1.53 mmol) and potassium acetate (225 mg, 2.30 mmol) was purged with argon for 10 minutes and then degassed anhydrous dioxane (5 mL) was added. The resulting mixture was placed in a preheated oil bath (80° C.) and stirred for 22 hours. LCMS showed remaining starting triflate and the mixture was cooled to room temperature, anhydrous dioxane (2 mL) was added and the mixture was purged with argon (10 min) followed by addition of bis[pinacolato]diboron (194 mg, 0.765 mmol), potassium acetate (113 mg, 1.15 mmol) and [1,1'-Bis(diphenylphosphino) ferrocene]dichloropalladium(II), complex with dichloromethane (62 mg, 0.076 mmol), further purged with argon and then stirred at 80° C. for further 24 hours. The mixture was cooled to room temperature and diluted in ethyl acetate (100 mL) and washed with water (2×15 mL) and brine (15 mL), dried over sodium sulfate, filtered and concentrated in vacuo. The residue was purified by DCVC on Silicagel (30 mL) (cyclohexane/ethyl acetate 100/0 up to 70/30) to provide methyl 2-(tert-butoxy)-2-[2-(3,4-dihydro-2H-1-benzopyran-6-yl)-3-(tetramethyl-1,3,2-dioxaborolan-2-yl)-6-(trifluoromethyl)phenyl]acetate (35a) (520 mg, quantitative yield) a yellow oil.

$^1$H NMR (300 MHz, CDCl$_3$) δ 0.92 and 0.95 (s, 9H), 1.06 (s, 6H), 1.13 (s, 6H), 2.04 (m, 2H), 2.75 (m, 2H), 3.67 (s, 3H), 4.21 (m, 2H), 5.18 (s, 1H), 6.74-6.93 (m, 2H), 7.05-7.10 (m, 1H), 7.26-7.67 (m, 2H).

Step 2: Preparation of intermediate methyl 2-(tert-butoxy)-2-[2-(3,4-dihydro-2H-1-benzopyran-6-yl)-3-(6-propylpyridin-2-yl)-6-(trifluoromethyl)phenyl]acetate (35b)

To a solution of methyl 2-(tert-butoxy)-2-[2-(3,4-dihydro-2H-1-benzopyran-6-yl)-3-(tetramethyl-1,3,2-dioxaborolan-2-yl)-6-(trifluoromethyl)phenyl]acetate (35a) (50 mg, 0.091 mmol) in dioxane (1.0 mL) was added 2-bromo-6-propylpyridine (36 mg, 0.182 mmol) and sodium carbonate saturated aqueous solution (1.0 mL). This mixture was stirred at room temperature for 20 minutes while passing a stream of argon. [1,1'-Bis(diphenylphosphino) ferrocene]dichloropalladium(II), complex with dichloromethane (7.45 mg, 0.009 mmol) was added and the resulting mixture was stirred at 80° C. for 16 hours. The reaction mixture was cooled to room temperature and diluted with ethyl acetate (15 mL). The organic phase were washed with water (2×10 mL) and brine (10 mL), dried over sodium sulfate and concentrated in vacuo. The crude residue was purified on preparative TLC (cyclohexane/ethyl acetate 70/30) to provide methyl 2-(tert-butoxy)-2-[2-(3,4-dihydro-2H-1-benzopyran-6-yl)-3-(6-propylpyridin-2-yl)-6-(trifluoromethyl)phenyl]acetate (35b) (22 mg, 0.041 mmol, 44%).

$^1$H NMR (300 MHz, CDCl$_3$) δ 0.90 (t, J=7.3 Hz, 3H), 0.94 and 0.95 (s, 9H), 1.58-1.73 (m, 2H), 1.82-2.04 (m, 2H), 2.31-2.59 (m, 1H), 2.63-2.76 (m, 3H), 3.73 (s, 3H), 4.07-4.20 (m, 2H), 5.20 and 5.22 (s, 1H), 6.43-6.65 (m, 2H), 6.71 (d, J=8.2 Hz, 1H), 6.90 (d, J=7.7 Hz, 1H), 7.13-7.20 (m, 1H), 7.26-7.35 (m, 1H), 7.61-7.66 (m, 1H), 8.76-7.81 (m, 1H).

MS m/z ([M+H]$^+$) 542.

Step 3: Preparation of 2-(tert-butoxy)-2-[2-(3,4-dihydro-2H-1-benzopyran-6-yl)-3-(6-propylpyridin-2-yl)-6-(trifluoromethyl)phenyl]acetic acid (Example 35)

Using the procedure described in example 25, step 4, the intermediate methyl 2-(tert-butoxy)-2-[2-(3,4-dihydro-2H-1-benzopyran-6-yl)-3-(6-propylpyridin-2-yl)-6-(trifluoromethyl)phenyl]acetate (35b) (22 mg, 0.041 mmol) is converted, after purification by triturating in diethyl ether into 2-(tert-butoxy)-2-[2-(3,4-dihydro-2H-1-benzopyran-6-yl)-3-(6-propylpyridin-2-yl)-6-(trifluoromethyl)phenyl]acetic acid (example 35) (20 mg, 0.038 mmol, 93%) as a white solid.

$^1$H NMR (400 MHz, DMSO) δ 0.76-0.87 (m, 12H), 1.39-1.65 (m, 2H), 1.68-1.98 (m, 2H), 2.50-2.73 (m, 4H), 3.97-4.17 (m, 2H), 5.03 (s, 1H), 6.31-6.76 (m, 2H), 6.80 and 6.88 (d, J=7.8 Hz, 1H), 7.02 (t, J=7.8 Hz, 1H), 7.07-7.29 (m, 1H), 7.44-7.52 (m, 1H), 7.59 and 7.63 (m, 1H), 7.82 (d, J=8.2 Hz, 1H).

MS m/z ([M+H]$^+$) 528.

Example 36

Synthesis of 2-(tert-butoxy)-2-[2-(3,4-dihydro-2H-1-benzopyran-6-yl)-3-(4-propylpyridin-2-yl)-6-(trifluoromethyl)phenyl]acetic acid

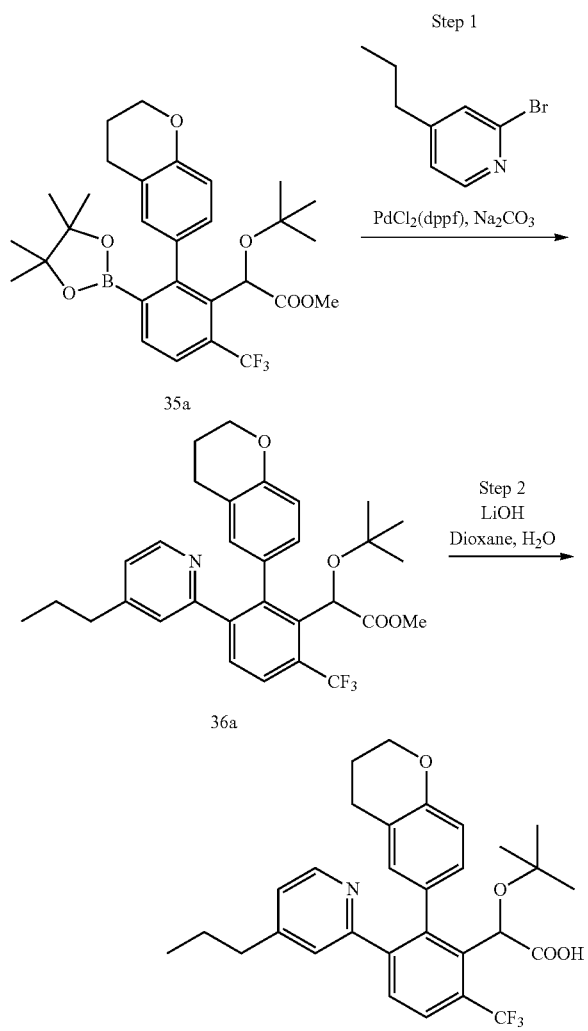

Example 36

Step 1: Preparation of Intermediate methyl 2-(tert-butoxy)-2-[2-(3,4-dihydro-2H-1-benzopyran-6-yl)-3-(4-propylpyridin-2-yl)-6-(trifluoromethyl)phenyl]acetate (36a)

Using the procedure described in example 35, step 2, the methyl 2-(tert-butoxy)-2-[2-(3,4-dihydro-2H-1-benzopyran-6-yl)-3-(tetramethyl-1,3,2-dioxaborolan-2-yl)-6-(trifluoromethyl)phenyl]acetate (35a) (50 mg, 0.091 mmol) is converted by reaction with 2-bromo-4-propyl-pyridine (36 mg, 0.180 mmol), after purification by preparative TLC (cyclohexane/ethyl acetate: 70/30) to methyl 2-(tert-butoxy)-2-[2-(3,4-dihydro-2H-1-benzopyran-6-yl)-3-(4-propyl pyridin-2-yl)-6-(trifluoromethyl)phenyl]acetate (36a) (39 mg, 0.072 mmol, 79%).

$^1$H NMR (400 MHz, CDCl$_3$) δ 0.71 and 0.75 (t, J=7.2 Hz, 3H), 0.91 and 0.92 (s, 9H), 1.25-1.40 (m, 2H), 1.80-2.07 (m, 2H), 2.28-2.57 (m, 3H), 2.75 (t, J=6.4 Hz, 1H), 3.75 (s, 3H), 4.04-4.22 (m, 2H), 5.22 (s, 1H), 6.47-6.76 (m, 3H), 6.85-6.88 (m, 1H), 7.20-7.23 (m, 1H), 7.70 and 7.72 (d, J=8.1 Hz, 1H), 7.80 (d, J=8.1 Hz, 1H), 8.43-8.46 (m, 1H).

MS m/z ([M+H]$^+$) 542.

Step 2: Preparation of 2-(tert-butoxy)-2-[2-(3,4-dihydro-2H-1-benzopyran-6-yl)-3-(4-propylpyridin-2-yl)-6-(trifluoromethyl)phenyl]acetic acid (Example 36)

Using the procedure described in example 25, step 4, the methyl 2-(tert-butoxy)-2-[2-(3,4-dihydro-2H-1-benzopyran-6-yl)-3-(4-propylpyridin-2-yl)-6-(trifluoromethyl)phenyl]acetate (36a) (39 mg, 0.072 mmol) is converted to 2-(tert-butoxy)-2-[2-(3,4-dihydro-2H-1-benzopyran-6-yl)-3-(4-propylpyridin-2-yl)-6-(trifluoromethyl)phenyl]acetic acid (example 36) (20 mg, 0.038 mmol, 52%) a white solid.

$^1$H NMR (400 MHz, CD$_3$OD) δ 0.74 and 0.75 (t, J=7.2 Hz, 3H), 0.92 (s, 9H), 1.30-1.45 (m, 2H), 1.81-2.04 (m, 2H), 2.32-2.61 (m, 3H), 2.78-2.81 (m, 1H), 4.04-4.20 (m, 2H), 5.26 and 5.27 (s, 1H), 6.46-6.77 (m, 3H), 7.05-7.08 (m, 1H), 7.30-7.37 (m, 1H), 7.65 and 7.66 (d, J=8.1 Hz, 1H), 7.85 (d, J=8.1 Hz, 1H), 8.34-8.37 (m, 1H).

MS m/z ([M+H]$^+$) 528.

Example 37

Synthesis of 2-(tert-butoxy)-2-[3-(1-cyclobutylmethyl-6-oxo-1,6-dihydro-pyridin-3-yl)-6-methyl-2-[5-methyl-(3,4-dihydro-2H-1-benzopyran-6-yl)]phenyl]acetic acid

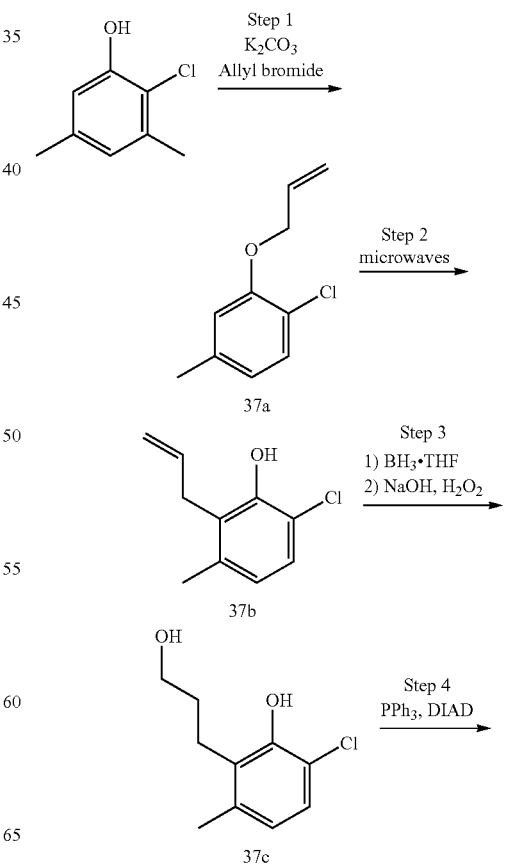

-continued

Step 12

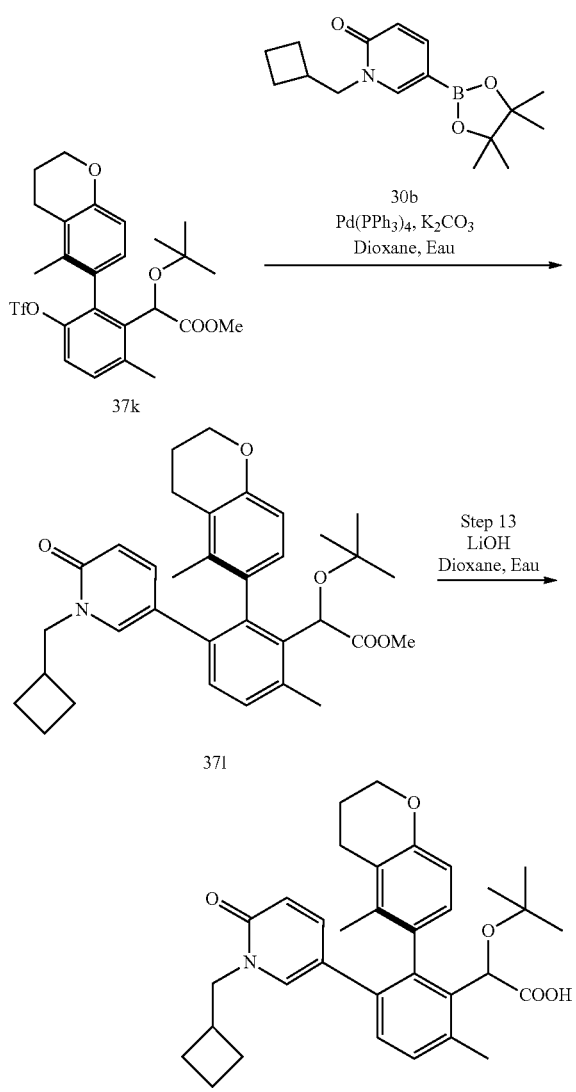

Step 1: Preparation of Intermediate 1-chloro-4-methyl-2-(prop-2-en-1-yloxy)benzene (37a)

To a suspension of 2-chloro-5-methylphenol (10.0 g, 0.07 mol) and potassium carbonate (11.7 g, 0.08 mol) in acetonitrile (200 mL) at 82° C., was dropwise added a solution of allyl bromide (9.6 mL, 0.11 mol) in acetonitrile (50 mL). The mixture was reflux overnight. Once at room temperature, the mixture was filtered and the precipitate rinsed with diethyl ether. The filtrate was then concentrated in vacuo. The residue was dissolved in diethyl ether (250 mL) and washed with a 2N sodium hydroxide solution (150 mL). The organic layer was dried over sodium sulfate and concentrated in vacuo to provide 1-chloro-4-methyl-2-(prop-2-en-1-yloxy)benzene (37a) (12.72 g, 0.07 mol, 99%) which was used without further purification.

$^1$H NMR (300 MHz, CDCl$_3$) δ 2.31 (s, 3H), 4.58-4.61 (m, 2H), 5.28-5.32 (m, 1H), 5.43-5.50 (m, 1H), 6.01-6.14 (m, 1H), 6.69-6.73 (m, 2H), 7.22 (d, J=8.0 Hz, 1H).
MS m/z ([M+H]$^+$) 183.

Step 2: Preparation of Intermediate 6-chloro-3-methyl-2-(prop-2-en-1-yl)phenol (37b)

1-chloro-4-methyl-2-(prop-2-en-1-yloxy)benzene (37a) (12.6 g, 0.07 mol) was irradiated in a microwaves for 20 minutes at 240° C. to provide 6-chloro-3-methyl-2-(prop-2-en-1-yl)phenol (37b) (12.6 g, 0.07 mol, 100%) which was used without further purification.

$^1$H NMR (300 MHz, CDCl$_3$) δ 2.26 (s, 3H), 3.45 (dt, J=5.9 Hz, J=1.6 Hz, 2H), 4.90-5.07 (m, 2H), 5.56 (s, 1H), 5.85-6.01 (m, 1H), 6.69 (d, J=8.2 Hz, 1H), 7.08 (d, J=8.2 Hz, 1H).

Step 3: Preparation of Intermediate 6-chloro-2-(3-hydroxypropyl)-3-methylphenol (37c)

Under nitrogen atmosphere, a solution of 6-chloro-3-methyl-2-(prop-2-en-1-yl)phenol (37b) (8.70 g, 47.6 mmol) in anhydrous tetrahydrofuran (300 mL) was cooled to 0° C. Borane-tetrahydrofuran complex, 1.0M solution in tetrahydrofuran (100 mL, 0.10 mol) was dropwise added. The reaction mixture was stirred at room temperature for 2 hours then cooled again to 0° C. A 10N sodium hydroxide solution (32.7 mL) was added dropwise, followed by a 30% hydrogen peroxide solution. The resulting mixture was warm to room temperature and stirred for 90 minutes. The reaction mixture was quenched with a 10% hydrochloric acid solution (163 mL). Layers were separated and the aqueous layer was extract with ethyl acetate (2×70 mL). The combined organics layers were washed with brine (3×100 mL) then cooled with an ice bath. A saturated solution of sodium sulfite (150 mL) was carefully added and the mixture was stirred for few minutes. The organic layer was separated, dried over sodium sulfate and concentrated in vacuo. The residue was purified by flash chromatography on silica gel (cyclohexane/ethyl acetate 100/0 to 75/25), to provide 6-chloro-2-(3-hydroxypropyl)-3-methylphenol (37c) (6.74 g, 33.6 mmol, 70%).

$^1$H NMR (300 MHz, CDCl$_3$) δ 1.76-1.88 (m, 2H), 2.28 (s, 3H), 2.81 (t, J=7.2 Hz, 2H), 3.63 (t, J=6.0 Hz, 2H), 6.69 (d, J=8.2 Hz, 1H), 7.08 (d, J=8.2 Hz, 1H).

Step 4: Preparation of Intermediate 8-chloro-5-methyl-3,4-dihydro-2H-1-benzopyran (37d)

Under nitrogen atmosphere, a solution of 6-chloro-2-(3-hydroxypropyl)-3-methylphenol (37c) (6.74 g, 33.6 mmol) in anhydrous tetrahydrofuran (500 mL) was cooled to 0° C. Triphenylphosphine (11.45 g, 43.7 mmol) was added, followed by diisopropyl azodicarboxylate (8.60 mL, 43.7 mmol). The reaction mixture was stirred for 16 hours at room temperature. After concentration in vacuo, the residue was dissolved in diethyl ether and the precipitate was filtered off. The filtrate was concentrated in vacuo and the residue was purified by flash chromatography on silica gel (cyclohexane/ethyl acetate 100/0 to 90/10), to provide 8-chloro-5-methyl-3,4-dihydro-2H-1-benzopyran (37d) (5.74 g, 31.4 mmol, 94%), as a light yellow oil.

$^1$H NMR (300 MHz, CDCl$_3$) δ 2.00-2.11 (m, 2H), 2.18 (s, 3H), 2.65 (t, J=6.6 Hz, 2H), 4.21-4.28 (m, 2H), 6.65 (d, J=8.1 Hz, 1H), 7.08 (d, J=8.1 Hz, 1H).

Step 5: Preparation of Intermediate 6-bromo-8-chloro-5-methyl-3,4-dihydro-2H-1-benzopyran (37e)

A mixture of the 8-chloro-5-methyl-3,4-dihydro-2H-1-benzopyran (37d) (5.74 g, 31.4 mmol) and acetic acid (75 mL) is treated with bromine (1.93 mL, 37.7 mmol) in AcOH (35 mL). The mixture was stirred at room temperature for 15 minutes, then diluted with toluene (100 mL). The mixture was concentrated in vacuo. The residue was dissolved in ethyl acetate (70 mL) and successively washed with a 15% sodium thiosulfate solution (50 mL) and a saturated solution of sodium hydrogenocarbonate (50 mL). The organic layer was dried over sodium sulfate and concentrated in vacuo. The product was recrystallized in ethanol, to provide 6-bromo-8-chloro-5-methyl-3,4-dihydro-2H-1-benzopyran (37e) (4.44 g, 17.0 mmol, 54%) as a white solid.

$^1$H NMR (300 MHz, CDCl$_3$) δ 1.99-2.11 (m, 2H), 2.27 (s, 3H), 2.71 (t, J=6.6 Hz, 2H), 4.18-4.26 (m, 2H), 7.41 (s, 1H).

Step 6: Preparation of Intermediate 2-(8-chloro-5-methyl-3,4-dihydro-2H-1-benzopyran-6-yl)-4,4,5,5-tetramethyl-1,3,2-dioxaborolane (37f)

[1,1'-Bis(diphenylphosphino)ferrocene]dichloropalladium(II) (761 mg, 0.93 mmol) was added to a previously degassed solution of 6-bromo-8-chloro-5-methyl-3,4-dihydro-2H-1-benzopyran (37e) (2.44g, 9.33 mmol), bis(pinacolato)diboron (3.55 g, 14.0 mmol) and potassium acetate (3.20 g, 32.6 mmol) in anhydrous N,N-dimethylformamide (100 mL). The reaction mixture was heated at 95° C. for 16 hours. Water (50 mL) was added and the reaction mixture was concentrated in vacuo. The residue was taken in water (50 mL) and extracted with ethyl acetate (2×50 mL). The organic layer was washed with brine (30 mL) then dried over sodium sulfate, concentrated in vacuo, and co-elutated with toluene. The crude was purified by flash chromatography on silica gel (cyclohexane/ethyl acetate 100/0 to 98/2). The product was triturated in cyclohexane and filtered to provide 2-(8-chloro-5-methyl-3,4-dihydro-2H-1-benzopyran-6-yl)-4,4,5,5-tetramethyl-1,3,2-dioxaborolane (37f) (1.62 g, 5.24 mmol, 58%) as a white solid.

$^1$H NMR (300 MHz, CDCl$_3$) δ 1.33 (s, 12H), 1.99-2.11 (m, 2H), 2.40 (s, 3H), 2.65 (t, J=6.6 Hz, 2H), 4.19-4.30 (m, 2H), 7.63 (s, 1H).

Step 7: Preparation of Intermediate 4,4,5,5-tetramethyl-2-(5-methyl-3,4-dihydro-2H-1-benzopyran-6-yl)-1,3,2-dioxaborolane (37g)

Palladium on activated charcoal (10% Pd by weight, 120 mg) was added to a solution of 2-(8-chloro-5-methyl-3,4-dihydro-2H-1-benzopyran-6-yl)-4,4,5,5-tetramethyl-1,3,2-dioxaborolane (37f) (1.20 g, 3.89 mmol) and ammonium formate (2.45 g, 38.89 mmol) in methanol (20 mL). The mixture was refluxed for 60 minutes. The mixture was then cooled to room temperature, filtered through a pad of Celite® and rinsed with methanol. The filtrate was concentrated in vacuo. The residue was dissolved in ethyl acetate (20 mL) and washed with water (20 mL). The organic layer was dried over sodium sulfate, concentrated in vacuo to provide 4,4,5,5-tetramethyl-2-(5-methyl-3,4-dihydro-2H-1-benzopyran-6-yl)-1,3,2-dioxaborolane (37g) (1.00 g, 3.66 mmol, 94%) as a white solid, which was used without further purification.

$^1$H NMR (300 MHz, CDCl$_3$) δ 1.32 (s, 12H), 1.96-2.10 (m, 2H), 2.43 (s, 3H), 2.65 (t, J=6.6 Hz, 2H), 4.09-4.17 (m, 2H), 6.66 (d, J=8.3 Hz, 1H), 7.55 (d, J=8.3 Hz, 1H).

Step 8: Preparation of Intermediate methyl 2-(3-benzyloxy-2-bromo-6-methylphenyl)-2-(tert-butoxy)-acetate (37h)

To a suspension of methyl 2-(3-benzyloxy-2-bromo-6-methylphenyl)-2-hydroxyacetate (34f) (500 mg, 1.37 mmol) in tert-butyl acetate (14 mL) at 0° C. was added sulfuric acid (0.292 mL, 5.48 mmol). The mixture was stirred at room temperature for 8 hours. The mixture was diluted with ethyl acetate (50 mL), washed with a saturated solution of sodium hydrogenocarbonate (50 mL), dried over sodium sulfate and concentrated in vacuo. The residue was purified by flash chromatography on silica gel (cyclohexane/ethyl acetate 90/10) to provide methyl 2-(3-benzyloxy-2-bromo-6-methylphenyl)-2-(tert-butoxy)-acetate (37h) (469 mg, 1.11 mmol, 81%) as a white solid.

$^1$H NMR (300 MHz, CDCl$_3$) δ 1.23 (s, 9H), 2.36 (s, 3H), 3.68 (s, 3H), 5.12 (s, 2H), 5.96 (s, 1H), 6.80 (d, J=8.4 Hz, 1H), 7.01 (d, J=8.4 Hz, 1H), 7.29-7.42 (m, 3H), 7.48-7.51 (m, 2H).

Step 9: Preparation of Intermediate methyl 2-[3-benzyloxy-6-methyl-2-[5-methyl-(3,4-dihydro-2H-1-benzopyran-6-yl)]]-2-(tert-butoxy)acetate (37i)

To a degassed mixture of methyl 2-(3-benzyloxy-2-bromo-6-methylphenyl)-2-(tert-butoxy)-acetate (37h) (70 mg, 0.17 mmol), sodium carbonate (53 mg, 0.50 mmol) and 3,4-dihydro-5-methyl-6-(4,4,5,5-tetramethyl-1,3,2-dioxaborolan-2-yl)-2H-1-benzopyran (37g) (55 mg, 0.20 mmol) in dioxane (1 mL) and water (0.2 mL) was added palladium tetrakis(triphenylphosphine) (19 mg, 0.02 mmol). The mixture was heated at 120° C. overnight. Water (5 mL) was added. The aqueous layer was extracted with ethyl acetate (2×5 mL), dichloromethane (2×5 mL) and tetrahydrofuran (2×5 mL). The combined organic layers were dried over sodium sulfate and concentrated in vacuo. The residue was purified by flash chromatography on silica gel (dichloromethane/ethyl acetate 100/0 up to 98/2) to provide a mixture of methyl 2-[3-benzyloxy-6-methyl-2-[5-methyl-(3,4-dihydro-2H-1-benzopyran-6-yl)]]-2-(tert-butoxy)acetate (37i) and methyl 2-(3-benzyloxy-6-methylphenyl)-2-(tert-butoxy)-acetate (37j) (84 mg, ratio 75/25) which was used without further purification.

$^1$H NMR (300 MHz, CDCl$_3$) δ 1.12 (s, 9H), 1.87 (s, 3H), 2.09-2.14 (m, 2H), 2.46 (s, 3H), 2.62-2.78 (m, 2H), 3.57 (s, 3H), 4.20-4.24 (m, 2H), 4.88-4.97 (m, 2H), 5.11 (s, 1H), 6.72 (d, J=8.3 Hz, 1H), 6.81 (d, J=8.3 Hz, 1H), 6.90 (d, J=8.3 Hz, 1H), 7.02-7.08 (m, 3H), 7.20-7.24 (m, 3H).

MS m/z ([M+Na]$^+$) 511.

Step 10: Preparation of Intermediate methyl 2-(tert-butoxy)-2-[3-hydroxy-6-methyl-2-[5-methyl-(3,4-dihydro-2H-1-benzopyran-6-yl)]-phenyl]acetate (37j)

A suspension of a mixture of methyl 2-[3-benzyloxy-6-methyl-2-[5-methyl-(3,4-dihydro-2H-1-benzopyran-6-yl)]]-2-(tert-butoxy)acetate (37i) and methyl 2-(3-benzyloxy-6-methylphenyl)-2-(tert-butoxy)-acetate (37j) (84 mg, 75/25) and palladium on carbon (18 mg) in methanol (5 mL) was stirred at room temperature under a 5 bar hydrogen pressure for 3.5 hours. The mixture was filtered over Millipore and concentrated in vacuo. The residue was purified by preparative TLC (dichloromethane/ethyl acetate 98/2) to provide methyl 2-(tert-butoxy)-2-[3-hydroxy-6-methyl-2-[5-methyl-(3,4-dihydro-2H-1-benzopyran-6-yl)]-phenyl]acetate (37j) (30 mg, 0.075 mmol, 45% over 2 steps).

$^1$H NMR (400 MHz, CDCl$_3$) δ 1.08 (s, 9H), 1.91 (s, 3H), 2.06-2.15 (m, 2H), 2.43 (s, 3H), 2.64-2.77 (m, 2H), 3.57 (s, 3H), 4.16-4.25 (m, 2H), 4.42 (bs, 1H), 4.93 (s, 1H), 6.76 (d, J=8.3 Hz, 1H), 6.83 (d, J=8.2 Hz, 1H), 6.93 (d, J=8.3 Hz, 1H), 7.05 (d, J=8.2 Hz, 1H).

MS m/z ([M+Na]+) 421.
MS m/z ([M−H]−) 397.

Step 11: Preparation of Intermediate methyl 2-(tert-butoxy)-2-[6-methyl-2-[5-methyl-(3,4-dihydro-2H-1-benzopyran-6-yl)]-3-trifluoromethanesulfonyloxy-phenyl]acetate (37k)

Using the procedure described in example 34, step 10, the intermediate methyl 2-(tert-butoxy)-2-[3-hydroxy-6-methyl-2-[5-methyl-(3,4-dihydro-2H-1-benzopyran-6-yl)]-phenyl]acetate (37j) (30 mg, 0.075 mmol) is converted into intermediate methyl 2-(tert-butoxy)-2-[6-methyl-2-[5-methyl-(3,4-dihydro-2H-1-benzopyran-6-yl)]-3-trifluoromethanesulfonyloxy-phenyl]acetate (37k) (40 mg, 0.075 mmol, 100%) as a colorless oil.

$^1$H NMR (300 MHz, CDCl$_3$) δ 1.09 (s, 9H), 1.84 (s, 3H), 2.06-2.13 (m, 2H), 2.53 (s, 3H), 2.68 (t, J=6.6 Hz, 2H), 3.58 (s, 3H), 4.17-4.21 (m, 2H), 5.08 (s, 1H), 6.72 (d, J=8.4 Hz, 1H), 6.88 (d, J=8.4 Hz, 1H), 7.16 (d, J=8.5 Hz, 1H), 7.21 (d, J=8.5 Hz, 1H).
MS m/z ([M+Na]+) 553.

Step 12: Preparation of Intermediate methyl 2-(tert-butoxy)-2-[3-(1-cyclobutylmethyl-6-oxo-1,6-dihydro-pyridin-3-yl)-6-methyl-2-[5-methyl-(3,4-dihydro-2H-1-benzopyran-6-yl)]phenyl]acetate (37l)

Using the procedure described in example 34, step 11, the intermediate methyl 2-(tert-butoxy)-2-[6-methyl-2-[5-methyl-(3,4-dihydro-2H-1-benzopyran-6-yl)]-3-trifluoromethanesulfonyloxy-phenyl]acetate (37k) (40 mg, 0.075 mmol) is converted, after purification by preparative TLC (dichloromethane/ethyl acetate 50/50) to intermediate methyl 2-(tert-butoxy)-2-[3-(1-cyclobutylmethyl-6-oxo-1,6-dihydro-pyridin-3-yl)-6-methyl-2-[5-methyl-(3,4-dihydro-2H-1-benzopyran-6-yl)]phenyl]acetate (37l) (27 mg, 0.049 mmol, 65%).

$^1$H NMR (300 MHz, CDCl$_3$) δ 1.12 (s, 9H), 1.60-1.70 (m, 5H), 1.81-2.06 (m, 6H), 2.39-2.63 (m, 6H), 3.55 (s, 3H), 3.76 (d, J=7.5 Hz, 2H), 4.04-4.18 (m, 2H), 5.12 (s, 1H), 6.30 (d, J=9.3 Hz, 1H), 6.67 (d, J=8.3 Hz, 1H), 6.78 (d, J=2.5 Hz, 1H), 6.90 (d, J=8.3 Hz, 1H), 7.00 (dd, J=2.5 Hz, J=9.3 Hz, 1H), 7.10 (d, J=7.8 Hz, 1H), 7.19 (d, J=7.8 Hz, 1H).
MS m/z ([M+H]+) 544.

Step 13: Preparation of 2-(tert-butoxy)-2-[3-(1-cyclobutylmethyl-6-oxo-1,6-dihydro-pyridin-3-yl)-6-methyl-2-[5-methyl-(3,4-dihydro-2H-1-benzopyran-6-yl)]phenyl]acetic acid (Example 37)

Using the procedure described in example 25, step 4, the intermediate methyl 2-(tert-butoxy)-2-[3-(1-cyclobutylmethyl-6-oxo-1,6-dihydro-pyridin-3-yl)-6-methyl-2-[5-methyl-(3,4-dihydro-2H-1-benzopyran-6-yl)]phenyl]acetate (37l) (27 mg, 0.049 mmol) is converted to 2-(tert-butoxy)-2-[3-(1-cyclobutylmethyl-6-oxo-1,6-dihydro-pyridin-3-yl)-6-methyl-2-[5-methyl-(3,4-dihydro-2H-1-benzopyran-6-yl)]phenyl]acetic acid (example 37) (15 mg, 0.028 mmol, 57%) as a white solid.

$^1$H NMR (300 MHz, CDCl$_3$) δ 1.12 (s, 9H), 1.60-1.69 (m, 2H), 1.75 (s, 3H), 1.80-1.94 (m, 4H), 1.97-2.04 (m, 2H), 2.41-2.62 (m, 6H), 3.77 (d, J=7.6 Hz, 2H), 4.07-4.16 (m, 2H), 5.19 (s, 1H), 6.34 (d, J=9.3 Hz, 1H), 6.65 (d, J=8.3 Hz, 1H), 6.80 (d, J=2.5 Hz, 1H), 6.85 (d, J=8.3 Hz, 1H), 7.04 (dd, J=2.5 Hz, J=9.3 Hz, 1H), 7.15 (d, J=7.8 Hz, 1H), 7.21 (d, J=7.8 Hz, 1H).

MS m/z ([M+H]+) 530.
MS m/z ([M−H]−) 528.

Example 38

Synthesis of 2-(tert-butoxy)-2-{3-[1-(cyclobutylmethyl)-2-oxo-1,2-dihydropyridin-3-yl]-2-(3,4-dihydro-2H-1-benzopyran-6-yl)-6-(trifluoromethyl)phenyl}acetic acid

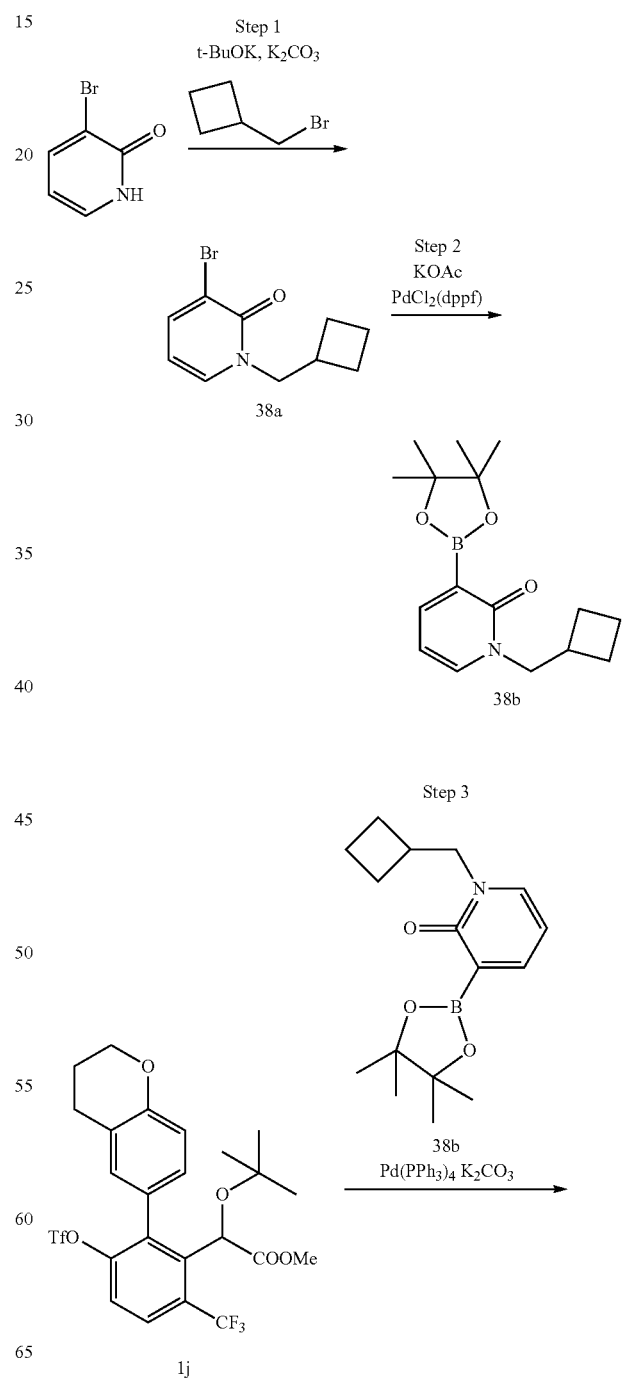

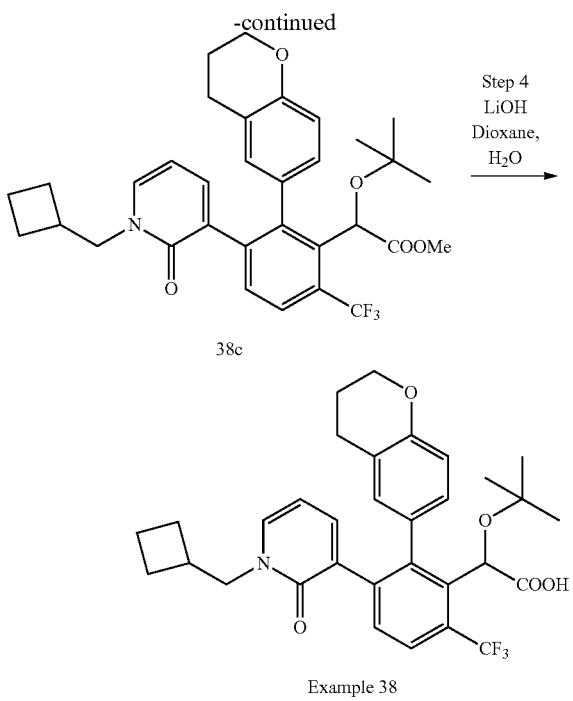

Step 4
LiOH
Dioxane,
H₂O

38c

Example 38

Step 1: Preparation of Intermediate 3-bromo-1-(cyclobutylmethyl)-1,2-dihydropyridin-2-one (38a)

Using the procedure described in example 30, step 1, the intermediate 3-bromo-2-hydroxypyridine (500 mg, 2.87 mmol) is converted, after purification by flash chromatography on silica gel (dichloromethane/ethyl acetate 100/0 to 80/20), into 3-bromo-1-(cyclobutylmethyl)-1,2-dihydropyridin-2-one (38a) (310 mg, 1.28 mmol, 45%).

$^1$H NMR (400 MHz, CDCl$_3$) δ 1.73-1.94 (m, 4H), 2.00-2.10 (m, 2H), 2.81 (sept, J=7.6 Hz, 1H), 4.00 (d, J=7.6 Hz, 2H), 6.03 (t, J=7.0 Hz, 1H), 7.23 (dd, J=1.9 Hz, J=7.0 Hz, 1H), 7.70 (dd, J=1.9 Hz, J=7.0 Hz, 1H).

MS m/z ([M+H]$^+$) 242/244.

Step 2: Preparation of Intermediate 1-(cyclobutylmethyl)-3-(tetramethyl-1,3,2-dioxaborolan-2-yl)-1,2-dihydropyridin-2-one (38b)

Using the procedure described in example 25, step 2, the intermediate 3-bromo-1-(cyclobutylmethyl)-1,2-dihydropyridin-2-one (38a) (300 mg, 1.24 mmol) is converted, after purification by preparative TLC (ethyl acetate/methanol 95/5) into 1-(cyclobutylmethyl)-3-(tetramethyl-1,3,2-dioxaborolan-2-yl)-1,2-dihydropyridin-2-one (38b) (60 mg, 0.21 mmol, 17%).

Step 3: Preparation of Intermediate methyl 2-(tert-butoxy)-2-{3-[1-(cyclobutylmethyl)-2-oxo-1,2-dihydropyridin-3-yl]-2-(3,4-dihydro-2H-1-benzopyran-6-yl)-6-(trifluoromethyl)phenyl}acetate (38c)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (70 mg, 0.123 mmol) is converted by reaction with 1-(cyclobutylmethyl)-3-(tetramethyl-1,3,2-dioxaborolan-2-yl)-1,2-dihydropyridin-2-one (38b) (60 mg, 0.207 mmol), after purification by preparative TLC (dichloromethane/ethyl acetate 80/20) to methyl 2-(tert-butoxy)-2-{3-[1-(cyclobutylmethyl)-2-oxo-1,2-dihydropyridin-3-yl]-2-(3,4-dihydro-2H-1-benzopyran-6-yl)-6-(trifluoromethyl)phenyl}acetate (38c) (45 mg, 0.077 mmol, 63%).

$^1$H NMR (400 MHz, CDCl$_3$) δ 0.96 and 0.97 (s, 9H), 1.64-1.74 (m, 2H), 1.81-2.01 (m, 6H), 2.49-2.76 (m, 3H), 3.69 and 3.70 (s, 3H), 3.76-3.86 (m, 1H), 3.90-4.02 (m, 1H), 4.09-4.20 (m, 2H), 5.15 (s, 1H), 5.94 and 5.95 (t, J=6.8 Hz, 1H), 6.53 and 6.66 (d, J=8.4 Hz, 1H), 6.68-6.79 (m, 1H), 6.88-6.95 (m, 1H), 7.00-7.05 (m, 1H), 7.06 and 7.08 (d, J=6.8 Hz, 1H), 7.36-7.43 (m, 1H), 7.71 (d, J=8.2 Hz, 1H).

MS m/z ([M+H]$^+$) 584.

Step 4: Preparation of 2-(tert-butoxy)-2-{3-[1-(cyclobutylmethyl)-2-oxo-1,2-dihydropyridin-3-yl]-2-(3,4-dihydro-2H-1-benzopyran-6-yl)-6-(trifluoromethyl)phenyl}acetic acid (Example 38)

Using the procedure described in example 25, step 4, methyl 2-(tert-butoxy)-2-{3-[1-(cyclobutylmethyl)-2-oxo-1,2-dihydropyridin-3-yl]-2-(3,4-dihydro-2H-1-benzopyran-6-yl)-6-(trifluoromethyl)phenyl}acetate (38c) (45 mg, 0.077 mmol) is converted into 2-(tert-butoxy)-2-{3-[1-(cyclobutylmethyl)-2-oxo-1,2-dihydropyridin-3-yl]-2-(3,4-dihydro-2H-1-benzopyran-6-yl)-6-(trifluoromethyl)phenyl}acetic acid (example 38) (15 mg, 0.026 mmol, 34%).

$^1$H NMR (400 MHz, CD$_3$OD) δ 0.94 and 0.96 (s, 9H), 1.59-1.80 (m, 2H), 1.80-2.10 (m, 6H), 2.50-2.70 (m, 2H), 2.72-2.77 (m, 1H), 3.65-4.05 (m, 2H), 4.05-4.25 (m, 2H), 5.19 (s, 1H), 6.17-6.24 (m, 1H), 6.50 and 6.66 (d, J=8.3 Hz, 1H), 6.67-6.79 (m, 1H), 7.06-7.30 (m, 2H), 7.38-7.49 (m, 2H), 7.76 (d, J=8.2 Hz, 1H).

MS m/z ([M+H]$^+$) 570.

Example 39

Synthesis of 2-(tert-butoxy)-2-[3-(1-cyclopropyl-6-oxo-1,6-dihydropyridin-3-yl)-2-(3,4-dihydro-2H-1-benzopyran-6-yl)-6-(trifluoromethyl)phenyl]acetic acid

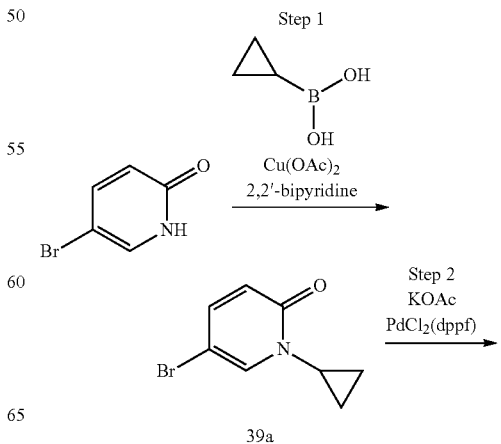

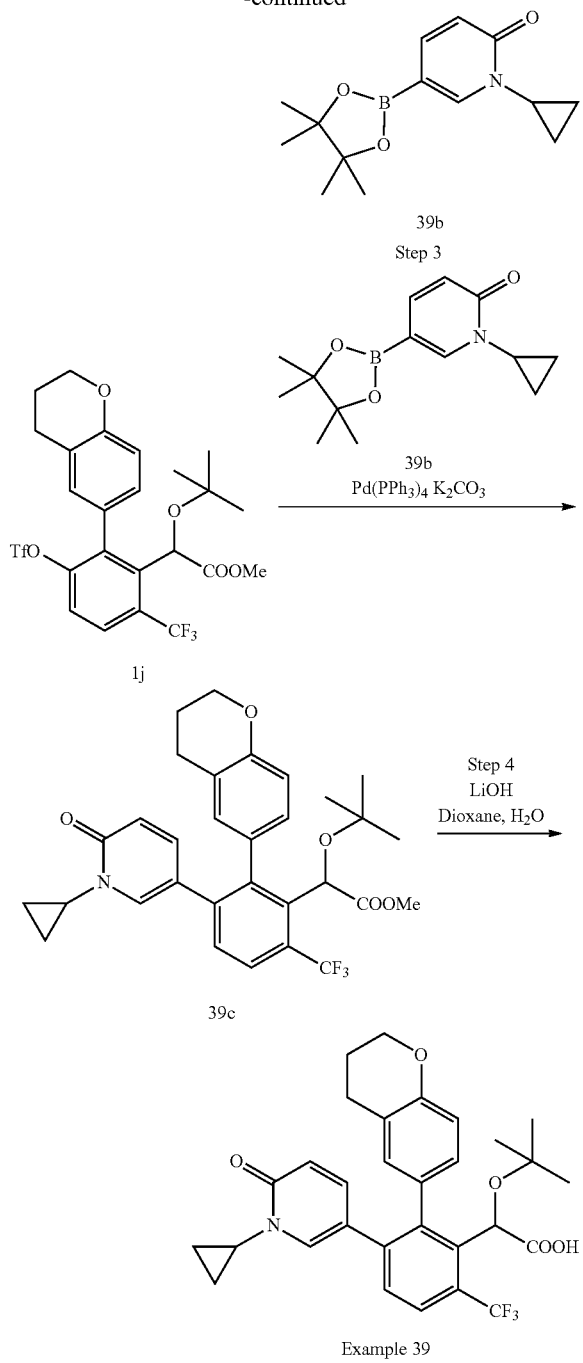

Step 1: Preparation of intermediate 5-bromo-1-cyclopropyl-1H-pyridin-2-one (39a)

A mixture of 5-bromo-2(1H)-pyridone (217 mg, 1.25 mmol), cyclopropylboronic acid (214 mg, 2.49 mmol), 2,2'-bipyridine (205 mg, 1.31 mmol), copper(I) acetate (236 mg, 1.30 mmol) and sodium carbonate (291 mg, 2.74 mmol) in 1,2-dichloroethane (7 mL) was stirred at 70° C. overnight. A saturated solution of ammonium chloride was added (20 mL). The layers were separated. The aqueous layer was extracted with dichloromethane (2×15 mL). The organic layer was washed with water (20 mL), dried over sodium sulfate and concentrated in vacuo. The residue was purified by flash chromatography on silica gel (cyclohexane/ethyl acetate 50/50 to 0/100) to provide 5-bromo-1-cyclopropyl-1H-pyridin-2-one (39a) (127 mg, 0.59 mmol, 47%).

$^1$H NMR (300 MHz, CDCl$_3$) δ 0.84-0.90 (m, 2H), 1.11-1.18 (m, 2H), 3.27-3.35 (m, 1H), 6.46 (d, J=9.6 Hz, 1H), 7.31 (dd, J=2.7 Hz, J=9.6 Hz, 1H), 7.40 (d, J=2.7 Hz, 1H).
MS m/z ([M+H]$^+$) 214/216.

Step 2: Preparation of Intermediate 1-cyclopropyl-5-(tetramethyl-1,3,2-dioxaborolan-2-yl)-1H-pyridin-2-one (39b)

Using the procedure described in example 25, step 2, the intermediate 35-bromo-1-cyclopropyl-1H-pyridin-2-one (39a) (127 mg, 0.59 mmol) is converted, after purification by preparative TLC (ethyl acetate) into 1-cyclopropyl-5-(tetramethyl-1,3,2-dioxaborolan-2-yl)-1H-pyridin-2-one (39b) (35 mg, 0.13 mmol, 22%).

$^1$H NMR (300 MHz, CDCl$_3$) δ 0.85-0.90 (m, 2H), 1.08-1.15 (m, 2H), 1.28 (s, 12H), 3.26-3.34 (m, 1H), 6.47 (d, J=9.5 Hz, 1H), 7.54 (dd, J=2.0 Hz, J=9.5 Hz, 1H), 7.72 (d, J=2.0 Hz, 1H).

Step 3: Preparation of Intermediate methyl 2-(tert-butoxy)-2-[3-(1-cyclopropyl-6-oxo-1,6-dihydropyridin-3-yl)-2-(3,4-dihydro-2H-1-benzopyran-6-yl)-6-(trifluoromethyl)phenyl]acetate (39c)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (50 mg, 0.087 mmol) is converted by reaction with 1-cyclopropyl-5-(tetramethyl-1,3,2-dioxaborolan-2-yl)-1H-pyridin-2-one (39b) (34 mg, 0.130 mmol), after purification by preparative TLC (ethyl acetate) to methyl 2-(tert-butoxy)-2-[3-(1-cyclopropyl-6-oxo-1,6-dihydropyridin-3-yl)-2-(3,4-dihydro-2H-1-benzopyran-6-yl)-6-(trifluoromethyl)phenyl]acetate (39c) (36 mg, 0.065 mmol, 73%).

$^1$H NMR (300 MHz, CDCl$_3$) δ 0.45-0.59 (m, 2H), 0.87-1.06 (m, 11H), 1.84-2.04 (m, 2H), 2.48-2.67 (m, 1H), 2.76 (t, J=6.3 Hz, 1H), 3.20-3.29 (m, 1H), 3.72 (s, 3H), 4.17-4.23 (m, 2H), 5.14 and 5.15 (s, 1H), 6.40 and 6.41 (d, J=9.3 Hz, 1H), 6.49-6.53 (m, 1H), 6.62-6.84 (m, 2H), 7.10-7.15 (m, 2H), 7.37 (d, J=8.2 Hz, 1H), 7.74 (d, J=8.2 Hz, 1H).
MS m/z ([M+H]$^+$) 556.

Step 4: Preparation of 2-(tert-butoxy)-2-[3-(1-cyclopropyl-6-oxo-1,6-dihydropyridin-3-yl)-2-(3,4-dihydro-2H-1-benzopyran-6-yl)-6-(trifluoromethyl)phenyl]acetic acid (Example 39)

Using the procedure described in example 25, step 4, the intermediate methyl 2-(tert-butoxy)-2-[3-(1-cyclopropyl-6-oxo-1,6-dihydropyridin-3-yl)-2-(3,4-dihydro-2H-1-benzopyran-6-yl)-6-(trifluoromethyl)phenyl]acetate (39c) (36 mg, 0.065 mmol) is converted into 2-(tert-butoxy)-2-[3-(1-cyclopropyl-6-oxo-1,6-dihydropyridin-3-yl)-2-(3,4-dihydro-2H-1-benzopyran-6-yl)-6-(trifluoromethyl)phenyl]acetic acid (example 39) (19 mg, 0.035 mmol, 54%) as a white solid.

$^1$H NMR (300 MHz, CDCl$_3$) δ 0.45-0.59 (m, 2H), 0.87-1.06 (m, 11H), 1.93-2.04 (m, 2H), 2.53-2.91 (m, 2H), 3.21-3.30 (m, 1H), 4.16-4.27 (m, 2H), 5.28 and 5.30 (s, 1H), 6.42-6.52 (m, 2H), 6.62-6.91 (m, 2H), 7.13-7.19 (m, 1H), 7.41 (d, J=8.2 Hz, 1H), 7.48 (bs, 1H), 7.75 (d, J=8.2 Hz, 1H).
MS m/z ([M+H]$^+$) 542.

Example 40

Synthesis of 2-(tert-butoxy)-2-{3-[1-(cyclobutylmethyl)-6-oxo-1,6-dihydropyridin-2-yl]-2-(3,4-dihydro-2H-1-benzopyran-6-yl)-6-(trifluoromethyl)phenyl}acetic acid

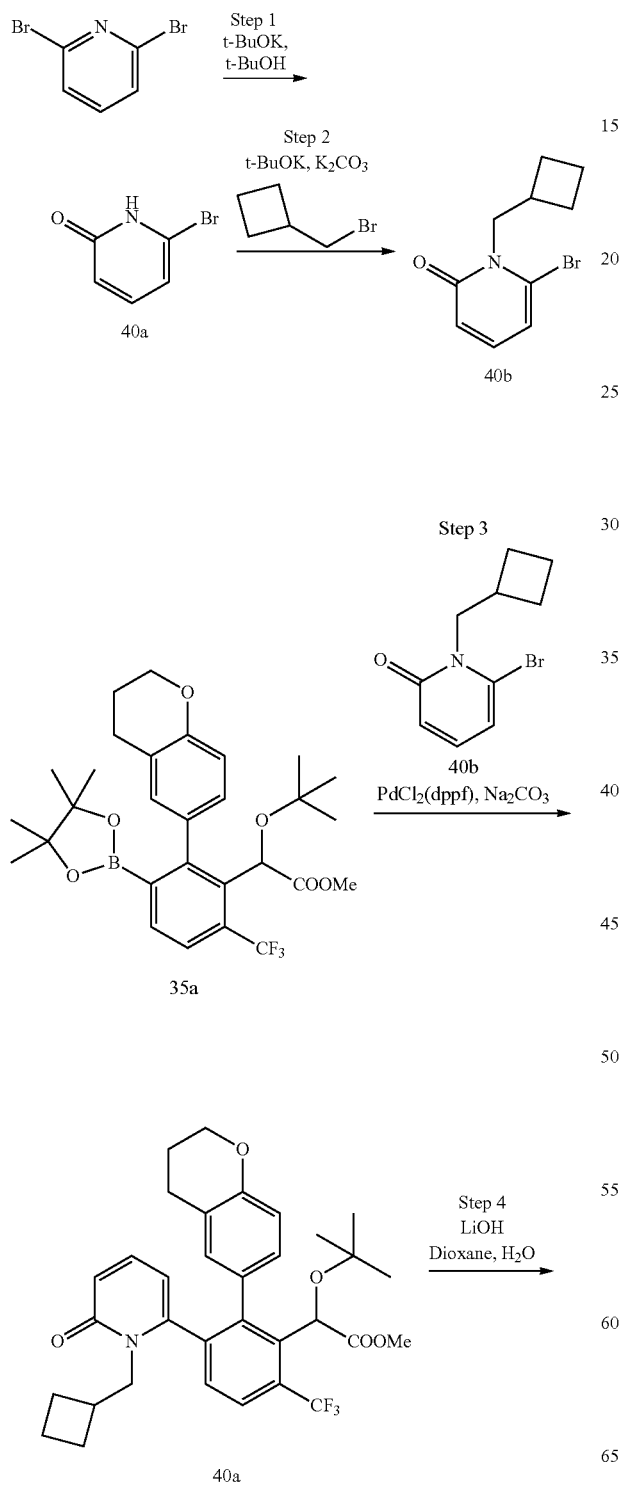

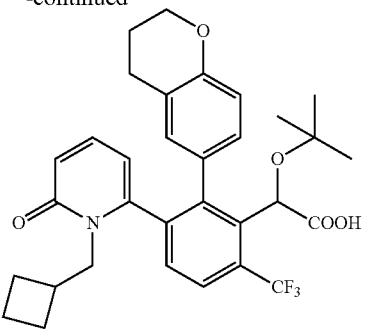

Example 40

Step 1: Preparation of Intermediate 6-bromo-1,2-dihydropyridin-2-one (40a)

Potassium tert-butoxide (4.74 g, 42.2 mmol) was added to a solution of 2,6-dibromopyridine (1.00 g, 4.22 mmol) in tert-Butyl alcohol (25 mL). The reaction mixture was refluxed for 18 hours, and concentrated in vacuo. A mixture of ice and water (20 mL) was added to the residue. The aqueous layer was washed with ethyl acetate (2×25 mL), acidified with concentrated hydrochloric acid until pH 3 and extracted with dichloromethane (2×30 mL). The organic layer was washed with brine (30 mL), then dried over sodium sulfate and concentrated in vacuo to provide 6-bromo-1,2-dihydropyridin-2-one (40a) (125 mg, 0.72 mmol, 17%).

$^1$H NMR (300 MHz, CDCl$_3$) δ 6.70 (dd, J=0.5 Hz, J=8.6 Hz, 1H), 6.83 (dd, J=0.5 Hz, J=7.4 Hz, 1H), 7.44 (dd, J=7.4 Hz, J=8.6 Hz, 1H), 12.05 (bs, 1H).

Step 2: Preparation of Intermediate 6-bromo-1-(cyclobutylmethyl)-1,2-dihydropyridin-2-one (40b)

Potassium tert-butoxide 1N in tetrahydrofuran (0.72 mL, 0.72 mmol) was added to a suspension of 6-bromo-1,2-dihydropyridin-2-one (40a) (125 mg, 0.72 mmol) in dimethoxyethane (1.2 mL). After 30 minutes stirring at room temperature, potassium carbonate (69 mg, 0.50 mmol) and (bromomethyl)cyclobutane (0.16 mL, 1.44 mmol) were added, and the reaction mixture was refluxed for 4 days. The resultant precipitate was filtered, and rinsed with ethyl acetate (5 mL). The filtrate was successively washed with water (20 mL) and brine (20 mL), then dried over sodium sulfate and concentrated in vacuo. The residue was purified by preparative TLC (cyclohexane/ethyl acetate 80/20) to provide 6-bromo-1-(cyclobutylmethyl)-1,2-dihydropyridin-2-one (40b) (61 mg, 40.25 mmol, 35%).

$^1$H NMR (400 MHz, CDCl$_3$) δ 1.79-1.97 (m, 4H), 1.99-2.07 (m, 2H), 2.83 (sept, J=7.5 Hz, 1H), 4.34 (d, J=7.5 Hz, 2H), 6.43 (dd, J=1.2 Hz, J=7.2 Hz, 1H), 6.48 (dd, J=1.2 Hz, J=9.1 Hz, 1H), 7.09 (dd, J=7.2 Hz, J=9.1 Hz, 1H).

MS m/z ([M+H]$^+$) 242/244.

Step 3: Preparation of Intermediate methyl 2-(tert-butoxy)-2-{3-[1-(cyclobutylmethyl)-6-oxo-1,6-dihydropyridin-2-yl]-2-(3,4-dihydro-2H-1-benzopyran-6-yl)-6-(trifluoromethyl)phenyl}acetate (40c)

Using the procedure described in example 35, step 2, the intermediate methyl 2-(tert-butoxy)-2-[2-(3,4-dihydro-2H-1-benzopyran-6-yl)-3-(tetramethyl-1,3,2-dioxaborolan-2- yl)-6-(trifluoromethyl)phenyl]acetate (35a) (70 mg, 0.128 mmol) is converted by reaction with 6-bromo-1-(cyclobutylmethyl)-1,2-dihydropyridin-2-one (40b) (46 mg, 0.191 mmol), after purification by preparative TLC (dichloromethane/ethyl acetate 60/40) to methyl 2-(tert-butoxy)-2-{3-[1-(cyclobutylmethyl)-6-oxo-1,6-dihydropyridin-2-yl]-2-(3,4-dihydro-2H-1-benzopyran-6-yl)-6-(trifluoromethyl)phenyl}acetate (40c) (50 mg, 0.086 mmol, 72%).

$^1$H NMR (300 MHz, CDCl$_3$) δ 0.91 and 0.93 and 1.02 and 1.03 (s, 9H), 1.24-1.37 (m, 1H), 1.46-1.80 (m, 4H), 1.80-2.10 (m, 3H), 2.40-2.80 (m, 3H), 2.98-3.10 and 3.27-3.42 (m, 1H), 3.68 and 3.69 and 3.74 and 3.75 (s, 3H), 3.86-3.95 and 4.10-4.24 (m, 3H), 5.11 and 5.15 and 5.17 and 5.18 (s, 1H), 5.66-5.72 and 6.01-6.08 (m, 1H), 6.31-6.42 (m, 1H), 6.53-7.24 (m, 4H), 7.40-7.48 (m, 1H), 7.82 (d, J=8.1 Hz, 1H).

MS m/z ([M+H]$^+$) 584.

Step 4: Preparation of 2-(tert-butoxy)-2-{3-[1-(cyclobutylmethyl)-6-oxo-1,6-dihydropyridin-2-yl]-2-(3,4-dihydro-2H-1-benzopyran-6-yl)-6-(trifluoromethyl)phenyl}acetic acid (Example 40)

Using the procedure described in example 25, step 4, methyl 2-(tert-butoxy)-2-{3-[1-(cyclobutylmethyl)-6-oxo-1,6-dihydropyridin-2-yl]-2-(3,4-dihydro-2H-1-benzopyran-6-yl)-6-(trifluoromethyl)phenyl}acetate (40c) (50 mg, 0.086 mmol) is converted to 2-(tert-butoxy)-2-{3-[1-(cyclobutylmethyl)-6-oxo-1,6-dihydro pyridin-2-yl]-2-(3,4-dihydro-2H-1-benzopyran-6-yl)-6-(trifluoromethyl)phenyl}acetic acid (example 40) (38 mg, 0.067 mmol, 78%).

$^1$H NMR (300 MHz, CDCl$_3$) δ 0.95 and 1.07 (s, 9H), 1.23-1.37 (m, 1H), 1.45-1.81 (m, 4H), 1.81-2.08 (m, 3H), 2.40-2.80 (m, 3H), 2.96-3.40 (m, 1H), 3.84-3.99 and 4.10-4.26 (m, 3H), 5.16-5.37 (m, 1H), 5.60-5.79 and 5.96-6.11 (m, 1H), 6.32-6.46 (m, 1H), 6.49-6.80 (m, 2H), 6.98-7.56 (m, 3H), 7.83 (d, J=8.1 Hz, 1H).

MS m/z ([M+H]$^+$) 570.

Example 41

Synthesis of 2-(tert-butoxy)-2-[2-(3,4-dihydro-2H-1-benzopyran-6-yl)-3-(pyridazin-4-yl)-6-(trifluoromethyl)phenyl]acetic acid

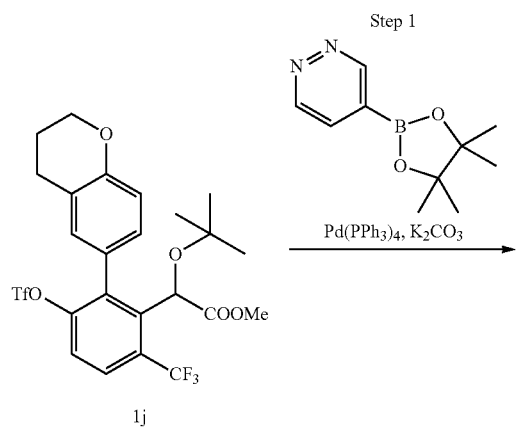

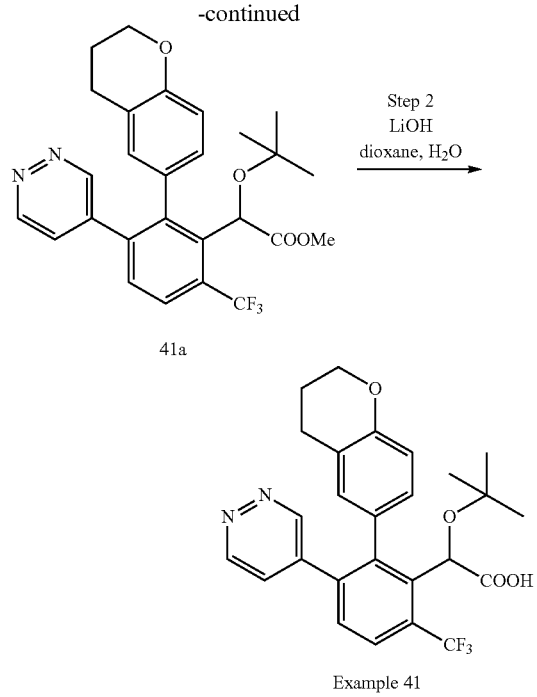

Example 41

Step 1: Preparation of Intermediate methyl 2-(tert-butoxy)-2-[2-(3,4-dihydro-2H-1-benzopyran-6-yl)-3-(pyridazin-4-yl)-6-(trifluoromethyl)phenyl]acetate (41a)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (70 mg, 0.122 mmol) is converted, by reaction with 4-(4,4,5,5-tetramethyl-1,3,2-dioxaborolan-2-yl)pyridazine (38 mg, 0.184 mmol), after purification by preparative TLC (dichloromethane/ethyl acetate 50/50) to methyl 2-(tert-butoxy)-2-[2-(3,4-dihydro-2H-1-benzopyran-6-yl)-3-(pyridazin-4-yl)-6-(trifluoromethyl)phenyl]acetate (41a) (19 mg, 0.038 mmol, 31%).

$^1$H NMR (400 MHz, CDCl$_3$) δ 0.95 and 0.96 (s, 9H), 1.87-1.93 (m, 1H), 1.99-2.05 (m, 1H), 2.38-2.63 (m, 1H), 2.66-2.81 (m, 1H), 3.73 (s, 3H), 4.12-4.20 (m, 2H), 5.18 (s, 1H), 6.37-6.43 (m, 1H), 6.53 and 6.77 (d, J=8.3 Hz, 1H), 7.14-7.22 (m, 2H), 7.44-7.48 (m, 1H), 7.86 (d, J=8.1 Hz, 1H), 8.87 and 8.93 (dd, J=1.1 Hz, J=2.3 Hz, 1H), 9.00 and 9.03 (dd, J=1.1 Hz, J=5.3 Hz, 1H).

MS m/z ([M+H]$^+$) 501.

Step 2: Preparation 2-(tert-butoxy)-2-[2-(3,4-dihydro-2H-1-benzopyran-6-yl)-3-(pyridazin-4-yl)-6-(trifluoromethyl)phenyl]acetic acid (Example 41)

Using the procedure described in example 2, step 2, the methyl 2-(tert-butoxy)-2-[2-(3,4-dihydro-2H-1-benzopyran-6-yl)-3-(pyridazin-4-yl)-6-(trifluoromethyl)phenyl]acetate (41a) (19 mg, 0.038 mmol) is converted to 2-(tert-butoxy)-2-[2-(3,4-dihydro-2H-1-benzopyran-6-yl)-3-(pyridazin-4-yl)-6-(trifluoromethyl)phenyl]acetic acid (example 41) (17 mg, 0.035 mmol, 92%) a yellow solid.

$^1$H NMR (400 MHz, CDCl$_3$) δ 0.97 (s, 9H), 1.85-1.95 (m, 1H), 1.96-2.08 (m, 1H), 2.33-2.58 (m, 1H), 2.76-2.80 (m, 1H), 4.12-4.21 (m, 2H), 5.30 and 5.33 (s, 1H), 6.36-6.83 (m, 2H), 7.16-7.26 (m, 1H), 7.49-7.53 (m, 2H), 7.89 (d, J=8.2 Hz, 1H), 8.91 and 8.98 (s, 1H), 9.03 and 9.06 (d, J=5.3 Hz, 1H).

MS m/z ([M+H]⁺) 487.

Example 42

Synthesis of 2-(tert-butoxy)-2-[2-(3,4-dihydro-2H-1-benzopyran-6-yl)-3-(1-methyl-1H-pyrrol-3-yl)-6-(trifluoromethyl)phenyl]acetic acid

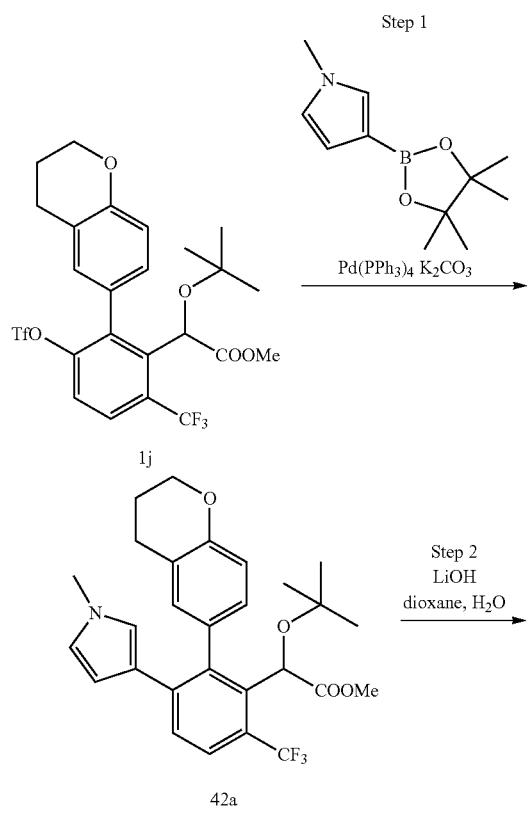

Example 42

Step 1: Preparation of Intermediate methyl 2-(tert-butoxy)-2-[2-(3,4-dihydro-2H-1-benzopyran-6-yl)-3-(1-methyl-1H-pyrrol-3-yl)-6-(trifluoromethyl)phenyl]acetate (42a)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (70 mg, 0.122 mmol) is converted, by reaction with 1-methylpyrrole-3-boronic acid, pinacol ester (38 mg, 0.183 mmol), after purification by preparative TLC (cyclohexane/ethyl acetate: 80/20) to methyl 2-(tert-butoxy)-2-[2-(3,4-dihydro-2H-1-benzopyran-6-yl)-3-(1-methyl-1H-pyrrol-3-yl)-6-(trifluoromethyl)phenyl]acetate (42a) (45 mg, 0.089 mmol, 73%).

¹H NMR (400 MHz, CDCl₃) δ 0.92 and 0.93 (s, 9H), 1.89-2.04 (m, 2H), 2.46-2.63 (m, 1H), 2.64-2.79 (m, 1H), 3.11 and 3.18 (s, 3H), 3.74 (s, 3H), 4.13-4.20 (m, 2H), 5.17 and 5.21 (s, 1H), 5.82 and 5.88 (d, J=3.5 Hz, 1H), 5.99 (d, J=3.5 Hz, 1H), 6.42 (bs, 1H), 6.52-6.70 (m, 2H), 7.08-7.14 (m, 1H), 7.41-7.47 (m, 1H), 7.72 (d, J=8.1 Hz, 1H).

MS m/z ([M+Na]⁺) 524, ([M+H]⁺) 502.

Step 2: Preparation 2-(tert-butoxy)-2-[2-(3,4-dihydro-2H-1-benzopyran-6-yl)-3-(1-methyl-1H-pyrrol-3-yl)-6-(trifluoromethyl)phenyl]acetic acid (Example 42)

Using the procedure described in example 2, step 2, the methyl 2-(tert-butoxy)-2-[2-(3,4-dihydro-2H-1-benzopyran-6-yl)-3-(1-methyl-1H-pyrrol-3-yl)-6-(trifluoromethyl)phenyl]acetate (42a) (45 mg, 0.089 mmol) is converted, after purification by preparative TLC (dichloromethane/methanol: 97/3) to 2-(tert-butoxy)-2-[2-(3,4-dihydro-2H-1-benzopyran-6-yl)-3-(1-methyl-1H-pyrrol-3-yl)-6-(trifluoromethyl)phenyl]acetic acid (example 42) (10 mg, 0.020 mmol, 23%) a white solid.

¹H NMR (300 MHz, CDCl₃) δ 0.94 (s, 9H), 1.90-1.96 (m, 1H), 1.97-2.04 (m, 1H), 2.48-2.60 (m, 1H), 2.70-2.84 (m, 1H), 3.08 and 3.15 (s, 3H), 4.14-4.20 (m, 2H), 5.32 and 5.40 (s, 1H), 5.86-6.02 (m, 2H), 6.40-6.76 (m, 3H), 7.46-7.51 (m, 2H), 7.73 (d, J=8.1 Hz, 1H).

MS m/z ([M+H]⁺) 488.
MS m/z ([M−H]⁻) 486.

Example 43

Synthesis of 4-{3-[(tert-butoxy)(carboxy)methyl]-2-(3,4-dihydro-2H-1-benzopyran-6-yl)-4-(trifluoromethyl)phenyl}benzoic acid

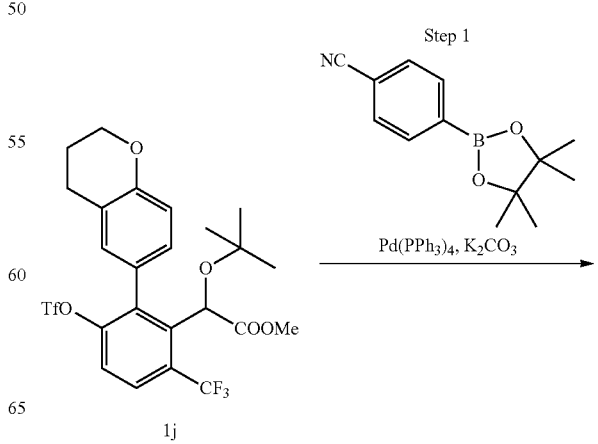

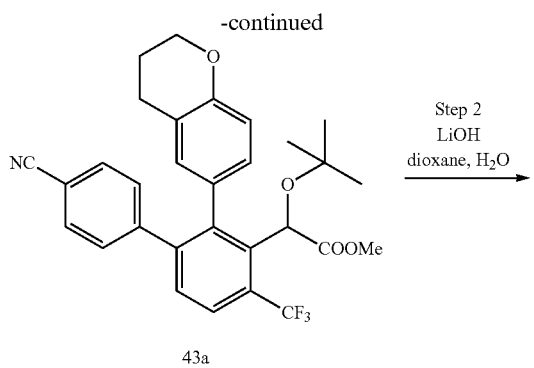

43a

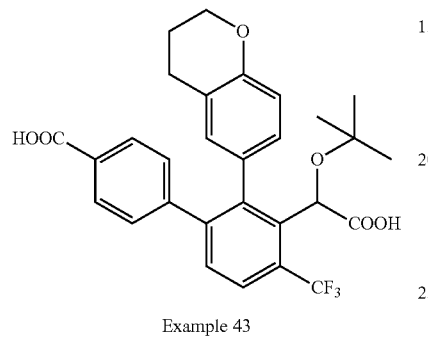

Example 43

Step 1: Preparation of Intermediate methyl 2-(tert-butoxy)-2-[3-(4-cyanophenyl)-2-(3,4-dihydro-2H-1-benzopyran-6-yl)-6-(trifluoromethyl)phenyl]acetate (43a)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (82 mg, 0.143 mmol) is converted by reaction with (4-cyanophenyl)boronic acid (32 mg, 0.218 mmol), after purification by preparative TLC (cyclohexane/ethyl acetate 80/20) to methyl 2-(tert-butoxy)-2-[3-(4-cyanophenyl)-2-(3,4-dihydro-2H-1-benzopyran-6-yl)-6-(trifluoromethyl)phenyl]acetate (43a) (48 mg, 0.091 mmol, 61%).

$^1$H NMR (400 MHz, CDCl$_3$) δ 0.93 and 0.94 (s, 9H), 1.88-1.92 (m, 1H), 1.98-2.03 (m, 1H), 2.33-2.56 (m, 1H), 2.66-2.80 (m, 1H), 3.73 (s, 1H), 4.12-4.20 (m, 2H), 5.17 and 5.18 (s, 1H), 6.33-6.40 (m, 1H), 6.49 and 6.72 (d, J=8.3 Hz, 1H), 7.09-7.15 (m, 3H), 7.40 and 7.41 (d, J=8.1 Hz, 1H), 7.44 and 7.46 (d, J=8.4 Hz, 2H), 7.78 (d, J=8.1 Hz, 1H).

Step 2: Preparation 4-{3-[(tert-butoxy)(carboxy)methyl]-2-(3,4-dihydro-2H-1-benzopyran-6-yl)-4-(trifluoromethyl)phenyl}benzoic acid (Example 43)

To a solution of methyl 2-(tert-butoxy)-2-[3-(4-cyanophenyl)-2-(3,4-dihydro-2H-1-benzopyran-6-yl)-6-(trifluoromethyl)phenyl]acetate (43a) (48 mg, 0.091 mmol) in dioxane (1.5 mL) and water (0.75 mL) was added lithium hydroxide (18 mg, 0.75 mmol). The mixture was heated at 95° C. for 18 hours. Further lithium hydroxide (18 mg, 0.75 mmol) was added and the mixture was heated at 110° C. for 24 hours. The mixture was poured in water (10 mL) and acidified with 1 M hydrochloric acid until ph 2. The mixture was extracted with ethyl acetate (2×5 mL). The organic layer was washed with brine (10 mL), dried over sodium sulfate and concentrated in vacuo to provide 4-{3-[(tert-butoxy)(carboxy) methyl]-2-(3,4-dihydro-2H-1-benzopyran-6-yl)-4-(trifluoromethyl)phenyl}benzoic acid (example 43) (39 mg, 0.073 mmol, 81%) as a white solid.

$^1$H NMR (300 MHz, CDCl$_3$) δ 0.97 (s, 9H), 1.86-1.91 (m, 1H), 1.97-2.05 (m, 1H), 2.30-2.50 (m, 1H), 2.75-2.80 (m, 1H), 4.10-4.20 (m, 2H), 5.33 and 5.37 (s, 1H), 6.37-6.80 (m, 2H), 7.13-7.17 (m, 2H), 7.46-7.50 (m, 2H), 7.80 (d, J=8.2 Hz, 1H), 7.91 (d, J=8.0 Hz, 2H).

MS m/z ([M−H]$^-$) 527.

Example 44

Synthesis of 3-{3-[(tert-butoxy)(carboxy)methyl]-2-(3,4-dihydro-2H-1-benzopyran-6-yl)-4-(trifluoromethyl)phenyl}benzoic acid

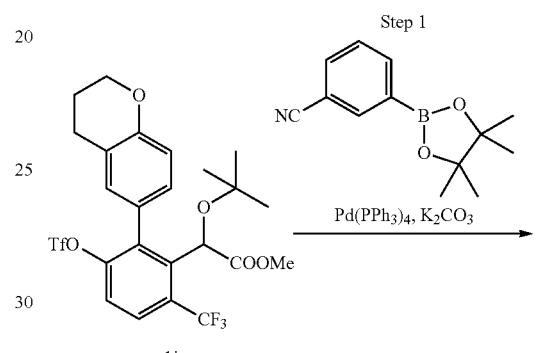

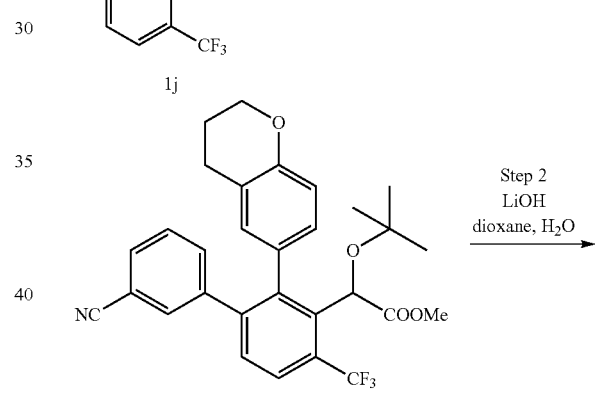

44a

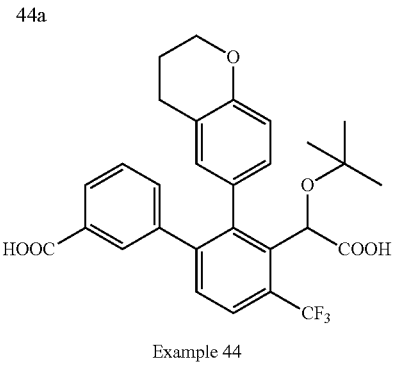

Example 44

Step 1: Preparation of Intermediate methyl 2-(tert-butoxy)-2-[3-(3-cyanophenyl)-2-(3,4-dihydro-2H-1-benzopyran-6-yl)-6-(trifluoromethyl)phenyl]acetate (44a)

Using the procedure described in example 1, step 11, the intermediate methyl 2-(tert-butoxy)-2-[2-(3,4-dihydro-2H-

1-benzopyran-6-yl)-3-[(trifluoromethane) sulfonyloxy]-6-(trifluoromethyl)phenyl]acetate (1j) (70 mg, 0.123 mmol) is converted by reaction with (3-cyanophenyl)boronic acid (27 mg, 0.184 mmol), after purification by preparative TLC (cyclohexane/ethyl acetate: 60/40) to methyl 2-(tert-butoxy)-2-[3-(3-cyanophenyl)-2-(3,4-dihydro-2H-1-benzopyran-6-yl)-6-(trifluoromethyl)phenyl]acetate (44a) (52 mg, 0.099 mmol, 81%).

$^1$H NMR (300 MHz, CDCl$_3$) δ 0.95 and 0.96 (s, 9H), 1.84-1.96 (m, 1H), 1.96-2.07 (m, 1H), 2.33-2.63 (m, 1H), 2.63-2.87 (m, 1H), 3.73 and 3.74 (s, 3H), 4.09-4.23 (m, 2H), 5.19 (s, 1H), 6.35-6.42 (m, 1H), 6.49 and 6.72 (d, J=8.4 Hz, 1H), 7.07-7.14 (m, 1H), 7.18-7.30 (m, 2H), 7.30-7.48 (m, 3H), 7.79 (d, J=8.2 Hz, 1H).

MS m/z ([M+Na]$^+$) 546.

Step 2: Preparation of 3-{3-[(tert-butoxy)(carboxy)methyl]-2-(3,4-dihydro-2H-1-benzopyran-6-yl)-4-(trifluoromethyl)phenyl}benzoic acid (Example 44)

Using the procedure described in example 43, step 2, the intermediate methyl 2-(tert-butoxy)-2-[3-(3-cyanophenyl)-2-(3,4-dihydro-2H-1-benzopyran-6-yl)-6-(trifluoromethyl)phenyl]acetate (51 mg, 0.097 mmol) is converted into 3-{3-[(tert-butoxy)(carboxy)methyl]-2-(3,4-dihydro-2H-1-benzopyran-6-yl)-4-(trifluoro methyl)phenyl}benzoic acid (example 44) (45 mg, 0.088 mmol, 91%).

$^1$H NMR (300 MHz, CDCl$_3$) δ 0.99 (s, 9H), 1.80-1.93 (m, 1H), 1.93-2.06 (m, 1H), 2.27-2.63 (m, 1H), 2.72-2.88 (m, 1H), 4.04-4.22 (m, 2H), 5.35 and 5.37 (s, 1H), 6.33-6.84 (m, 2H), 7.14-7.32 (m, 2H), 7.42-7.56 (m, 2H), 7.80 (d, J=8.2 Hz, 1H), 7.83-7.95 (m, 2H).

Example 45

Synthesis of 2-(tert-butoxy)-2-[2-(3,4-dihydro-2H-1-benzopyran-6-yl)-3-(1-methyl-1H-imidazol-4-yl)-6-(trifluoromethyl)phenyl]acetic acid Step 1

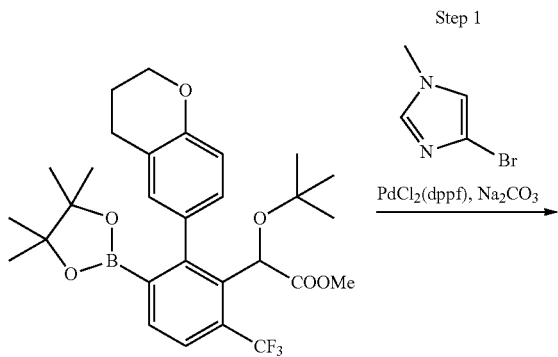

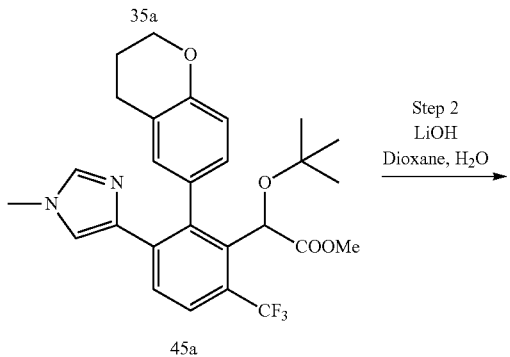

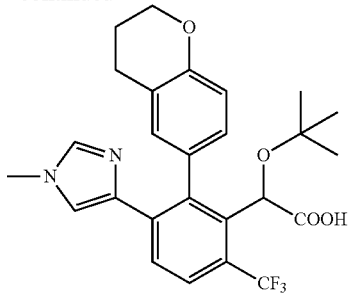

Example 45

Step 1-2: Preparation of 2-(tert-butoxy)-2-[2-(3,4-dihydro-2H-1-benzopyran-6-yl)-3-(1-methyl-1iH-imidazol-4-yl)-6-(trifluoromethyl)phenyl]acetic acid (Example 45)

To a solution of methyl 2-(tert-butoxy)-2-[2-(3,4-dihydro-2H-1-benzopyran-6-yl)-3-(tetramethyl-1,3,2-dioxaborolan-2-yl)-6-(trifluoromethyl)phenyl]acetate (35a) (100 mg, 0.182 mmol) in dioxane (1 mL) was added 4-bromo-1-methylimidazole (36 µL, 0.36 mmol) and sodium carbonate saturated aqueous solution (1 mL). This mixture was stirred at room temperature for 20 minutes while passing a stream of argon. [1,1'-Bis(diphenylphosphino) ferrocene]dichloropalladium(II), complex with dichloromethane (14 mg, 0.018 mmol) was added and the resulting mixture was stirred at 80° C. for 24 hours. Further 4-bromo-1-methylimidazole (36 µL, 0.36 mmol) and [1,1'-Bis(diphenylphosphino) ferrocene]dichloropalladium(II), complex with dichloromethane (14 mg, 0.018 mmol) were added and the resulting mixture was stirred at 80° C. for 24 hours. Water (10 mL) was added and the mixture was extracted with ethyl acetate (2×10 mL). The organic phase were washed with brine (10 mL), dried over sodium sulfate and concentrated in vacuo. The crude residue was purified on preparative TLC (dichloromethane/ethyl acetate: 90/10). The residue (42 mg) was dissolved in a mixture of dioxane (1.5 mL) and water (0.75 mL) and lithium hydroxide (16 mg, 0.67 mmol) was added. The mixture was heated at 110° C. overnight. The mixture was poured in water (5 mL), acidified with a 1 M hydrochloric acid solution until pH 4 followed by extraction with ethyl acetate (2×5 mL). The combined organic layers were washed with brine (5 mL), dried over sodium sulfate and concentrated in vacuo. The residue was purified by trituration in diethyl ether (2 mL) to provide 2-(tert-butoxy)-2-[2-(3,4-dihydro-2H-1-benzopyran-6-yl)-3-(1-methyl-1H-imidazol-4-yl)-6-(trifluoromethyl)phenyl]acetic acid (example 45) (3 mg, 0.006 mmol, 3%) as a white solid.

$^1$H NMR (400 MHz, CDCl$_3$) δ 1.00 (s, 9H), 2.02-2.05 (m, 2H), 2.69-2.80 (m, 2H), 3.58 (s, 3H), 4.24-4.27 (m, 2H), 5.20 (bs, 1H), 5.52-5.56 (m, 1H), 6.76-6.94 (m, 2H), 7.40-7.44 (m, 1H), 7.81-7.83 (m, 1H), 8.02-8.12 (m, 1H), 8.28-8.30 (m, 1H).

MS m/z ([M+H]$^+$) 489.

MS m/z ([M-H]$^-$) 487.

Example 46

Synthesis of 2-(tert-butoxy)-2-[2-(3,4-dihydro-2H-1-benzopyran-6-yl)-3-(1,2-thiazol-4-yl)-6-(trifluoromethyl)phenyl]acetic acid

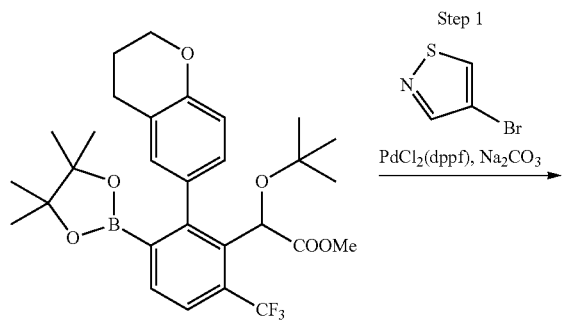

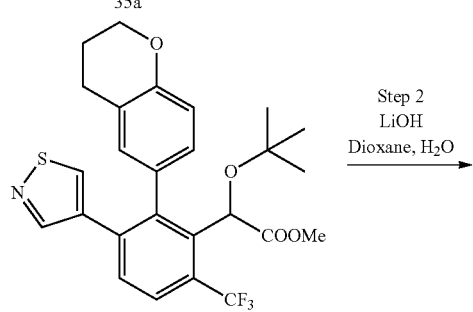

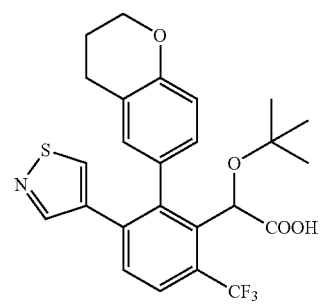

Example 46

Step 1: Preparation of Intermediate methyl 2-(tert-butoxy)-2-[2-(3,4-dihydro-2H-1-benzopyran-6-yl)-3-(1,2-thiazol-4-yl)-6-(trifluoromethyl)phenyl]acetate (46a)

Using the procedure described in example 35, step 2, the methyl 2-(tert-butoxy)-2-[2-(3,4-dihydro-2H-1-benzopyran-6-yl)-3-(tetramethyl-1,3,2-dioxaborolan-2-yl)-6-(trifluoromethyl)phenyl]acetate (35a) (100 mg, 0.182 mmol) is converted by reaction with 4-bromoisothiazole (59 mg, 0.36 mmol), after purification by preparative TLC (cyclohexane/ethyl acetate 70/30) into methyl 2-(tert-butoxy)-2-[2-(3,4-dihydro-2H-1-benzopyran-6-yl)-3-(1,2-thiazol-4-yl)-6-(trifluoromethyl)phenyl]acetate (46a) (51 mg, 0.100 mmol, 56%).

$^1$H NMR (400 MHz, CDCl$_3$) δ 0.97 (s, 9H), 1.92-1.98 (m, 1H), 2.01-2.07 (m, 1H), 2.47-2.63 (m, 1H), 2.68-2.82 (m, 1H), 3.72 (s, 3H), 4.17-4.23 (m, 2H), 5.17 and 5.18 (s, 1H), 6.49-6.80 (m, 2H), 7.10-7.15 (m, 1H), 7.52 and 7.53 (d, J=8.1 Hz, 1H), 7.77 (d, J=8.1 Hz, 1H), 8.08 (s, 1H), 8.12 (s, 1H).

MS m/z ([M+H]$^+$) 506.
MS m/z ([M−H]$^−$) 504.

Step 2: Preparation of 2-(tert-butoxy)-2-[2-(3,4-dihydro-2H-1-benzopyran-6-yl)-3-(1,2-thiazol-4-yl)-6-(trifluoromethyl)phenyl]acetic acid (Example 46)

To a solution of methyl 2-(tert-butoxy)-2-[2-(3,4-dihydro-2H-1-benzopyran-6-yl)-3-(1,2-thiazol-4-yl)-6-(trifluoromethyl)phenyl]acetate (46a) (51 mg, 0.100 mmol) in a mixture of dioxane (1.5 mL) and water (0.75 mL) was added lithium hydroxide (19 mg, 0.81 mmol). The mixture was heated at 90° C. for 3 days. Further lithium hydroxide (19 mg, 0.81 mmol) was added and the mixture was stirred at 110° C. for 18 hours. The mixture was poured in water (5 mL), acidified with a 1 M hydrochloric acid solution until pH 2 followed by extraction with ethyl acetate (2×5 mL). The combined organic layers were washed with brine (5 mL), dried over sodium sulfate and concentrated in vacuo. The residue was purified by preparative TLC (dichloromethane/methanol 97/3) to provide 2-(tert-butoxy)-2-[2-(3,4-dihydro-2H-1-benzopyran-6-yl)-3-(1,2-thiazol-4-yl)-6-(trifluoromethyl)phenyl]acetic acid (example 46) (22 mg, 0.044 mmol, 44%) as a white solid.

$^1$H NMR (400 MHz, CDCl$_3$) δ 1.00 (s, 9H), 1.91-1.97 (m, 1H), 2.01-2.07 (m, 1H), 2.47-2.60 (m, 1H), 2.79-2.83 (m, 1H), 4.17-4.23 (m, 2H), 5.31 and 5.35 (s, 1H), 6.46-6.86 (m, 2H), 7.52 and 7.48 (bs, 1H), 7.57 and 7.58 (d, J=8.2 Hz, 1H), 7.79 (d, J=8.2 Hz, 1H), 8.08-8.14 (m, 2H).

MS m/z ([M+H]$^+$) 492.

Example 47

Synthesis of 2-(tert-butoxy)-2-[2-(3,4-dihydro-2H-1-benzopyran-6-yl)-3-(pyridin-2-yl)-6-(trifluoromethyl)phenyl]acetic acid

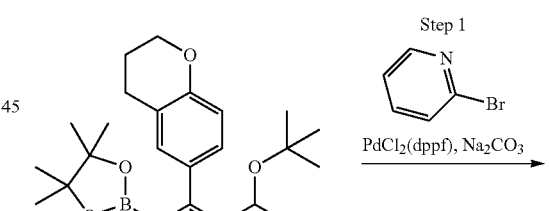

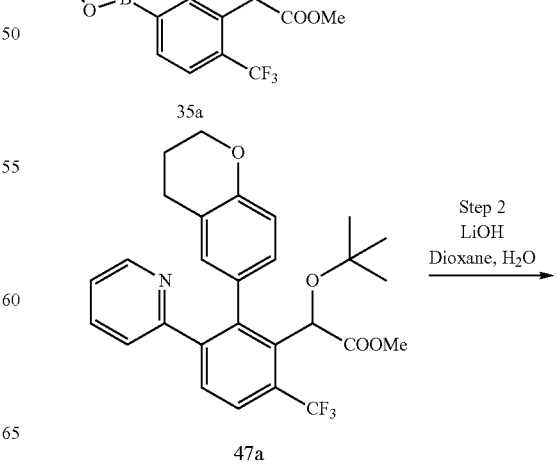

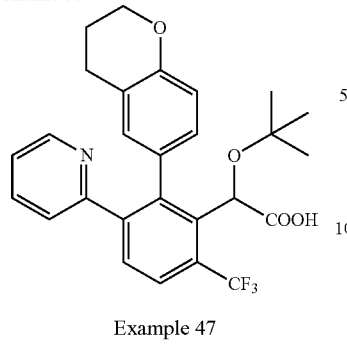

Example 47

Step 1: Preparation of Intermediate methyl 2-(tert-butoxy)-2-[2-(3,4-dihydro-2H-1-benzopyran-6-yl)-3-(pyridin-2-yl)-6-(trifluoromethyl)phenyl]acetate (47a)

Using the procedure described in example 35, step 2, the methyl 2-(tert-butoxy)-2-[2-(3,4-dihydro-2H-1-benzopyran-6-yl)-3-(tetramethyl-1,3,2-dioxaborolan-2-yl)-6-(trifluoromethyl)phenyl]acetate (35a) (100 mg, 0.182 mmol) is converted by reaction with 2-bromopyridine (57 mg, 0.36 mmol), after purification by preparative TLC (cyclohexane/ethyl acetate 70/30) into methyl 2-(tert-butoxy)-2-[2-(3,4-dihydro-2H-1-benzopyran-6-yl)-3-(pyridin-2-yl)-6-(trifluoromethyl)phenyl]acetate (47a) (31 mg, 0.062 mmol, 34%).

$^1$H NMR (400 MHz, CDCl$_3$) δ 0.91 and 0.92 (s, 9H), 1.83-1.91 (m, 1H), 1.98-2.04 (m, 1H), 2.32-2.56 (m, 1H), 2.67-2.81 (m, 1H), 3.74 (s, 3H), 4.12-4.19 (m, 2H), 5.20 and 5.21 (s, 1H), 6.47-6.80 (m, 3H), 7.06 and 7.08 (dd, J=1.0 Hz, J=4.9 Hz, 1H), 7.17-7.22 (m, 1H), 7.33-7.39 (m, 1H), 7.68 and 7.70 (d, J=8.1 Hz, 1H), 7.81 (d, J=8.1 Hz, 1H), 8.55-8.59 (m, 1H).

MS m/z ([M+H]$^+$) 500.

Step 2: Preparation of 2-(tert-butoxy)-2-[2-(3,4-dihydro-2H-1-benzopyran-6-yl)-3-(pyridin-2-yl)-6-(trifluoromethyl)phenyl]acetic acid (Example 47)

Using the procedure described in example 2, step 2, the methyl 2-(tert-butoxy)-2-[2-(3,4-dihydro-2H-1-benzopyran-6-yl)-3-(pyridin-2-yl)-6-(trifluoromethyl)phenyl]acetate (47a) (31 mg, 0.062 mmol) is converted into 2-(tert-butoxy)-2-[2-(3,4-dihydro-2H-1-benzopyran-6-yl)-3-(pyridin-2-yl)-6-(trifluoromethyl)phenyl]acetic acid (example 47) (24 mg, 0.049 mmol, 79%) as a white solid.

$^1$H NMR (400 MHz, CDCl$_3$) δ 0.91 (s, 9H), 1.94 (m, 1H), 1.83-1.88 (m, 1H), 1.96 (bs, 1H), 2.26-2.55 (m, 2H), 4.10-4.16 (m, 2H), 5.24-5.29 (m, 1H), 6.40-6.69 (m, 2H), 6.86-7.04 (m, 1H), 7.15 (bs, 1H), 7.37-7.53 (m, 2H), 7.64-7.70 (m, 1H), 7.82-7.85 (m, 1H), 8.60-8.62 (m, 1H).

MS m/z ([M+H]$^+$) 486.

Example 48

Synthesis of 2-(tert-butoxy)-2-[2-(3,4-dihydro-2H-1-benzopyran-6-yl)-3-(pyridin-3-yl)-6-(trifluoromethyl)phenyl]acetic acid

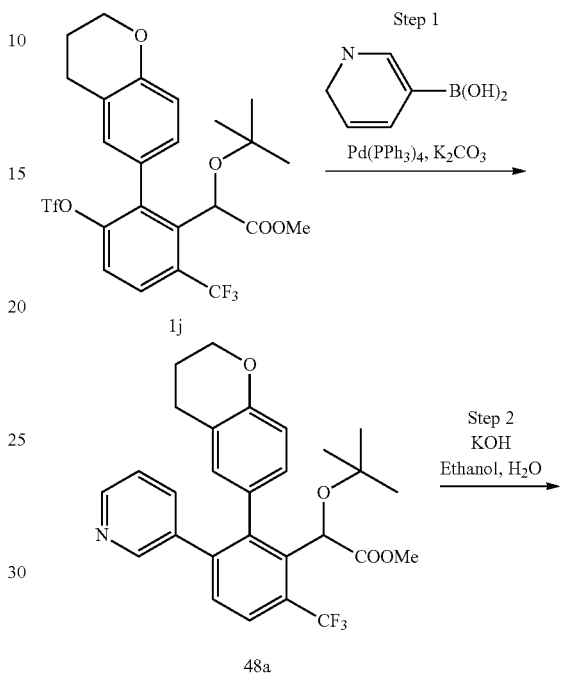

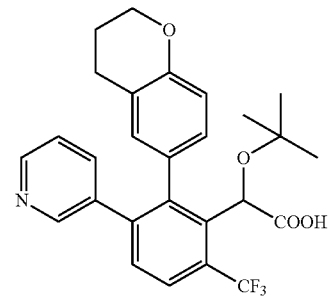

Example 48

Step 1: Preparation of Intermediate methyl 2-(tert-butoxy)-2-[2-(3,4-dihydro-2H-1-benzopyran-6-yl)-3-(pyridin-3-yl)-6-(trifluoromethyl)phenyl]acetate (48a)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (70 mg, 0.122 mmol) is converted by reaction with 3-Pyridineboronic acid (29 mg, 0.244 mmol) into methyl 2-(tert-butoxy)-2-[2-(3,4-dihydro-2H-1-benzopyran-6-yl)-3-(pyridin-3-yl)-6-(trifluoromethyl)phenyl]acetate (48a) (46 mg, 0.092 mmol, 75%) after purification by preparative TLC (cyclohexane/ethyl acetate 50/50).

$^1$H NMR (400 MHz, CDCl$_3$) δ 0.96 (s, 9H), 1.86-1.93 (m, 1H), 1.98-2.04 (m, 1H), 2.38-2.57 (m, 1H), 2.66-2.81 (m, 1H), 3.72 and 3.73 (s, 3H), 4.10-4.19 (m, 2H), 5.18 (s, 1H), 6.39-6.43 (m, 1H), 6.51 and 6.73 (d, J=8.4 Hz, 1H), 7.11-7.23 (m, 2H), 7.38-7.48 (m, 2H), 7.81 (d, J=8.2 Hz, 1H), 8.34-8.43 (m, 2H).

MS m/z ([M+H]⁺) 500.

Step 2: Preparation of 2-(tert-butoxy)-2-[2-(3,4-dihydro-2H-1-benzopyran-6-yl)-3-(pyridin-3-yl)-6-(trifluoromethyl)phenyl]acetic acid (Example 48)

Using the procedure described in example 5, step 4, the intermediate methyl 2-(tert-butoxy)-2-[2-(3,4-dihydro-2H-1-benzopyran-6-yl)-3-(pyridin-3-yl)-6-(tri fluoromethyl) phenyl]acetate (48a) (46 mg, 0.092 mmol) is converted into 2-(tert-butoxy)-2-[2-(3,4-dihydro-2H-1-benzopyran-6-yl)-3-(pyridin-3-yl)-6-(trifluoromethyl)phenyl]acetic acid (example 48) (20 mg, 0.041 mmol, 44%) as a yellow solid, after purification by preparative TLC (dichloromethane/methanol 95/5).

¹H NMR (300 MHz, CDCl₃) δ 0.97 (s, 9H), 1.86-1.91 (m, 1H), 1.95-2.04 (m, 1H), 2.22-2.55 (m, 1H), 2.75-2.80 (m, 1H), 4.10-4.19 (m, 2H), 5.30 and 5.33 (s, 1H), 6.39-6.78 (m, 2H), 7.09-7.16 (m, 1H), 7.29-7.49 (m, 3H), 7.81 (d, J=8.2 Hz, 1H), 8.38-8.44 (m, 2H).

MS m/z ([M+H]⁺) 486.

Example 49

Synthesis of 2-[3-(1,3-benzothiazol-2-yl)-2-(3,4-dihydro-2H-1-benzopyran-6-yl)-6-(trifluoromethyl)phenyl]-2-(tert-butoxy)acetic acid

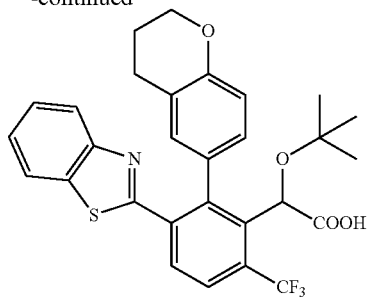

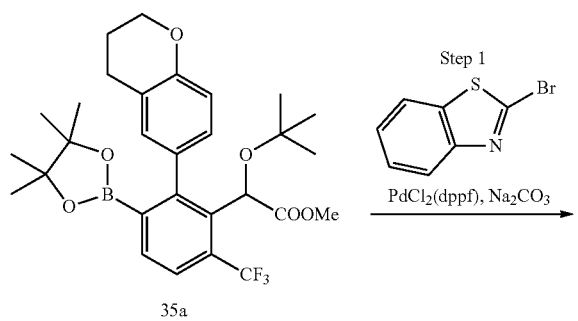

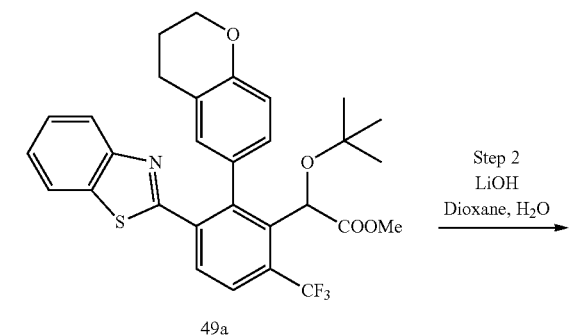

Example 49

Step 1: Preparation of Intermediate methyl 2-[3-(1,3-benzothiazol-2-yl)-2-(3,4-dihydro-2H-1-benzopyran-6-yl)-6-(trifluoromethyl)phenyl]-2-(tert-butoxy)acetate (49a)

Using the procedure described in example 35, step 2, the methyl 2-(tert-butoxy)-2-[2-(3,4-dihydro-2H-1-benzopyran-6-yl)-3-(tetramethyl-1,3,2-dioxaborolan-2-yl)-6-(trifluoromethyl)phenyl]acetate (35a) (110 mg, 0.200 mmol) is converted by reaction with 2-bromobenzothiazole (85 mg, 0.4 mmol), after purification by preparative TLC (cyclohexane/ethyl acetate 70/30), into methyl 2-[3-(1,3-benzothiazol-2-yl)-2-(3,4-dihydro-2H-1-benzopyran-6-yl)-6-(trifluoromethyl)phenyl]-2-(tert-butoxy)acetate (49a) (35 mg, 0.063 mmol, 31%).

¹H NMR (300 MHz, CDCl₃) δ 0.99 (s, 9H), 1.96 (m, 1H), 2.07 (m, 1H), 2.61 (m, 1H), 2.78 (m, 1H), 3.72 (s, 3H), 4.22-4.26 (m, 2H), 5.16 and 5.17 (s, 1H), 6.70-6.89 (m, 2H), 7.17 (m, 1H), 7.38-7.50 (m, 2H), 7.73 (m, 1H), 7.85 (m, 1H), 8.04 (m, 1H), 8.28 (m, 1H).

MS m/z ([M+H]⁺) 556

Step 2: Preparation of 2-[3-(1,3-benzothiazol-2-yl)-2-(3,4-dihydro-2H-1-benzopyran-6-yl)-6-(trifluoromethyl)phenyl]-2-(tert-butoxy)acetic acid (Example 49)

Using the procedure described in example 2, step 2, the methyl 2-[3-(1,3-benzothiazol-2-yl)-2-(3,4-dihydro-2H-1-benzopyran-6-yl)-6-(trifluoromethyl)phenyl]-2-(tert-butoxy)acetate (49a) (35 mg, 0.063 mmol) is converted after purification by preparative TLC (cyclohexane/ethyl acetate/acetic acid: 70/30/0.1) into 2-[3-(1,3-benzothiazol-2-yl)-2-(3,4-dihydro-2H-1-benzopyran-6-yl)-6-(trifluoromethyl)phenyl]-2-(tert-butoxy)acetic acid (example 49) (24 mg, 0.044 mmol, 70%) as a white solid.

¹H NMR (300 MHz, CDCl₃) δ 1.03 (s, 9H), 1.94 (m, 1H), 2.05-2.10 (m, 1H), 2.56 (m, 1H), 2.81-2.89 (m, 1H), 4.20-4.29 (m, 2H), 5.31 and 5.41 (s, 1H), 6.68-6.96 (m, 2H), 7.32 (t, J=8.1 Hz, 1H), 7.44-7.47 (m, 1H), 7.55-7.60 (m, 1H), 7.74 (d, J=8.1 Hz, 1H), 7.87 (d, J=8.4 Hz, 1H), 8.06 (d, J=8.1 Hz, 1H), 8.31 (d, J=8.4 Hz, 1H).

MS m/z ([M+H]⁺) 542.

Example 50

Synthesis of 2-(tert-butoxy)-2-[2-(3,4-dihydro-2H-1-benzopyran-6-yl)-3-(1,3-thiazol-2-yl)-6-(trifluoromethyl)phenyl]acetic acid

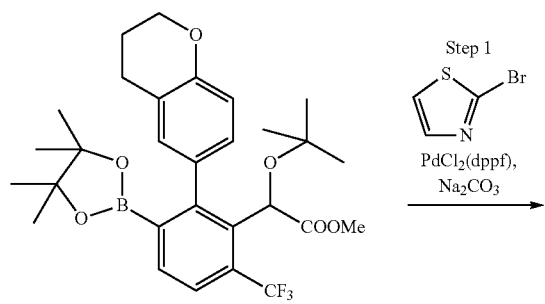

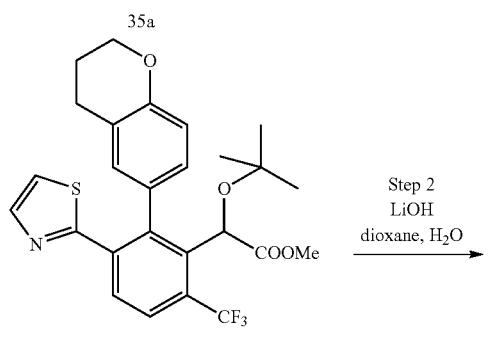

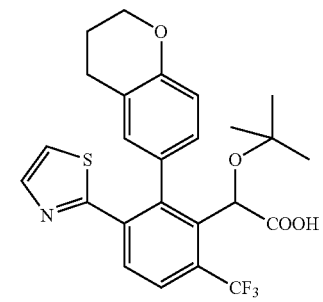

Example 40

Step 1: Preparation of intermediate methyl 2-(tert-butoxy)-2-[2-(3,4-dihydro-2H-1-benzopyran-6-yl)-3-(1,3-thiazol-2-yl)-6-(trifluoromethyl)phenyl]acetate (50a)

Using the procedure described in example 35, step 2, the methyl 2-(tert-butoxy)-2-[2-(3,4-dihydro-2H-1-benzopyran-6-yl)-3-(tetramethyl-1,3,2-dioxaborolan-2-yl)-6-(trifluoromethyl)phenyl]acetate (35a) (120 mg, 0.218 mmol) is converted by reaction with 2-bromothiazole (72 mg, 0.438 mmol), after purification by preparative TLC (cyclohexane/ethyl acetate 70/30) into (3-cyanophenyl)boronic acid (27 mg, 0.184 mmol), methyl 2-(tert-butoxy)-2-[2-(3,4-dihydro-2H-1-benzopyran-6-yl)-3-(1,3-thiazol-2-yl)-6-(trifluoromethyl)phenyl]acetate (40a) (38 mg, 0.075 mmol, 35%).

$^1$H NMR (300 MHz, CDCl$_3$) δ 1.01 (s, 9H), 2.03-2.07 (m, 2H), 2.67 (m, 1H), 2.78 (m, 1H), 3.69 (s, 3H), 4.25-4.28 (m, 2H), 5.16 (s, 1H), 6.78-6.88 (m, 2H), 7.12 (m, 1H), 7.45 (m, 1H), 7.78 (m, 1H), 7.80 (m, 1H), 8.28 (m, 1H).

MS m/z ([M+H]$^+$) 506.

Step 2: Preparation of 2-(tert-butoxy)-2-[2-(3,4-dihydro-2H-1-benzopyran-6-yl)-3-(1,3-thiazol-2-yl)-6-(trifluoromethyl)phenyl]acetic acid (Example 50)

Using the procedure described in example 2, step 2, the methyl 2-(tert-butoxy)-2-[2-(3,4-dihydro-2H-1-benzopyran-6-yl)-3-(1,3-thiazol-2-yl)-6-(trifluoromethyl)phenyl]acetate (50a) (38 mg, 0.075 mmol) is converted into 2-(tert-butoxy)-2-[2-(3,4-dihydro-2H-1-benzopyran-6-yl)-3-(1,3-thiazol-2-yl)-6-(trifluoromethyl)phenyl]acetic acid (example 50) (20 mg, 0.040 mmol, 54%) as a white solid after purification by preparative TLC (cyclohexane/ethyl acetate/acetic acid 70/30/0.1).

$^1$H NMR (300 MHz, CDCl$_3$) δ 1.02 (s, 9H), 2.07 (m, 2H), 2.85 (m, 2H), 4.26 (m, 2H), 5.28 (s, 1H), 6.77 (m, 2H), 7.26 (s, 1H), 7.48 (m, 1H), 7.78-7.82 (m, 2H), 8.29 (m, 1H), 9.53 (bs, 1H).

MS m/z ([M+H]$^+$) 492.

MS m/z ([M−H]$^−$) 490.

Example 51

Synthesis of 2-(tert-butoxy)-2-[2-(3,4-dihydro-2H-1-benzopyran-6-yl)-3-(1-methyl-1H-pyrazol-3-yl)-6-(trifluoromethyl)phenyl]acetic acid

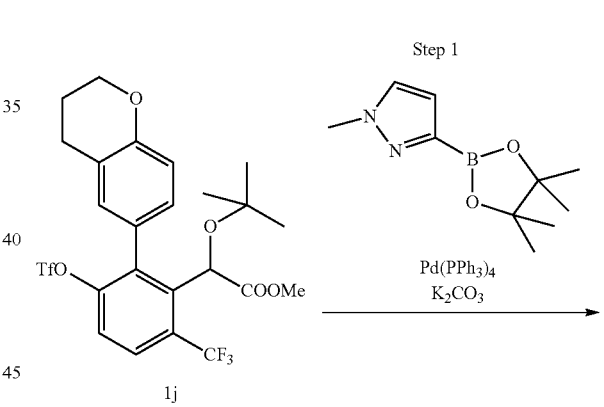

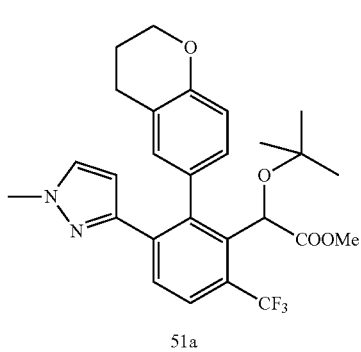

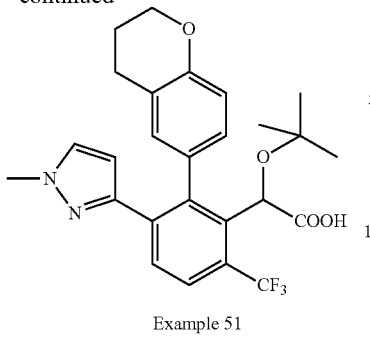

Example 51

Step 1: Preparation of Intermediate methyl 2-(tert-butoxy)-2-[2-(3,4-dihydro-2H-1-benzopyran-6-yl)-3-(1-methyl-1H-pyrazol-3-yl)-6-(trifluoromethyl)phenyl]acetate (51a)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (100 mg, 0.175 mmol) is converted by reaction with 1-methyl-3-(4,4,5,5-tetramethyl-1,3,2-dioxaborolan-2-yl)-1H-pyrazole (55 mg, 0.264 mmol), after purification by preparative TLC (cyclohexane/ethyl acetate 70/30) into methyl 2-(tert-butoxy)-2-[2-(3,4-dihydro-2H-1-benzopyran-6-yl)-3-(1-methyl-1H-pyrazol-3-yl)-6-(trifluoromethyl)phenyl]acetate (51a) (47 mg, 0.093 mmol, 53%).

$^1$H NMR (300 MHz, CDCl$_3$) δ 0.96 (s, 9H), 1.99-2.04 (m, 2H), 2.63 (m, 1H), 2.76 (m, 1H), 3.70 (s, 3H), 3.86 (s, 3H), 4.20 (m, 2H), 5.15-5.19 (m, 2H), 6.67-6.82 (m, 2H), 7.03 (s, 1H), 7.05-7.13 (m, 1H), 7.73 (d, J=8.4 Hz, 1H), 7.96 (d, J=8.4 Hz, 1H).

MS m/z ([M+H]$^+$) 503.

Step 2: Preparation of 2-(tert-butoxy)-2-[2-(3,4-dihydro-2H-1-benzopyran-6-yl)-3-(1-methyl-1H-pyrazol-3-yl)-6-(trifluoromethyl)phenyl]acetic acid (Example 51)

Using the procedure described in example 2, step 2, the methyl 2-(tert-butoxy)-2-[2-(3,4-dihydro-2H-1-benzopyran-6-yl)-3-(1-methyl-1H-pyrazol-3-yl)-6-(trifluoromethyl)phenyl]acetate (47 mg, 0.093 mmol) is converted after purification by preparative TLC (cyclohexane/ethyl acetate/acetic acid 50/50/0.1) into 2-(tert-butoxy)-2-[2-(3,4-dihydro-2H-1-benzopyran-6-yl)-3-(1-methyl-1H-pyrazol-3-yl)-6-(trifluoromethyl)phenyl]acetic acid (example 51) (43 mg, 0.088 mmol, 95%) as a white solid.

$^1$H NMR (300 MHz, CDCl$_3$) δ 0.96 (s, 9H), 1.95-2.06 (m, 2H), 2.60 (m, 1H), 2.83 (m, 1H), 3.87 (s, 3H), 4.11-4.25 (m, 2H), 5.16 and 5.19 (s, 1H), 5.30 (m, 1H), 6.65-6.88 (m, 2H), 7.04 (m, 1H), 7.47 (bs, 1H), 7.73 (d, J=8.4 Hz, 1H), 7.99 (d, J=8.4 Hz, 1H), 9.50 (bs, 1H)

MS m/z ([M+H]$^+$) 489.
MS m/z ([M−H]$^−$) 487.

Example 52

Synthesis of 2-(tert-butoxy)-2-[2-(3,4-dihydro-2H-1-benzopyran-6-yl)-3-(1-methyl-1H-pyrazol-5-yl)-6-(trifluoromethyl)phenyl]acetic acid

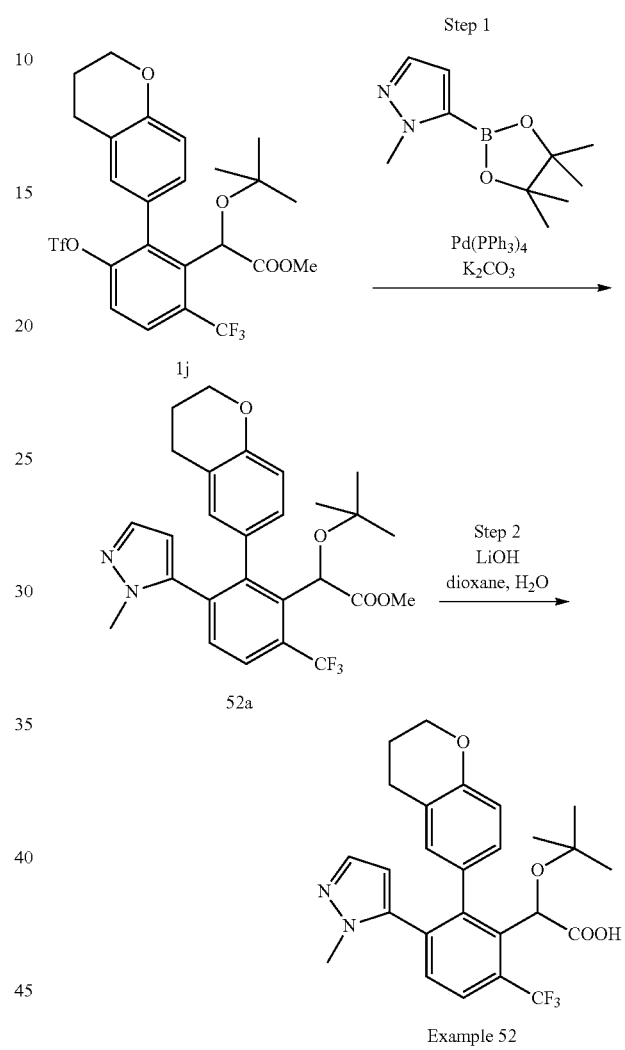

Example 52

Step 1: Preparation of Intermediate methyl 2-(tert-butoxy)-2-[2-(3,4-dihydro-2H-1-benzopyran-6-yl)-3-(1-methyl-1H-pyrazol-5-yl)-6-(trifluoromethyl)phenyl]acetate (52a)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (100 mg, 0.175 mmol) is converted by reaction with 1-methyl-5-(4,4,5,5-tetramethyl-1,3,2-dioxaborolan-2-yl)-1H-pyrazole (44 mg, 0.210 mmol, after purification by preparative TLC (cyclohexane/ethyl acetate 60/40) into methyl 2-(tert-butoxy)-2-[2-(3,4-dihydro-2H-1-benzopyran-6-yl)-3-(1-methyl-1H-pyrazol-5-yl)-6-(trifluoromethyl)phenyl]acetate (52a) (41 mg, 0.082 mmol, 47%).

$^1$H NMR (300 MHz, CDCl$_3$) δ 0.94 and 0.95 (s, 9H), 1.95 (m, 2H), 2.55 (m, 1H), 2.70 (m, 1H), 3.43 and 3.46 (s, 3H), 3.74 (s, 3H), 4.14 (m, 2H), 5.16 and 5.18 (s, 1H), 5.98 (m, 1H), 6.49-6.72 (m, 2H), 7.03-7.10 (m, 1H), 7.31 (s, 1H), 7.41 (m, 1H), 7.78 (d, J=8.1 Hz, 1H).

MS m/z ([M+H]⁺) 503.

Step 2: Preparation of 2-(tert-butoxy)-2-[2-(3,4-dihydro-2H-1-benzopyran-6-yl)-3-(1-methyl-1H-pyrazol-5-yl)-6-(trifluoromethyl)phenyl]acetic acid (Example 52)

Using the procedure described in example 2, step 2, the methyl 2-(tert-butoxy)-2-[2-(3,4-dihydro-2H-1-benzopyran-6-yl)-3-(1-methyl-1H-pyrazol-5-yl)-6-(trifluoromethyl)phenyl]acetate (52a) (41 mg, 0.082 mmol) is converted, after purification by preparative TLC (cyclohexane/ethyl acetate/acetic acid 50/50/0.1) into 2-(tert-butoxy)-2-[2-(3,4-dihydro-2H-1-benzopyran-6-yl)-3-(1-methyl-1H-pyrazol-5-yl)-6-(trifluoromethyl)phenyl]acetic acid (example 52) (33 mg, 0.067 mmol, 83%) as a white solid.

¹H NMR (300 MHz, CDCl₃) δ 0.98 (s, 9H), 1.99 (m, 2H), 2.25 (m, 1H), 2.74 (m, 1H), 3.42 and 3.45 (s, 3H), 4.17 (m, 2H), 5.30 and 5.36 (s, 1H), 6.01 (m, 1H), 6.49-6.75 (m, 2H), 7.32 (s, 1H), 7.47 (m, 2H), 7.79 (d, J=8.1 Hz, 1H), 9.59 (bs, 1H).

MS m/z ([M+H]⁺) 489.
MS m/z ([M−H]⁻) 487.

Example 53

Synthesis of 2-(tert-butoxy)-2-[2-(3,4-dihydro-2H-1-benzopyran-6-yl)-3-(2,5-dimethyl-thiophen-3-yl)-6-(trifluoromethyl)phenyl]acetic acid

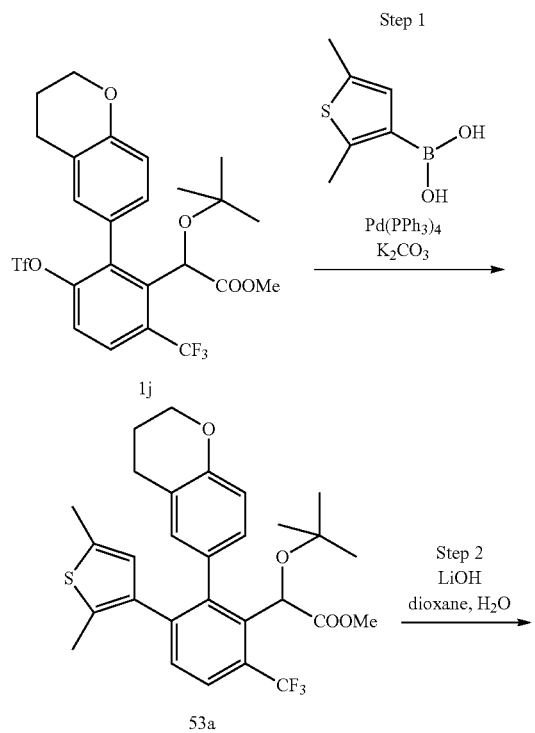

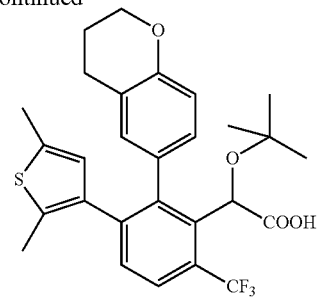

Example 53

Step 1: Preparation of Intermediate methyl 2-(tert-butoxy)-2-[2-(3,4-dihydro-2H-1-benzopyran-6-yl)-3-(2,5-dimethyl-thiophen-3-yl)-6-(trifluoromethyl)phenyl]acetate (53a)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (200 mg, 0.350 mmol) is converted by reaction with (2,5-dimethyl-3-thienyl)boronic acid (66 mg, 0.420 mmol), after purification by preparative TLC (cyclohexane/ethyl acetate 85/15) to methyl 2-(tert-butoxy)-2-[2-(3,4-dihydro-2H-1-benzopyran-6-yl)-3-(2,5-dimethyl-thiophen-3-yl)-6-(trifluoromethyl)phenyl]acetate (53a) (154 mg, 0.289 mmol, 82%) as a yellow oil.

¹H NMR (300 MHz, CDCl₃) δ 0.94 (s, 9H), 1.84-2.12 (m, 5H), 2.24 (s, 3H), 2.38-2.80 (m, 2H), 3.73 (s, 3H), 4.03-4.26 (m, 2H), 5.17 and 5.20 (s, 1H), 6.07 and 6.11 (s, 1H), 6.40-6.71 (m, 2H), 6.97-7.10 (m, 1H), 7.28-7.37 (m, 1H), 7.69 (d, J=8.1 Hz, 1H).

Step 2: Preparation of 2-(tert-butoxy)-2-[2-(3,4-dihydro-2H-1-benzopyran-6-yl)-3-(2,5-dimethyl-thiophen-3-yl)-6-(trifluoromethyl)phenyl]acetic acid (Example 53)

Using the procedure described in example 2, step 2, the methyl 2-(tert-butoxy)-2-[2-(3,4-dihydro-2H-1-benzopyran-6-yl)-3-(2,5-dimethyl-thiophen-3-yl)-6-(trifluoromethyl)phenyl]acetate (53a) (50 mg, 0.094 mmol) is converted into 2-(tert-butoxy)-2-[2-(3,4-dihydro-2H-1-benzopyran-6-yl)-3-(2,5-dimethyl-thiophen-3-yl)-6-(trifluoromethyl)phenyl]acetic acid (example 53) (46 mg, 0.088 mmol, 94%) as a white solid.

¹H NMR (300 MHz, CDCl₃) δ 0.94 (s, 9H), 1.83-2.04 (m, 2H), 2.05 (s, 3H), 2.24 (s, 3H), 2.39-2.86 (m, 2H), 4.05-4.26 (m, 2H), 5.31 and 5.38 (s, 1H), 6.10 and 6.12 (s, 1H), 6.35-6.80 (m, 2H), 7.37-7.48 (m, 2H), 7.70 (d, J=8.1 Hz, 1H), 9.57 (bs, 1H).

MS m/z ([M−H]⁻) 517.

Example 54
Synthesis of 2-(tert-butoxy)-2-[2-(3,4-dihydro-2H-1-benzopyran-6-yl)-3-[3-(dimethylamino)-1H-pyrazol-1-yl]-6-(trifluoromethyl)phenyl]acetic acid
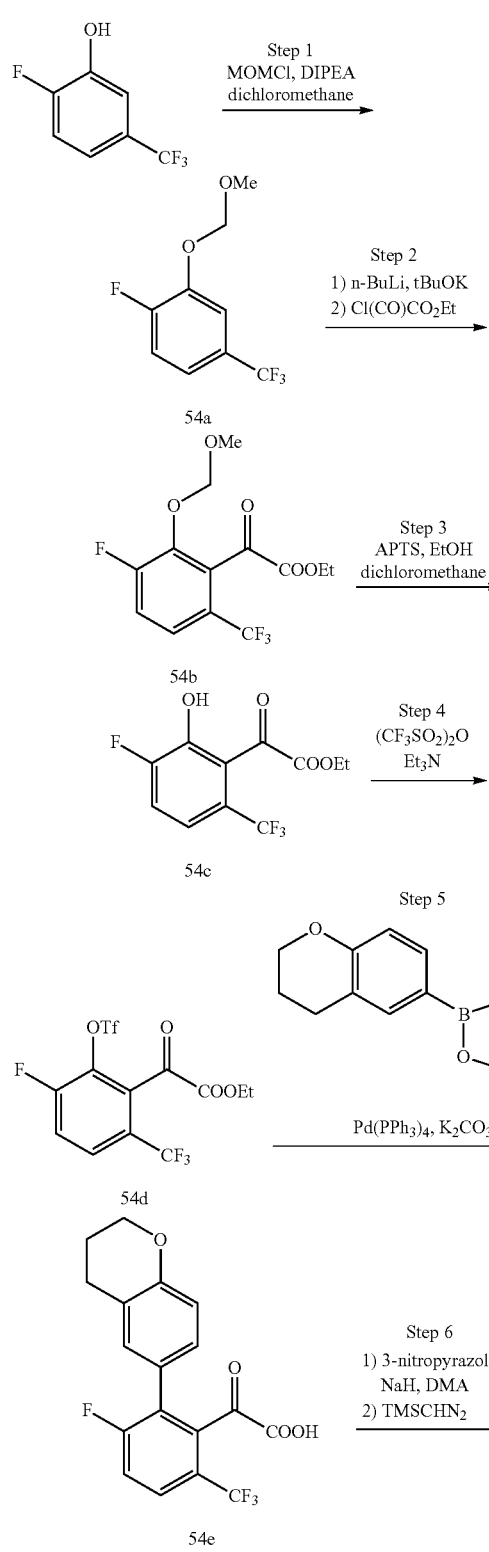
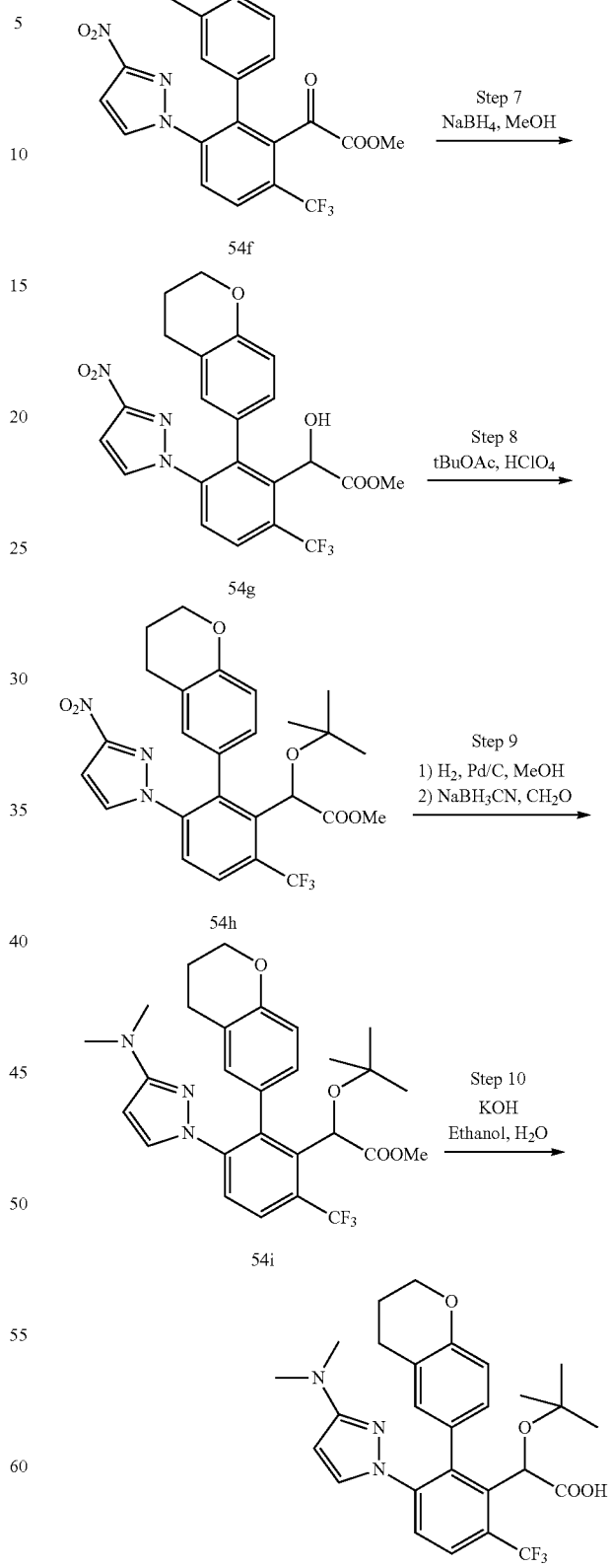

Step 1: Preparation of Intermediate 1-fluoro-2-(methoxymethoxy)-4-(trifluoromethyl)benzene (54a)

To a solution of 2-fluoro-5-(trifluoromethyl)phenol (2.0 g, 11.1 mmol) in anhydrous dichloromethane (20 mL) under nitrogen atmosphere at 0° C. were successively added diisopropylethylamine (3.87 mL, 22.2 mmol) and chloromethyl methyl ether (1.26 mL, 16.6 mmol). The mixture was stirred at 0° C. for 45 minutes before adding water (20 mL). Layers were separated and the aqueous one was extracted with dichloromethane (30 mL). The combined organic layers were washed with a 2 M sodium hydroxide solution (20 mL), dried over sodium sulfate and concentrated in vacuo to provide 1-fluoro-2-(methoxymethoxy)-4-(trifluoromethyl)benzene (54a) (2.49 g, 11.1 mmol, 100%) as a lightly yellow oil.

$^1$H NMR (400 MHz, CDCl$_3$) δ 3.53 (s, 3H), 5.25 (s, 2H), 7.16-7.20 (m, 1H), 7.24-7.27 (m, 1H), 7.46 (dd, J=1.8 Hz, J=7.4 Hz, 1H).

Step 2: Preparation of Intermediate ethyl 2-[3-fluoro-2-(methoxymethoxy)-6-(trifluoromethyl)phenyl]-2-oxoacetate (54b)

Under nitrogen atmosphere, a 1.6 M n-butyllithium solution in hexanes (3.5 mL, 5.6 mmol) and a 1M potassium tert-butoxide solution in tetrahydrofuran (5.6 mL, 5.6 mmol) were added to anhydrous tetrahydrofuran (30 mL) at −78° C. The mixture was stirred for 15 minutes before adding dropwise a solution of 1-fluoro-2-(methoxymethoxy)-4-(trifluoromethyl)benzene (54a) (1.0 g, 4.46 mmol) in tetrahydrofuran (10 mL). The mixture was stirred at −78° C. for 2 hours and was added via cannulation to a solution of ethyl oxalyl chloride (1.4 mL, 9.0 mmol) in tetrahydrofuran (20 mL) at −78° C. The mixture was stirred at −78° C. for 45 minutes and water (50 mL) was added. Layers were separated and the aqueous layer was extracted with ethyl acetate (2×30 mL). The combined organic layers were washed with a saturated solution of sodium hydrogenocarbonate (30 mL), brine (30 mL), dried over sodium sulfate and concentrated in vacuo. The residue was purified by flash chromatography on silica gel (cyclohexane/ethyl acetate 90/10) to provide ethyl 2-[3-fluoro-2-(methoxymethoxy)-6-(trifluoromethyl)phenyl]-2-oxoacetate (34b) (840 mg, 2.59 mmol, 58%) as a yellow oil.

$^1$H NMR (300 MHz, CDCl$_3$) δ 1.36 (t, J=7.2 Hz, 3H), 3.45 (s, 3H), 4.38 (q, J=7.2 Hz, 2H), 5.16 (s, 2H), 7.28-7.34 (m, 1H), 7.43 (dd, J=4.4 Hz, J=8.8 Hz, 1H).

Step 3: Preparation of Intermediate ethyl 2-[3-fluoro-2-hydroxy-6-(trifluoromethyl)phenyl]-2-oxoacetate (54c)

To a solution of ethyl 2-[3-fluoro-2-(methoxymethoxy)-6-(trifluoromethyl)phenyl]-2-oxoacetate (54b) (500 mg, 1.54 mmol) and p-toluenesulfonic acid (59 mg, 0.31 mmol) in dichloromethane (7.5 mL) and ethanol (1.5 mL) was heated at 50° C. overnight. The mixture was concentrated in vacuo. The residue was purified by flash chromatography on silica gel (cyclohexane/ethyl acetate 60/40) to provide ethyl 2-[3-fluoro-2-hydroxy-6-(trifluoromethyl)phenyl]-2-oxoacetate (54c) (394 mg, 1.40 mmol, 91%) as a yellow oil.

$^1$H NMR (300 MHz, CDCl$_3$) δ 1.38 (t, J=7.2 Hz, 3H), 4.38 (q, J=7.2 Hz, 2H), 6.91 (d, J=2.7 Hz), 7.26-7.35 (m, 2H).

Step 4: Preparation of Intermediate ethyl 2-{3-fluoro-2-[(trifluoromethane)sulfonyloxy]-6-(trifluoromethyl)phenyl}-2-oxoacetate (54d)

To a solution of ethyl 2-[3-fluoro-2-hydroxy-6-(trifluoromethyl)phenyl]-2-oxoacetate (54c) (394 mg, 1.41 mmol) in anhydrous dichloromethane (5 mL) under nitrogen atmosphere at −78° C. were successively added triethylamine (0.24 mL, 1.69 mmol) and triflic anhydride (0.26 mL, 1.55 mmol). The mixture was stirred at −78° C. for 45 minutes before adding water (10 mL). Layers were separated. The aqueous layer was extracted with dichloromethane (10 mL). The combined organic layers were washed with a saturated solution of sodium hydrogenocarbonate (10 mL), dried over sodium sulfate and concentrated in vacuo to ethyl 2-{3-fluoro-2-[(trifluoromethane)sulfonyloxy]-6-(trifluoromethyl)phenyl}-2-oxoacetate (54d) (548 mg, 1.32 mmol, 94%) as a yellow oil which was used without further purification.

$^1$H NMR (300 MHz, CDCl$_3$) δ 1.37 (t, J=7.2 Hz, 3H), 4.42 (q, J=7.2 Hz, 2H), 7.55 (t, J=8.7 Hz), 7.78 (dd, J=4.5 Hz, J=8.7 Hz, 1H).

Step 5: Preparation of Intermediate 2-[2-(3,4-dihydro-2H-1-benzopyran-6-yl)-3-fluoro-6-(trifluoromethyl)phenyl]-2-oxoacetic acid (54e)

A degassed solution of ethyl 2-{3-fluoro-2-[(trifluoromethane)sulfonyloxy]-6-(trifluoromethyl)phenyl}-2-oxoacetate (54d) (2.00 g, 4.88 mmol), potassium carbonate (2.68 g, 19.4 mmol), 6-(4,4,5,5-tetramethyl-1,3,2-dioxaborolan-2-yl)chroman (1.64 g, 6.31 mmol) and palladium tetrakis(triphenylphosphine) (0.56 g, 0.49 mmol) in dioxane (40 mL) and water (10 mL) was heated at 85° C. overnight. Dioxane was evaporated in vacuo. Diethyl ether (20 mL) was added and the layers were separated. The organic layer was washed with a saturated solution of sodium hydrogenocarbonate (10 mL). The combined aqueous layers were acidified with 37% hydrochloric acid until pH 2 then extracted with diethyl ether (2×20 mL). The organic layer was dried over sodium sulfate and concentrated in vacuo. The residue was dissolved in toluene (30 mL) and concentrated in vacuo. The operation was repeated twice to provide 2-[2-(3,4-dihydro-2H-1-benzopyran-6-yl)-3-fluoro-6-(trifluoromethyl)phenyl]-2-oxoacetic acid (54e) (0.736 mg, 2.0 mmol, 41%) as an oil which crystallized.

$^1$H NMR (400 MHz, CDCl$_3$) δ 1.98-2.05 (m, 2H), 2.76 (t, J=6.4 Hz, 2H), 4.19-4.22 (m, 2H), 4.35 (bs, 1H), 6.80 (d, J=8.3 Hz, 1H), 6.90-6.94 (m, 2H), 7.28-7.39 (m, 2H), 7.72 (dd, J=4.5 Hz, J=8.7 Hz, 1H).

MS m/z ([M−H]$^-$) 367.

Step 6: Preparation of Intermediate methyl 2-[2-(3,4-dihydro-2H-1-benzopyran-6-yl)-3-(3-nitro-1H-pyrazol-1-yl)-6-(trifluoromethyl)phenyl]-2-oxoacetate (54f)

To a solution of 2-[2-(3,4-dihydro-2H-1-benzopyran-6-yl)-3-fluoro-6-(trifluoromethyl)phenyl]-2-oxoacetic acid (54e) (100 mg, 0.27 mmol) and 3-nitro-1H-pyrazole (61 mg, 0.54 mmol) in anhydrous dimethylacetamide (2 mL) at room temperature under nitrogen atmosphere, was added sodium hydride 60% in oil (33 mg, 0.81 mmol). The mixture was heated at 150° C. overnight. The mixture was poured in water (10 mL), acidified with 1 M hydrochloric acid until pH 2 and extracted with ethyl acetate (2×10 mL). The organic layer was washed with brine (10 mL), dried over sodium sulfate and concentrated in vacuo. The residue was dissolved in methanol (2 mL) and cyclohexane (4 mL) and a 2 M solution of trimethylsilyldiazomethane in diethyl ether (0.9 mL, 1.8 mmol) was added. The mixture was stirred at 0° C. for 30 minutes and a few drops of acetic acid were added. The mixture was concentrated in vacuo. The residue was dissolved in ethyl acetate (10 mL) and washed with a saturated solution of sodium hydrogenocarbonate (10 mL). The organic layer was dried over sodium sulfate and concentrated in vacuo. The residue was purified by flash chromatography on silica gel (cyclohexane/ethyl acetate 70/30) to provide methyl 2-[2-(3,4-dihydro-2H-1-benzopyran-6-yl)-3-(3-nitro-1H-pyrazol-1-yl)-6-(trifluoromethyl)phenyl]-2-oxoacetate (54f) (69 mg, 0.145 mmol, 53%).

$^1$H NMR (300 MHz, CDCl$_3$) δ 1.95-2.04 (m, 2H), 2.60-2.75 (m, 2H), 3.57 (s, 3H), 4.19 (t, J=5.2 Hz, 2H), 6.71 (s, 2H), 6.73 (s, 1H), 6.78 (d, J=2.8 Hz, 1H), 7.05 (d, J=2.8 Hz, 1H), 7.90 (d, J=8.4 Hz, 1H), 7.98 (d, J=8.4 Hz, 1H).

Step 7: Preparation of Intermediate methyl 2-[2-(3,4-dihydro-2H-1-benzopyran-6-yl)-3-(3-nitro-1H-pyrazol-1-yl)-6-(trifluoromethyl)phenyl]-2-hydroxyacetate (54g)

To a solution of methyl 2-[2-(3,4-dihydro-2H-1-benzopyran-6-yl)-3-(3-nitro-1H-pyrazol-1-yl)-6-(trifluoromethyl)phenyl]-2-oxoacetate (54f) (69 mg, 0.145 mmol) in anhydrous methanol (4 mL) at 0° C. was added sodium borohydride (12 mg, 0.29 mmol). The mixture was stirred at room temperature for 45 minutes before adding water (2 mL). Methanol was evaporated in vacuo. The resulting solution was extracted with ethyl acetate (2×5 mL). The organic layer was washed with brine (5 mL) and dried over sodium sulfate to provide methyl 2-[2-(3,4-dihydro-2H-1-benzopyran-6-yl)-3-(3-nitro-1H-pyrazol-1-yl)-6-(trifluoromethyl)phenyl]-2-hydroxyacetate (54g) (66 mg, 0.138 mmol, 95%).

$^1$H NMR (400 MHz, CDCl$_3$) δ 1.93-2.06 (m, 2H), 2.52-2.65 (m, 1H), 2.68-2.82 (m, 1H), 3.52 and 3.55 (s, 3H), 4.17-4.23 (m, 2H), 5.45 (s, 1H), 6.52-6.78 (m, 3H), 6.99-7.01 (m, 1H), 7.14-7.16 (m, 1H), 7.78 (d, J=8.5 Hz, 1H), 7.90 (d, J=8.0 Hz, 1H).

MS m/z ([M+H]$^+$) 478.

Step 8: Preparation of Intermediate methyl 2-(tert-butoxy)-2-[2-(3,4-dihydro-2H-1-benzopyran-6-yl)-3-(3-nitro-1H-pyrazol-1-yl)-6-(trifluoromethyl)phenyl]acetate (54h)

Using the procedure described in example 1, step 8, the intermediate methyl 2-[2-(3,4-dihydro-2H-1-benzopyran-6-yl)-3-(3-nitro-1H-pyrazol-1-yl)-6-(trifluoromethyl)phenyl]-2-hydroxyacetate (54g) (66 mg, 0.138 mmol) is converted, after purification by preparative TLC (cyclohexane/ethyl acetate 70/30) into intermediate methyl 2-(tert-butoxy)-2-[2-(3,4-dihydro-2H-1-benzopyran-6-yl)-3-(3-nitro-1H-pyrazol-1-yl)-6-(trifluoromethyl)phenyl]acetate (54h) (32 mg, 0.060 mmol, 43%) as a colorless oil.

$^1$H NMR (400 MHz, CDCl$_3$) δ 0.93 and 0.94 (s, 9H), 1.91-2.06 (m, 2H), 2.47-2.64 (m, 1H), 2.68-2.81 (m, 1H), 3.74 (s, 3H), 4.17-4.22 (m, 2H), 5.16 and 5.17 (s, 1H), 6.58-6.82 (m, 3H), 6.98 and 7.00 (d, J=2.6 Hz, 1H), 7.13-7.18 (m, 1H), 7.71 and 7.73 (d, J=8.5 Hz, 1H), 7.87 and 7.88 (d, J=8.5 Hz, 1H).

Step 9: Preparation of Intermediate methyl 2-(tert-butoxy)-2-[2-(3,4-dihydro-2H-1-benzopyran-6-yl)-3-[3-(dimethylamino)-1H-pyrazol-1-yl]-6-(trifluoromethyl)phenyl]acetate (54i)

A suspension of methyl 2-(tert-butoxy)-2-[2-(3,4-dihydro-2H-1-benzopyran-6-yl)-3-(3-nitro-1H-pyrazol-1-yl)-6-(trifluoromethyl)phenyl]acetate (54g) (32 mg, 0.060 mmol) and palladium on carbon (8 mg) in methanol (3 mL) was stirred at room temperature for 1 hour. The mixture was filtered over Millipore and concentrated in vacuo. The residue was dissolved in methanol (1 mL) and tetrahydrofurane (1 mL). To the mixture was added 37% aqueous formaldehyde (47 µL, 0.60 mmol) and sodium cyanoborohydride (19 mg, 0.30 mmol) maintaining at pH 5 with addition of acetic acid. The mixture was stirred at room temperature for 1 hour before adding a saturated solution of sodium hydrogenocarbonate (5 mL). The Aqueous layer was extracted with ethyl acetate (2×5 mL). The organic layer was washed with brine (5 mL), dried over sodium sulfate and concentrated in vacuo. The residue was purified by preparative TLC (cyclohexane/ethyl acetate: 60/40) to provide methyl 2-(tert-butoxy)-2-[2-(3,4-dihydro-2H-1-benzopyran-6-yl)-3-[3-(dimethylamino)-1H-pyrazol-1-yl]-6-(trifluoromethyl)phenyl]acetate (54i) (20 mg, 0.037 mmol, 62%) as a colorless oil.

$^1$H NMR (400 MHz, CDCl$_3$) δ 0.93 and 0.94 (s, 9H), 1.94-2.07 (m, 2H), 2.62 (t, J=6.4 Hz, 1H), 2.69-2.82 (m, 1H), 2.86 and 2.87 (s, 6H), 3.71 (s, 3H), 4.19-4.24 (m, 2H), 5.15 (s, 1H), 5.52 and 5.53 (d, J=2.6 Hz, 1H), 6.59 (d, J=2.6 Hz, 1H), 6.70-6.84 (m, 2H), 7.14-7.18 (m, 1H), 7.75 (d, J=8.5 Hz, 1H), 7.81 and 7.82 (d, J=8.5 Hz, 1H).

MS m/z ([M+H]$^+$) 532.

Step 10: Preparation of 2-(tert-butoxy)-2-[2-(3,4-dihydro-2H-1-benzopyran-6-yl)-3-[3-(dimethylamino)-1H-pyrazol-1-yl]-6-(trifluoromethyl)phenyl]acetic acid (Example 54)

Using the procedure described in example 5, step 4, the methyl 2-(tert-butoxy)-2-[2-(3,4-dihydro-2H-1-benzopyran-6-yl)-3-[3-(dimethylamino)-1H-pyrazol-1-yl]-6-(trifluoromethyl)phenyl]acetate (54i) (20 mg, 0.037 mmol) is converted into 2-(tert-butoxy)-2-[2-(3,4-dihydro-2H-1-benzopyran-6-yl)-3-[3-(dimethylamino)-1H-pyrazol-1-yl]-6-(trifluoromethyl)phenyl]acetic acid (example 54) (9 mg, 0.017 mmol, 47%) as a white solid.

$^1$H NMR (300 MHz, CDCl$_3$) δ 0.94 (s, 9H), 1.95-2.06 (m, 2H), 2.61-2.63 (m, 1H), 2.82-2.89 (m, 7H), 4.19-4.25 (m, 2H), 5.28 and 5.30 (s, 1H), 5.55-5.57 (m, 1H), 6.58-6.91 (m, 3H), 7.53 (bs, 1H), 7.77 (d, J=8.6 Hz, 1H), 7.87 (d, J=8.6 Hz, 1H).

MS m/z ([M+H]$^+$) 518.

Example 55

Synthesis of 2-(tert-butoxy)-2-[2-(3,4-dihydro-2H-1-benzopyran-6-yl)-3-[4-(dimethylamino)-1H-pyrazol-1-yl]-6-(trifluoromethyl)phenyl]acetic acid

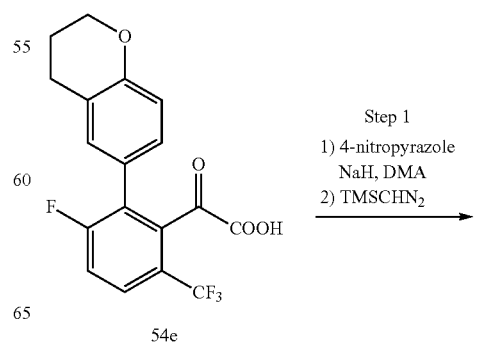

54e

Step 1
1) 4-nitropyrazole
NaH, DMA
2) TMSCHN$_2$

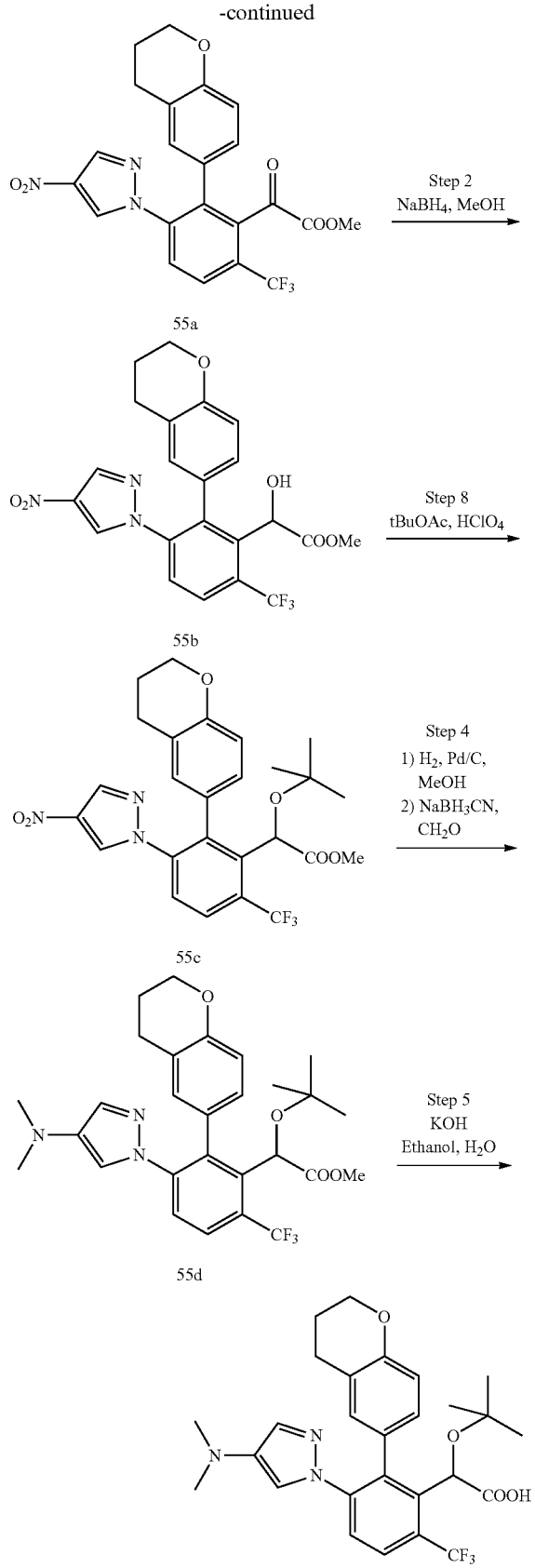

Step 1: Preparation of Intermediate methyl 2-[2-(3,4-dihydro-2H-1-benzopyran-6-yl)-3-(4-nitro-1H-pyrazol-1-yl)-6-(trifluoromethyl)phenyl]-2-oxoacetate (55a)

To a solution of 2-[2-(3,4-dihydro-2H-1-benzopyran-6-yl)-3-fluoro-6-(trifluoromethyl)phenyl]-2-oxoacetic acid (54e) (150 mg, 0.41 mmol) and 4-nitro-1H-pyrazole (92 mg, 0.81 mmol) in anhydrous dimethylacetamide (2 mL) at room temperature under nitrogen atmosphere, was added sodium hydride 60% in oil (49 mg, 1.22 mmol). The mixture was heated at 70° C. for 1 hour then at 110° C. for 2 hours. The mixture was poured in water (10 mL) and washed with ethyl acetate (10 mL). The aqueous layer was acidified with 1 M hydrochloric acid until pH 2 and extracted with ethyl acetate (2×10 mL). The organic layer was washed with brine (10 mL), dried over sodium sulfate and concentrated in vacuo. The residue was dissolved in methanol (2 mL) and cyclohexane (4 mL) and a 2 M solution of trimethylsilyldiazomethane in diethyl ether (0.5 mL, 1 mmol) was added. The mixture was stirred at 0° C. for 30 minutes and a few drops of acetic acid were added. The mixture was concentrated in vacuo. The residue was dissolved in ethyl acetate (10 mL) and washed with a saturated solution of sodium hydrogenocarbonate (10 mL). The organic layer was dried over sodium sulfate and concentrated in vacuo. The residue was purified by flash chromatography on silica gel (cyclohexane/ethyl acetate: 75/25) to provide methyl 2-[2-(3,4-dihydro-2H-1-benzopyran-6-yl)-3-(4-nitro-1H-pyrazol-1-yl)-6-(trifluoromethyl)phenyl]-2-oxoacetate (55a) (104 mg, 0.218 mmol, 53%) as a white solid.

$^1$H NMR (300 MHz, CDCl$_3$) δ 1.96-2.02 (m, 2H), 2.70 (t, J=6.3 Hz, 2H), 3.58 (s, 3H), 4.18-4.22 (m, 2H), 6.65-6.74 (m, 3H), 6.70-6.78 (m, 3H), 7.73 (s, 1H), 7.88-7.95 (m, 2H), 8.18 (s, 1H).

MS m/z ([M+H]$^+$) 476.
MS m/z ([M−H]$^−$) 474.

Step 2: Preparation of Intermediate methyl 2-[2-(3,4-dihydro-2H-1-benzopyran-6-yl)-3-(4-nitro-1H-pyrazol-1-yl)-6-(trifluoromethyl)phenyl]-2-hydroxyacetate (55b)

Using the procedure described in example 54, step 7, the intermediate methyl 2-[2-(3,4-dihydro-2H-1-benzopyran-6-yl)-3-(4-nitro-1H-pyrazol-1-yl)-6-(trifluoromethyl)phenyl]-2-oxoacetate (55a) (104 mg, 0.219 mmol) is converted into methyl 2-[2-(3,4-dihydro-2H-1-benzopyran-6-yl)-3-(4-nitro-1H-pyrazol-1-yl)-6-(trifluoromethyl)phenyl]-2-hydroxyacetate (55b) (100 mg, 0.209 mmol, 96%) as a white solid.

$^1$H NMR (300 MHz, CDCl$_3$) δ 1.93-2.07 (m, 2H), 2.62 and 2.78 (t, J=6.4 Hz), 3.53 and 3.58 (s, 3H), 4.17-4.23 (m, 2H), 5.46 (s, 1H), 6.47-6.53 (m, 1H), 6.64 and 6.80 (d, J=8.4 Hz, 1H), 7.09-7.15 (m, 1H), 7.64 and 7.65 (s, 1H), 7.75 (d, J=8.6 Hz, 1H), 7.92 (d, J=8.6 Hz, 1H), 8.08 and 8.09 (s, 1H).

Step 3: Preparation of Intermediate methyl 2-(tert-butoxy)-2-[2-(3,4-dihydro-2H-1-benzopyran-6-yl)-3-(4-nitro-1H-pyrazol-1-yl)-6-(trifluoromethyl)phenyl]acetate (55c)

Using the procedure described in example 1, step 8, the intermediate methyl 2-[2-(3,4-dihydro-2H-1-benzopyran-6-yl)-3-(4-nitro-1H-pyrazol-1-yl)-6-(trifluoromethyl)phenyl]-2-hydroxyacetate (55b) (100 mg, 0.209 mmol) is converted, after purification by preparative TLC (cyclohexane/ethyl acetate 75/25) into intermediate methyl 2-(tert-butoxy)-2-[2-(3,4-dihydro-2H-1-benzopyran-6-yl)-3-(4-nitro-1H-pyrazol-1-yl)-6-(trifluoromethyl)phenyl]acetate (55c) (44 mg, 0.082 mmol, 39%) as a colorless oil.

$^1$H NMR (300 MHz, CDCl$_3$) δ 0.96 and 0.97 (s, 9H), 1.91-2.08 (m, 2H), 2.49-2.87 (m, 2H), 3.73 (s, 3H), 4.17-4.23 (m, 2H), 5.18 (s, 1H), 6.54-6.58 (m, 1H), 6.65 and 6.84 (d, J=8.4 Hz, 1H), 7.14-7.17 (m, 1H), 7.63 and 7.66 (s, 1H), 7.69 and 7.71 (d, J=8.4 Hz, 1H), 7.89 (d, J=8.4 Hz, 1H), 8.10 and 8.12 (s, 1H).

Step 4: Preparation of Intermediate methyl 2-(tert-butoxy)-2-[2-(3,4-dihydro-2H-1-benzopyran-6-yl)-3-[4-(dimethylamino)-1H-pyrazol-1-yl]-6-(trifluoromethyl)phenyl]acetate (55d)

Using the procedure described in example 54, step 9, the intermediate methyl 2-(tert-butoxy)-2-[2-(3,4-dihydro-2H-1-benzopyran-6-yl)-3-(4-nitro-1H-pyrazol-1-yl)-6-(trifluoromethyl)phenyl]acetate (55c) (44 mg, 0.082 mmol) is converted, after purification by preparative TLC (dichloromethane/methanol 97/3) into methyl 2-(tert-butoxy)-2-[2-(3,4-dihydro-2H-1-benzopyran-6-yl)-3-[4-(dimethyl amino)-1H-pyrazol-1-yl]-6-(trifluoromethyl)phenyl]acetate (55d) (23 mg, 0.043 mmol, 52%)

$^1$H NMR (400 MHz, CDCl$_3$) δ 0.93 and 0.95 (s, 9H), 1.93-2.05 (m, 2H), 2.47 and 2.48 (s, 6H), 2.52-2.64 (m, 1H), 2.74-2.77 (m, 1H), 3.72 and 3.73 (s, 3H), 4.15-4.22 (m, 2H), 5.21 (s, 1H), 6.24 and 6.29 (s, 1H), 6.54-6.62 (m, 1H), 6.67 and 6.82 (d, J=8.4 Hz, 1H), 7.13-7.20 (m, 1H), 7.25 and 7.27 (s, 1H), 7.71 and 7.72 (d, J=8.5 Hz, 1H), 7.78 and 7.79 (d, J=8.5 Hz, 1H).

MS m/z ([M+H]$^+$) 532.

Step 5: Preparation of 2-(tert-butoxy)-2-[2-(3,4-dihydro-2H-1-benzopyran-6-yl)-3-[4-(dimethylamino)-1H-pyrazol-1-yl]-6-(trifluoromethyl)phenyl] acetic acid (Example 55)

Using the procedure described in example 5, step 4, the methyl 2-(tert-butoxy)-2-[2-(3,4-dihydro-2H-1-benzopyran-6-yl)-3-[4-(dimethylamino)-1H-pyrazol-1-yl]-6-(trifluoromethyl)phenyl]acetate (55d) (23 mg, 0.043 mmol) is converted into 2-(tert-butoxy)-2-[2-(3,4-dihydro-2H-1-benzopyran-6-yl)-3-[4-(dimethylamino)-1H-pyrazol-1-yl]-6-(trifluoromethyl)phenyl]acetic acid (example 55) (18 mg, 0.034 mmol, 81%) as a white solid.

$^1$H NMR (400 MHz, CDCl$_3$) δ 0.96 (s, 9H), 1.94-2.03 (m, 2H), 2.47 and 2.49 (s, 6H), 2.52-2.60 (m, 1H), 2.74-2.78 (m, 1H), 4.13-4.22 (m, 2H), 5.33 and 5.37 (s, 1H), 6.25 and 6.32 (s, 1H), 6.52-6.89 (m, 2H), 7.28 and 7.30 (s, 1H), 7.51-7.56 (m, 1H), 7.74-7.82 (m, 2H).

MS m/z ([M+H]$^+$) 518.

Example 56

Synthesis of 2-(tert-butoxy)-2-[2-(3,4-dihydro-2H-1-benzopyran-6-yl)-3-[1-methyl-3-(trifluoromethyl)-1H-pyrazol-5-yl]-6-(trifluoromethyl)phenyl]acetic acid

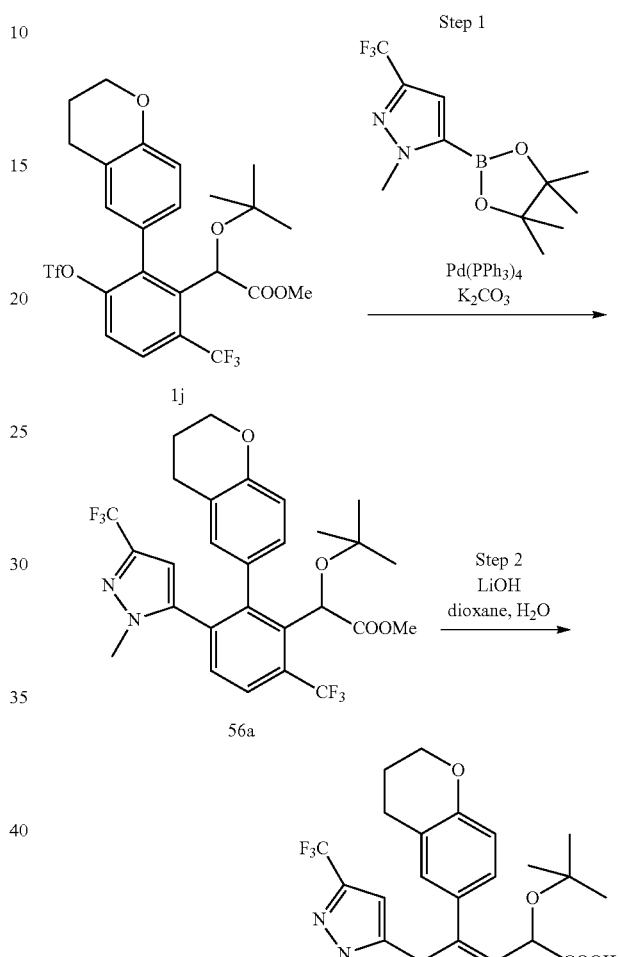

Step 1: Preparation of Intermediate methyl 2-(tert-butoxy)-2-[2-(3,4-dihydro-2H-1-benzopyran-6-yl)-3-[1-methyl-3-(trifluoromethyl)-1H-pyrazol-5-yl]-6-(trifluoromethyl)phenyl]acetate (56a)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (100 mg, 0.175 mmol) is converted by reaction with (1-methyl-3-(trifluoromethyl)-1H-pyrazol-5-yl)boronic acid (41 mg, 0.210 mmol), after purification by preparative TLC (cyclohexane/ethyl acetate 25/75) into methyl 2-(tert-butoxy)-2-[2-(3,4-dihydro-2H-1-benzopyran-6-yl)-3-[1-methyl-3-(trifluoromethyl)-1H-pyrazol-5-yl]-6-(trifluoromethyl)phenyl]acetate (56a) (39 mg, 0.068 mmol, 39%) as a colourless oil.

¹H NMR (300 MHz, CDCl₃) δ 0.93 and 0.95 (s, 9H), 1.86-2.07 (m, 2H), 2.42-2.82 (m, 2H), 3.42 and 3.47 (s, 3H), 3.73 and 3.74 (s, 3H), 4.10-4.23 (m, 2H), 5.17 and 5.21 (s, 1H), 6.25 and 6.29 (s, 1H), 6.45-6.76 (m, 2H), 7.01-7.12 (m, 1H), 7.40-7.45 (m, 1H), 7.79 (d, J=8.1 Hz, 1H).

Step 2: Preparation of 2-(tert-butoxy)-2-[2-(3,4-dihydro-2H-1-benzopyran-6-yl)-3-[1-methyl-3-(trifluoromethyl)-1H-pyrazol-5-yl]-6-(trifluoromethyl)phenyl]acetic acid (Example 56)

Using the procedure described in example 2, step 12, the intermediate 2-(tert-butoxy)-2-[2-(3,4-dihydro-2H-1-benzopyran-6-yl)-3-[1-methyl-3-(trifluoromethyl)-1H-pyrazol-5-yl]-6-(trifluoromethyl)phenyl]acetate (56a) (39 mg, 0.068 mmol) is converted after purification by preparative TLC (cyclohexane/ethyl acetate/acetic acid 70/30/0.1) into 2-(tert-butoxy)-2-[2-(3,4-dihydro-2H-1-benzopyran-6-yl)-3-[1-methyl-3-(trifluoromethyl)-1H-pyrazol-5-yl]-6-(trifluoromethyl)phenyl]acetic acid (example 56) (24 mg, 0.043 mmol, 63%) as a beige solid.

¹H NMR (300 MHz, CDCl₃) δ 0.97 (s, 9H), 1.83-2.18 (m, 2H), 2.34-2.90 (m, 2H), 3.41 and 3.46 (s, 3H), 4.05-4.31 (m, 2H), 5.30 and 5.38 (s, 1H), 6.27-6.85 (m, 3H), 7.40-7.50 (m, 2H), 7.81 (d, J=8.1 Hz, 1H).

MS m/z ([M−H]⁻) 557.

Example 57

Synthesis of 2-(tert-butoxy)-2-[2-(3,4-dihydro-2H-1-benzopyran-6-yl)-3-(5-methyl-1H-pyrazol-1-yl)-6-(trifluoromethyl)phenyl]acetic acid

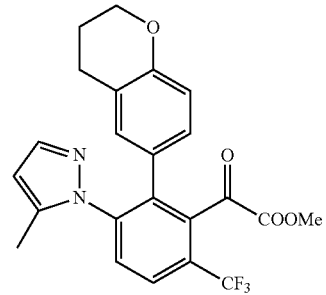

54e

Step 1
1) 3-methylpyrazole NaH, DMA
2) TMSCHN₂

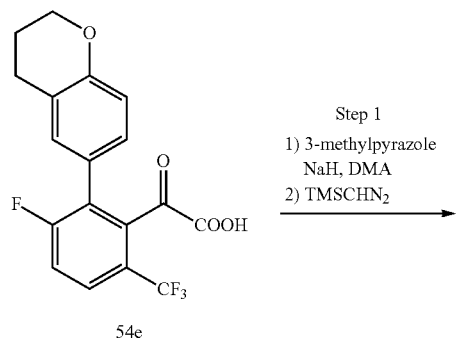

57a

+

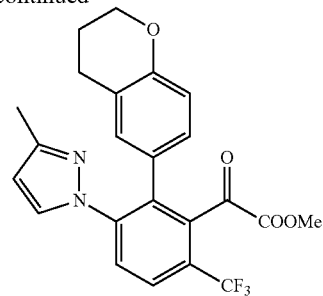

57b

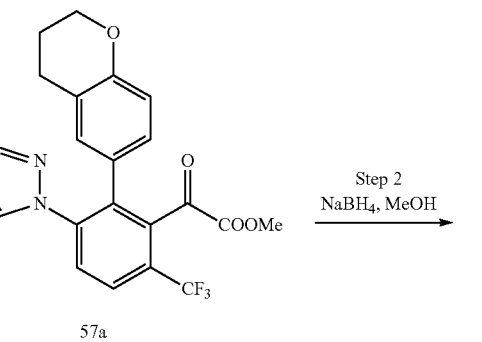

57a

Step 2
NaBH₄, MeOH

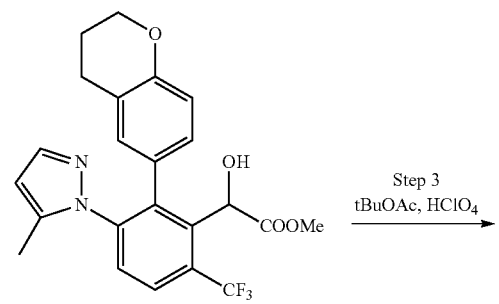

57c

Step 3
tBuOAc, HClO₄

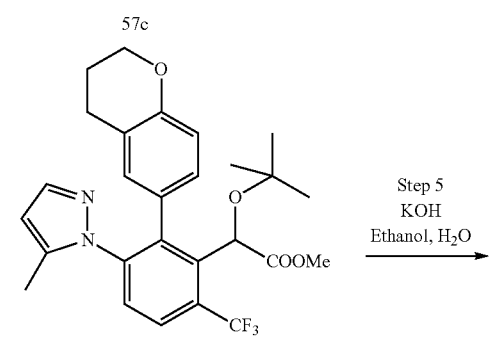

57d

Step 5
KOH
Ethanol, H₂O

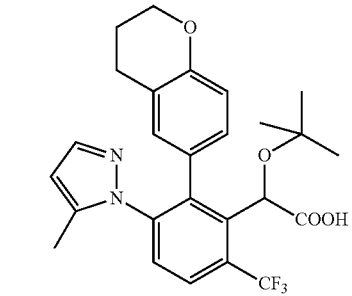

Example 57

Step 1: Preparation of Intermediate methyl 2-[2-(3,4-dihydro-2H-1-benzopyran-6-yl)-3-(5-methyl-1H-pyrazol-1-yl)-6-(trifluoromethyl)phenyl]-2-oxoacetate (57a) and methyl 2-[2-(3,4-dihydro-2H-1-benzopyran-6-yl)-3-(3-methyl-1H-pyrazol-1-yl)-6-(trifluoromethyl)phenyl]-2-oxoacetate (57b)

To a solution of 2-[2-(3,4-dihydro-2H-1-benzopyran-6-yl)-3-fluoro-6-(trifluoromethyl)phenyl]-2-oxoacetic acid (54e) (150 mg, 0.41 mmol) and 3-methylpyrazole (66 µL, 0.81 mmol) in anhydrous dimethylacetamide (2 mL) at room temperature under nitrogen atmosphere, was added sodium hydride 60% in oil (49 mg, 1.22 mmol). The mixture was heated at 70° C. for 5 hours then poured in water (10 mL). The mixture was acidified with 1 M hydrochloric acid until pH 2 and extracted with diethyl ether (2×10 mL). The organic layer was washed with brine (10 mL), dried over sodium sulfate and concentrated in vacuo. The residue was dissolved in methanol (2 mL) and cyclohexane (4 mL) and a 2 M solution of trimethylsilyldiazomethane in diethyl ether (0.5 mL, 1 mmol) was added. The mixture was stirred at 0° C. for 30 minutes and a few drops of acetic acid was added. The mixture was concentrated in vacuo. The residue was dissolved in ethyl acetate (10 mL) and washed with a saturated solution of sodium hydrogenocarbonate (10 mL). The organic layer was dried over sodium sulfate and concentrated in vacuo. The residue was purified by preparative TLC (cyclohexane/ethyl acetate 75/25) to provide and methyl 2-[2-(3,4-dihydro-2H-1-benzopyran-6-yl)-3-(5-methyl-1H-pyrazol-1-yl)-6-(trifluoro methyl)phenyl]-2-oxoacetate (57a) (30 mg, 0.067 mmol, 16%) as a colorless oil and methyl 2-[2-(3,4-dihydro-2H-1-benzopyran-6-yl)-3-(3-methyl-1H-pyrazol-1-yl)-6-(trifluoromethyl)phenyl]-2-oxoacetate (57b) (90 mg, 0.20 mmol, 49%) as a colorless oil.

(57b) $^1$H NMR (400 MHz, CDCl$_3$) δ 1.96-1.99 (m, 2H), 2.30 (s, 3H), 2.65-2.71 (m, 2H), 3.53 (s, 3H), 4.17-4.19 (m, 2H), 5.94 (d, J=2.4 Hz, 1H), 6.70 (s, 2H), 6.73 (s, 1H), 6.80 (d, J=2.4 Hz, 1H), 7.79 (d, J=8.8 Hz, 1H), 7.96 (d, J=8.8 Hz, 1H).
MS m/z ([M+H]$^+$) 445.

(57a) $^1$H NMR (400 MHz, CDCl$_3$) δ 1.79 (s, 3H), 1.90-1.96 (m, 2H), 2.61 (bs, 2H), 3.48 (s, 3H), 4.12-4.15 (m, 2H), 5.93 (d, J=1.6 Hz, 1H), 6.58-6.65 (m, 3H), 7.48 (d, J=1.6 Hz, 1H), 7.67 (d, J=8.4 Hz, 1H), 7.84 (d, J=8.4 Hz, 1H).
MS m/z ([M+H]$^+$) 445.

Step 2: Preparation of Intermediate methyl 2-[2-(3,4-dihydro-2H-1-benzopyran-6-yl)-3-(5-methyl-1H-pyrazol-1-yl)-6-(trifluoromethyl)phenyl]-2-hydroxyacetate (57c)

Using the procedure described in example 54, step 7, the intermediate methyl 2-[2-(3,4-dihydro-2H-1-benzopyran-6-yl)-3-(5-methyl-1H-pyrazol-1-yl)-6-(trifluoromethyl)phenyl]-2-oxoacetate (54a) (30 mg, 0.067 mmol) is converted into methyl 2-[2-(3,4-dihydro-2H-1-benzopyran-6-yl)-3-(5-methyl-1H-pyrazol-1-yl)-6-(trifluoromethyl)phenyl]-2-hydroxyacetate (57c) (25 mg, 0.056 mmol, 83%) as a white solid.

$^1$H NMR (300 MHz, CDCl$_3$) δ 1.86 (s, 3H), 1.90-1.99 (m, 2H), 2.26 (s, 3H), 2.53-2.77 (m, 2H), 3.32 (bs, 1H), 3.49 and 3.51 (s, 3H), 4.10-4.17 (m, 2H), 5.43 and 5.44 (s, 1H), 5.83-5.84 (m, 1H), 6.51-6.63 (m, 2H), 7.05-7.07 (m, 1H), 7.35 (s, 1H), 7.15 (m, 1H), 7.48 and 7.49 (d, J=8.3 Hz, 1H), 7.84 (d, J=8.3 Hz, 1H).
MS m/z ([M+H]$^+$) 447.
MS m/z ([M−H]$^-$) 445.

Step 3: Preparation of Intermediate methyl 2-(tert-butoxy)-2-[2-(3,4-dihydro-2H-1-benzopyran-6-yl)-3-(5-methyl-1H-pyrazol-1-yl)-6-(trifluoromethyl)phenyl]acetate (57d)

Using the procedure described in example 1, step 8, the intermediate methyl 2-[2-(3,4-dihydro-2H-1-benzopyran-6-yl)-3-(5-methyl-1H-pyrazol-1-yl)-6-(trifluoromethyl)phenyl]-2-hydroxyacetate (57c) (25 mg, 0.56 mmol) is converted, after purification by preparative TLC (cyclohexane/ethyl acetate 60/40) into methyl 2-(tert-butoxy)-2-[2-(3,4-dihydro-2H-1-benzopyran-6-yl)-3-(5-methyl-1H-pyrazol-1-yl)-6-(trifluoromethyl)phenyl]acetate (57d) (11 mg, 0.022 mmol, 39%) as a colorless oil.

$^1$H NMR (400 MHz, CDCl$_3$) δ 0.91 and 0.93 (s, 9H), 1.81-2.01 (m, 5H), 2.46-2.63 (m, 1H), 2.64-2.73 (m, 1H), 3.74 and 3.75 (s, 3H), 4.12-4.18 (m, 2H), 5.17 and 5.20 (s, 1H), 5.84 and 5.87 (s, 1H), 6.53-6.69 (m, 2H), 7.06-7.11 (m, 1H), 7.38 and 7.40 (s, 1H), 7.46 and 7.49 (d, J=8.3 Hz, 1H), 7.82 and 7.83 (d, J=8.3 Hz, 1H).
MS m/z ([M+H]$^+$) 503.
MS m/z ([M−H]$^-$) 501.

Step 4: Preparation of 2-(tert-butoxy)-2-[2-(3,4-dihydro-2H-1-benzopyran-6-yl)-3-(5-methyl-1H-pyrazol-1-yl)-6-(trifluoromethyl)phenyl]acetic acid (Example 57)

Using the procedure described in example 5, step 4, the intermediate methyl 2-(tert-butoxy)-2-[2-(3,4-dihydro-2H-1-benzopyran-6-yl)-3-(5-methyl-1H-pyrazol-1-yl)-6-(trifluoromethyl)phenyl]acetate (57d) (11 mg, 0.022 mmol) is converted into 2-(tert-butoxy)-2-[2-(3,4-dihydro-2H-1-benzopyran-6-yl)-3-(5-methyl-1H-pyrazol-1-yl)-6-(trifluoromethyl)phenyl]acetic acid (example 57) (10 mg, 0.020 mmol, 91%) as a white solid.

$^1$H NMR (400 MHz, CDCl$_3$) δ 0.94 (s, 9H), 1.80-1.99 (m, 5H), 2.46-2.76 (m, 2H), 4.13-4.18 (m, 2H), 5.28 and 5.36 (s, 1H), 5.85 and 5.88 (s, 1H), 6.53-6.73 (m, 2H), 7.43-7.56 (m, 3H), 7.85 (d, J=8.3 Hz, 1H).
MS m/z ([M+H]$^+$) 489.
MS m/z ([M−H]$^-$) 487.

Example 58

Synthesis of 2-(tert-butoxy)-2-[3-(cyclohex-1-en-1-yl)-2-(3,4-dihydro-2H-1-benzopyran-6-yl)-6-(trifluoromethyl)phenyl]acetic acid

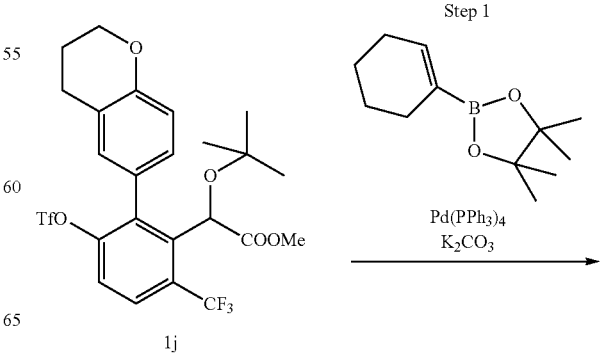

1j

Hz, 2H), 5.30 and 5.36 (s, 1H), 5.52 (s, 1H), 6.70-6.88 (m, 2H), 7.29-7.86 (m, 2H), 7.62 (d, J=8.1 Hz, 1H), 9.59 (bs, 1H).
MS m/z ([M–H]⁻) 487.

Example 59

Synthesis of 2-(tert-butoxy)-2-[2-(3,4-dihydro-2H-1-benzopyran-6-yl)-3-(3-methyl-1H-pyrazol-1-yl)-6-(trifluoromethyl)phenyl]acetic acid

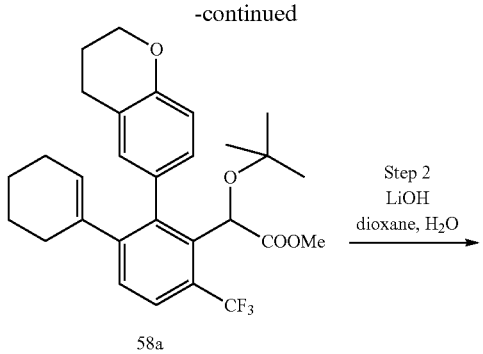

58a

Step 2
LiOH
dioxane, H₂O
→

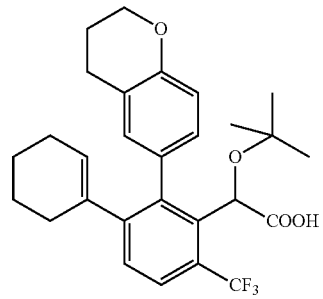

Example 58

Step 1: Preparation of Intermediate methyl 2-(tert-butoxy)-2-[3-(cyclohex-1-en-1-yl)-2-(3,4-dihydro-2H-1-benzopyran-6-yl)-6-(trifluoromethyl)phenyl] acetate (58a)

Using the procedure described in example 1, step 11, the intermediate methyl 2-(tert-butoxy)-2-[2-(3,4-dihydro-2H-1-benzopyran-6-yl)-3-[(trifluoromethane) sulfonyloxy]-6-(trifluoromethyl)phenyl]acetate (1j) (100 mg, 0.175 mmol) is converted by reaction with (1-cyclohexen-1-yl-boronic acid pinacol ester (44 mg, 0.210 mmol), after purification by preparative TLC (cyclohexane/ethyl acetate 90/10) into methyl 2-(tert-butoxy)-2-[3-(cyclohex-1-en-1-yl)-2-(3,4-dihydro-2H-1-benzopyran-6-yl)-6-(trifluoromethyl)phenyl] acetate (58a) (58 mg, 0.115 mmol, 66%) as a colourless oil.

¹H NMR (300 MHz, CDCl₃) δ 0.93 and 0.94 (s, 9H), 1.21-1.80 (m, 6H), 1.92-2.08 (m, 4H), 2.65-2.80 (m, 2H), 3.70 (s, 3H), 4.22 (t, J=5.02 Hz, 2H), 5.15 and 5.18 (s, 1H), 5.46-5.55 (m, 1H), 6.72-6.89 (m, 2H), 6.98-7.08 (m, 1H), 7.22 (d, J=8, 1 Hz, 1H), 7.60 (d, J=8.1 Hz, 1H).
MS m/z ([M+Na]⁺) 525.

Step 2: Preparation of 2-(tert-butoxy)-2-[3-(cyclohex-1-en-1-yl)-2-(3,4-dihydro-2H-1-benzopyran-6-yl)-6-(trifluoromethyl)phenyl]acetic acid (Example 58)

Using the procedure described in example 2, step 12, the intermediate 2-(tert-butoxy)-2-[3-(cyclohex-1-en-1-yl)-2-(3,4-dihydro-2H-1-benzopyran-6-yl)-6-(trifluoromethyl) phenyl]acetate (58a) (57 mg, 0.113 mmol) is converted after purification by preparative TLC (cyclohexane/ethyl acetate/acetic acid 20/80/0.1) into 2-(tert-butoxy)-2-[3-(cyclohex-1-en-1-yl)-2-(3,4-dihydro-2H-1-benzopyran-6-yl)-6-(trifluoromethyl)phenyl]acetic acid (example 58) (30 mg, 0.061 mmol, 54%) as a white solid.

¹H NMR (300 MHz, CDCl₃) 0.95 (s, 9H), 1.17-1.78 (m, 6H), 1.92-2.08 (m, 4H), 2.69-2.82 (m, 2H), 4.23 (t, J=5.1

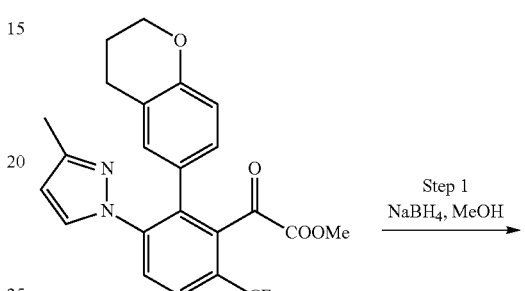

57b

Step 1
NaBH₄, MeOH
→

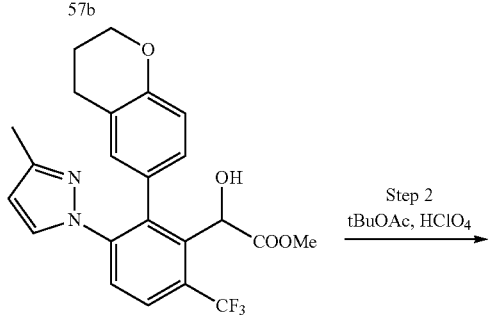

59a

Step 2
tBuOAc, HClO₄
→

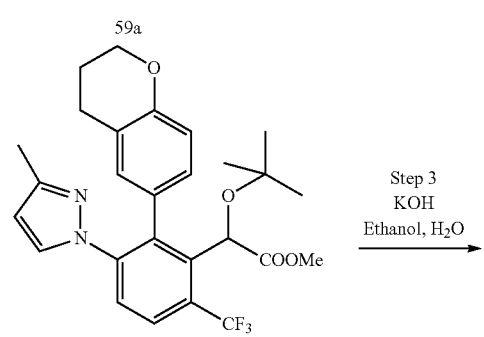

59b

Step 3
KOH
Ethanol, H₂O
→

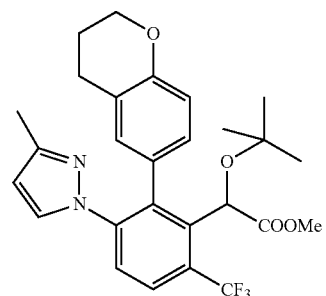

Example 59

Step 1: Preparation of Intermediate methyl 2-[2-(3,4-dihydro-2H-1-benzopyran-6-yl)-3-(3-methyl-1H-pyrazol-1-yl)-6-(trifluoromethyl)phenyl]-2-hydroxyacetate (59a)

Using the procedure described in example 54, step 7, the intermediate methyl 2-[2-(3,4-dihydro-2H-1-benzopyran-6-yl)-3-(3-methyl-1H-pyrazol-1-yl)-6-(trifluoromethyl)phenyl]-2-oxoacetate (57b) (90 mg, 0.20 mmol) is converted to methyl 2-[2-(3,4-dihydro-2H-1-benzopyran-6-yl)-3-(3-methyl-1H-pyrazol-1-yl)-6-(trifluoromethyl)phenyl]-2-hydroxyacetate (59a) (90 mg, 0.20 mmol, 100%) as a white solid.

$^1$H NMR (300 MHz, CDCl$_3$) δ 1.93-2.07 (m, 2H), 2.26 (s, 3H), 2.58-2.62 (m, 1H), 2.63-2.85 (m, 1H), 3.21 (bs, 1H), 3.50 and 3.53 (s, 3H), 4.17-4.23 (m, 2H), 5.43 and 5.44 (s, 1H), 5.86-5.87 (m, 1H), 6.50-6.79 (m, 3H), 7.12-7.15 (m, 1H), 7.77-7.83 (m, 2H).

MS m/z ([M+H]$^+$) 447.

Step 2: Preparation of Intermediate methyl 2-(tert-butoxy)-2-[2-(3,4-dihydro-2H-1-benzopyran-6-yl)-3-(3-methyl-1H-pyrazol-1-yl)-6-(trifluoromethyl)phenyl]acetate (59b)

Using the procedure described in example 1, step 8, the intermediate methyl 2-[2-(3,4-dihydro-2H-1-benzopyran-6-yl)-3-(3-methyl-1H-pyrazol-1-yl)-6-(trifluoromethyl)phenyl]-2-hydroxyacetate (59a) (90 mg, 0.20 mmol) is converted, after purification by preparative TLC (cyclohexane/ethyl acetate 80/20) into methyl 2-(tert-butoxy)-2-[2-(3,4-dihydro-2H-1-benzopyran-6-yl)-3-(3-methyl-1H-pyrazol-1-yl)-6-(trifluoromethyl)phenyl]acetate (59b) (48 mg, 0.095 mmol, 45%) as a colorless oil.

$^1$H NMR (400 MHz, CDCl$_3$) δ 0.91 and 0.92 (s, 9H), 1.92-1.97 (m, 1H), 2.00-2.06 (m, 1H), 2.27 and 2.28 (s, 3H), 2.49-2.64 (m, 1H), 2.68-2.83 (m, 1H), 3.73 (s, 3H), 4.16-4.22 (m, 2H), 5.15 and 5.16 (s, 1H), 5.85 and 5.87 (d, J=2.4 Hz, 1H), 6.57-6.81 (m, 3H), 7.13-7.18 (m, 1H), 7.72 (d, J=8.6 Hz, 1H), 7.79 (d, J=8.6 Hz, 1H).

MS m/z ([M+H]$^+$) 503.

Step 3: Preparation of 2-(tert-butoxy)-2-[2-(3,4-dihydro-2H-1-benzopyran-6-yl)-3-(3-methyl-1H-pyrazol-1-yl)-6-(trifluoromethyl)phenyl]acetic acid (Example 59)

Using the procedure described in example 5, step 4, the intermediate methyl 2-(tert-butoxy)-2-[2-(3,4-dihydro-2H-1-benzopyran-6-yl)-3-(3-methyl-1H-pyrazol-1-yl)-6-(trifluoromethyl)phenyl]acetate (59b) (45 mg, 0.089 mmol) is converted to 2-(tert-butoxy)-2-[2-(3,4-dihydro-2H-1-benzopyran-6-yl)-3-(3-methyl-1H-pyrazol-1-yl)-6-(trifluoromethyl)phenyl]acetic acid (example 59) (30 mg, 0.061 mmol, 68%) as a white solid.

$^1$H NMR (400 MHz, CDCl$_3$) δ 0.94 (s, 9H), 1.92-1.99 (m, 1H), 2.00-2.07 (m, 1H), 2.29 and 2.30 (s, 3H), 2.52-2.60 (m, 1H), 2.82-2.85 (m, 1H), 4.18-4.24 (m, 2H), 5.29 and 5.33 (s, 1H), 5.88 and 5.90 (d, J=2.4 Hz, 1H), 6.56-6.89 (m, 3H), 7.54-7.57 (m, 1H), 7.78-7.83 (m, 2H).

MS m/z ([M+H]$^+$) 489.
MS m/z ([M−H]$^-$) 487.

Example 60

Synthesis of 2-(tert-butoxy)-2-[2-(4,4-dimethylcyclohex-1-en-1-yl)-3-(1H-pyrazol-1-yl)-6-(trifluoromethyl)phenyl]acetic acid

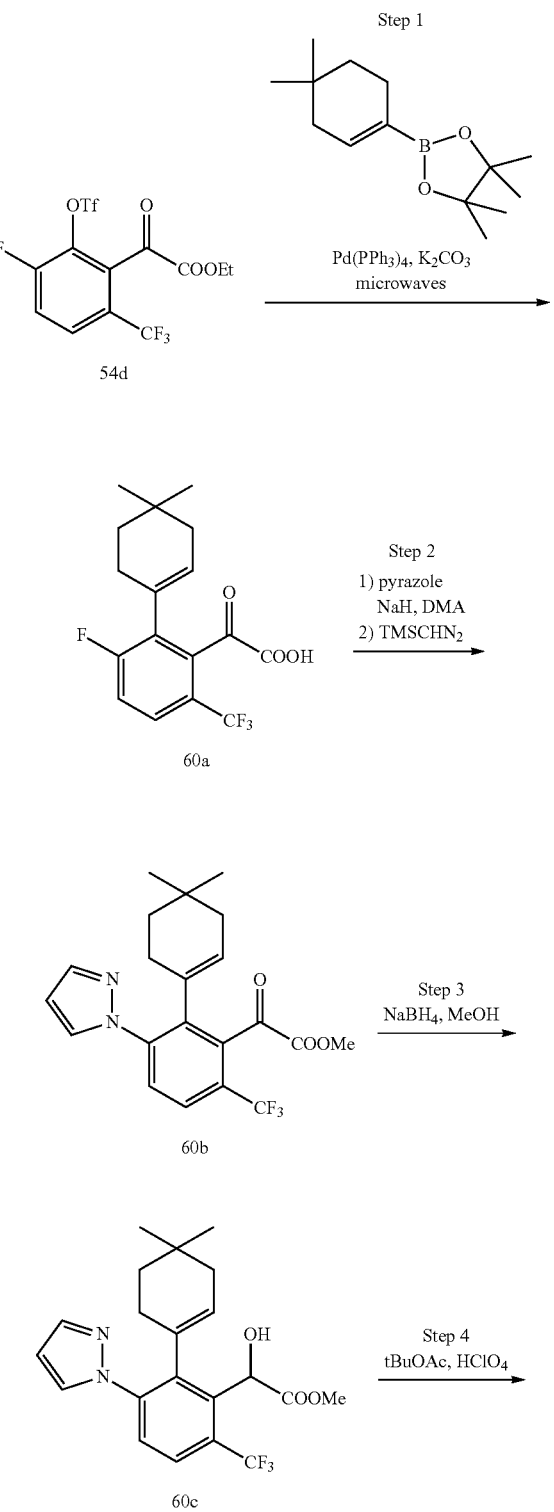

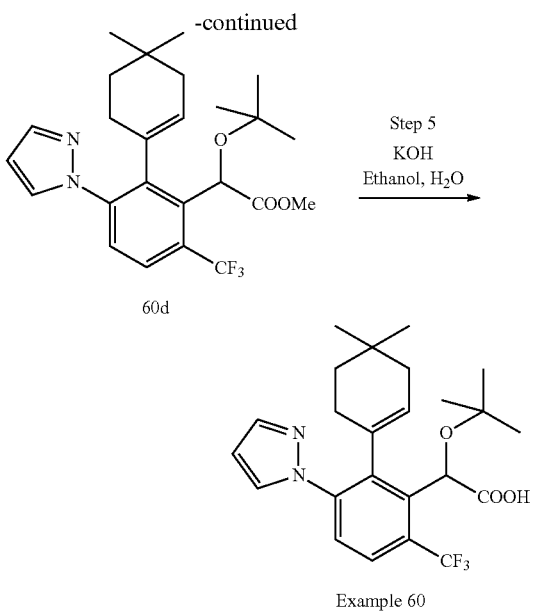

Example 60

Step 1: preparation of intermediate 2-[2-(4,4-dimethylcyclohex-1-en-1-yl)-3-fluoro-6-(trifluoromethyl)phenyl]-2-oxoacetic acid (60a)

A degassed solution of ethyl 2-{3-fluoro-2-[(trifluoromethane)sulfonyloxy]-6-(trifluoromethyl)phenyl}-2-oxoacetate (54d) (100 mg, 0.24 mmol), sodium carbonate (77 mg, 0.73 mmol), 2-(4,4-dimethyl-1-cyclohexen-1-yl)-4,4,5,5-tetramethyl-1,3,2-dioxaborolane (74 mg, 0.32 mmol) and palladium tetrakis(triphenylphosphine) (28 mg, 0.02 mmol) in tetrahydrofurane (1.7 mL) and water (0.3 mL) was irradiated at 60° C. for 1 hour. The mixture was poured in water (5 mL) and extracted with ethyl acetate. The organic layer was washed with a saturated solution of sodium hydrogenocarbonate (5 mL), dried over sodium sulfate and concentrated in vacuo. The residue was purified by flash chromatography on silica gel (cyclohexane/ethyl acetate 90/10) to provide 2-[2-(4,4-dimethylcyclohex-1-en-1-yl)-3-fluoro-6-(trifluoromethyl)phenyl]-2-oxoacetic acid (60a) (64 mg, 0.17 mmol, 71%) as a colorless oil.

$^1$H NMR (300 MHz, CDCl$_3$) δ 0.94 (s, 6H), 1.33-1.43 (m, 5H), 1.88-1.91 (m, 2H), 2.24-2.29 (m, 2H), 4.31 (q, J=7.2 Hz, 2H), 5.55-5.58 (m, 1H), 7.23 (t, J=8.7 Hz, 1H), 7.63 (dd, J=4.8 Hz, J=8.7 Hz, 1H).

Step 2: Preparation of Intermediate methyl 2-[2-(4,4-dimethylcyclohex-1-en-1-yl)-3-(1H-pyrazol-1-yl)-6-(trifluoromethyl)phenyl]-2-oxoacetate (60b)

Using the procedure described in example 57, step 1, the intermediate 2-[2-(4,4-dimethylcyclohex-1-en-1-yl)-3-fluoro-6-(trifluoromethyl)phenyl]-2-oxo acetic acid (60a) (311 mg, 0.84 mmol) is converted by reaction with pyrazole (114 mg, 1.67 mmol), after purification by flash chromatography on silica gel (cyclohexane/ethyl acetate 80/20) into methyl 2-[2-(4,4-dimethylcyclohex-1-en-1-yl)-3-(1H-pyrazol-1-yl)-6-(trifluoromethyl)phenyl]-2-oxoacetate (60b) (177 mg, 0.43 mmol, 52%) as a colorless oil.

$^1$H NMR (300 MHz, CDCl$_3$) δ 0.84 (s, 6H), 1.13-1.32 (m, 3H), 1.71-1.93 (m, 3H), 3.86 (s, 3H), 5.74-5.76 (m, 1H), 6.44-6.46 (m, 1H), 7.72-7.76 (m, 4H).

MS m/z ([M+H]$^+$) 407.

Step 3: Preparation of Intermediate methyl 2-[2-(4,4-dimethylcyclohex-1-en-1-yl)-3-(1H-pyrazol-1-yl)-6-(trifluoromethyl)phenyl]-2-hydroxyacetate (60c)

Using the procedure described in example 54, step 7, the intermediate methyl 2-[2-(4,4-dimethylcyclohex-1-en-1-yl)-3-(1H-pyrazol-1-yl)-6-(trifluoromethyl)phenyl]-2-oxoacetate (177 mg, 0.44 mmol) (60b) (90 mg, 0.20 mmol) is converted into methyl 2-[2-(4,4-dimethylcyclohex-1-en-1-yl)-3-(1H-pyrazol-1-yl)-6-(trifluoromethyl)phenyl]-2-hydroxyacetate (60c) (178 mg, 0.44 mmol, 100%) as a colorless oil.

$^1$H NMR (400 MHz, CDCl$_3$) δ 0.72 (s, 3H), 0.93 (s, 3H), 1.14-1.19 (m, 1H), 1.30-1.35 (m, 1H), 1.55-2.17 (m, 4H), 3.74 and 3.76 (s, 3H), 5.41 and 5.95 (bs, 1H), 5.61 (s, 1H), 6.39 (s, 1H), 7.53-7.56 (m, 1H), 7.62 (s, 1H), 7.67-7.69 (m, 1H), 7.74-7.76 (m, 1H).

MS m/z ([M+H]$^+$) 409.

MS m/z ([M−H]$^−$) 407.

Step 4: Preparation of Intermediate methyl 2-(tert-butoxy)-2-[2-(4,4-dimethylcyclohex-1-en-1-yl)-3-(1H-pyrazol-1-yl)-6-(trifluoromethyl)phenyl]acetate (60d)

Using the procedure described in example 1, step 8, the intermediate methyl 2-[2-(4,4-dimethylcyclohex-1-en-1-yl)-3-(1H-pyrazol-1-yl)-6-(trifluoromethyl)phenyl]-2-hydroxyacetate (60c) (178 mg, 0.44 mmol) is converted, after purification by flash chromatography on silica gel (cyclohexane/ethyl acetate 90/10) into methyl 2-(tert-butoxy)-2-[2-(4,4-dimethylcyclohex-1-en-1-yl)-3-(1H-pyrazol-1-yl)-6-(trifluoromethyl)phenyl]acetate (60d) (69 mg, 0.148 mmol, 34%) as a colorless oil.

$^1$H NMR (300 MHz, CDCl$_3$) δ 0.79 and 0.84 (s, 3H), 0.95 and 0.97 (s, 3H), 1.12-1.40 (m, 12H), 1.79 (s, 1H), 1.92-1.94 (m, 1H), 2.21-2.27 (m, 1H), 3.67 and 3.73 (s, 3H), 5.32 and 5.80 and 5.88 (bs, 1H), 6.37 and 6.39 and 6.42 (t, J=2.1 Hz, 1H), 7.48-7.54 (m, 1H), 7.61-7.76 (m, 3H).

MS m/z ([M+H]$^+$) 465.

Step 4: Preparation of 2-(tert-butoxy)-2-[2-(4,4-dimethylcyclohex-1-en-1-yl)-3-(1H-pyrazol-1-yl)-6-(trifluoromethyl)phenyl]acetic acid (Example 60)

Using the procedure described in example 5, step 4, the intermediate methyl 2-(tert-butoxy)-2-[2-(4,4-dimethylcyclohex-1-en-1-yl)-3-(1H-pyrazol-1-yl)-6-(trifluoromethyl)phenyl]acetate (60d) (69 mg, 0.15 mmol) is converted into 2-(tert-butoxy)-2-[2-(4,4-dimethylcyclohex-1-en-1-yl)-3-(1H-pyrazol-1-yl)-6-(trifluoromethyl)phenyl]acetic acid (example 60) (50 mg, 0.11 mmol, 74%) as a white solid.

$^1$H NMR (300 MHz, CDCl$_3$) δ 0.78 and 0.85 (s, 3H), 0.94 (s, 3H), 1.13-1.30 (m, 11H), 1.40-1.50 (m, 1H), 1.79-2.01 (m, 3H), 5.51-5.59 and 6.31-5.35 (m, 2H), 6.39 and 6.42 and 6.42 (t, J=2.1 Hz, 1H), 7.54-7.71 (m, 3H), 7.75 and 7.76 (d, J=8.5 Hz, 1H).

MS m/z ([M+H]$^+$) 451.

MS m/z ([M−H]$^−$) 449.

Example 61

Synthesis of 2-(tert-butoxy)-2-[2-(3,4-dihydro-2H-1-benzopyran-6-yl)-3-(4-methyl-1H-pyrazol-1-yl)-6-(trifluoromethyl)phenyl]acetic acid

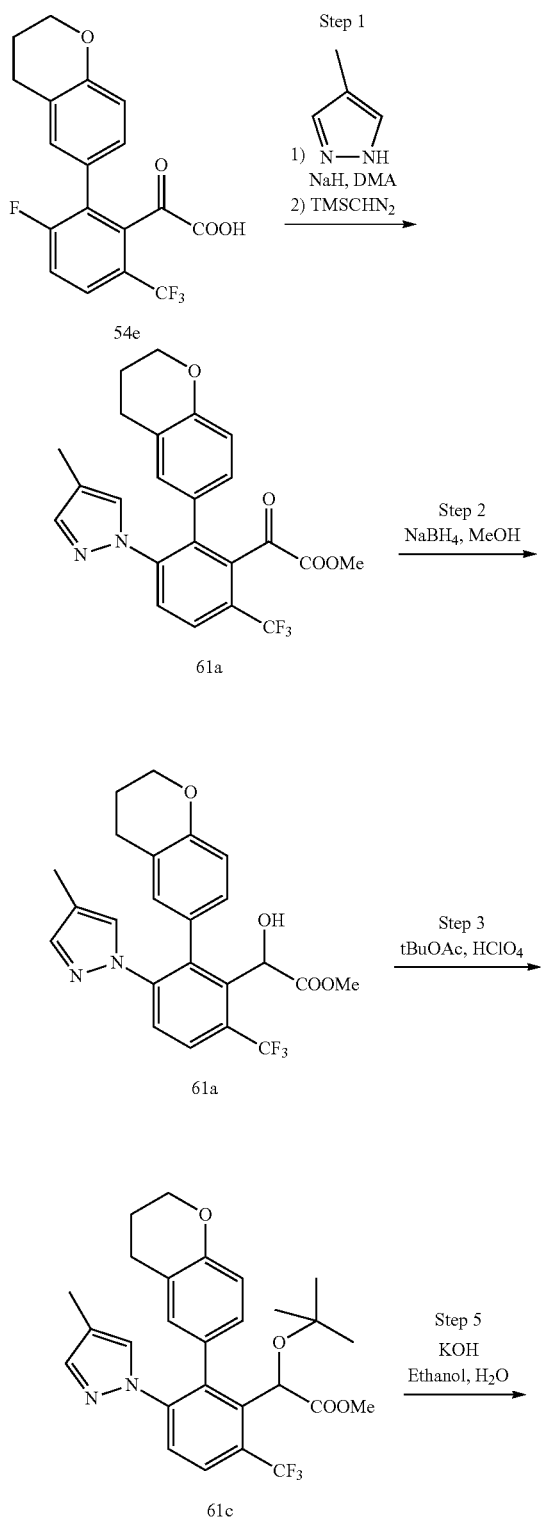

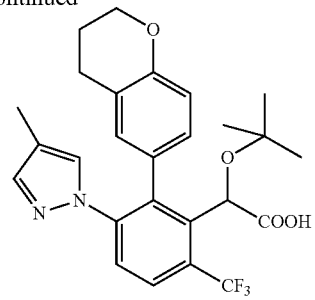

Example 61

Step 1: Preparation of Intermediate methyl 2-[2-(3,4-dihydro-2H-1-benzopyran-6-yl)-3-(4-methyl-1H-pyrazol-1-yl)-6-(trifluoromethyl)phenyl]-2-oxoacetate (61a)

Using the procedure described in example 57, step 1, the intermediate 2-[2-(3,4-dihydro-2H-1-benzopyran-6-yl)-3-fluoro-6-(trifluoromethyl)phenyl]-2-oxoacetic acid (54e) (150 mg, 0.39 mmol) is converted by reaction with 4-methylpyrazole (65 μL, 0.78 mmol), after purification by flash chromatography on silica gel (cyclohexane/ethyl acetate 80/20) into methyl 2-[2-(3,4-dihydro-2H-1-benzopyran-6-yl)-3-(4-methyl-1H-pyrazol-1-yl)-6-(trifluoromethyl)phenyl]-2-oxoacetate (61a) (116 mg, 0.26 mmol, 66%) as a colorless oil.

$^1$H NMR (300 MHz, CDCl$_3$) δ 1.92 (s, 3H), 1.96-2.02 (m, 2H), 2.66-2.73 (m, 2H), 3.53 (s, 3H), 4.17-4.20 (m, 2H), 6.69-6.72 (m, 4H), 7.43 (s, 1H), 7.80 (d, J=8.4 Hz, 1H), 7.92 (d, J=8.4 Hz, 1H).

MS m/z ([M+H]$^+$) 445.

Step 2: Preparation of Intermediate methyl 2-[2-(3,4-dihydro-2H-1-benzopyran-6-yl)-3-(4-methyl-1H-pyrazol-1-yl)-6-(trifluoromethyl)phenyl]-2-hydroxyacetate (61 b)

Using the procedure described in example 54, step 7, the intermediate methyl 2-[2-(3,4-dihydro-2H-1-benzopyran-6-yl)-3-(4-methyl-1H-pyrazol-1-yl)-6-(trifluoromethyl)phenyl]-2-oxoacetate (61a) (116 mg, 0.26 mmol) is converted, after recrystallization in cyclohexane, into methyl 2-[2-(3,4-dihydro-2H-1-benzopyran-6-yl)-3-(4-methyl-1H-pyrazol-1-yl)-6-(trifluoromethyl)phenyl]-2-hydroxyacetate (61 b) (32 mg, 0.07 mmol, 27%) as a white solid.

$^1$H NMR (300 MHz, CDCl$_3$) δ 1.89 (s, 3H), 1.93-2.06 (m, 2H), 2.57-2.61 (m, 1H), 2.74-2.78 (m, 1H), 3.51 and 3.54 (s, 3H), 4.17-4.23 (m, 2H), 5.44 and 5.45 (s, 1H), 6.51-6.97 (m, 3H), 7.12-7.16 (m, 1H), 7.35 (s, 1H), 7.74 (d, J=8.7 Hz, 1H), 7.22 (d, J=8.7 Hz, 1H).

MS m/z ([M+H]$^+$) 447.
MS m/z ([M−H]$^-$) 445.

Step 3: Preparation of Intermediate methyl 2-(tert-butoxy)-2-[2-(3,4-dihydro-2H-1-benzopyran-6-yl)-3-(4-methyl-1H-pyrazol-1-yl)-6-(trifluoromethyl)phenyl]acetate (61c)

Using the procedure described in example 1, step 8, the intermediate methyl 2-[2-(3,4-dihydro-2H-1-benzopyran-6-yl)-3-(4-methyl-1H-pyrazol-1-yl)-6-(trifluoromethyl)phenyl]-2-hydroxyacetate (61b) (32 mg, 0.07 mmol) (178 mg, 0.44 mmol) is converted, after purification by preparative TLC (cyclohexane/ethyl acetate 70/30) into methyl 2-(tert-butoxy)-2-[2-(3,4-dihydro-2H-1-benzopyran-6-yl)-3-(4-methyl-1H-pyrazol-1-yl)-6-(trifluoromethyl)phenyl]acetate (61c) (20 mg, 0.039 mmol, 55%) as a colorless oil.

$^1$H NMR (300 MHz, CDCl$_3$) δ 0.93 and 0.94 (s, 9H), 1.89 and 1.90 (s, 3H), 1.90-2.07 (m, 2H), 2.47-2.66 (m, 1H), 2.67-2.86 (m, 1H), 3.73 and 3.74 (s, 3H), 4.16-4.23 (m, 2H), 5.16 and 5.18 (s, 1H), 6.52-6.82 (m, 3H), 7.12-7.19 (m, 1H), 7.35 and 7.36 (s, 1H), 7.67 and 7.68 (d, J=8.6 Hz, 1H), 7.77 and 7.80 (d, J=8.6 Hz, 1H).

MS m/z ([M+H]$^+$) 503.

Step 4: Preparation of 2-(tert-butoxy)-2-[2-(3,4-dihydro-2H-1-benzopyran-6-yl)-3-(4-methyl-1H-pyrazol-1-yl)-6-(trifluoromethyl)phenyl]acetic acid (Example 61)

Using the procedure described in example 5, step 4, the intermediate methyl 2-(tert-butoxy)-2-[2-(3,4-dihydro-2H-1-benzopyran-6-yl)-3-(4-methyl-1H-pyrazol-1-yl)-6-(trifluoromethyl)phenyl]acetate (61c) (20 mg, 0.039 mmol) is converted into 2-(tert-butoxy)-2-[2-(3,4-dihydro-2H-1-benzopyran-6-yl)-3-(4-methyl-1H-pyrazol-1-yl)-6-(trifluoromethyl)phenyl]acetic acid (example 61) (12 mg, 0.024 mmol, 63%) as a white solid.

$^1$H NMR (300 MHz, CDCl$_3$) δ 0.94 (s, 9H), 1.88-2.07 (m, 5H), 2.47-2.66 (m, 1H), 2.79-2.83 (m, 1H), 4.16-4.24 (m, 2H), 5.29 and 5.35 (s, 1H), 6.51-6.89 (m, 3H), 7.38 and 7.39 (s, 1H), 7.51-7.55 (m, 1H), 7.71-7.83 (m, 2H).

MS m/z ([M+H]$^+$) 489.
MS m/z ([2M−H]$^−$) 975.

Example 62

Synthesis of 2-(tert-butoxy)-2-[2-(3,4-dihydro-2H-1-benzopyran-6-yl)-3-(1H-imidazol-1-yl)-6-(trifluoromethyl)phenyl]acetic acid

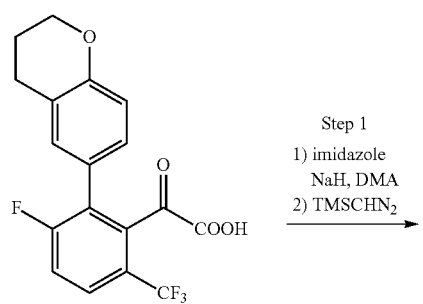

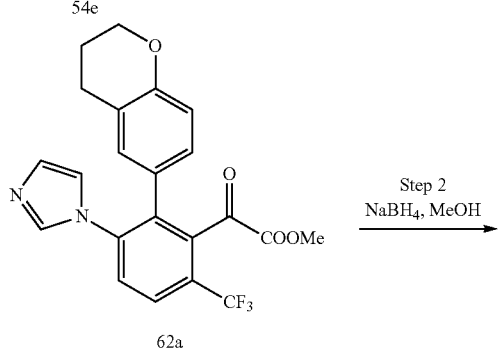

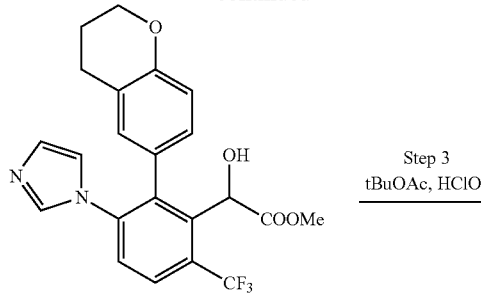

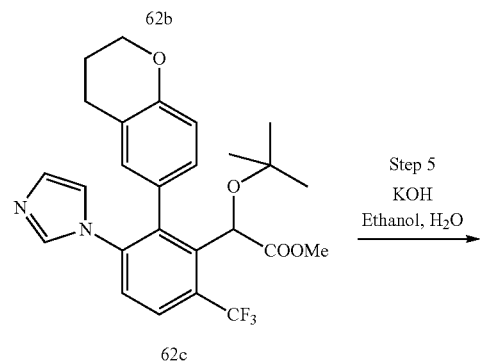

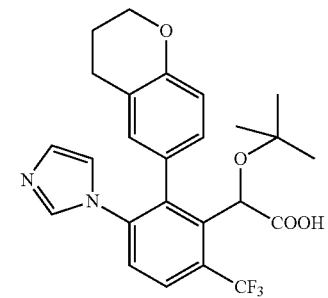

Example 62

Step 1: Preparation of Intermediate methyl 2-[2-(3,4-dihydro-2H-1-benzopyran-6-yl)-3-(1H-imidazol-1-yl)-6-(trifluoromethyl)phenyl]-2-oxoacetate (62a)

To a solution of 2-[2-(3,4-dihydro-2H-1-benzopyran-6-yl)-3-fluoro-6-(trifluoromethyl)phenyl]-2-oxoacetic acid (54a) (117 mg, 0.32 mmol) and imidazole (43 mg, 0.64 mmol) in anhydrous dimethylacetamide (2 mL) at 0° C. under nitrogen atmosphere, was added sodium hydride 60% in oil (51 mg, 1.27 mmol). The mixture was heated at 110° C. for 3 hours. At room temperature, 5 drops of water were added to the mixture. The mixture was then diluted with ethyl acetate, dried over sodium sulfate and concentrated in vacuo. The residue was dissolved in toluene and concentrated in vacuo. The procedure was carried out twice. The residue was dissolved in methanol (5 mL) and a 2 M solution of trimethylsilyldiazomethane in diethyl ether (1 mL, 2 mmol) was added. The mixture was stirred at room temperature for 30 minutes and concentrated in vacuo. The residue was purified by flash chromatography on silica gel (100% ethyl acetate) to provide methyl 2-[2-(3,4-dihydro-2H-1-benzopyran-6-yl)-3-(1H-imidazol-1-yl)-6-(trifluoromethyl)phenyl]-2-oxoacetate (62a) (57 mg, 0.13 mmol, 41%) as a colorless oil.

$^1$H NMR (400 MHz, CDCl$_3$) δ 1.91-1.98 (m, 2H), 2.62-2.70 (m, 2H), 3.55 (s, 3H), 4.14-4.17 (t, J=5.2 Hz, 2H), 6.60-6.67 (m, 3H), 6.82 (s, 1H), 6.99 (s, 1H), 7.35 (s, 1H), 7.59 (d, J=8.4 Hz, 1H), 7.84 (d, J=8.4 Hz, 1H).

Step 2: Preparation of Intermediate methyl 2-[2-(3,4-dihydro-2H-1-benzopyran-6-yl)-3-(1H-imidazol-1-yl)-6-(trifluoromethyl)phenyl]-2-hydroxyacetate (62b)

Using the procedure described in example 54, step 7, the intermediate methyl 2-[2-(3,4-dihydro-2H-1-benzopyran-6-yl)-3-(1H-imidazol-1-yl)-6-(trifluoro methyl)phenyl]-2-oxoacetate (62a) (56 mg, 0.13 mmol) is converted, after purification by preparative TLC (dichloromethane/methanol 95/5) into methyl 2-[2-(3,4-dihydro-2H-1-benzopyran-6-yl)-3-(1H-imidazol-1-yl)-6-(trifluoromethyl)phenyl]-2-hydroxyacetate (62b) (40 mg, 0.095 mmol, 71%) as a colorless oil.

$^1$H NMR (400 MHz, CDCl$_3$) δ 1.92-2.03 (m, 2H), 2.56-2.60 (m, 1H), 2.63-2.78 (m, 1H), 3.54 and 3.57 (s, 3H), 4.14-4.20 (m, 2H), 5.44 and 5.45 (s, 1H), 6.45-6.74 (m, 3H), 6.89-6.91 (m, 1H), 7.05-7.07 (m, 1H), 7.28 (s, 1H), 7.46 (d, J=8.4 Hz, 1H), 7.85 (d, J=8.4 Hz, 1H).

MS m/z ([M+H]$^+$) 433.

Step 3: Preparation of Intermediate methyl 2-(tert-butoxy)-2-[2-(3,4-dihydro-2H-1-benzopyran-6-yl)-3-(1H-imidazol-1-yl)-6-(trifluoromethyl)phenyl]acetate (62c)

Using the procedure described in example 1, step 8, the intermediate methyl 2-[2-(3,4-dihydro-2H-1-benzopyran-6-yl)-3-(1H-imidazol-1-yl)-6-(trifluoro methyl)phenyl]-2-hydroxyacetate (62b) (40 mg, 0.09 mmol) is converted, after purification by preparative TLC (cyclohexane/ethyl acetate 80/20) into methyl 2-(tert-butoxy)-2-[2-(3,4-dihydro-2H-1-benzopyran-6-yl)-3-(1H-imidazol-1-yl)-6-(trifluoromethyl)phenyl]acetate (62c) (16 mg, 0.032 mmol, 35%) as a colorless oil.

$^1$H NMR (400 MHz, CDCl$_3$) δ 0.95 and 0.96 (s, 9H), 1.92-2.04 (m, 2H), 2.50-2.60 (m, 1H), 2.65-2.79 (m, 1H), 3.72 (s, 3H), 4.15-4.20 (m, 2H), 5.17 (s, 1H), 6.45-6.78 (m, 3H), 6.91 and 6.93 (s, 1H), 7.05-7.11 (m, 1H), 7.25-7.31 (m, 1H), 7.41 (d, J=8.4 Hz, 1H), 7.82 (d, J=8.4 Hz, 1H).

MS m/z ([M+H]$^+$) 489.

Step 4: Preparation of 2-(tert-butoxy)-2-[2-(3,4-dihydro-2H-1-benzopyran-6-yl)-3-(1H-imidazol-1-yl)-6-(trifluoromethyl)phenyl]acetic acid (Example 62)

Using the procedure described in example 5, step 4, the intermediate methyl 2-(tert-butoxy)-2-[2-(3,4-dihydro-2H-1-benzopyran-6-yl)-3-(1H-imidazol-1-yl)-6-(trifluoromethyl)phenyl]acetate (62c) (16 mg, 0.032 mmol) is converted into 2-(tert-butoxy)-2-[2-(3,4-dihydro-2H-1-benzopyran-6-yl)-3-(1H-imidazol-1-yl)-6-(trifluoromethyl)phenyl]acetic acid (example 62) (11 mg, 0.023 mmol, 68%) as a white solid.

$^1$H NMR (300 MHz, CDCl$_3$) δ 0.98 (s, 9H), 1.92-2.05 (m, 2H), 2.53-2.57 (m, 1H), 2.75-2.79 (m, 1H), 4.14-4.21 (m, 2H), 5.26 and 5.29 (s, 1H), 6.45-6.82 (m, 3H), 6.94 and 6.95 (s, 1H), 7.42-7.47 (m, 3H), 7.84 (d, J=8.4 Hz, 1H).

MS m/z ([M+H]$^+$) 475.

Example 63

Synthesis of 2-(tert-butoxy)-2-[2-(3,4-dihydro-2H-1-benzopyran-6-yl)-3-(1H-pyrazol-1-yl)-6-(trifluoromethyl)phenyl]acetic acid

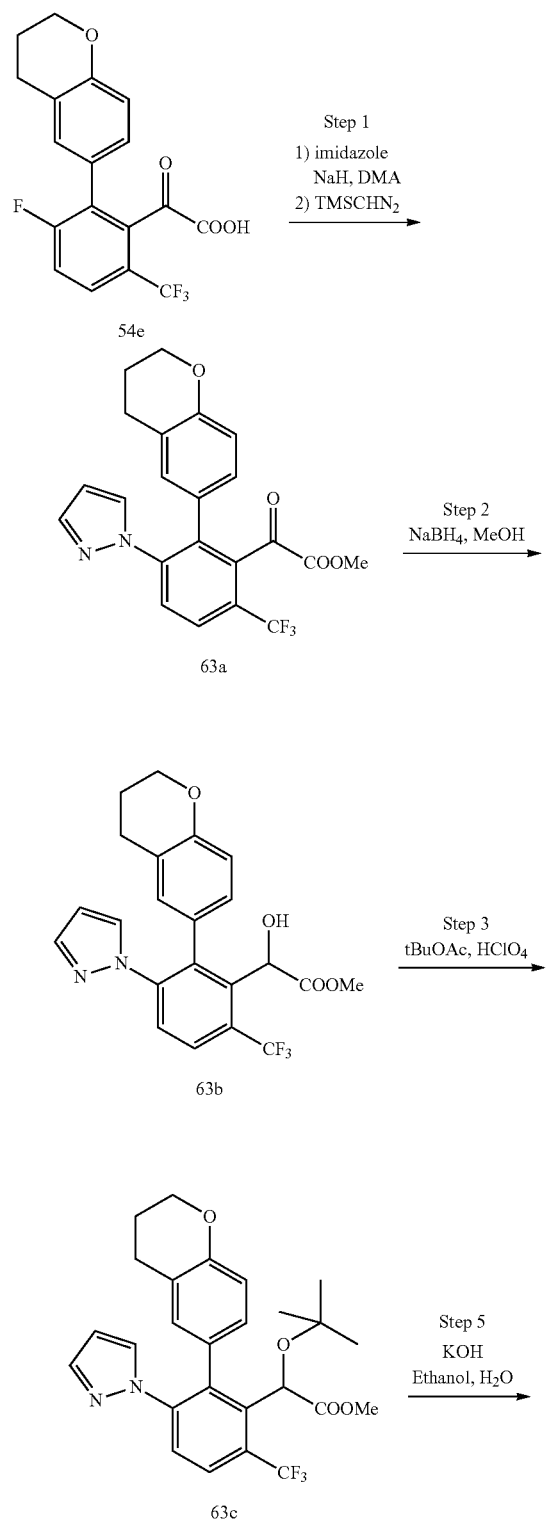

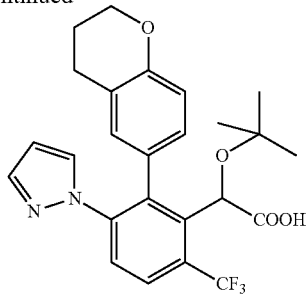

Example 63

Step 1: Preparation of Intermediate methyl 2-[2-(3,4-dihydro-2H-1-benzopyran-6-yl)-3-(1H-pyrazol-1-yl)-6-(trifluoromethyl)phenyl]-2-oxoacetate (63a)

Using the procedure described in example 62, step 1, the intermediate 2-[2-(3,4-dihydro-2H-1-benzopyran-6-yl)-3-fluoro-6-(trifluoromethyl)phenyl]-2-oxoacetic acid (54e) (50 mg, 0.14 mmol) is converted by reaction with pyrazole (18 mg, 0.27 mmol), after purification by flash chromatography on silica gel (cyclohexane/ethyl acetate 70/30) to provide methyl 2-[2-(3,4-dihydro-2H-1-benzopyran-6-yl)-3-(1H-pyrazol-1-yl)-6-(trifluoromethyl)phenyl]-2-oxoacetate (63a) (33 mg, 0.076 mmol, 57%) as a colorless oil.

$^1$H NMR (400 MHz, CDCl$_3$) δ 1.94-2.03 (m, 2H), 2.61-2.72 (m, 2H), 3.54 (s, 3H), 4.16-4.19 (m, 2H), 6.16-6.17 (m, 1H), 6.68 (s, 2H), 6.71 (s, 1H), 6.97 (d, J=2.5 Hz, 1H), 7.63 (d, J=1.4 Hz, 1H), 7.82 (d, J=8.5 Hz, 1H), 7.95 (d, J=8.5 Hz, 1H).

MS m/z ([M+H]$^+$) 431.

Step 2: Preparation of Intermediate methyl 2-[2-(3,4-dihydro-2H-1-benzopyran-6-yl)-3-(1H-pyrazol-1-yl)-6-(trifluoromethyl)phenyl]-2-hydroxyacetate (63b)

Using the procedure described in example 54, step 7, the intermediate methyl 2-[2-(3,4-dihydro-2H-1-benzopyran-6-yl)-3-(1H-pyrazol-1-yl)-6-(trifluoromethyl)phenyl]-2-oxoacetate (63a) (33 mg, 0.076 mmol) is converted into methyl 2-[2-(3,4-dihydro-2H-1-benzopyran-6-yl)-3-(1H-pyrazol-1-yl)-6-(trifluoromethyl)phenyl]-2-hydroxyacetate (63b) (30 mg, 0.07 mmol, 91%) as a colorless oil.

$^1$H NMR (300 MHz, CDCl$_3$) δ 1.90-2.06 (m, 2H), 2.49-2.66 (m, 1H), 2.67-2.84 (m, 1H), 3.50 and 3.53 (s, 3H), 4.14-4.22 (m, 2H), 5.44 and 5.45 (s, 1H), 6.07-6.10 (m, 1H), 6.49-6.53 (m, 1H), 6.61 and 6.76 (d, J=8.4 Hz, 1H), 6.88 (d, J=2.4 Hz, 1H), 7.13-7.17 (m, 1H), 7.54 (d, J=1.7 Hz, 1H), 7.76 (d, J=8.6 Hz, 1H), 7.84 (d, J=8.6 Hz, 1H).

MS m/z ([M+H]$^+$) 433.

Step 3: Preparation of Intermediate methyl 2-(tert-butoxy)-2-[2-(3,4-dihydro-2H-1-benzopyran-6-yl)-3-(1H-pyrazol-1-yl)-6-(trifluoromethyl)phenyl]acetate (63c)

Using the procedure described in example 1, step 8, the intermediate methyl 2-[2-(3,4-dihydro-2H-1-benzopyran-6-yl)-3-(1H-pyrazol-1-yl)-6-(trifluoro methyl)phenyl]-2-hydroxyacetate (63b) (30 mg, 0.07 mmol) is converted, after purification by preparative TLC (cyclohexane/ethyl acetate 70/30) into methyl 2-(tert-butoxy)-2-[2-(3,4-dihydro-2H-1-benzopyran-6-yl)-3-(1H-pyrazol-1-yl)-6-(trifluoromethyl)phenyl]acetate (63c) (20 mg, 0.04 mmol, 58%) as a colorless oil.

$^1$H NMR (300 MHz, CDCl$_3$) δ 0.93 and 0.94 (s, 9H), 1.90-2.07 (m, 2H), 2.45-2.64 (m, 1H), 2.67-2.84 (m, 1H), 3.73 and 3.74 (s, 3H), 4.16-4.23 (m, 2H), 5.17 and 5.18 (s, 1H), 6.08-6.11 (m, 1H), 6.52-6.58 (m, 1H), 6.62 and 6.80 (d, J=8.4 Hz, 1H), 6.87 and 6.90 (d, J=2.4 Hz, 1H), 7.14-7.20 (m, 1H), 7.55-7.56 (m, 1H), 7.72 (d, J=8.5 Hz, 1H), 7.83 (d, J=8.5 Hz, 1H).

MS m/z ([M+H]$^+$) 489.

Step 4: Preparation of 2-(tert-butoxy)-2-[2-(3,4-dihydro-2H-1-benzopyran-6-yl)-3-(1H-pyrazol-1-yl)-6-(trifluoromethyl)phenyl]acetic acid (Example 63)

Using the procedure described in example 5, step 4, the intermediate methyl 2-(tert-butoxy)-2-[2-(3,4-dihydro-2H-1-benzopyran-6-yl)-3-(1H-pyrazol-1-yl)-6-(trifluoromethyl)phenyl]acetate (63c) (20 mg, 0.04 mmol) is converted to 2-(tert-butoxy)-2-[2-(3,4-dihydro-2H-1-benzopyran-6-yl)-3-(1H-pyrazol-1-yl)-6-(trifluoromethyl)phenyl]acetic acid (example 63) (12 mg, 0.025 mmol, 63%) as a white solid.

$^1$H NMR (300 MHz, CDCl$_3$) 0.95 (s, 9H), 1.90-1.96 (m, 1H), 2.00-2.07 (m, 1H), 2.46-2.59 (m, 1H), 2.79-2.84 (m, 1H), 4.16-4.23 (m, 2H), 5.30 and 5.34 (s, 1H), 6.09-6.12 (m, 1H), 6.50-6.90 (m, 3H), 7.52-7.58 (m, 2H), 7.77 (d, J=8.5 Hz, 1H), 7.84 (d, J=8.5 Hz, 1H).

MS m/z ([M+H]$^+$) 475.
MS m/z ([M−H]$^-$) 473.

Antiviral Activity

The antiviral activity, particularly against HIV, of compounds according to the invention is evaluated by the protocol described below.

Preparation of Virus Stock of the NL4-3 Strain of HIV-1 (Adachi et al, J Virol, 1986, 59(2):284-91).

The virus was prepared as described in Lopez et al (Lopez et al, Proc Natl Acad Sci USA., 2006, 103(40):14947-52, by transfecting 2×10$^6$ 293 T cells (CRL-1573, ATCC) with following modifications: 6 μg of NL4-3 proviral DNA molecular clone were mixed with Fugene 6 transfection reagent from Roche, and used according to manufacturer's instructions. Forty eight hours later, transfected cell supernatants were harvested, filtered through 0.45-μm-pore-size filters, quantified for HIV-1 p24 antigen by using a Innotest HIV antigen mAb assay (Ingen) according to manufacturer's instructions, and used in infection experiments.

Preparation of Compounds:

Serial dilutions of compounds to be tested were prepared in complete RPMI medium from 10 mM DMSO stock solutions, and distributed in a volume of 20 μL in 96 well Falcon 353072 Microtest™ tissue culture plate, in order to get 0.5% DMSO final concentration in each well, after the addition of infected cells. Control wells contained also 0.5% DMSO final concentration but no compound.

Infection of Cells:

MT$^4$ cells (from the NIH AIDS Research and Reference Reagent Program) in RPMI complete medium were counted (10×10$^6$ cells per well in Falcon 353047 Multiwell™ 24 well) and infected for 2 hours at 37°, at a multiplicity of infection (moi) of 0.0001-0.00001. Cells were then centrifuged 3 min at 3000 rpm, and washed two times in 1 ml PBS to remove viruses that have not entered in cells. Infected cells were resuspended in complete RPMI at 1.25×10$^6$ cells/ml, and 80 μl of infected cells were distributed in each well containing compounds to be tested or control wells. The plates were then incubated at 37° for 5 days.

Assay Used to Measure the Inhibition of HIV Replication by the Compounds (According to (According to Gregg S. Jones et al., Antimicrobial Agents and Chemotherapy, 2009, 53 (3): 1194-1203).

After 5 days of incubation, 50 μl of CellTiter-Glo reagent (Promega Biosciences, Inc., Madison Wis., USA) were added to each well. Cell lysis was carried out at room temperature during 10 min, 150 μl of lysates were transferred in Packard Optiplate 96 well, and luminescence was read on a Fluoroskan (Thermo Scientific).

The EC50, or effective concentration 50, is the concentration of compound leading to 50% of cyto-protection in a Cell-Titer-Glo® viability assay based on $MT^4$ cells infected with NL4-3 virus (table 1).

TABLE 1

| Example number | EC50 (μM) | Example number | EC50 (μM) |
|---|---|---|---|
| 1 | 0.26 | 17 | 0.25 |
| 2 | 0.25 | 19 | 0.33 |
| 3 | 0.40 | 20 | 0.15 |
| 4 | 0.12 | 21 | 0.17 |
| 5 | 0.76 | 22 | 0.32 |
| 6 | 0.26 | 23 | 0.19 |
| 7 | 0.30 | 24 | 0.29 |
| 8 | 0.24 | 25 | 0.22 |
| 9 | 0.36 | 26 | 0.44 |
| 10 | 0.48 | 27 | 0.079 |
| 11 | 0.91 | 28 | 0.078 |
| 12 | 0.42 | 29 | 0.43 |
| 13 | 0.83 | 30 | 0.067 |
| 14 | 0.78 | 31 | 0.26 |
| 15 | 0.15 | 32 | 0.085 |
| 16 | 0.94 | 37 | 0.31 |
| 38 | 0.13 | 39 | 0.33 |

The results show that the compounds according to the invention can inhibit the HIV replication and thus can be used as anti-HIV compounds.

The invention claimed is:
1. A compound according to formula (I):

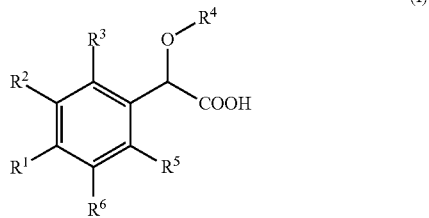

(I)

wherein:
$R^1$ and $R^6$, identical or different, independently represent a hydrogen atom; —CN; —OH; —$CF_3$; a halogen atom; a linear or branched $C_1$-$C_3$ alkyl a linear or branched $C_1$-$C_3$ heteroalkyl;

$R^2$, non-substituted or substituted by at least one $T^1$, represents a partially or totally unsaturated or aromatic 5-, 6- or 7-membered carbocycle; a partially or totally unsaturated or aromatic 5-, 6- or 7-membered heterocycle; a partially or totally unsaturated or aromatic 5-, 6- or 7-membered carbocycle fused with a saturated, partially or totally unsaturated or aromatic 5-, 6- or 7-membered carbocycle; a partially or totally unsaturated or aromatic 5-, 6- or 7-membered carbocycle fused with a saturated, partially or totally unsaturated or aromatic 5-, 6- or 7-membered heterocycle; a partially or totally unsaturated or aromatic 5-, 6- or 7-membered heterocycle fused with a saturated, partially or totally unsaturated or aromatic 5-, 6- or 7-membered carbocycle; a partially or totally unsaturated or aromatic 5-, 6- or 7-membered heterocycle fused with a saturated, partially or totally unsaturated or aromatic 5-, 6- or 7-membered heterocycle;

$R^3$, non-substituted or substituted by at least one $T^2$, represents an aryl; an aryl fused with a saturated, partially or totally unsaturated or aromatic 5-, 6- or 7-membered carbocycle; an aryl fused with a saturated, partially or totally unsaturated or aromatic 5-, 6- or 7-membered heterocycle; an aryl fused with a saturated, partially or totally unsaturated or aromatic 4-, 5-, 6- or 7-membered heterocycle and further fused with a saturated, partially or totally unsaturated or aromatic 4-, 5-, 6- or 7-membered heterocycle; a heteroaryl; a heteroaryl fused with a saturated, partially or totally unsaturated or aromatic 5-, 6- or 7-membered carbocycle; a heteroaryl fused with a saturated, partially or totally unsaturated or aromatic 5-, 6- or 7-membered heterocycle; a $C_5$-$C_7$ cycloalkenyl; a $C_5$-$C_7$ cycloalkenyl fused with a saturated, partially or totally unsaturated or aromatic 4-, 5-, 6- or 7-membered heterocycle; or a saturated, partially or totally unsaturated or aromatic 5-, 6- or 7-membered heterocycle;

$R^4$ represents a linear or branched $C_1$-$C_6$-alkyl; a linear or branched $C_1$-$C_6$ fluoroalkyl or a $C_3$-$C_6$ cycloalkyl;

$R^5$ represents a halogen atom; —$CF_3$; a linear or branched $C_1$-$C_6$ alkyl; a linear or branched $C_2$-$C_6$ alkenyl; a linear or branched $C_2$-$C_6$ alkynyl; a linear or branched fluoroalkyl; a $C_3$-$C_6$ cycloalkyl; —$CH_2OH$; or —$CH_2$—O—$CH_3$;

$T^1$ independently represents a hydrogen atom; a halogen atom; an alkyl; —$(X)_x$—$C_1$-$C_6$ alkyl; a linear or branched fluoroalkyl; a linear or branched —O—$C_1$-$C_3$ fluoroalkyl; —$(X)_x$—$C_3$-$C_6$ cycloalkyl; —$(X)_x$—$(CT^5T^6)_y$-$C_3$-$C_6$ cycloalkyl; —$(X)_x$—$(CT^5T^6)_y$-aryl; —$(X)_x$—$(CT^5T^6)_y$CN; —$(X)_x$—$(CT^5T^6)_y$OT$^3$; —$(X)_x$—$(CT^5T^6)_y$ST$^3$; —$(X)_x$—$(CT^5T^6)_y$S(O)T$^3$; —$(X)_x$—$(CT^5T^6)_y$S(O)$_2$T$^3$; —$(X)_x$—$(CT^5T^6)_y$NT$^3$T$^4$; —$(X)_x$—$(CT^5T^6)_y$C(O)T$^3$; —$(X)_x$—$(CT^5T^6)_y$C(O)OT$^3$; —$(X)_x$—$(CT^5T^6)_y$C(O)NT$^3$T$^4$; —$(X)_x$—$(CT^5T^6)_y$NT$^3$C(O)NT$^3$T$^4$; —$(X)_x$—$(CT^5T^6)_y$NT$^3$C(O)T$^4$; —$(X)_x$—$(CT^5T^6)_y$NT$^3$C(O)OT$^4$; —$(X)_x$—$(CT^5T^6)_y$OC(O)NT$^3$T$^4$; —$(X)_x$—$(CT^5T^6)_y$ S(O)$_2$NT$^3$T$^4$ or —$(X)_x$—$(CT^5T^6)_y$NT$^3$S(O)$_2$T$_4$;

$T^2$ independently represents a hydrogen atom; a halogen atom; a linear or branched —O—$C_1$-$C_3$ alkyl; a linear or branched $C_1$-$C_3$ fluoroalkyl; a linear or branched —O—$C_1$-$C_3$ fluoroalkyl; a linear or branched $C_1$-$C_3$ alkyl; or —CN; optionally two geminal $T^2$ form with the carbon atom to which they are bonded, a $C_3$-$C_7$ cycloalkyl;

X independently represents an oxygen atom; a sulphur atom; NT$^3$; S=O or S(O)$_2$;

$T^3$ and $T^4$, identical or different, independently represent a hydrogen atom; a branched or linear $C_1$-$C_6$ alkyl or a $C_3$-$C_6$ cycloalkyl; optionally $T^3$, $T^4$ and the nitrogen atom to which they are bonded form a $C_4$-$C_6$ heterocycloalkyl;

$T^5$ and $T^6$, identical or different, independently represent a hydrogen atom; a fluorine atom or a linear or branched $C_1$-$C_3$ alkyl or a $C_3$-$C_6$ cycloalkyl; optionally $T^5$, $T^6$ and the carbon atom to which they are bonded form a cyclopropyl;

x independently represents 0 or 1;

y independently represents 0, 1, 2 or 3;

or $R^5$ and $R^6$ form, with the carbon atoms to which they are bonded, a heteroaryl comprising at least one nitrogen atom; and a racemate, enantiomer, atropisomer, diastereoisomer or a pharmaceutically acceptable salt thereof.

2. The compound according to claim 1, wherein:

$R^1$ and $R^6$ represent a hydrogen atom;

$R^2$, non-substituted or substituted by at least one $T^1$, represents a partially or totally unsaturated or aromatic 5-, 6- or 7-membered carbocycle; a partially or totally unsaturated or aromatic 5-, 6- or 7-membered heterocycle; a partially or totally unsaturated or aromatic 5-, 6- or 7-membered carbocycle fused with a saturated, partially or totally unsaturated or aromatic 5-, 6- or 7-membered carbocycle; a partially or totally unsaturated or aromatic 5-, 6- or 7-membered carbocycle fused with a saturated, partially or totally unsaturated or aromatic 5-, 6- or 7-membered heterocycle; a partially or totally unsaturated or aromatic 5-, 6- or 7-membered heterocycle fused with a saturated, partially or totally unsaturated or aromatic 5-, 6- or 7-membered carbocycle; a partially or totally unsaturated or aromatic 5-, 6- or 7-membered heterocycle fused with a saturated, partially or totally unsaturated or aromatic 5-, 6- or 7-membered heterocycle;

$R^3$, non-substituted or substituted by at least one $T^2$, represents an aryl; an aryl fused with a saturated, partially or totally unsaturated or aromatic 5-, 6- or 7-membered carbocycle; an aryl fused with a saturated, partially or totally unsaturated or aromatic 5-, 6- or 7-membered heterocycle; an aryl fused with a saturated, partially or totally unsaturated or aromatic 4-, 5-, 6- or 7-membered heterocycle and further fused with a saturated, partially or totally unsaturated or aromatic 4-, 5-, 6- or 7-membered heterocycle; a heteroaryl; a heteroaryl fused with a saturated, partially or totally unsaturated or aromatic 5-, 6- or 7-membered carbocycle; a heteroaryl fused with a saturated, partially or totally unsaturated or aromatic 5-, 6- or 7-membered heterocycle; a $C_5$-$C_7$ cycloalkenyl; a $C_5$-$C_7$ cycloalkenyl fused with a saturated, partially or totally unsaturated or aromatic 4-, 5-, 6- or 7-membered heterocycle; or a saturated, partially or totally unsaturated or aromatic 5-, 6- or 7-membered heterocycle;

$R^4$ represents a linear or branched $C_1$-$C_6$-alkyl; a linear or branched $C_1$-$C_6$ fluoroalkyl or a $C_3$-$C_6$ cycloalkyl;

$R^5$ represents a halogen atom; a linear or branched $C_1$-$C_6$ alkyl; a linear or branched fluoroalkyl; a $C_3$-$C_6$ cycloalkyl or —$CH_2OH$;

$T^1$ independently represents a hydrogen atom; a halogen atom; an alkyl; —$(X)_x$—$C_1$-$C_6$ alkyl; a linear or branched fluoroalkyl; a linear or branched —O—$C_1$-$C_3$ fluoroalkyl; —$(X)_x$—$C_3$-$C_6$ cycloalkyl; —$(X)_x$—$(CT^5T^6)_y$-$C_3$-$C_6$ cycloalkyl; —$(X)_x$—$(CT^5T^6)_y$-aryl; —$(X)_x$—$(CT^5T^6)_y$CN; —$(X)_n$—$(CT^5T^6)_y$OT$^3$; —$(X)_x$—$(CT^5T^6)_y$ST$^3$; —$(X)_x$—$(CT^5T^6)_y$S(O)T$^3$; —$(X)_x$—$(CT^5T^6)_y$S(O)$_2$T$^3$; —$(X)_x$—$(CT^5T^6)_y$NT$^3$T$^4$; —$(X)_x$—$(CT^5T^6)_y$C(O)T$^3$; —$(X)_x$—$(CT^5T^6)_y$C(O)OT$^3$; —$(X)_x$—$(CT^5T^6)_y$C(O)NT$^3$T$^4$; —$(X)_x$—$(CT^5T^6)_y$NT$^3$C(O)NT$^3$T$^4$; —$(X)_x$—$(CT^5T^6)_y$NT$^3$C(O)T$^4$; —$(X)_x$—$(CT^5T^6)_y$NT$^3$C(O)OT$^4$; —$(X)_x$—$(CT^5T^6)_y$OC(O)NT$^3$T$^4$; —$(X)_x$—$(CT^5T^6)_y$ S(O)$_2$NT$^3$T$^4$ or —$(X)_x$—$(CT^5T^6)_y$NT$^3$S(O)$_2$T$^4$;

$T^2$ independently represents a hydrogen atom; a halogen atom; a linear or branched —O—$C_1$-$C_3$ alkyl; a linear or branched $C_1$-$C_3$ fluoroalkyl; a linear or branched —O—$C_1$-$C_3$ fluoroalkyl; a linear or branched $C_1$-$C_3$ alkyl; or —CN; optionally two geminal $T^2$ form with the carbon atom to which they are bonded, a $C_3$-$C_7$ cycloalkyl;

X independently represents an oxygen atom; a sulphur atom; NT$^3$; S=O or S(O)$_2$;

$T^3$ and $T^4$, identical or different, independently represent a hydrogen atom; a branched or linear $C_1$-$C_6$ alkyl or a $C_3$-$C_6$ cycloalkyl; optionally $T^3$, $T^4$ and the nitrogen atom to which they are bonded form a $C_4$-$C_6$ heterocycloalkyl;

$T^5$ and $T^6$, identical or different, independently represent a hydrogen atom; a fluorine atom or a linear or branched $C_1$-$C_3$ alkyl or a $C_3$-$C_6$ cycloalkyl; optionally $T^5$, $T^6$ and the carbon atom to which they are bonded form a cyclopropyl;

x independently represents 0 or 1;

y independently represents 0, 1, 2 or 3.

3. The compound according to claim 1 wherein $R^4$ represents tBu.

4. The compound according to claim 1, wherein:

$R^2$ represents a partially or totally unsaturated or aromatic 5-, 6- or 7-membered carbocycle; a partially or totally unsaturated or aromatic 5-, 6- or 7-membered heterocycle; a partially or totally unsaturated or aromatic 5-, 6- or 7-membered heterocycle fused with a saturated, partially or totally unsaturated or aromatic 5-, 6- or 7-membered heterocycle; or a partially or totally unsaturated or aromatic 5-, 6- or 7-membered heterocycle fused with a saturated, partially or totally unsaturated or aromatic 5-, 6- or 7-membered carbocycle;

$T^1$ independently represents a hydrogen atom; a halogen atom; —$CH_3$; —$CH_2CH_3$; —$(CH_2)_2CH_3$; —$CH(CH_3)_2$; —$CH_2CF_3$; —$OCH_3$; —$NH_2$; —$N(CH_3)_2$; —$CH_2F$; —$CHF_2$; —$CF_3$; —$OCH_2F$; —$OCHF_2$; —$OCF_3$; —$(X)_x$—$C_3$-$C_6$ cycloalkyl; —$(X)_x$—$(CT^5T^6)_y$-$C_3$-$C_6$ cycloalkyl; —$(X)_x$—$(CT^5T^6)_y$-aryl; —$(X)_x$—$(CT^5T^6)_y$CN; —$(X)_x$—$(CT^5T^6)_y$OT$^3$; —$(X)_x$—$(CT^5T^6)_y$ST$^3$; —$(X)_x$—$(CT^5T^6)_y$S(O)T$^3$; —$(X)_x$—$(CT^5T^6)_y$S(O)$_2$T$^3$; —$(X)_x$—$(CT^5T^6)_y$NT$^3$T$^4$; —$(X)_x$—$(CT^5T^6)_y$C(O)T$^3$; —$(X)_x$—$(CT^5T^6)_y$C(O)OT$^3$; —$(X)_x$—$(CT^5T^6)_y$C(O)NT$^3$T$^4$; —$(X)_x$—$(CT^5T^6)_y$NT$^3$C(O)NT$^3$T$^4$; —$(X)_x$—$(CT^5T^6)_y$NT$^3$C(O)T$^4$; —$(X)_x$—$(CT^5T^6)_y$NT$^3$C(O)OT$^4$; —$(X)_x$—$(CT^5T^6)_y$OC(O)NT$^3$T$^4$; —$(X)_x$—$(CT^5T^6)_y$ S(O)$_2$NT$^3$T$^4$ or —$(X)_x$—$(CT^5T^6)_y$NT$^3$S(O)$_2$T$^4$;

X independently represents an oxygen atom; a sulphur atom; NT$^3$; S=O or S(O)$_2$;

$T^3$ and $T^4$, identical or different, independently represent a hydrogen atom; a branched or linear $C_1$-$C_6$ alkyl or a $C_3$-$C_6$ cycloalkyl;

$T^5$ and $T^6$, identical or different, independently represent a hydrogen atom; a fluorine atom or methyl;

x independently represents 0 or 1;

y independently represents 0, 1, 2 or 3.

5. The compound according to claim 1 wherein $R^5$ represents a linear or branched $C_1$-$C_3$ alkyl; a linear or branched $C_1$-$C_3$ fluoroalkyl; a halogen atom; a $C_3$-$C_6$ cycloalkyl or —$CH_2OH$.

6. The compound according to claim 1 wherein $R^2$, non-substituted or substituted by at least one $T^1$, represents a partially or totally unsaturated or aromatic 5-, 6- or 7-membered heterocycle; a partially or totally unsaturated or aromatic 5-, 6- or 7-membered heterocycle fused with a saturated, partially or totally unsaturated or aromatic 5-, 6- or 7-membered heterocycle; or a partially or totally unsaturated or aromatic 5-, 6- or 7-membered heterocycle fused with a saturated, partially or totally unsaturated or aromatic 5-, 6- or 7-membered carbocycle.

7. The compound according to claim 1 wherein $R^3$, non-substituted or substituted by at least one $T^2$, represents an aryl fused with a saturated, partially or totally unsaturated or aromatic 5-, 6- or 7-membered heterocycle; or a $C_5$-$C_7$ cycloalkenyl.

8. The compound according to claim 1 wherein:
  $T^1$ independently represents a hydrogen atom; a halogen atom; an alkyl; —(X)$_x$—$C_1$-$C_6$ alkyl; a linear or branched fluoroalkyl; —(X)$_x$—$C_3$-$C_6$ cycloalkyl; —(X)$_x$—(CT$^5$T$^6$)$_y$-$C_3$-$C_6$ cycloalkyl; —(X)$_x$—(CT$^5$T$^6$)$_y$OT$^3$; —(X)$_x$—(CT$^5$T$^6$)$_y$-aryl; —(X)$_x$—(CT$^5$T$^6$)$_y$NT$^3$T$^4$; —(X)$_x$—(CT$^5$T$^6$)$_y$C(O)OT$^3$; —(X)$_x$—(CT$^5$T$^6$)$_y$C(O)NT$^3$T$^4$; or —(X)$_x$—(CT$^5$T$^6$)$_y$NT$^3$C(O)T$^4$;
  $T^2$ independently represents a hydrogen atom; a halogen atom; a linear or branched $C_1$-$C_3$ fluoroalkyl; or a linear or branched $C_1$-$C_3$ alkyl;
  X represents an oxygen atom;
  $T^3$ and $T^4$, identical or different, independently represent a hydrogen atom; or a branched or linear $C_1$-$C_6$ alkyl;
  x independently represents 0 or 1;
  y independently represents 0, 1, 2 or 3.

9. The compound according to claim 1 selected in the group consisting of:
  2-(tert-butoxy)-2-[2-(3,4-dihydro-2H-1-benzopyran-6-yl)-3-phenyl-6-(trifluoromethyl)phenyl]acetic acid;
  2-(tert-butoxy)-2-[2-(3,4-dihydro-2H-1-benzopyran-6-yl)-3-(4-methoxyphenyl)-6-(trifluoromethyl)phenyl]acetic acid;
  2-(tert-butoxy)-2-[3-(4-carbamoylphenyl)-2-(3,4-dihydro-2H-1-benzopyran-6-yl)-6-(trifluoromethyl)phenyl]acetic acid;
  2-(tert-butoxy)-2-[3-(3-carbamoylphenyl)-2-(3,4-dihydro-2H-1-benzopyran-6-yl)-6-(trifluoromethyl)phenyl]acetic acid;
  2-(tert-butoxy)-2-[2-(3,4-dihydro-2H-1-benzopyran-6-yl)-3-[4-(methylcarbamoyl)phenyl]-6-(trifluoromethyl)phenyl]acetic acid;
  2-[3-(4-aminophenyl)-2-(3,4-dihydro-2H-1-benzopyran-6-yl)-6-(trifluoromethyl)phenyl]-2-(tert-butoxy)acetic acid;
  2-(tert-butoxy)-2-[3-(4-acetamidophenyl)-2-(3,4-dihydro-2H-1-benzopyran-6-yl)-6-(trifluoromethyl)phenyl]acetic acid;
  2-[3-(3-aminophenyl)-2-(3,4-dihydro-2H-1-benzopyran-6-yl)-6-(trifluoromethyl)phenyl]-2-(tert-butoxy)acetic acid;
  2-(tert-butoxy)-2-[3-(3-acetamidophenyl)-2-(3,4-dihydro-2H-1-benzopyran-6-yl)-6-(trifluoromethyl)phenyl]acetic acid;
  2-(tert-butoxy)-2-[2-(3,4-dihydro-2H-1-benzopyran-6-yl)-3-(3-propylphenyl)-6-(trifluoromethyl)phenyl]acetic acid;
  4-{3-[(tert-butoxy)(carboxy)methyl]-2-(3,4-dihydro-2H-1-benzopyran-6-yl)-4-(trifluoromethyl)phenyl}benzoic acid;
  3-{3-[(tert-butoxy)(carboxy)methyl]-2-(3,4-dihydro-2H-1-benzopyran-6-yl)-4-(trifluoromethyl)phenyl}benzoic acid;
  2-(tert-butoxy)-2-[2-(3,4-dihydro-2H-1-benzopyran-6-yl)-3-(6-propylpyridin-2-yl)-6-(trifluoromethyl)phenyl]acetic acid;
  2-(tert-butoxy)-2-[2-(3,4-dihydro-2H-1-benzopyran-6-yl)-3-(4-propylpyridin-2-yl)-6-(trifluoromethyl)phenyl]acetic acid;
  2-(tert-butoxy)-2-[2-(3,4-dihydro-2H-1-benzopyran-6-yl)-3-(pyridin-2-yl)-6-(trifluoromethyl)phenyl]acetic acid;
  2-(tert-butoxy)-2-[2-(4,4-dimethylcyclohex-1-en-1-yl)-3-(pyridin-4-yl)-6-(trifluoromethyl)phenyl]acetic acid;
  2-{3-[2-(benzyloxy)pyridin-4-yl]-2-(3,4-dihydro-2H-1-benzopyran-6-yl)-6-(trifluoromethyl)phenyl}-2-(tert-butoxy)acetic acid;
  2-(tert-butoxy)-2-[2-(3,4-dihydro-2H-1-benzopyran-6-yl)-3-(3-fluoropyridin-4-yl)-6-(trifluoromethyl)phenyl]acetic acid;
  2-(tert-butoxy)-2-[2-(3,4-dihydro-2H-1-benzopyran-6-yl)-3-(2-propylpyridin-4-yl)-6-(trifluoromethyl)phenyl]acetic acid;
  2-(tert-butoxy)-2-[2-(3,4-dihydro-2H-1-benzopyran-6-yl)-3-(pyridin-4-yl)-6-(trifluoromethyl)phenyl]acetic acid;
  2-(tert-butoxy)-2-[2-(3,4-dihydro-2H-1-benzopyran-6-yl)-3-(pyridin-3-yl)-6-(trifluoromethyl)phenyl]acetic acid;
  2-(tert-butoxy)-2-[2-(3,4-dihydro-2H-1-benzopyran-6-yl)-3-(pyrimidin-4-yl)-6-(trifluoromethyl)phenyl]acetic acid;
  2-(tert-butoxy)-2-[2-(3,4-dihydro-2H-1-benzopyran-6-yl)-3-(pyridazin-4-yl)-6-(trifluoromethyl)phenyl]acetic acid;
  2-(tert-butoxy)-2-[2-(3,4-dihydro-2H-1-benzopyran-6-yl)-3-(thiophen-2-yl)-6-(trifluoromethyl)phenyl]acetic acid;
  2-(tert-butoxy)-2-[2-(3,4-dihydro-2H-1-benzopyran-6-yl)-3-(1-methyl-1H-pyrazol-5-yl)-6-(trifluoromethyl)phenyl]acetic acid;
  2-(tert-butoxy)-2-[2-(3,4-dihydro-2H-1-benzopyran-6-yl)-3-[4-(dimethylamino)-1H-pyrazol-1-yl]-6-(trifluoromethyl)phenyl]acetic acid;
  2-(tert-butoxy)-2-[2-(3,4-dihydro-2H-1-benzopyran-6-yl)-3-(1-methyl-1H-pyrazol-3-yl)-6-(trifluoromethyl)phenyl]acetic acid;
  2-(tert-butoxy)-2-[2-(3,4-dihydro-2H-1-benzopyran-6-yl)-3-(3-methyl-1H-pyrazol-1-yl)-6-(trifluoromethyl)phenyl]acetic acid;
  2-(tert-butoxy)-2-[2-(3,4-dihydro-2H-1-benzopyran-6-yl)-3-(3-phenyl-1H-pyrazol-1-yl)-6-(trifluoromethyl)phenyl]acetic acid;
  2-[3-(4-bromo-1H-pyrazol-1-yl)-2-(3,4-dihydro-2H-1-benzopyran-6-yl)-6-(trifluoromethyl)phenyl]-2-(tert-butoxy)acetic acid;
  2-[3-(4-chloro-1H-pyrazol-1-yl)-2-(3,4-dihydro-2H-1-benzopyran-6-yl)-6-(trifluoromethyl)phenyl]-2-(tert-butoxy)acetic acid;
  2-(tert-butoxy)-2-[2-(3,4-dihydro-2H-1-benzopyran-6-yl)-3-(4-methyl-1H-pyrazol-1-yl)-6-(trifluoromethyl)phenyl]acetic acid;
  2-(tert-butoxy)-2-[2-(3,4-dihydro-2H-1-benzopyran-6-yl)-3-[3-(dimethylamino)-1H-pyrazol-1-yl]-6-(trifluoromethyl)phenyl]acetic acid;
  2-(tert-butoxy)-2-[2-(3,4-dihydro-2H-1-benzopyran-6-yl)-3-[1-methyl-3-(trifluoromethyl)-1H-pyrazol-5-yl]-6-(trifluoromethyl)phenyl]acetic acid;

2-(tert-butoxy)-2-[3-(cyclohex-1-en-1-yl)-2-(3,4-dihydro-2H-1-benzopyran-6-yl)-6-(trifluoromethyl)phenyl]acetic acid;

2-(tert-butoxy)-2-[2-(4,4-dimethylcyclohex-1-en-1-yl)-3-(1H-pyrazol-1-yl)-6-(trifluoromethyl)phenyl]acetic acid;

2-(tert-butoxy)-2-[2-(3,4-dihydro-2H-1-benzopyran-6-yl)-3-(1H-pyrazol-1-yl)-6-(trifluoromethyl)phenyl]acetic acid;

2-(tert-butoxy)-2-[2-(3,4-dihydro-2H-1-benzopyran-6-yl)-3-(1H-imidazol-1-yl)-6-(trifluoromethyl)phenyl]acetic acid;

2-[3-(1,3-benzothiazol-2-yl)-2-(3,4-dihydro-2H-1-benzopyran-6-yl)-6-(trifluoromethyl)phenyl]-2-(tert-butoxy)acetic acid;

2-(tert-butoxy)-2-[2-(3,4-dihydro-2H-1-benzopyran-6-yl)-3-(1,3-thiazol-2-yl)-6-(trifluoromethyl)phenyl]acetic acid;

2-(tert-butoxy)-2-[2-(3,4-dihydro-2H-1-benzopyran-6-yl)-3-(1,2-thiazol-4-yl)-6-(trifluoromethyl)phenyl]acetic acid;

2-(tert-butoxy)-2-[2-(3,4-dihydro-2H-1-benzopyran-6-yl)-3-(1-methyl-1H-imidazol-4-yl)-6-(trifluoromethyl)phenyl]acetic acid;

2-(tert-butoxy)-2-[2-(4,4-dimethylcyclohex-1-en-1-yl)-3-(1-methyl-1H-pyrazol-4-yl)-6-(trifluoromethyl)phenyl]acetic acid;

2-(tert-butoxy)-2-[2-(3,4-dihydro-2H-1-benzopyran-6-yl)-3-(1-methyl-1H-pyrazol-4-yl)-6-(trifluoromethyl)phenyl]acetic acid;

2-(tert-butoxy)-2-[2-(3,4-dihydro-2H-1-benzopyran-6-yl)-3-{pyrazolo[1,5-a]pyridin-3-yl}-6-(trifluoromethyl)phenyl]acetic acid;

2-(tert-butoxy)-2-{2-(3,4-dihydro-2H-1-benzopyran-6-yl)-3-[1-(2,2,2-trifluoroethyl)-1H-pyrazol-4-yl]-6-(trifluoromethyl)phenyl}acetic acid;

2-(tert-butoxy)-2-[2-(3,4-dihydro-2H-1-benzopyran-6-yl)-3-(1-methyl-1H-pyrrol-3-yl)-6-(trifluoromethyl)phenyl] acetic acid;

2-(tert-butoxy)-2-[3-(cyclopent-1-en-1-yl)-2-(3,4-dihydro-2H-1-benzopyran-6-yl)-6-(trifluoromethyl)phenyl]acetic acid;

2-(tert-butoxy)-2-{3-[1-(cyclobutylmethyl)-6-oxo-1,6-dihydropyridin-2-yl]-2-(3,4-dihydro-2H-1-benzopyran-6-yl)-6-(trifluoromethyl)phenyl}acetic acid;

2-(tert-butoxy)-2-{3-[1-(cyclobutylmethyl)-2-oxo-1,2-dihydropyridin-3-yl]-2-(3,4-dihydro-2H-1-benzopyran-6-yl)-6-(trifluoromethyl)phenyl}acetic acid;

2-(tert-butoxy)-2-[2-(3,4-dihydro-2H-1-benzopyran-6-yl)-3-(1-methyl-1H-pyridin-2-one-5-yl)-6-(trifluoromethyl)phenyl]acetic acid;

2-(tert-butoxy)-2-[2-(3,4-dihydro-2H-1-benzopyran-6-yl)-3-(6-oxo-1-propyl-1,6-dihydropyridin-3-yl)-6-(trifluoromethyl)phenyl]acetic acid;

2-[3-(1-benzyl-6-oxo-1,6-dihydropyridin-3-yl)-2-(3,4-dihydro-2H-1-benzopyran-6-yl)-6-(trifluoromethyl)phenyl]-2-(tert-butoxy)acetic acid;

2-(tert-butoxy)-2-{3-[1-(cyclopropylmethyl)-6-oxo-1,6-dihydropyridin-3-yl]-2-(3,4-dihydro-2H-1-benzopyran-6-yl)-6-(trifluoromethyl)phenyl}acetic acid;

2-(tert-butoxy)-2-{3-[1-(cyclobutylmethyl)-6-oxo-1,6-dihydropyridin-3-yl]-2-(3,4-dihydro-2H-1-benzopyran-6-yl)-6-(trifluoromethyl)phenyl}acetic acid;

2-(tert-butoxy)-2-{3-[1-(2-cyclopropylethyl)-6-oxo-1,6-dihydropyridin-3-yl]-2-(3,4-dihydro-2H-1-benzopyran-6-yl)-6-(trifluoro methyl)phenyl}acetic acid;

2-(tert-butoxy)-2-[2-(3,4-dihydro-2H-1-benzopyran-6-yl)-3-[1-(2-methylpropyl)-6-oxo-1,6-dihydropyridin-3-yl]-6-(trifluoromethyl)phenyl]acetic acid;

2-(tert-butoxy)-2-[3-(1-cyclobutylmethyl-6-oxo-1,6-dihydro-pyridin-3-yl)-2-(3,4-dihydro-2H-1-benzopyran-6-yl)-6-methylphenyl]acetic acid;

2-(tert-butoxy)-2-[3-(1-cyclobutylmethyl-6-oxo-1,6-dihydro-pyridin-3-yl)-6-methyl-2-[5-methyl-(3,4-dihydro-2H-1-benzopyran-6-yl)]phenyl]acetic acid;

2-(tert-butoxy)-2-[3-(1-cyclopropyl-6-oxo-1,6-dihydropyridin-3-yl)-2-(3,4-dihydro-2H-1-benzopyran-6-yl)-6-(trifluoromethyl)phenyl]acetic acid;

2-(tert-butoxy)-2-[2-(3,4-dihydro-2H-1-benzopyran-6-yl)-3-(1-ethyl-2-oxo-1,2-dihydropyridin-4-yl)-6-(trifluoromethyl)phenyl]acetic;

2-(tert-butoxy)-2-[2-(3,4-dihydro-2H-1-benzopyran-6-yl)-3-(5-methyl-1H-pyrazol-1-yl)-6-(trifluoromethyl)phenyl]acetic acid.

10. A method for treating a viral infection comprising administering to patient in need thereof a compound according claim 1.

11. The method according to claim 10, wherein said viral infection is a retroviral infection.

12. The method accord to claim 10, wherein said viral infection is an HIV infection.

13. A pharmaceutical composition comprising a compound according to claim 1 as an active ingredient and at least a pharmaceutically acceptable carrier.

14. A pharmaceutical composition according to claim 13 further comprising a further antiviral agent.

15. A method for treating a viral infection comprising administering to patient in need thereof a pharmaceutical composition according claim 13.

16. The method according to claim 15, wherein said viral infection is a retroviral infection.

17. The method according to claim 15, wherein said viral infection is an HIV infection.

* * * * *